United States Patent
Beaulieu et al.

(10) Patent No.: US 9,315,475 B2
(45) Date of Patent: Apr. 19, 2016

(54) HIV PROTEASE INHIBITORS

(71) Applicants: Christian Beaulieu, Laval (CA); David J. Bennett, New Hope, PA (US); Christopher J. Bungard, Lansdale, PA (US); Ronald K. Chang, Oreland, PA (US); Sheldon Crane, Ile Perrot (CA); Thomas J. Greshock, Collegeville, PA (US); Li Hao, Singapore (SG); Kate Holloway, Lansdale, PA (US); Jesse J. Manikowski, Norristown, PA (US); John A. McCauley, Maple Glen, PA (US); Daniel McKay, Milton, MA (US); Carmela Molinaro, West Point, PA (US); Oscar Miguel Moradei, Kirkland (CA); Philippe G. Nantermet, Lansdale, PA (US); Christian Nadeau, Montreal (CA); Satyanarayana Tummanapalli, Singapore (SG); William Shipe, Chalfont, PA (US); Sanjay Kumar Singh, Singapore (SG); Vouy Linh Truong, Pierrefonds (CA); Sivalenka Vijayasaradhi, Singapore (SG); Peter D. Williams, Harleysville, PA (US); Catherine M. Wiscount, Allentown, PA (US)

(72) Inventors: Christian Beaulieu, Laval (CA); David J. Bennett, New Hope, PA (US); Christopher J. Bungard, Lansdale, PA (US); Ronald K. Chang, Oreland, PA (US); Sheldon Crane, Ile Perrot (CA); Thomas J. Greshock, Collegeville, PA (US); Li Hao, Singapore (SG); Kate Holloway, Lansdale, PA (US); Jesse J. Manikowski, Norristown, PA (US); John A. McCauley, Maple Glen, PA (US); Daniel McKay, Milton, MA (US); Carmela Molinaro, West Point, PA (US); Oscar Miguel Moradei, Kirkland (CA); Philippe G. Nantermet, Lansdale, PA (US); Christian Nadeau, Montreal (CA); Satyanarayana Tummanapalli, Singapore (SG); William Shipe, Chalfont, PA (US); Sanjay Kumar Singh, Singapore (SG); Vouy Linh Truong, Pierrefonds (CA); Sivalenka Vijayasaradhi, Singapore (SG); Peter D. Williams, Harleysville, PA (US); Catherine M. Wiscount, Allentown, PA (US)

(73) Assignees: MERCK SHARP & DOHME CORP., Rahway, NJ (US); MERCK CANADA INC., Kirkland, Province of Quebec (CA)

(*) Notice: Subject to any disclaimer, the term of this patent is extended or adjusted under 35 U.S.C. 154(b) by 124 days.

(21) Appl. No.: 14/021,930

(22) Filed: Sep. 9, 2013

(65) Prior Publication Data

US 2014/0200197 A1 Jul. 17, 2014

Related U.S. Application Data

(60) Provisional application No. 61/699,343, filed on Sep. 11, 2011.

(51) Int. Cl.
*C07D 413/06* (2006.01)
*C07D 413/12* (2006.01)
(Continued)

(52) U.S. Cl.
CPC .......... *C07D 265/30* (2013.01); *A61K 31/5375* (2013.01); *A61K 31/5377* (2013.01); *A61K 31/695* (2013.01); *A61K 45/06* (2013.01); *C07D 413/06* (2013.01); *C07D 413/12* (2013.01); *C07D 413/14* (2013.01); *C07D 417/12* (2013.01); *C07D 487/04* (2013.01); *C07D 493/04* (2013.01); *C07F 7/0814* (2013.01)

(58) Field of Classification Search
CPC .. C07D 265/30; C07D 413/06; C07D 413/12; C07D 413/14; C07D 417/12; C07D 487/04; C07D 493/04
See application file for complete search history.

(56) References Cited

U.S. PATENT DOCUMENTS

| | | | |
|---|---|---|---|
| 5,196,438 | A | 3/1993 | Martin et al. |
| 5,413,999 | A | 5/1995 | Vacca et al. |
| 5,484,801 | A | 1/1996 | Al-Razzak et al. |
| 5,484,926 | A | 1/1996 | Dressman et al. |
| 5,852,195 | A | 12/1998 | Romines et al. |
| 5,858,397 | A | 1/1999 | Lim et al. |
| 8,497,383 | B2 | 7/2013 | Coburn et al. |
| 2014/0018325 | A1 | 1/2014 | Boyd et al. |
| 2014/0018326 | A1 | 1/2014 | Moradei |
| 2014/0303171 | A1 | 10/2014 | Boyd et al. |

FOREIGN PATENT DOCUMENTS

| | | | |
|---|---|---|---|
| WO | 0138332 | A1 | 5/2001 |
| WO | 0230930 | A2 | 4/2002 |
| WO | 2009042093 | A1 | 4/2009 |
| WO | 2009042094 | A2 | 4/2009 |
| WO | 2012030685 | A2 | 3/2012 |

(Continued)

OTHER PUBLICATIONS

Huff, Joel R., Journal of Medicinal Chemistry, vol. 34, No. 8, Aug. 1991, pp. 2305-2314.*

(Continued)

*Primary Examiner* — Rebecca Anderson
(74) *Attorney, Agent, or Firm* — Carol S. Quagliato; Mark R. Daniel

(57) ABSTRACT

The compounds encompassed by Formula I include compounds which are HIV protease inhibitors and other compounds which can be metabolized in vivo to HIV protease inhibitors. The compounds and their pharmaceutically acceptable salts are useful for the prophylaxis or treatment of infection by HIV and the prophylaxis, treatment, or delay in the onset of AIDS. The compounds and their salts can be employed as ingredients in pharmaceutical compositions, optionally in combination with other antivirals, immunomodulators, antibiotics or vaccines.

23 Claims, No Drawings

(51) Int. Cl.

| | |
|---|---|
| *C07D 413/14* | (2006.01) |
| *C07D 417/12* | (2006.01) |
| *C07D 265/30* | (2006.01) |
| *C07D 487/04* | (2006.01) |
| *C07D 493/04* | (2006.01) |
| *A61K 31/5375* | (2006.01) |
| *A61K 31/5377* | (2006.01) |
| *A61K 31/695* | (2006.01) |
| *A61K 45/06* | (2006.01) |
| *C07F 7/08* | (2006.01) |

(56) References Cited

FOREIGN PATENT DOCUMENTS

| WO | 2015017393 A2 | 2/2015 |
|---|---|---|
| WO | 2015095265 A1 | 6/2015 |
| WO | 2015095276 A1 | 6/2015 |

OTHER PUBLICATIONS

Daniel E. Patterson, et al, "Developement of a Practical Large-Scale Synthesis of Denagliptin Tosylate", Organic Process Research & Dev., 2009, pp. 900-906, vol. 13, US.

Hiroyuki Toh, et al, "Close Structural Resemblance Between Putative Polymerase of a *Drosophila* Transposable Genetic Element 17.5 and Pol Gene Product of Moloney Murine Leukaemia Virus", The EMBO Journal, 1985, pp. 1267-1272, vol. 4, No. 5, US.

J.P. Vacca, et al, "L-735,524: An Orally Bioavailable Human Immunodeficiency Virus Type 1 Protease Inhibitor", Proc. Natl. Acad. Sci., Apr. 1994, pp. 4096-4100, vol. 91, US.

Laurence H. Pearl, et al, "A Structural Model for the Retroviral Proteases", Nature, 1987, pp. 351-354, vol. 329, US.

Lee Ratner, et al, "Complete Nucleotide Sequence of AIDS Virus", HTLV-III, Nature, 1985, pp. 277-284, vol. 313, US.

Michael D. Power, et al, "Nucleotide Sequence of SRV-1, a Type D Simian", Science, 1986, pp. 1567-1572, vol. 231, US.

Nancy E. Kohl, et al, "Active Human Immunodeficiency Virus Protease is Required for Viral Infectivity", Proc. Natl. Acad. Sci., 1988, pp. 4686-4690, vol. 85, US.

Roy M. Gulick, et al, "Treatment With Indinavir, Zidovudine, and Lamivudine in Adults With Human Immunodeficiency Virus Infection and Prior Antiretroviral Therapy", New England Journal of Medicine, 1997, pp. 734-739, vol. 337, US.

Scott M. Hammer, et al, "A Controlled Trial of Two Nucleoside Analogues Plus Indinavir in Persons With Human Immunodeficiency Virus Infection and CD4 Cell Counts of 200 Per Cubic Millimeter or Less", The New England Journal of Medicine, 1997, pp. 725-733, vol. 337, No. 11, US.

* cited by examiner

HIV PROTEASE INHIBITORS

REFERENCE TO SEQUENCE LISTING SUBMITTED ELECTRONICALLY

The sequence listing of the present application is submitted electronically via EFS-Web as an ASCII formatted sequence listing with a file name "MCCIFD00008-25MAR2014.txt", creation date of Mar. 25, 2014, and a size of 1243 bytes. This sequence listing submitted via EFS-Web is part of the specification and is herein incorporated by reference in its entirety.

BACKGROUND OF THE INVENTION

A retrovirus designated human immunodeficiency virus (HIV), particularly the strains known as HIV type-1 (HIV-1) virus and type-2 (HIV-2) virus, is the etiological agent of acquired immunodeficiency syndrome (AIDS), a disease characterized by the destruction of the immune system, particularly of CD4 T-cells, with attendant susceptibility to opportunistic infections, and its precursor AIDS-related complex ("ARC"), a syndrome characterized by symptoms such as persistent generalized lymphadenopathy, fever and weight loss. This virus was previously known as LAV, HTLV-III, or ARV. A common feature of retrovirus replication is the extensive post-translational processing of precursor polyproteins by a virally encoded protease to generate mature viral proteins required for virus assembly and function. Inhibition of this processing prevents the production of normally infectious virus. For example, Kohl et al., *Proc. Nat'l Acad. Sci.* 1988, 85: 4686, demonstrated that genetic inactivation of the HIV encoded protease resulted in the production of immature, non-infectious virus particles. These results indicated that inhibition of the HIV protease represents a viable method for the treatment of AIDS and the prevention or treatment of infection by HIV.

Nucleotide sequencing of HIV shows the presence of a pol gene in one open reading frame [Ratner et al., *Nature* 1985, 313: 277]. Amino acid sequence homology provides evidence that the pol sequence encodes reverse transcriptase, an endonuclease, HIV protease and gag, which encodes the core proteins of the virion (Toh et al., *EMBO J.* 1985, 4: 1267; Power et al., *Science* 1986, 231: 1567; Pearl et al., *Nature* 1987, 329: 351].

Several HIV protease inhibitors are presently approved for clinical use in the treatment of AIDS and HIV infection, including indinavir (see U.S. Pat. No. 5,413,999), amprenavir (U.S. Pat. No. 5,585,397), saquinavir (U.S. Pat. No. 5,196,438), ritonavir (U.S. Pat. No. 5,484,801) and nelfinavir (U.S. Pat. No. 5,484,926). Each of these protease inhibitors is a peptide-derived peptidomimetic, competitive inhibitor of the viral protease which prevents cleavage of the HIV gag-pol polyprotein precursor. Tipranavir (U.S. Pat. No. 5,852,195) is a non-peptide peptidomimetic protease inhibitors also approved for use in treating HIV infection. The protease inhibitors are administered in combination with at least one and typically at least two other HIV antiviral agents, particularly nucleoside reverse transcriptase inhibitors such as zidovudine (AZT) and lamivudine (3TC) and/or non-nucleoside reverse transcriptase inhibitors such as efavirenz and nevirapine. Indinavir, for example, has been found to be highly effective in reducing HIV viral loads and increasing CD4 cell counts in HIV-infected patients, when used in combination with nucleoside reverse transcriptase inhibitors. See, for example, Hammer et al., *New England J. Med.* 1997, 337: 725-733 and Gulick et al., *New England J. Med.* 1997, 337: 734-739.

The established therapies employing a protease inhibitor are not suitable for use in all HIV-infected subjects. Some subjects, for example, cannot tolerate these therapies due to adverse effects. Many HIV-infected subjects often develop resistance to particular protease inhibitors. Furthermore, the currently available protease inhibitors are rapidly metabolized and cleared from the bloodstream, requiring frequent dosing and use of a boosting agent. Accordingly, there is a continuing need for new compounds which are capable of inhibiting HIV protease and suitable for use in the treatment or prophylaxis of infection by HIV and/or for the treatment or prophylaxis or delay in the onset or progression of AIDS.

SUMMARY OF THE INVENTION

The present invention is directed to 2,5-morpholine derivatives and their use in the inhibition of HIV protease, the inhibition of HIV replication, the prophylaxis of infection by HIV, the treatment of infection by HIV, and the prophylaxis, treatment, and delay in the onset or progression of AIDS.

DETAILED DESCRIPTION OF THE INVENTION

The invention encompasses a genus of compounds of Formula I:

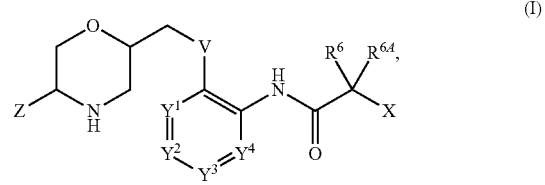

or a pharmaceutically acceptable salt thereof, wherein:

V is $CH_2$ or O;

$Y^1, Y^2, Y^3$ and $Y^4$ are independently selected from C(R) and N;

each X is independently selected from H and $NR^7R^8$;

Z is selected from the group consisting of

-continued (4) 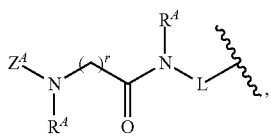

(5) 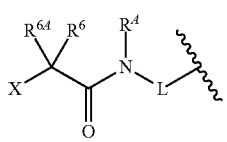

(6) 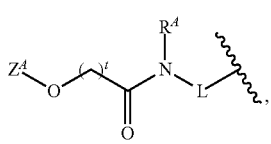

(7) 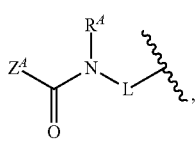

(8) 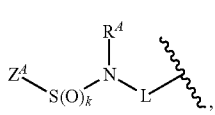

(9) 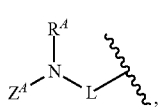

(10) 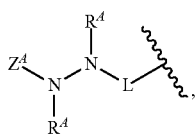

(11) 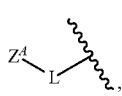

(12) 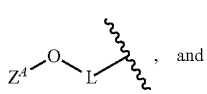, and

(13) 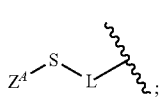;

L is a linker selected from
(a) a bond,
(b) —CH$_2$—,
(c) —C(O)—,
(d) —CH$_2$—C(O)— or —C(O)—CH$_2$—,
(e) —CH$_2$—CH$_2$—C(O)— or —C(O)—CH$_2$—CH$_2$—, and (f) 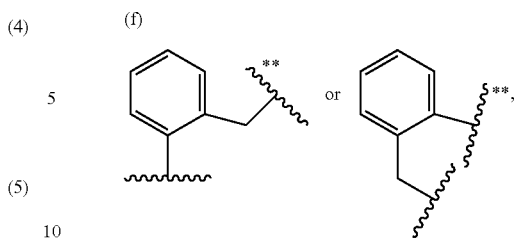

wherein ** shows the point of attachment to the morpholine and when Z is

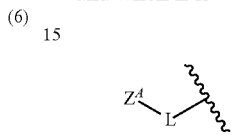

then L is not a bond;

R is selected from H, halo, hydroxy, C$_{1-4}$alkyl, C$_{1-4}$alkoxy, C$_{1-4}$alkyl-S(O)$_k$—, CF$_3$, CN, benzyl, or two R groups on adjacent atoms may be joined together with the atoms to which they are attached to form a fused phenyl, pyridine, pyridazine, pyrimidine, pyrazine, or triazine, each of which is optionally substituted with 1 to 4 substituents independently selected from the group consisting of: halo, C$_{1-4}$alkyl, C$_{1-4}$alkoxy, CF$_3$ and CN;

each k is independently 0, 1 or 2;
each r and t are independently 1, 2, 3 or 4;
Z$^A$ is selected from the group consisting of:
(1) hydrogen,
(2) C$_{1-10}$ alkyl,
(3) C$_{2-10}$alkenyl,
(4) C$_{3-7}$ cycloalkyl,
(5) AryA,
(6) HetA,
(7) HetB,
wherein said C$_{1-10}$ alkyl, C$_{2-10}$alkenyl and C$_{3-7}$ cycloalkyl are optionally substituted with 1 to 6 substituents as allowed by valence independently selected from the group consisting of: fluoro, hydroxy, carbamoyl, C$_{3-6}$ cycloalkyl, C(O)O—C$_{1-6}$ alkyl, C(O)OH, C(O)—C$_{1-6}$ alkyl, N(H)—C$_{1-6}$ alkyl, N(—C$_{1-6}$ alkyl)$_2$, ArylA, HetA and HetB;

each R$^A$ is independently H or C$_{1-6}$ alkyl;
or Z$^A$ and R$^A$ and the nitrogen atom to which they are attached may be joined together to form a 5-, 6 or 7-membered mono-cyclic, or 9- or 10-membered bi-cyclic, saturated, aromatic or partially aromatic ring, said ring optionally containing 1 to 3 additional heteroatoms selected from O, S and N, and said ring optionally substituted with from 1 to 3 X$^A$;

each R$^6$ independently is:

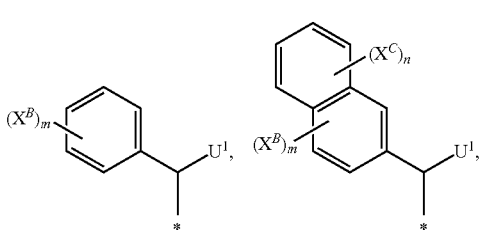

-continued

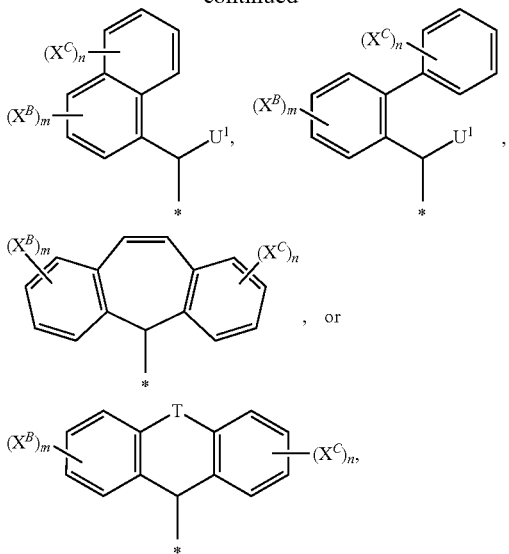

wherein the asterisk (*) denotes the point of attachment to the rest of the compound and $U^1$ is selected from H, $C_{1-10}$alkyl, ArylA, HetA and HetB;

each $R^{6A}$ independently is H or $C_{1-6}$ alkyl;

alternatively, $R^6$ and $R^{6A}$ together with the carbon to which they are attached form a $C_{3-6}$ cycloalkyl which is optionally substituted with phenyl, wherein the phenyl is optionally substituted with from 1 to 3 $X^D$.

each $X^A$, each $X^B$, each $X^C$, each $X^D$, each $Y^B$ and each $Y^C$ are independently selected from the group consisting of:
(1) $C_{1-6}$ alkyl,
(2) $C_{3-6}$ cycloalkyl,
(3) $C_{1-6}$ haloalkyl,
(4) OH,
(5) O—$C_{1-6}$ alkyl,
(6) O—$C_{1-6}$ haloalkyl,
(7) O—$C_{3-6}$ cycloalkyl,
(8) SH,
(9) S—$C_{1-6}$ alkyl,
(10) S—$C_{1-6}$ haloalkyl,
(11) S—$C_{3-6}$ cycloalkyl,
(12) halo,
(13) CN,
(14) $NO_2$,
(15) $NH_2$,
(16) N(H)—$C_{1-6}$ alkyl,
(17) N(—$C_{1-6}$ alkyl)$_2$,
(18) N(H)C(O)—$C_{1-6}$ alkyl,
(19) N(H)CH(O),
(20) CH(O),
(21) C(O)—$C_{1-6}$ alkyl,
(22) C(O)OH,
(23) C(O)O—$C_{1-6}$ alkyl,
(24) C(O)$NH_2$,
(25) C(O)N(H)—$C_{1-6}$ alkyl,
(26) C(O)N(—$C_{1-6}$ alkyl)$_2$,
(27) C(O)N(H)C(O)—$C_{1-6}$ alkyl,
(28) C(O)N(H)CH(O)
(29) $SO_2$H,
(30) $SO_2$—$C_{1-6}$ alkyl;
(31) phenyl, benzyl or phenoxy, each optionally substituted with 1 to 5 substituents selected from halogen and $C_{1-6}$ alkyl,
(32) HetA, —O-HetA or $CH_2$-HetA, optionally substituted with 1 to 5 substituents selected from halogen and $C_{1-6}$ alkyl,
(33) trimethylsilyl, and
(34) $C_{2-6}$alkenyl, wherein $C_{1-6}$ alkyl in each instance of (1), (3) (5), (6), (9), (10), (16), (17), (18), (21), (23), (25), (26), (27), (30), (31) and (32) above is optionally substituted with 1 to 6 substituents as allowed by valence selected from the group consisting of:
(a) $C_{1-6}$ haloalkyl,
(b) OH
(c) O—$C_{1-6}$ alkyl,
(d) O—$C_{1-6}$ haloalkyl,
(e) O—$C_{3-6}$ cycloalkyl,
(f) SH,
(g) S—$C_{1-6}$ alkyl,
(h) halo,
(i) CN,
(j) $NO_2$,
(k) $NH_2$,
(l) N(H)—$C_{1-6}$ alkyl,
(m) N(—$C_{1-6}$ alkyl)$_2$,
(n) C(O)—$C_{1-6}$ alkyl,
(o) C(O)OH,
(p) C(O)O—$C_{1-6}$ alkyl, and
(q) $SO_2$—$C_{1-6}$ alkyl;

T is O, S, S(O), or $SO_2$;
m is an integer equal to 0, 1, 2, or 3;
n is an integer equal to 0, 1, 2, or 3;
$R^7$ is H, $C_{1-6}$ alkyl, $C_{3-6}$ cycloalkyl, $C_{1-6}$ alkyl substituted with $C_{3-6}$ cycloalkyl, C(O)—$R^K$ or $SO_2$—$R^K$;
$R^8$ is H, $C_{1-6}$ alkyl, $C_{1-6}$ haloalkyl and $C_{3-6}$ cycloalkyl;
$R^K$ is:
(1) $C_{1-6}$ alkyl,
(2) $C_{3-6}$ cycloalkyl,
(3) $C_{1-6}$ alkyl substituted with $C_{3-6}$ cycloalkyl,
(4) O—$C_{1-6}$ alkyl,
(5) O—$C_{1-6}$ alkyl substituted with O—$C_{1-6}$ alkyl,
(6) O—$C_{1-6}$ fluoroalkyl,
(7) C(O)O—$C_{1-6}$ alkyl,
(8) $C_{1-6}$ alkyl substituted with C(O)O—$C_{1-6}$ alkyl,
(9) $C_{1-6}$ alkyl substituted with C(O)OH,
(10) $C_{1-6}$ alkyl substituted with C(O)—$C_{1-6}$ alkyl,
(11) N(H)—$C_{1-6}$ alkyl,
(12) N(—$C_{1-6}$ alkyl)$_2$,
(13) $C_{1-6}$ alkyl substituted with $NH_2$, N(H)—$C_{1-6}$ alkyl, or N(—$C_{1-6}$ alkyl)$_2$,
(14) AryA,
(15) $C_{1-6}$ alkyl substituted with AryA,
(16) O—$C_{1-6}$ alkyl substituted with AryA,
(17) HetA,
(18) $C_{1-6}$ alkyl substituted with HetA,
(19) O—$C_{1-6}$ alkyl substituted with HetA,
(20) HetB,
(21) O-HetB, or
(22) O—$C_{1-6}$ alkyl substituted with HetB;

each AryA is an aryl which is independently phenyl or naphthyl, wherein the phenyl or naphthyl is optionally substituted with from 1 to 3 $Y^B$;

each HetA is a heteroaryl which is independently (i) a 5- or 6-membered monocyclic heteroaromatic ring containing from 1 to 3 heteroatoms independently selected from N, O and S, or (ii) is a 9-, 10- or 11-membered bicyclic heteroaromatic ring containing from 1 to 4 heteroatoms independently selected from N, O and S; wherein the monocyl- cic ring (i) or the bicyclic ring (ii) is optionally substituted with from 1 to 3 $Y^C$; and each HetB is independently a 4- to 7-membered, saturated or unsaturated, non-aromatic heterocyclic ring containing at least one carbon atom and from 1 to 4 heteroatoms independently selected from N, O and S, where each S is optionally oxidized to S(O) or S(O)$_2$, and wherein the saturated or unsaturated heterocyclic ring is optionally substituted with from 1 to 3 substituents each of which is independently halogen, CN, $C_{1-6}$ alkyl, OH, oxo, O—$C_{1-6}$ alkyl, $C_{1-6}$ haloalkyl, O—$C_{1-6}$ haloalkyl, C(O)NH$_2$, C(O)N(H)—$C_{1-6}$ alkyl, C(O)N(—$C_{1-6}$ alkyl)$_2$, C(O)H, C(O)—$C_{1-6}$ alkyl, CO$_2$H, CO$_2$—$C_{1-6}$ alkyl, SO$_2$H, or SO$_2$—$C_{1-6}$ alkyl.

Within the genus, the invention encompasses a first subgenus of compounds of Formula I wherein $R^6$ is:

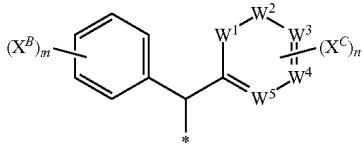

wherein $W^1$ to $W^5$ are independently C or N, with the proviso that no more that three are N, and $R^{6A}$ is H. Although not explicitly depicted, when any of $W^1$ to $W^5$ is C, said carbon is bonded to a hydrogen atom to satisfy the valence, unless said carbon is substituted with $X^C$.

Also within the genus, the invention encompasses a second sub-genus of compounds of Formula I wherein Z is

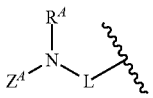

and L is —C(O)—, and all other variables are as provided in the genus or first sub-genus.

Also within the genus, the invention encompasses a third sub-genus of compounds of Formula I wherein Z is

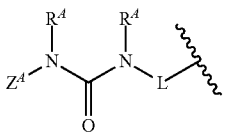

and L is —CH$_2$—, and all other variables are as provided in the genus or first sub-genus.

Also within the genus, the invention encompasses a fourth sub-genus of compounds of Formula I wherein Z is

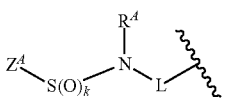

and L is —CH$_2$—, and all other variables are as provided in the genus or first sub-genus.

Also within the genus, the invention encompasses a fifth sub-genus of compounds of Formula I wherein Z is

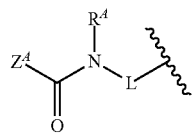

and L is —CH$_2$—, and all other variables are as provided in the genus or first sub-genus.

Also within the genus, the invention encompasses a sixth sub-genus of compounds of Formula I wherein Z is

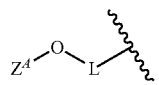

and L is —CH$_2$—, and all other variables are as provided in the genus or first sub-genus.

Also within the genus, the invention encompasses a seventh sub-genus of compounds of Formula I wherein Z is

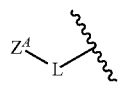

and L is —CH$_2$—, and all other variables are as provided in the genus or first sub-genus.

Also within the genus, the invention encompasses an eighth sub-genus of compounds of Formula I wherein Z is

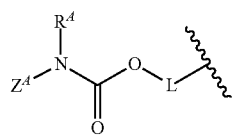

and L is —CH$_2$—, and all other variables are as provided in the genus or first sub-genus.

Also within the genus, the invention encompasses a ninth sub-genus of compounds of Formula I wherein Z is

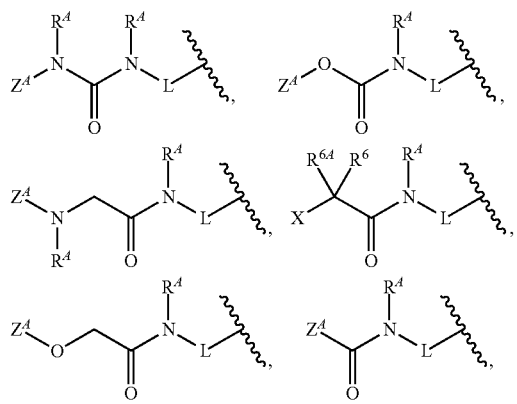

-continued

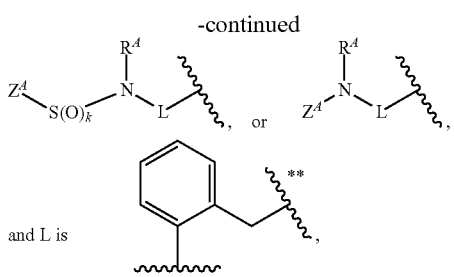

and L is and all other variables are as provided in the genus or first sub-genus.

Also within the genus, the invention encompasses a tenth sub-genus of compounds of Formula I of Formula Ia

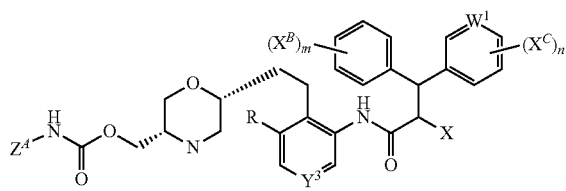

(Ia)

or a pharmaceutically acceptable salt thereof, wherein $W^1$ is C or N. $X^B$ and $X^C$ may be substituted on any substitutable position including, for $X^C$, $W^1$ when $W^1$ is C, and all other variables are as provided in the genus.

Within the tenth sub-genus, the invention encompasses a class of compounds of Formula Ia wherein:
R is H or fluoro,
$Y^3$ is CH or N,
$X^B$ and $X^C$ are independently selected from halo, —$OCH_3$, —$CF_3$ and —$OCF_3$, and
m and n are independently 0, 1 or 2.

The invention encompasses a sub-class of compounds of Formula Ia wherein X is selected from: H, —$NH_2$ and —N(H)—C(O)—$OR^8$, and all other variables are as provided in the tenth sub-genus or class. The invention encompasses a group of compounds of Formula Ia wherein $W^1$ is C, one $X^B$ group is present and substituted at the 4-position, one or two $X^C$ groups are present and substituted at the 3- or 3,5-positions respectively, and the $X^B$ group is a different group with respect to either $X^C$ group, and all other variables are as provided in the tenth sub-genus, class or sub-class.

The invention encompasses a group of compounds of Formula Ia wherein $Z^A$ is selected from the group consisting of:
(1) hydrogen,
(2) $C_{1-10}$ alkyl,
(3) $C_{2-10}$ alkenyl, and
(4) $C_{3-7}$ cycloalkyl,
wherein said $C_{1-10}$ alkyl, $C_{2-10}$ alkenyl and $C_{3-7}$ cycloalkyl are optionally substituted with 1 to 6 substituents as allowed by valence independently selected from the group consisting of: fluoro, hydroxy, carbamoyl, $C_{3-6}$ cycloalkyl, C(O)O—$C_{1-6}$ alkyl, C(O)OH, C(O)—$C_{1-6}$ alkyl, N(H)—$C_{1-6}$ alkyl, N(—$C_{1-6}$ alkyl)$_2$, ArylA, HetA and HetB, and all other variables are as provided in the tenth sub-genus, class or sub-class as described above.

The invention encompasses a sub-group of compounds of Formula Ia wherein $Z^A$ is $C_{1-10}$ alkyl, optionally substituted with 1 to 6 substituents as allowed by valence independently selected from the group consisting of: fluoro and hydroxyl, and all other variables are as provided in the tenth sub-genus, class, sub-class or group as described above. The invention encompasses compounds of Formula Ia wherein $Z^A$ is —$(CH_2)_{0-4}$—$CF_3$, and all other variables are as provided in the tenth sub-genus, class, sub-class, group or sub-group as described above.

The present invention includes compounds of Formula I above and pharmaceutically acceptable salts thereof.

Compounds of Formula Ia form a subset of the compounds included in Formula I. Any description which follows that refers to a compound of Formula I also applies to a compound of Formula Ia.

Another embodiment of the present invention is a compound of Formula I, or a pharmaceutically acceptable salt thereof, as originally defined or as defined in any of the foregoing embodiments, aspects, classes, or subclasses, wherein the compound or its salt is in a substantially pure form. As used herein "substantially pure" means suitably at least about 60 wt. %, typically at least about 70 wt. %, preferably at least about 80 wt. %, more preferably at least about 90 wt. % (e.g., from about 90 wt. % to about 99 wt. %), even more preferably at least about 95 wt. % (e.g., from about 95 wt. % to about 99 wt. %, or from about 98 wt. % to 100 wt. %), and most preferably at least about 99 wt. % (e.g., 100 wt. %) of a product containing a compound of Formula I or its salt (e.g., the product isolated from a reaction mixture affording the compound or salt) consists of the compound or salt. The level of purity of the compounds and salts can be determined using a standard method of analysis such as thin layer chromatography, gel electrophoresis, high performance liquid chromatography, and/or mass spectrometry. If more than one method of analysis is employed and the methods provide experimentally significant differences in the level of purity determined, then the method providing the highest level of purity governs. A compound or salt of 100% purity is one which is free of detectable impurities as determined by a standard method of analysis. The compounds of the invention have two or more asymmetric centers and can occur as mixtures of stereoisomers. It is understood that a substantially pure compound can be either a substantially pure mixture of stereoisomers or a substantially pure individual diastereomer or enantiomer.

Other embodiments of the present invention include the following:

(a) A pharmaceutical composition comprising an effective amount of a compound of Formula I as defined above, or a pharmaceutically acceptable salt thereof, and a pharmaceutically acceptable carrier.

(b) A pharmaceutical composition which comprises the product prepared by combining (e.g., mixing) an effective amount of a compound of Formula I as defined above, or a pharmaceutically acceptable salt thereof, and a pharmaceutically acceptable carrier.

(c) The pharmaceutical composition of (a) or (b), further comprising an effective amount of an anti-HIV agent selected from the group consisting of HIV antiviral agents, immunomodulators, and anti-infective agents.

(d) The pharmaceutical composition of (c), wherein the anti-HIV agent is an antiviral selected from the group consisting of HIV protease inhibitors, HIV reverse transcriptase inhibitors, HIV integrase inhibitors, HIV fusion inhibitors, HIV entry inhibitors, and HIV maturation inhibitors.

(e) The pharmaceutical composition of (d), wherein the antiviral is selected from the group consisting of HIV reverse transcriptase inhibitors and HIV integrase inhibitors.

(f) A combination which is (i) a compound of Formula I as defined above, or a pharmaceutically acceptable salt thereof, and (ii) an anti-HIV agent selected from the group consisting of HIV antiviral agents, immunomodulators, and anti-infective agents; wherein Compound I and the anti-HIV agent are each employed in an amount that renders the combination effective for inhibition of HIV protease, for treatment or prophylaxis of infection by HIV, or for treatment, prophylaxis of, or delay in the onset or progression of AIDS.

(g) The combination of (f), wherein the anti-HIV agent is an antiviral selected from the group consisting of HIV protease inhibitors, HIV reverse transcriptase inhibitors, HIV integrase inhibitors, HIV fusion inhibitors, HIV entry inhibitors, and HIV maturation inhibitors.

(h) The combination of (g), wherein the antiviral is selected from the group consisting of HIV reverse transcriptase inhibitors and HIV integrase inhibitors.

(i) A method for the inhibition of HIV protease in a subject in need thereof which comprises administering to the subject an effective amount of a compound of Formula I or a pharmaceutically acceptable salt thereof.

(j) A method for the prophylaxis or treatment of infection by HIV (e.g., HIV-1) in a subject in need thereof which comprises administering to the subject an effective amount of a compound of Formula I or a pharmaceutically acceptable salt thereof (k) The method of (j), wherein the compound of Formula I is administered in combination with an effective amount of at least one other HIV antiviral selected from the group consisting of HIV protease inhibitors, HIV reverse transcriptase inhibitors, HIV integrase inhibitors, HIV fusion inhibitors, HIV entry inhibitors, and HIV maturation inhibitors.

(l) The method of (k), wherein the at least one other HIV antiviral is selected from the group consisting of HIV reverse transcriptase inhibitors and HIV integrase inhibitors.

(m) A method for the prophylaxis, treatment or delay in the onset or progression of AIDS in a subject in need thereof which comprises administering to the subject an effective amount of a compound of Formula I or a pharmaceutically acceptable salt thereof (n) The method of (m), wherein the compound is administered in combination with an effective amount of at least one other HIV antiviral, selected from the group consisting of HIV protease inhibitors, HIV reverse transcriptase inhibitors, HIV integrase inhibitors, HIV fusion inhibitors, HIV entry inhibitors, and HIV maturation inhibitors.

(o) The method of (n), wherein the at least one other HIV antiviral is selected from the group consisting of HIV reverse transcriptase inhibitors and HIV integrase inhibitors.

(p) A method for the inhibition of HIV protease in a subject in need thereof which comprises administering to the subject the pharmaceutical composition of (a), (b), (c) or (d) or the combination of (e) or (f).

(q) A method for the prophylaxis or treatment of infection by HIV (e.g., HIV-1) in a subject in need thereof which comprises administering to the subject the pharmaceutical composition of (a), (b), (c), (d) or (e).

(r) A method for the prophylaxis, treatment, or delay in the onset or progression of AIDS in a subject in need thereof which comprises administering to the subject the pharmaceutical composition of (a), (b), (c), (d) or (e).

The present invention also includes a compound of Formula I, or a pharmaceutically acceptable salt thereof, (i) for use in, (ii) for use as a medicament for, or (iii) for use in the manufacture/preparation of a medicament for: (a) therapy (e.g., of the human body), (b) medicine, (c) inhibition of HIV protease, (d) treatment or prophylaxis of infection by HIV, or (e) treatment, prophylaxis of, or delay in the onset or progression of AIDS. In these uses, the compounds of the present invention can optionally be employed in combination with one or more other anti-HIV agents selected from HIV antiviral agents, anti-infective agents, and immunomodulators.

Additional embodiments of the invention include the pharmaceutical compositions, combinations and methods set forth in (a)-(r) above and the uses (i)(a)-(e) through (iii)(a)-(e) set forth in the preceding paragraph, wherein the compound of the present invention employed therein is a compound of one of the embodiments, aspects, classes or subclasses described above. In all of these embodiments etc., the compound can optionally be used in the form of a pharmaceutically acceptable salt.

Additional embodiments of the present invention include each of the pharmaceutical compositions, combinations, methods and uses set forth in the preceding paragraphs, wherein the compound of the present invention or its salt employed therein is substantially pure. With respect to a pharmaceutical composition comprising a compound of Formula I or a pharmaceutically acceptable carrier and optionally one or more excipients, it is understood that the term "substantially pure" is in reference to a compound of Formula I or its salt per se.

As used herein, the term "alkyl" refers to a monovalent straight or branched chain, saturated aliphatic hydrocarbon radical having a number of carbon atoms in the specified range. Thus, for example, "$C_{1-6}$ alkyl" (or "$C_1$-$C_6$ alkyl") refers to any of the hexyl alkyl and pentyl alkyl isomers as well as n-, iso-, sec- and t-butyl, n- and iso-propyl, ethyl and methyl. As another example, "$C_{1-4}$ alkyl" refers to n-, iso-, sec- and t-butyl, n- and isopropyl, ethyl and methyl. As another example, "$C_{1-3}$ alkyl" refers to n-propyl, isopropyl, ethyl and methyl.

The term "alkylene" refers to any divalent linear or branched chain aliphatic hydrocarbon radical having a number of carbon atoms in the specified range. Thus, for example, "—$C_{1-6}$ alkylene-" refers to any of the $C_1$ to $C_6$ linear or branched alkylenes, and "—$C_{1-4}$ alkylene-" refers to any of the $C_1$ to $C_4$ linear or branched alkylenes. A class of alkylenes of interest with respect to the invention is —$(CH_2)_{1-6}$—, and sub-classes of particular interest include —$(CH_2)_{1-4}$—, —$(CH_2)_{2-4}$—, —$(CH_2)_{1-3}$—, —$(CH_2)_{2-3}$—, —$(CH_2)_{1-2}$—, and —$CH_2$—. Another sub-class of interest is an alkylene selected from the group consisting of —$CH_2$—, —$CH(CH_3)$—, and —$C(CH_3)_2$—.

The term "cycloalkyl" refers to any monocyclic ring of an alkane having a number of carbon atoms in the specified range. Thus, for example, "$C_{3-6}$ cycloalkyl" (or "$C_3$-$C_6$ cycloalkyl") refers to cyclopropyl, cyclobutyl, cyclopentyl, and cyclohexyl, and "$C_{3-5}$ cycloalkyl" refers to cyclopropyl, cyclobutyl, and cyclopentyl.

The term "halogen" (or "halo") refers to fluorine, chlorine, bromine and iodine (alternatively referred to as fluoro, chloro, bromo, and iodo).

The term "haloalkyl" refers to an alkyl group as defined above in which one or more of the hydrogen atoms have been replaced with a halogen (i.e., F, Cl, Br and/or I). Thus, for example, "$C_{1-6}$ haloalkyl" (or "$C_1$-$C_6$ haloalkyl") refers to a $C_1$ to $C_6$ linear or branched alkyl group as defined above with one or more halogen substituents. The term "fluoroalkyl" has an analogous meaning except that the halogen substituents are restricted to fluoro. Suitable fluoroalkyls include the series $(CH_2)_{0-4}CF_3$ (i.e., trifluoromethyl, 2,2,2-trifluoroethyl, 3,3,3-trifluoro-n-propyl, etc.). A fluoroalkyl of particular interest is $CF_3$.

The term "C(O)" refers to carbonyl. The terms "$S(O)_2$" and "$SO_2$" each refer to sulfonyl. The term "S(O)" refers to sulfinyl.

The term "aryl" refers to phenyl and naphthyl. The aryl of particular interest is phenyl.

The term "heteroaryl" refers to (i) a 5- or 6-membered heteroaromatic ring containing from 1 to 3 heteroatoms independently selected from N, O and S, or (ii) is a heterobicyclic ring selected from quinolinyl, isoquinolinyl, and quinoxalinyl. Suitable 5- and 6-membered heteroaromatic rings include, for example, pyridyl (also referred to as pyridinyl), pyrrolyl, pyrazinyl, pyrimidinyl, pyridazinyl, triazinyl, thienyl, furanyl, imidazolyl, pyrazolyl, triazolyl, oxazolyl, isooxazolyl, oxadiazolyl, oxatriazolyl, thiazolyl, isothiazolyl, and thiadiazolyl. Heteroaryls of particular interest are pyrrolyl, imidazolyl, pyridyl, pyrazinyl, quinolinyl (or quinolyl), isoquinolinyl (or isoquinolyl), and quinoxalinyl.

Examples of 4- to 7-membered, saturated heterocyclic rings within the scope of this invention (see HetB) include, for example, azetidinyl, piperidinyl, morpholinyl, thiomorpholinyl, thiazolidinyl, isothiazolidinyl, oxazolidinyl, isoxazolidinyl, pyrrolidinyl, imidazolidinyl, piperazinyl, tetrahydrofuranyl, tetrahydrothienyl, pyrazolidinyl, hexahydropyrimidinyl, thiazinanyl, thiazepanyl, azepanyl, diazepanyl, tetrahydropyranyl, tetrahydrothiopyranyl, and dioxanyl. Examples of 4- to 7-membered, unsaturated heterocyclic rings within the scope of this invention (see HetB) include mono-unsaturated heterocyclic rings corresponding to the saturated heterocyclic rings listed in the preceding sentence in which a single bond is replaced with a double bond (e.g., a carbon-carbon single bond is replaced with a carbon-carbon double bond).

It is understood that the specific rings listed above are not a limitation on the rings which can be used in the present invention. These rings are merely representative.

Unless expressly stated to the contrary in a particular context, any of the various cyclic rings and ring systems described herein may be attached to the rest of the compound at any ring atom (i.e., any carbon atom or any heteroatom) provided that a stable compound results.

Unless expressly stated to the contrary, all ranges cited herein are inclusive. For example, a heteroaromatic ring described as containing from "1 to 4 heteroatoms" means the ring can contain 1, 2, 3 or 4 heteroatoms. It is also understood that any range cited herein includes within its scope all of the sub-ranges within that range. Thus, for example, a heterocyclic ring described as containing from "1 to 4 heteroatoms" is intended to include as aspects thereof, heterocyclic rings containing 2 to 4 heteroatoms, 3 or 4 heteroatoms, 1 to 3 heteroatoms, 2 or 3 heteroatoms, 1 or 2 heteroatoms, 1 heteroatom, 2 heteroatoms, 3 heteroatoms, and 4 heteroatoms. As another example, an aryl or heteroaryl described as optionally substituted with "from 1 to 4 substituents" is intended to include as aspects thereof, an aryl or heteroaryl substituted with 1 to 4 substituents, 2 to 4 substituents, 3 to 4 substituents, 4 substituents, 1 to 3 substituents, 2 to 3 substituents, 3 substituents, 1 to 2 substituents, 2 substituents, and 1 substituent.

When any variable (e.g., $X^A$ or $X^B$) occurs more than one time in any constituent or in Formula I or in any other formula depicting and describing compounds of the present invention, its definition on each occurrence is independent of its definition at every other occurrence. Also, combinations of substituents and/or variables are permissible only if such combinations result in stable compounds.

Unless expressly stated to the contrary, substitution by a named substituent is permitted on any atom in a ring (e.g., cycloalkyl, aryl, or heteroaryl) provided such ring substitution is chemically allowed and results in a stable compound.

The compounds of the invention contain chiral centers and, as a result of the selection of substituents and substituent patterns, can contain additional chiral centers, and thus can occur as mixtures of stereoisomers, or as individual diastereomers, or enantiomers. All isomeric forms of these compounds, whether individually or in mixtures, are within the scope of the present invention.

To the extent substituents and substituent patterns provide for the existence of tautomers (e.g., keto-enol tautomers) in the compounds of the invention, all tautomeric forms of these compounds, whether present individually or in mixtures, are within the scope of the present invention. Compounds of the present invention having a hydroxy substituent on a carbon atom of a heteroaromatic ring are understood to include compounds in which only the hydroxy is present, compounds in which only the tautomeric keto form (i.e., an oxo substitutent) is present, and compounds in which the keto and enol forms are both present.

A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject). The compounds of the present invention are limited to stable compounds embraced by Formula I.

The methods of the present invention involve the use of compounds of the present invention in the inhibition of HIV protease (e.g., wild type HIV-1 and/or mutant strains thereof), the prophylaxis or treatment of infection by human immunodeficiency virus (HIV) and the prophylaxis, treatment or delay in the onset or progression of consequent pathological conditions such as AIDS. Prophylaxis of AIDS, treating AIDS, delaying the onset or progression of AIDS, or treating or prophylaxis of infection by HIV is defined as including, but not limited to, treatment of a wide range of states of HIV infection: AIDS, ARC (AIDS related complex), both symptomatic and asymptomatic, and actual or potential exposure to HIV. For example, the present invention can be employed to treat infection by HIV after suspected past exposure to HIV by such means as blood transfusion, exchange of body fluids, bites, accidental needle stick, or exposure to patient blood during surgery.

The compounds can be administered in the form of pharmaceutically acceptable salts. The term "pharmaceutically acceptable salt" refers to a salt which possesses the effectiveness of the parent compound and which is not biologically or otherwise undesirable (e.g., is neither toxic nor otherwise deleterious to the recipient thereof). Suitable salts include acid addition salts which may, for example, be formed by mixing a solution of the compound of the present invention with a solution of a pharmaceutically acceptable acid such as hydrochloric acid, sulfuric acid, acetic acid, or benzoic acid. When compounds employed in the present invention carry an acidic moiety (e.g., —COOH or a phenolic group), suitable pharmaceutically acceptable salts thereof can include alkali metal salts (e.g., sodium or potassium salts), alkaline earth metal salts (e.g., calcium or magnesium salts), and salts formed with suitable organic ligands such as quaternary ammonium salts.

The term "administration" and variants thereof (e.g., "administering" a compound) in reference to a compound of Formula I mean providing the compound to the individual in need of treatment or prophylaxis. When a compound is provided in combination with one or more other active agents (e.g., antiviral agents useful for treating or prophylaxis of HIV infection or AIDS), "administration" and its variants are each understood to include provision of the compound and other agents at the same time or at different times. When the agents of a combination are administered at the same time, they can be administered together in a single composition or they can be administered separately.

As used herein, the term "composition" is intended to encompass a product comprising the specified ingredients, as well as any product which results from combining the specified ingredients.

By "pharmaceutically acceptable" is meant that the ingredients of the pharmaceutical composition must be compatible with each other and not deleterious to the recipient thereof.

The term "subject" as used herein refers to an animal, preferably a mammal, most preferably a human, who has been the object of treatment, observation or experiment.

The term "effective amount" as used herein means that amount of active compound or pharmaceutical agent that elicits the biological or medicinal response in a tissue, system, animal or human that is being sought by a researcher, veterinarian, medical doctor or other clinician. In one embodiment, the effective amount is a "therapeutically effective amount" for the alleviation of the symptoms of the disease or condition being treated. In another embodiment, the effective amount is a "prophylactically effective amount" for reduced likelihood of the symptoms of the disease or condition being prevented. The term also includes herein the amount of active compound sufficient to inhibit HIV protease (wild type and/or mutant strains thereof) and thereby elicit the response being sought (i.e., an "inhibition effective amount"). When the active compound (i.e., active ingredient) is administered as the salt, references to the amount of active ingredient are to the free form (i.e., the non-salt form) of the compound.

In the methods of the present invention (e.g., inhibiting HIV protease, treating or prophylaxis of HIV infection or treating, prophylaxis of, or delaying the onset or progression of AIDS), the compounds of Formula I, optionally in the form of a salt, can be administered by any means that produces contact of the active agent with the agent's site of action. They can be administered by any conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice. The compounds of the invention can, for example, be administered by one or more of the following routes: orally, parenterally (including subcutaneous injections, intravenous, intramuscular, intrasternal injection or infusion techniques), by inhalation spray, or rectally, in the form of a unit dosage of a pharmaceutical composition containing an effective amount of the compound and conventional non-toxic pharmaceutically acceptable carriers, adjuvants and vehicles. Liquid preparations suitable for oral administration (e.g., suspensions, syrups, elixirs and the like) can be prepared according to techniques known in the art and can employ any of the usual media such as water, glycols, oils, alcohols and the like. Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Parenteral compositions can be prepared according to techniques known in the art and typically employ sterile water as a carrier and optionally other ingredients, such as a solubility aid. Injectable solutions can be prepared according to methods known in the art wherein the carrier comprises a saline solution, a glucose solution or a solution containing a mixture of saline and glucose. Further description of methods suitable for use in preparing pharmaceutical compositions for use in the present invention and of ingredients suitable for use in said compositions is provided in *Remington's Pharmaceutical Sciences*, 18$^{th}$ edition, edited by A. R. Gennaro, Mack Publishing Co., 1990 and in *Remington—The Science and Practice of Pharmacy*, 21st edition, Lippincott Williams & Wilkins, 2005.

The compounds of Formula I can be administered orally in a dosage range of 0.001 to 1000 mg/kg of mammal (e.g., human) body weight per day in a single dose or in divided doses. One dosage range is 0.01 to 500 mg/kg body weight per day orally in a single dose or in divided doses. Another dosage range is 0.1 to 100 mg/kg body weight per day orally in single or divided doses. For oral administration, the compositions can be provided in the form of tablets or capsules containing 1.0 to 500 milligrams of the active ingredient, particularly 1, 5, 10, 15, 20, 25, 50, 75, 100, 150, 200, 250, 300, 400, and 500 milligrams of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

As noted above, the present invention is also directed to use of a compound of Formula I with one or more anti-HIV agents. An "anti-HIV agent" is any agent which is directly or indirectly effective in the inhibition of HIV reverse transcriptase, protease, or another enzyme required for HIV replication or infection, the inhibition of HIV replication, the treatment or prophylaxis of HIV infection, and/or the treatment, prophylaxis or delay in the onset or progression of AIDS. It is understood that an anti-HIV agent is effective in treating, preventing, or delaying the onset or progression of HIV infection or AIDS and/or diseases or conditions arising therefrom or associated therewith. For example, the compounds of this invention may be effectively administered, whether at periods of pre-exposure and/or post-exposure, in combination with effective amounts of one or more anti-HIV agents selected from HIV antiviral agents, immunomodulators, antiinfectives, or vaccines useful for treating HIV infection or AIDS, such as those disclosed in Table 1 of WO 01/38332 or in the Table in WO 02/30930. Suitable HIV antivirals for use in combination with the compounds of the present invention include, for example, those listed in Table A as follows:

TABLE A

| Antiviral Agents for Treating HIV infection or AIDS | |
|---|---|
| Name | Type |
| abacavir, ABC, Ziagen ® | nRTI |
| abacavir + lamivudine, Epzicom ® | nRTI |
| abacavir + lamivudine + zidovudine, Trizivir ® | nRTI |
| amprenavir, Agenerase ® | PI |
| atazanavir, Reyataz ® | PI |
| AZT, zidovudine, azidothymidine, Retrovir ® | nRTI |
| capravirine | nnRTI |
| darunavir, Prezista ® | PI |
| ddC, zalcitabine, dideoxycytidine, Hivid ® | nRTI |
| ddI, didanosine, dideoxyinosine, Videx ® | nRTI |
| ddI (enteric coated), Videx EC ® | nRTI |
| delavirdine, DLV, Rescriptor ® | nnRTI |
| efavirenz, EFV, Sustiva ®, Stocrin ® | nnRTI |
| efavirenz + emtricitabine + tenofovir DF, Atripla ® | nnRTI + nRTI |
| EFdA (4'-ethynyl-2-fluoro-2'-deoxyadenosine) | nRTI |
| emtricitabine, FTC, Emtriva ® | nRTI |

TABLE A-continued

Antiviral Agents for Treating HIV infection or AIDS

| Name | Type |
| --- | --- |
| emtricitabine + tenofovir DF, Truvada ® | nRTI |
| emvirine, Coactinon ® | nnRTI |
| enfuvirtide, Fuzeon ® | FI |
| enteric coated didanosine, Videx EC ® | nRTI |
| etravirine, TMC-125 | nnRTI |
| fosamprenavir calcium, Lexiva ® | PI |
| indinavir, Crixivan ® | PI |
| lamivudine, 3TC, Epivir ® | nRTI |
| lamivudine + zidovudine, Combivir ® | nRTI |
| lopinavir | PI |
| lopinavir + ritonavir, Kaletra ® | PI |
| maraviroc, Selzentry ® | EI |
| nelfinavir, Viracept ® | PI |
| nevirapine, NVP, Viramune ® | nnRTI |
| PPL-100 (also known as PL-462) (Ambrilia) | PI |
| raltegravir, MK-0518, Isentress ™ | InI |
| ritonavir, Norvir ® | PI |
| saquinavir, Invirase ®, Fortovase ® | PI |
| stavudine, d4T, didehydrodeoxythymidine, Zerit ® | nRTI |
| tenofovir DF (DF = disoproxil fumarate), TDF, Viread ® | nRTI |
| Tenofovir, hexadecyloxypropyl (CMX-157) | nRTI |
| tipranavir, Aptivus ® | PI |

EI = entry inhibitor; FI = fusion inhibitor; InI = integrase inhibitor; PI = protease inhibitor; nRTI = nucleoside reverse transcriptase inhibitor; nnRTI = non-nucleoside reverse transcriptase inhibitor. Some of the drugs listed in the table are used in a salt form; e.g., abacavir sulfate, indinavir sulfate, atazanavir sulfate, nelfinavir mesylate.

It is understood that the scope of combinations of the compounds of this invention with anti-HIV agents is not limited to the HIV antivirals listed in Table A and/or listed in the above-referenced Tables in WO 01/38332 and WO 02/30930, but includes in principle any combination with any pharmaceutical composition useful for the treatment or prophylaxis of AIDS. The HIV antiviral agents and other agents will typically be employed in these combinations in their conventional dosage ranges and regimens as reported in the art, including, for example, the dosages described in the *Physicians' Desk Reference*, Thomson PDR, Thomson PDR, 57$^{th}$ edition (2003), the 58$^{th}$ edition (2004), or the 59$^{th}$ edition (2005). The dosage ranges for a compound of the invention in these combinations are the same as those set forth above.

The compounds of this invention are also useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HIV protease, e.g., by competitive inhibition. Thus the compounds of this invention are commercial products to be used for these purposes.

In the compounds of Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

Abbreviations employed herein include the following: Bn=benzyl; BOC (or Boc)=t-butyloxycarbonyl; Boc$_2$O=di-t-butyl carbonate; BOP=benzotriazol-1-yloxytris-(dimethylamino)phosphonium; BSA=bovine serum albumin; CBS=Corey, Bakshi, Shibata chiral oxazaborolidine mediated ketone reduction; Cbz=benzyloxycarbonyl; DBU=1,8-diazabicyclo[5.4.0]undec-7-one; DCAD=di-(4-chlorobenzyl) azodicarboxylate; DCE=1,2-dichloroethane; DCM=dichloromethane; DEAD=diethyl azodicarboxylate; DIAD=diisopropylazodicarboxylate; Dibal-H=diisobutylaluminum hydride; DMAP=4-dimethylaminopyridine; DMF=dimethylformamide; DMSO=dimethyl sulfoxide; EDC=1-ethyl-3-(3-dimethylaminopropyl) carbodiimide; Et=ethyl; EtOAc=ethyl acetate; EtOH=ethanol; G-2G=Grubbs catalyst, 2$^{nd}$ generation; HOAt=1-hydroxy-7-azabenzotriazole; HPLC=high performance liquid chromatography; HSU=hydroxysuccinimide; i-PrOH=isopropanol; LAH=lithium aluminum hydride; LC-MS=liquid chromatography-mass spectroscopy; Me=methyl; MeOH=methanol; MOC=methoxycarbonyl; Ms=mesyl or methanesulfonyl; NMR=nuclear magnetic resonance; Ph=phenyl; RCM=ring closing metathesis; Piv=pivaloyl; PPTS=pyridinium p-toluene sulfonate; PyBrOP=bromo-tris-pyrrolidinophosphonium hexafluorophosphate; SCX=strong cation exchange resin; STP=standard temperature and pressure (i.e., 25° C. & 1 atmosphere); TBS=tert-butyldimethylsilyl; TBDPS=tert-butyl(diphenyl) silyl; TBDPSCl=tert-butyl(dimethyl)silyl chloride; TEA=triethylamine; TFA=trifluoroacetic acid; THF=tetrahydrofuran; TLC=thin layer chromatography; TMAF=tetramethyl ammonium fluoride; TMSCHN$_2$=trimethylsilyl diazomethane; TPAP=tetrapropylammonium perruthenate; TPP=triphenylphosphine.

The compounds of the present invention can be readily prepared according to the following reaction schemes and examples, or modifications thereof, using readily available starting materials, reagents and conventional synthesis procedures. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the following reaction schemes and examples. Unless otherwise indicated, all variables are as defined above. The term "Ar" appears in several of the schemes and refers to phenyl optionally substituted with one or more X$^A$. In the examples that follow, when a nitrogen atom is depicted without the necessary hydrogen atoms to complete the valence, it is assumed those nitrogen atoms are present unless specifically depicted to the contrary.

INTERMEDIATE 1

Synthesis of morpholine intermediate (tert-butyl (2S, 5S)-5-({[tert-butyl(dimethyl)silyl]oxy}methyl)-2-(hydroxymethyl)morpholine-4-carboxylate)

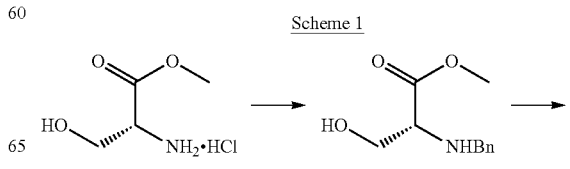

Scheme 1

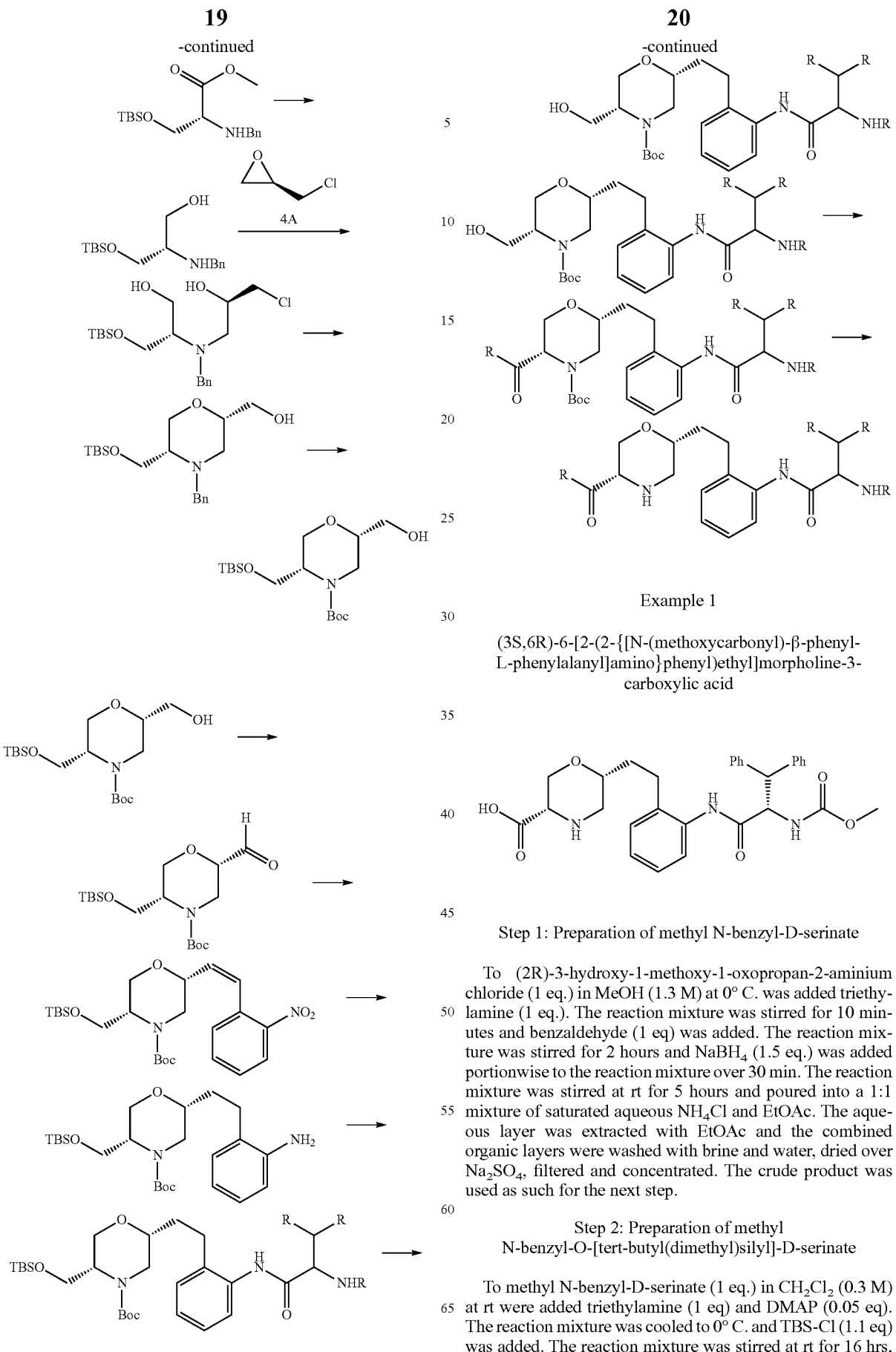

Example 1

(3S,6R)-6-[2-(2-{[N-(methoxycarbonyl)-β-phenyl-L-phenylalanyl]amino}phenyl)ethyl]morpholine-3-carboxylic acid Step 1: Preparation of methyl N-benzyl-D-serinate To (2R)-3-hydroxy-1-methoxy-1-oxopropan-2-aminium chloride (1 eq.) in MeOH (1.3 M) at 0° C. was added triethylamine (1 eq.). The reaction mixture was stirred for 10 minutes and benzaldehyde (1 eq) was added. The reaction mixture was stirred for 2 hours and NaBH$_4$ (1.5 eq.) was added portionwise to the reaction mixture over 30 min. The reaction mixture was stirred at rt for 5 hours and poured into a 1:1 mixture of saturated aqueous NH$_4$Cl and EtOAc. The aqueous layer was extracted with EtOAc and the combined organic layers were washed with brine and water, dried over Na$_2$SO$_4$, filtered and concentrated. The crude product was used as such for the next step.

Step 2: Preparation of methyl N-benzyl-O-[tert-butyl(dimethyl)silyl]-D-serinate

To methyl N-benzyl-D-serinate (1 eq.) in CH$_2$Cl$_2$ (0.3 M) at rt were added triethylamine (1 eq) and DMAP (0.05 eq). The reaction mixture was cooled to 0° C. and TBS-Cl (1.1 eq) was added. The reaction mixture was stirred at rt for 16 hrs, water was added and the aqueous layer was extracted with CH$_2$Cl$_2$. The combined organic layers were washed with saturated aqueous NH$_4$Cl, dried over Na$_2$SO$_4$, filtered and concentrated. The crude product was used as such for the next step.

Step 3: Preparation of (2S)-2-(benzylamino)-3-{[tert-butyl(dimethyl)silyl]oxy}propan-1-ol To methyl N-benzyl-O-[tert-butyl(dimethyl)silyl]-D-serinate (1 eq.) in THF (0.4 M) at rt were added 2M LiBH$_4$ in THF (1.2 eq.) and MeOH (1.2 eq). The mixture was stirred at rt for 16 hrs and quenched by the slow addition of saturated aqueous NH$_4$Cl. The aqueous layer was extracted with EtOAc. The combined organic layers were dried over Na$_2$SO$_4$, filtered and concentrated. The crude product was used as such for the next step.

Step 4: Preparation of [(2S,5S)-4-benzyl-5-({[tert-butyl(dimethyl)silyl]oxy}methyl)morpholin-2-yl]methanol To (2S)-2-(benzylamino)-3-{[tert-butyl(dimethyl)silyl]oxy}propan-1-ol (1 eq) in Toluene (0.3 M) at rt was added (R)-(−)-epichlorohydrin (1.3 eq.) and Lithium perchlorate (1.3 eq) was then slowly added over 2 hours. The mixture was stirred at rt for 48 hrs and sodium methoxide (2.5 eq of a 25% solution of NaOMe in MeOH) was added. MeOH was then added to the reaction mixture to obtain a 4:1 ratio of toluene:MeOH as solvent. The reaction mixture was stirred for 48 hrs at rt and diluted with saturated aqueous NH$_4$Cl. The aqueous layer was extracted with EtOAc. The combined organic layers were washed with brine, dried over Na$_2$SO$_4$, filtered and concentrated. The crude product was purified by automated SiO$_2$ flash chromatography system using solvent gradient of 0% EtOAc/Hex to 25% EtOAc/Hex to afford the desired compound.

Step 5: Preparation of tert-butyl (2S,5S)-5-({[tert-butyl(dimethyl)silyl]oxy}methyl)-2-(hydroxymethyl)morpholine-4-carboxylate To ethyl [(2S,5S)-4-benzyl-5-({[tert-butyl(dimethyl)silyl]oxy}methyl)morpholin-2-yl]methanol (1 eq.) in EtOH (0.4 M) at rt were added Boc$_2$O (1.2 eq), triethylamine (1 eq) and 20% Pd(OH)$_2$ (0.2 eq.). The reaction was degassed and then shaken in a parr apparatus under 45 psi of H$_2$ for 16 hrs. The reaction mixture was filtered on celite and concentrated. The residue was diluted in EtOAc and the organic layer was washed with water and brine, dried over Na$_2$SO$_4$, filtered and concentrated. The crude product was used as such for the next step.

Step 6: Preparation of tert-butyl (2S,5S)-5-({[tert-butyl(dimethyl)silyl]oxy}methyl)-2-formylmorpholine-4-carboxylate To a stirred solution of oxalyl chloride (2 eq) in DCM (0.3 M) at −78° C. was added a solution of DMSO (5 eq) in DCM (0.5M). The reaction mixture was stirred at −78° C. for 30 min. A solution of tert-butyl (2S,5S)-5-({[tert-butyl(dimethyl)silyl]oxy}methyl)-2-(hydroxymethyl)morpholine-4-carboxylate (1 eq) in CH$_2$Cl$_2$ (0.2M) was added dropwise and stirred at −40° C. for 1.5 hours. It was then cooled to −78° C. and triethylamine (7 eq) was added and the reaction mixture was stirred at 0° C. for 1 h. Water was added and the reaction mixture was warmed to rt for 30 min. The mixture was diluted with CH$_2$Cl$_2$, the organic layer was washed with water and brine, dried over Na$_2$SO$_4$, filtered and concentrated. The crude product was used as such for the next step.

Step 7: Preparation of tert-butyl (2R,5S)-5-({[tert-butyl(dimethyl)silyl]oxy}methyl)-2-[(E)-2-(2-nitrophenyl)ethenyl]morpholine-4-carboxylate To tert-butyl (2S,5S)-5-({[tert-butyl(dimethyl)silyl]oxy}methyl)-2-formylmorpholine-4-carboxylate (1 eq.) in DME (0.2 M) at rt were added (2-nitrobenzyl)(triphenyl)phosphonium bromide (1.1 eq.), potassium carbonate (2 eq.) and 18-C-6 (0.1 eq.). The reaction mixture was stirred at rt for 12 hrs, filtered on celite and the filtrate was concentrated under reduced pressure. The crude product was purified by automated SiO$_2$ flash chromatography system using solvent gradient of 10% to 60% EtOAc/Hex to afford the desired compound

Step 8: Preparation of tert-butyl (2R,5S)-2-[2-(2-aminophenyl)ethyl]-5-({[tert-butyl(dimethyl)silyl]oxy}methyl)morpholine-4-carboxylate To tert-butyl (2R,5S)-5-({[tert-butyl(dimethyl)silyl]oxy}methyl)-2-[(E)-2-(2-nitrophenyl)ethenyl]morpholine-4-carboxylate (1 eq.) in 2,2,2,-trifluoroethanol (0.4 M) at rt was added 20% Pd(OH)$_2$ (0.2 eq.). The reaction was degassed and then shaken under 1 atm of H$_2$ for 24 hrs. The reaction mixture was filtered on celite and concentrated to afford the desired compound.

Step 9: Preparation of tert-butyl (2R,5S)-5-({[tert-butyl(dimethyl)silyl]oxy}methyl)-2-[2-(2-{[N-(methoxycarbonyl)-β-phenyl-L-phenylalanyl]amino}phenyl)ethyl]morpholine-4-carboxylate To tert-butyl (2R,5S)-2-[2-(2-aminophenyl)ethyl]-5-({[tert-butyl(dimethyl)silyl]oxy}methyl)morpholine-4-carboxylate (1 eq.) in DMF (0.15 M) at rt was added N-(methoxycarbonyl)-β-phenyl-L-phenylalanine (1.1 eq.), HATU (1.4 eq) and 2,6-lutidine (3 eq.). The reaction mixture was stirred at rt for 16 h and diluted with EtOAc and saturated aqueous NaHCO$_3$. The aqueous layer was extracted with EtOAc. The combined organic layers were washed with brine, dried over Na$_2$SO$_4$, filtered and concentrated. The crude product was purified by automated SiO$_2$ flash chromatography system using solvent gradient of 10% to 100% EtOAc/Hex to afford the desired compound.

Step 10: Preparation of tert-butyl (2R,5R)-5-(hydroxymethyl)-2-[2-(2-{[N-(methoxycarbonyl)-β-phenyl-L-phenylalanyl]amino}phenyl)ethyl]morpholine-4-carboxylate To tert-butyl (2R,5S)-5-({[tert-butyl(dimethyl)silyl]oxy}methyl)-2-[2-(2-{[N-(methoxycarbonyl)-β-phenyl-L-phenylalanyl]amino}phenyl)ethyl]morpholine-4-carboxylate in THF (0.1 M) at rt was added TBAF (1M in THF) (4 eq.). The mixture was stirred at rt for 2 hrs, diluted with EtOAc and saturated aqueous NH$_4$Cl and the aqueous layer was extracted with EtOAc. The combined organic layers were washed with brine, dried over Na$_2$SO$_4$, filtered and concentrated. The crude product was purified by automated SiO$_2$ flash chromatography system using solvent gradient of 0-5% MeOH/CH$_2$Cl$_2$ to afford the desired compound.

Step 11: Preparation of (3S,6R)-4-(tert-butoxycarbonyl)-6-[2-(2-{[N-(methoxycarbonyl)-β-phenyl-L-phenylalanyl]amino}phenyl)ethyl]morpholine-3-carboxylic acid To tert-butyl (2R,5R)-5-(hydroxymethyl)-2-[2-(2-{[N-(methoxycarbonyl)-β-phenyl-L-phenylalanyl]amino}phenyl)ethyl]morpholine-4-carboxylate (1 eq) in DMF (0.1M) at rt were added PDC (10 eq) and 4A molecular sieve (1 g/mmol of substrate). The reaction mixture was stirred at rt for 16 hrs. The reaction mixture was then filtered on a celite and the celite pad was washed with EtOAc and water. The filtrate was extracted with EtOAc. The combined organic layers were washed with brine, 1N aqueous HCl and brine, dried over $Na_2SO_4$, filtered and concentrated. The crude product was used as such for next step.

Step 12: Preparation of (3S,6R)-6-[2-(2-{[N-(methoxycarbonyl)-β-phenyl-L-phenylalanyl]amino}phenyl)ethyl]morpholine-3-carboxylic acid 4M HCl in dioxane was added to a solution of (3S,6R)-4-(tert-butoxycarbonyl)-6-[2-(2-{[N-(methoxycarbonyl)-β-phenyl-L-phenylalanyl]amino}phenyl)ethyl]morpholine-3-carboxylic acid in Dioxane at room temperature and the reaction stirred until complete by LC/MS (8 hrs). The solvent was removed in vacuo to afford the title compound, LC/MS.M+1, +ESI=532.3

EXAMPLE 2

N-(2-{2-[(2R,5S)-5-(benzylcarbamoyl)morpholin-2-yl]ethyl}phenyl)-Nα-(methoxycarbonyl)-β-phenyl-L-phenylalaninamide

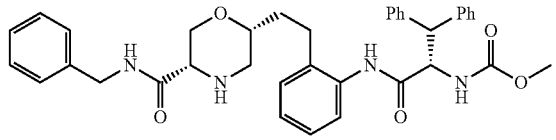 [SMILES: COC(=O)N[C@H](C(=O)Nc1ccccc1CC[C@@H]1CN[C@H](C(=O)NCc2ccccc2)CO1)C(c1ccccc1)c1ccccc1]

Step 1: Preparation of tert-butyl (2R,5S)-5-(benzylcarbamoyl)-2-[2-(2-{[N-(methoxycarbonyl)-β-phenyl-L-phenylalanyl]amino}phenyl)ethyl]morpholine-4-carboxylate HATU (1.4 eq) was added to a stirred mixture a solution of (3S,6R)-4-(tert-butoxycarbonyl)-6-[2-(2-{[N-(methoxycarbonyl)-β-phenyl-L-phenylalanyl]amino}phenyl)ethyl]morpholine-3-carboxylic acid (Example 1, step 11) (1 eq), benzyl amine (1.2 eq) and 2,6-lutidine (2 eq) in DMF (0.05 M) and the mixture was stirred at room temperature for 16 hrs. The mixture was diluted in EtOAc. The organic layer was washed with aqueous saturated $NH_4Cl$ and brine. The organic layer was dried over $Na_2SO_4$, filtered and evaporated. The residue was purified by automated silica gel flash chromatography system eluted with a gradient 10% to 100% of EtOAc/Hex to afford title compound.

Step 2: Preparation of N-(2-{2-[(2R,5S)-5-(benzylcarbamoyl)morpholin-2-yl]ethyl}phenyl)-Nα-(methoxycarbonyl)-β-phenyl-L-phenylalaninamide Tert-butyl (2R,5S)-5-(benzylcarbamoyl)-2-[2-(2-{[N-(methoxycarbonyl)-β-phenyl-L-phenylalanyl]amino}phenyl)ethyl]morpholine-4-carboxylate in a 1:1 mixture of $CH_2Cl_2$/TFA (0.1 M) was stirred at rt for 1 hr. The reaction mixture was concentrated under reduced pressure and the residue was co-evaporated twice with heptane and triturated in $Et_2O$ to afford the desired product as a TFA salt. Alternatively, the TFA salt, after concentration, could be neutralized with aqueous saturated $NaHCO_3$, extracted with EtOAc, dried over $Na_2SO_4$, filtered and concentrated and then purified by automated $SiO_2$ flash chromatography system using solvent gradient of 0% to 10% MeOH/$CH_2Cl_2$ to afford the desired compound. Alternatively, the free base could be purified by filtration on SCX SPE cartridge made of pTSA-$SiO_2$ eluted first with MeOH to remove non basic impurities and eluted then with 10% $NH_4OH$/MeOH to elute the free base and afford the desired compound after concentration under reduced pressure.

M+1, +ESI=621.2

The following examples (3 to 11) were synthesized from (3S,6R)-4-(tert-butoxycarbonyl)-6-[2-(2-{[N-(methoxycarbonyl)-β-phenyl-L-phenylalanyl]amino}phenyl)ethyl]morpholine-3-carboxylic acid (Example 1, step 11) according to the procedures described for the preparation of Example 2 and by using the appropriate reagents.

| Ex | | Compound name | Characterization data |
|---|---|---|---|
| 3 | 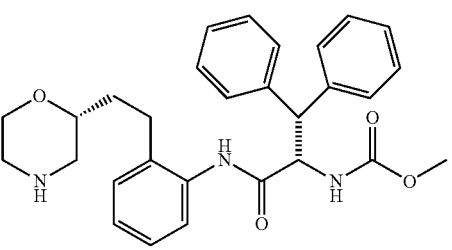 | N-(2-{2-[(2R,5S)-5-(ethylcarbamoyl)morpholin-2-yl]ethyl}phenyl)-Nα-(methoxycarbonyl)-β-phenyl-L-phenylalaninamide | M + 1, +ESI = 559.3 |

-continued

| Ex | Compound name | Characterization data |
|---|---|---|
| 4 | Nα-(methoxycarbonyl)-β-phenyl-N-(2-{2-[(2R,5S)-5-(tetrahydrofuran-3-ylcarbamoyl)morpholin-2-yl]ethyl}phenyl)-L-phenylalaninamide | M + 1, +ESI = 601.3 |
| 5 | Nα-(methoxycarbonyl)-β-phenyl-N-(2-{2-[(2R,5S)-5-(pyrrolidin-1-ylcarbonyl)morpholin-2-yl]ethyl}phenyl)-L-phenylalaninamide | M + 1, +ESI = 585.3 |
| 6 | Nα-(methoxycarbonyl)-β-phenyl-N-[2-(2-{(2R,5S)-5-[(2-phenylethyl)carbamoyl]morpholin-2-yl}ethyl)phenyl]-L-phenylalaninamide | M + 1, +ESI = 635.3 |
| 7 | Nα-(methoxycarbonyl)-β-phenyl-N-(2-{2-[(2R,5S)-5-(phenylcarbamoyl)morpholin-2-yl]ethyl}phenyl)-L-phenylalaninamide | M + 1, +ESI = 607.2 |
| 8 | N-(2-{2-[(2R,5S)-5-(tert-butylcarbamoyl)morpholin-2-yl]ethyl}phenyl)-Nα-(methoxycarbonyl)-β-phenyl-L-phenylalaninamide | M + 1, +ESI = 587.2 |
| 9 | Nα-(methoxycarbonyl)-β-phenyl-N-[2-(2-{(2R,5S)-5-[(2-phenylhydrazinyl)carbonyl]morpholin-2-yl}ethyl)phenyl]-L-phenylalaninamide | M + 1, +ESI = 622.2 |

EXAMPLE 10

Nα-(methoxycarbonyl)-β-phenyl-N-[2-(2-{(2R,5S)-5-[(phenylsulfonyl)carbamoyl]morpholin-2-yl}ethyl)phenyl]-L-phenylalaninamide

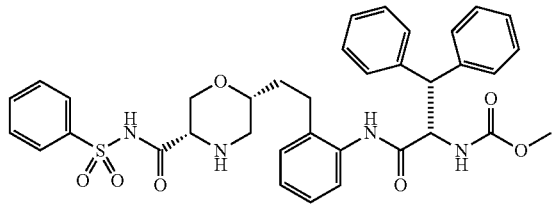 [SMILES: COC(=O)N[C@H](C(=O)Nc1ccccc1CC[C@@H]1CN[C@H](C(=O)NS(=O)(=O)c2ccccc2)CO1)C(c1ccccc1)c1ccccc1]

Step 1: Preparation of Nα-(methoxycarbonyl)-β-phenyl-N-[2-(2-{(2R,5S)-5-[(phenylsulfonyl)carbamoyl]morpholin-2-yl}ethyl)phenyl]-L-phenylalaninamide EDC (1.5 eq) was added to a stirred mixture of (3S,6R)-4-(tert-butoxycarbonyl)-6-[2-(2-{[N-(methoxycarbonyl)-β-phenyl-L-phenylalanyl]amino}phenyl)ethyl]morpholine-3-carboxylic (Example 1, Step 11) (1 eq), benzenesulfonamide (1.3 eq) and DMAP (1.5 eq) in DCM (0.06 M). The mixture was stirred at room temperature for 16 hrs and then evaporated to dryness. The residue was purified by automated silica gel flash chromatography system eluted with a gradient 0% to 10% of MeOH/CH$_2$Cl$_2$ to afford tert-butyl (2R,5S)-2-[2-(2-{[N-(methoxycarbonyl)-β-phenyl-L-phenylalanyl]amino}phenyl)ethyl]-5-[(phenylsulfonyl)carbamoyl]morpholine-4-carboxylate which was then treated with TFA following the procedure described in step 2 of Example 2 to afford the title compound.

M+1, +ESI=671.7

EXAMPLE 11 methyl [(1S)-2-[(2-{2-[(2R,5S)-5-(aminocarbonyl)morpholin-2-yl]ethyl}phenyl)amino]-1-(diphenylmethyl)-2-oxoethyl]carbamate

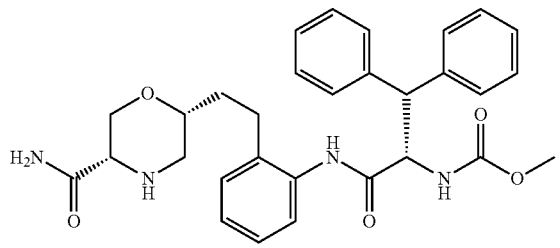 [SMILES: COC(=O)N[C@H](C(=O)Nc1ccccc1CC[C@@H]1CN[C@H](C(N)=O)CO1)C(c1ccccc1)c1ccccc1]

Step 1: Preparation of methyl [(1S)-2-[(2-{2-[(2R,5S)-5-(aminocarbonyl)morpholin-2-yl]ethyl}phenyl)amino]-1-(diphenylmethyl)-2-oxoethyl]carbamate Methyl [(1S)-2-[(2-{2-[(2R,5S)-5-(aminocarbonyl)morpholin-2-yl]ethyl}phenyl)amino]-1-(diphenylmethyl)-2-oxoethyl]carbamate was prepared from (3S,6R)-4-(tert-butoxycarbonyl)-6-[2-(2-{[N-(methoxycarbonyl)-β-phenyl-L-phenylalanyl]amino}phenyl)ethyl]morpholine-3-carboxylic acid by following procedures described in Example 2 and by using the appropriate reagents.

M+1, +ESI=531.40

Scheme 2

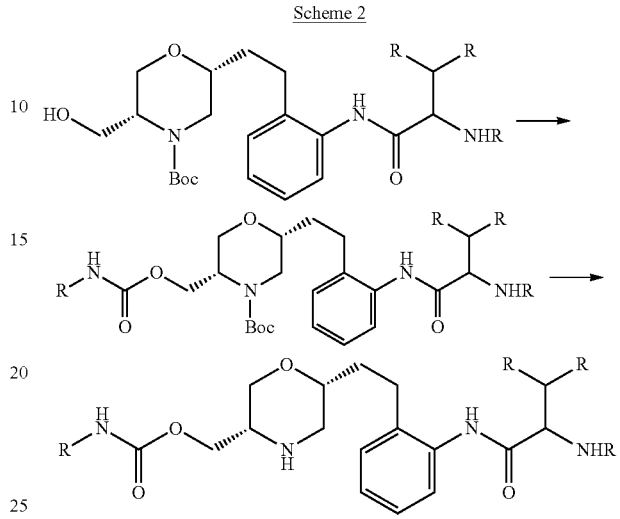

EXAMPLE 12

N-(2-{2-[(2R,5S)-5-({[(2-fluorobenzyl)carbamoyl]oxy}methyl)morpholin-2-yl]ethyl}phenyl)-Nα-(methoxycarbonyl)-β-phenyl-L-phenylalaninamide

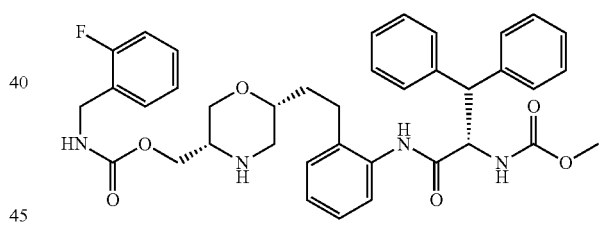

Step 1: Preparation of tert-butyl (2R,5S)-5-({[(2-fluorobenzyl)carbamoyl]oxy}methyl)-2-[2-(2-{[N-(methoxycarbonyl)-β-phenyl-L-phenylalanyl]amino}phenyl)ethyl]morpholine-4-carboxylate A mixture of tert-butyl (2R,5R)-5-(hydroxymethyl)-2-[2-(2-{[N-(methoxycarbonyl)-β-phenyl-L-phenylalanyl]amino}phenyl)ethyl]morpholine-4-carboxylate (Example 1, step 10) (1 eq) and CDI (2.05 eq.) was dissolved in dry Pyridine (0.04 M) and the resulting solution stirred under N$_2$ at rt for 5 h and then at 49° C. for 0.5 h; then neat 2-fluorobenzylamine (6 eq.) was added and the resulting mixture further stirred at the same temperature for 12 h. The crude reaction mixture was diluted with EtOAc, washed with 5% aq. KHSO$_4$ then sat. NaHCO$_3$, dried over Na$_2$SO$_4$, filtered and concentrated. The residue was purified by automated silicagel flash chromatography system eluted with a gradient 0% to 5% MeOH in DCM, to afford title compound.

Step 2: Preparation of N-(2-{2-[(2R,5S)-5-({[(2-fluorobenzyl)carbamoyl]oxy}methyl)morpholin-2-yl]ethyl}phenyl)-Nα-(methoxycarbonyl)-β-phenyl-L-phenylalaninamide Tert-butyl (2R,5S)-5-({[(2-fluorobenzyl)carbamoyl]oxy}methyl)-2-[2-(2-{[N-(methoxycarbonyl)-β-phenyl-L-phenylalanyl]amino}phenyl)ethyl] morpholine-4-carboxylate in a 1:1 mixture of CH$_2$Cl$_2$/TFA (0.1 M) was stirred at rt for 1 hr. The reaction mixture was concentrated under reduced pressure and the residue was co-evaporated twice with heptane and triturated in Et$_2$O to afford the desired product as a TFA salt. Alternatively, the TFA salt, after concentration, could be neutralized with aqueous saturated NaHCO$_3$, extracted with EtOAc, dried over Na$_2$SO$_4$, filtered and concentrated and then purified by automated SiO$_2$ flash chromatography system using solvent gradient of 0% to 10% MeOH/CH$_2$Cl$_2$ to afford the desired compound. Alternatively, the free base could be purified by filtration on SCX SPE cartridge made of pTSA-SiO$_2$ eluted first with MeOH to remove non basic impurities and eluted then with 10% NH$_4$OH/MeOH to elute the free base and afford the desired compound after concentration under reduced pressure.

M+1, +EST=669.3

The following examples (13 to 31) were synthesized from tert-butyl (2S,5S)-5-({[tert-butyl(dimethyl)silyl]oxy}methyl)-2-formylmorpholine-4-carboxylate (Example 1, step 6) according to the procedures described in steps 7-10 of Example 1 and steps 1 and 2 from Example 12 and by using the appropriate reagents.

| Example | | Compound name | Characterization data |
|---|---|---|---|
| 13 | 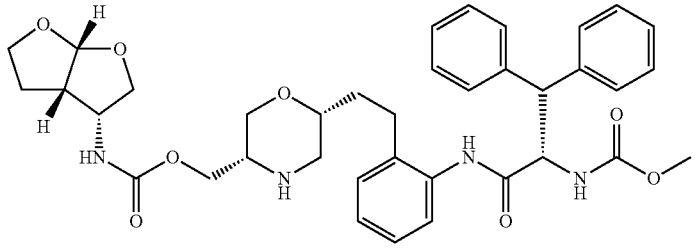 [SMILES: COC(=O)N[C@H](C(=O)Nc1ccccc1CC[C@@H]1CN[C@H](COC(=O)N[C@H]2CO[C@H]3OCC[C@H]32)CO1)C(c1ccccc1)c1ccccc1] | N-(2-{2-[(2R,5S)-5-({[(3R,3aS,6aR)-hexahydrofuro[2,3-b]furan-3-ylcarbamoyl]oxy}methyl)morpholin-2-yl]ethyl}phenyl)-Nα-(methoxycarbonyl)-β-phenyl-L-phenylalaninamide | M + 1, +ESI = 673.2 |
| 14 | 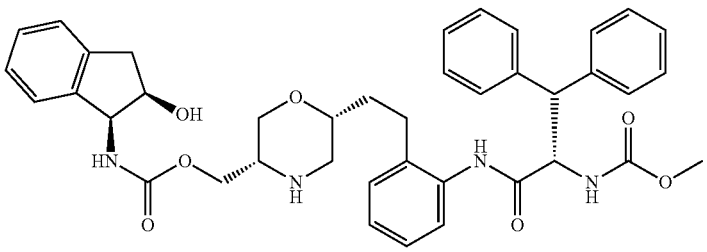 [SMILES: COC(=O)N[C@H](C(=O)Nc1ccccc1CC[C@@H]1CN[C@H](COC(=O)N[C@H]2c3ccccc3C[C@H]2O)CO1)C(c1ccccc1)c1ccccc1] | N-[2-(2-{(2R,5S)-5-[({[(1S,2R)-2-hydroxy-2,3-dihydro-1H-inden-1-yl]carbamoyl}oxy)methyl]morpholin-2-yl}ethyl)phenyl]-Nα-(methoxycarbonyl)-β-phenyl-L-phenylalaninamide | M + 1, +ESI = 693.2 |
| 15 | 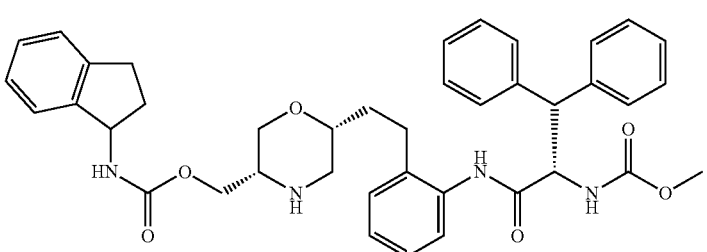 | N-(2-{2-[(2R,5S)-5-{[(2,3-dihydro-1H-inden-1-ylcarbamoyl)oxy]methyl}morpholin-2-yl]ethyl}phenyl)-Nα-(methoxycarbonyl)-β-phenyl-L-phenylalaninamide | M + 1, +ESI = 677.2 |
| 16 | 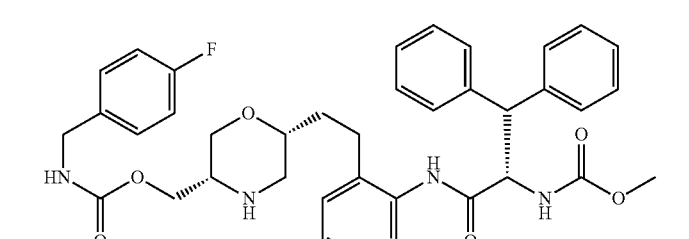 | methyl N-[(1S)-1-benzhydryl-2-[[2-[2-[(2R,5S)-5-[(4-fluorophenyl)methylcarbamoyloxymethyl]morpholin-2-yl]ethyl]phenyl]amino]-2-oxo-ethyl]carbamate | M + 1, +ESI = 669.3 |

-continued

| Example | | Compound name | Characterization data |
|---|---|---|---|
| 17 | 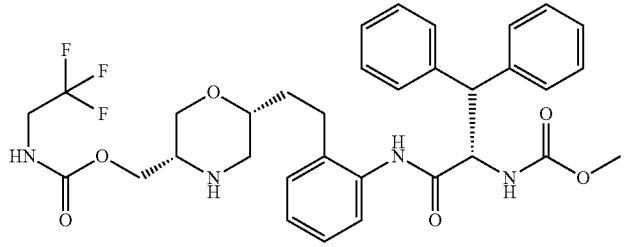 [SMILES: COC(=O)N[C@H](C(=O)Nc1ccccc1CC[C@@H]1CN[C@H](COC(=O)NCC(F)(F)F)CO1)C(c1ccccc1)c1ccccc1] | methyl N-[(1S)-1-benzhydryl-2-oxo-2-[[2-[2-[(2R,5S)-5-(2,2,2-trifluoroethylcarbamoyloxymethyl)morpholin-2-yl]ethyl]phenyl]amino]ethyl]carbamate | M + 1, +ESI = 643.4 |
| 18 | 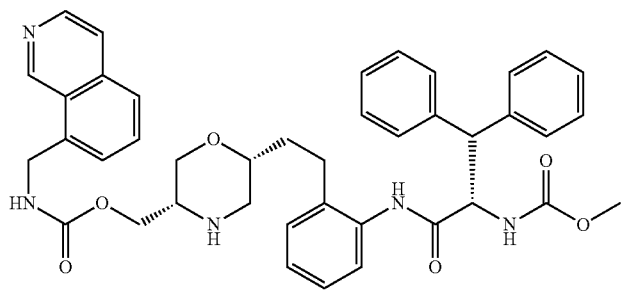 [SMILES: COC(=O)N[C@H](C(=O)Nc1ccccc1CC[C@@H]1CN[C@H](COC(=O)NCc2cccc3ccncc23)CO1)C(c1ccccc1)c1ccccc1] | methyl N-[(1S)-1-benzhydryl-2-[[2-[2-[(2R,5S)-5-(8-isoquinolylmethylcarbamoyloxymethyl)morpholin-2-yl]ethyl]phenyl]amino]-2-oxo-ethyl]carbamate | M + 1, +ESI = 702.6 |
| 19 | 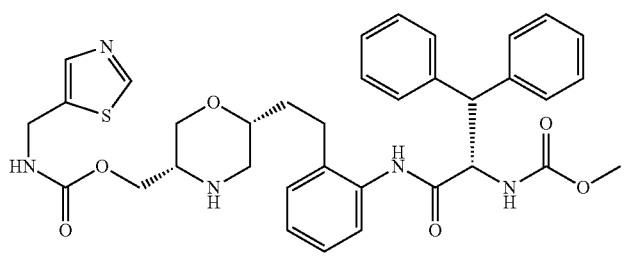 [SMILES: COC(=O)N[C@H](C(=O)Nc1ccccc1CC[C@@H]1CN[C@H](COC(=O)NCc2cncs2)CO1)C(c1ccccc1)c1ccccc1] | methyl N-[(1S)-1-benzhydryl-2-oxo-2-[[2-[2-[(2R,5S)-5-(thiazol-5-ylmethylcarbamoyloxymethyl)morpholin-2-yl]ethyl]phenyl]amino]ethyl]carbamate | M + 1, +ESI = 658.3 |
| 20 | 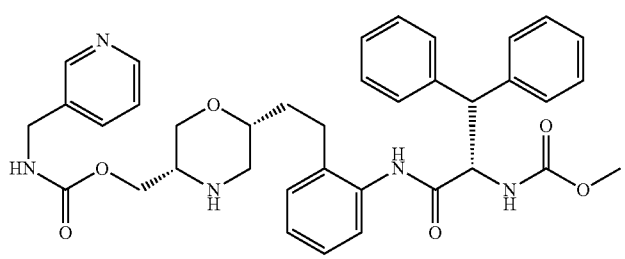 [SMILES: COC(=O)N[C@H](C(=O)Nc1ccccc1CC[C@@H]1CN[C@H](COC(=O)NCc2cccnc2)CO1)C(c1ccccc1)c1ccccc1] | methyl N-[(1S)-1-benzhydryl-2-oxo-2-[[2-[2-[(2R,5S)-5-(3-pyridylmethylcarbamoyloxymethyl)morpholin-2-yl]ethyl]phenyl]amino]ethyl]carbamate | M + 1, +ESI = 652.3 |
| 21 | 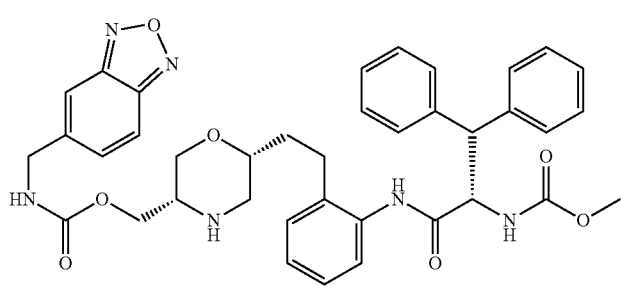 [SMILES: COC(=O)N[C@H](C(=O)Nc1ccccc1CC[C@@H]1CN[C@H](COC(=O)NCc2ccc3nonc3c2)CO1)C(c1ccccc1)c1ccccc1] | methyl N-[(1S)-1-benzhydryl-2-[[2-[2-[(2R,5S)-5-(2,1,3-benzoxadiazol-5-ylmethylcarbamoyloxymethyl)morpholin-2-yl]ethyl]phenyl]amino]-2-oxo-ethyl]carbamate | M + 1, +ESI = 693.2 |

-continued

| Example | Compound name | Characterization data |
|---|---|---|
| 22 | methyl N-[(1S)-1-benzhydryl-2-[[2-[2-[(2R,5S)-5-(cyclopropylmethylcarbamoyloxymethyl)morpholin-2-yl]ethyl]phenyl]amino]-2-oxo-ethyl]carbamate | M + 1, +ESI = 615.3 |
| 23 | methyl N-[(1S)-1-benzhydryl-2-[[2-[2-[(2R,5S)-5-(cyclobutylcarbamoyloxymethyl)morpholin-2-yl]ethyl]phenyl]amino]-2-oxo-ethyl]carbamate | M + 1, +ESI = 615.3 |
| 24 | methyl N-[(1S)-1-benzhydryl-2-[[2-[2-[(2R,5S)-5-(2,2-difluoroethylcarbamoyloxymethyl)morpholin-2-yl]ethyl]phenyl]amino]-2-oxo-ethyl]carbamate | M + 1, +ESI = 625.4 |
| 25 | methyl N-(1S)-1-benzhydryl-2-[[2-[2-[(2R,5S)-5-(diethylcarbamoyloxymethyl)morpholin-2-yl]ethyl]phenyl]amino]-2-oxo-ethyl]carbamate | M + 1, +ESI = 617.3 |
| 26 | methyl N-[(1S)-1-benzhydryl-2-[[2-[2-[(2R,5S)-5-(dimethylcarbamoyloxymethyl)morpholin-2-yl]ethyl]phenyl]amino]-2-oxo-ethyl]carbamate | M + 1, +ESI = 589.3 |
| 27 | [(3S,6R)-6-[2-[2-[[(2S)-2-(methoxycarbonylamino)-3,3-diphenyl-propanoyl]amino]phenyl]ethyl]morpholin-3-yl]methyl pyrrolidine-1-carboxylate | M + 1, +ESI = 615.3 |

| Example | Compound name | Characterization data |
|---|---|---|
| 28 | methyl N-[(1S)-1-benzhydryl-2-[[2-[2-[(2R,5S)-5-(2-dimethylaminoethylcarbamoyloxymethyl)morpholin-2-yl]ethyl]phenyl]amino]-2-oxo-ethyl]carbamate | M + 1, +ESI = 632.3 |
| 29 | N-[2-(2-{(2R,5S)-5-[({[(3S,4R)-4-fluorotetrahydrofuran-3-yl]carbamoyl}oxy)methyl]morpholin-2-yl}ethyl)phenyl]-Nα-(methoxycarbonyl)-β-phenyl-L-phenylalaninamide | M + 1, +ESI = 649.3 |
| 30 | Nα-(methoxycarbonyl)-N-(2-{2-[(2R,5S)-5-{[(methylcarbamoyl)oxy]methyl}morpholin-2-yl]ethyl}phenyl)-β-phenyl-L-phenylalaninamide | M + 1, +ESI = 575.2 |
| 31 | N-(2-{2-[(2R,5S)-5-({[(1-cyclopropyl-2,2,2-trifluoroethyl)carbamoyl]oxy}methyl)morpholin-2-yl]ethyl}phenyl)-Nα-(methoxycarbonyl)-β-phenyl-L-phenylalaninamide | M + 1, +ESI = 683.2 |

EXAMPLE 32

N-(3-{2-[(2R,5S)-5-({[(4-fluorobenzyl)carbamoyl]oxy}methyl)morpholin-2-yl]ethyl}pyridin-2-yl)-Nα-(methoxycarbonyl)-β-phenyl-L-phenylalaninamide

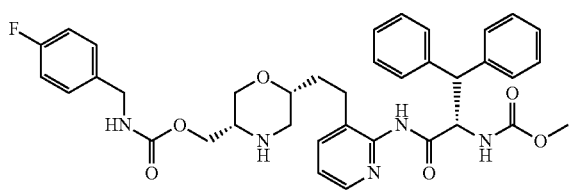 [SMILES: COC(=O)N[C@H](C(=O)Nc1ncccc1CC[C@@H]1CN[C@H](COC(=O)NCc2ccc(F)cc2)CO1)C(c1ccccc1)c1ccccc1]

Step 1: Preparation of tert-butyl (2R,5S)-2-[(2-aminopyridin-3-yl)ethynyl]-5-({[tert-butyl(dimethyl)silyl]oxy}methyl)morpholine-4-carboxylate A solution of tert-butyl (2R,5S)-5-({[tert-butyl(dimethyl)silyl]oxy}methyl)-2-ethynylmorpholine-4-carboxylate (1 eq) and 3-bromopyridin-2-amine (1.4 eq) in acetonitrile (0.1M) and triethylamine (25 eq) was flushed with nitrogen for 10 minutes. Then bis(triphenylphosphine)palladium(ii) chloride (0.1 eq) and copper(i) iodide (1.2 eq) were added and the mixture was flushed again with nitrogen for 10 minutes. The reaction mixture was stirred at 60° C. for 2 hours in the dark. It was concentrated to dryness and the residue was purified by automated SiO₂ flash chromatography system using solvent gradient of 0% to 10% MeOH/CH₂Cl2 to afford the desired compound.

Step 2: Preparation of tert-butyl (2R,5S)-2-[2-(2-aminopyridin-3-yl)ethyl]-5-({[tert-butyl(dimethyl)silyl]oxy}methyl)morpholine-4-carboxylate To tert-butyl (2R,5S)-2-[(2-aminopyridin-3-yl)ethynyl]-5-({[tert-butyl(dimethyl)silyl]oxy}methyl)morpholine-4-carboxylate (1 eq.) in 2,2,2,-trifluoroethanol (0.4 M) at rt was added 10% Pd/C (0.2 eq.). The reaction was degassed and then shaken under 1 atm of $H_2$ for 24 hrs. The reaction mixture was filtered on celite and concentrated to afford the desired compound.

Step 3: Preparation of tert-butyl (2R,5S)-5-({[tert-butyl(dimethyl)silyl]oxy}methyl)-2-[2-(2-{[N-(methoxycarbonyl)-β-phenyl-L-phenylalanyl]amino}pyridin-3-yl)ethyl]morpholine-4-carboxylate To N-(methoxycarbonyl)-β-phenyl-L-phenylalanine (1.1 eq.) in DMF (0.15 M) at rt were added HATU (1.4 eq.) and 2,6-lutidine (3 eq.). The reaction mixture was stirred for 30 min and tert-butyl (2R,5S)-2-[2-(2-aminopyridin-3-yl)ethyl]-5-({[tert-butyl(dimethyl)silyl]oxy}methyl)morpholine-4-carboxylate (1 eq) was added. The reaction mixture was stirred at 60° C. for 16 h and diluted with EtOAc and saturated aqueous $NaHCO_3$. The aqueous layer was extracted with EtOAc. The combined organic layers were washed with brine, dried over $Na_2SO_4$, filtered and concentrated. The crude product was purified by automated $SiO_2$ flash chromatography system using solvent gradient of 0% to 10% MeOH/$CH_2Cl_2$ to afford the desired compound. Alternatively, DMF could be replaced as solvent by pyridine to ease coupling involving less reactive amine.

Step 4: Preparation of tert-butyl (2R,5R)-5-(hydroxymethyl)-2-[2-(2-{[N-(methoxycarbonyl)-β-phenyl-L-phenylalanyl]amino}pyridin-3-yl)ethyl]morpholine-4-carboxylate To tert-butyl (2R,5S)-5-({[tert-butyl(dimethyl)silyl]oxy}methyl)-2-[2-(2-{[N-(methoxycarbonyl)-β-phenyl-L-phenylalanyl]amino}pyridin-3-yl)ethyl]morpholine-4-carboxylate in THF (0.1 M) at rt was added TBAF (1M in THF) (4 eq.). The mixture was stirred at rt for 2 hrs, diluted with EtOAc and saturated aqueous $NH_4Cl$ and the aqueous layer was extracted with EtOAc. The combined organic layers were washed with brine, dried over $Na_2SO_4$, filtered and concentrated. The crude product was purified by automated $SiO_2$ flash chromatography system using solvent gradient of 0-10% MeOH/$CH_2Cl_2$ to afford the desired compound.

Step 5: Preparation of tert-butyl (2R,5S)-5-({[(4-fluorobenzyl)carbamoyl]oxy}methyl)-2-[2-(2-{[N-(methoxycarbonyl)-β-phenyl-L-phenylalanyl]amino}pyridin-3-yl)ethyl]morpholine-4-carboxylate A mixture of tert-butyl (2R,5R)-5-(hydroxymethyl)-2-[2-(2-{[N-(methoxycarbonyl)-β-phenyl-L-phenylalanyl]amino}pyridin-3-yl)ethyl]morpholine-4-carboxylate (1 eq) and CDI (2.05 eq.) was dissolved in dry Pyridine (0.04 M) and the resulting solution stirred under $N_2$ at rt for 5 h and then at 49° C. for 0.5 h; then neat 4-fluorobenzylamine (6 eq.) was added and the resulting mixture further stirred at the same temperature for 12 h. The crude reaction mixture was diluted with EtOAc, washed with 5% aq. $KHSO_4$ then sat. $NaHCO_3$, dried over $Na_2SO_4$, filtered and concentrated. The residue was purified by automated silicagel flash chromatography system eluted with a gradient 0% to 5% MeOH in DCM, to afford title compound.

Step 6: Preparation of N-(3-{2-[(2R,5S)-5-({[(4-fluorobenzyl)carbamoyl]oxy}methyl)morpholin-2-yl]ethyl}pyridin-2-yl)-Nα-(methoxycarbonyl)-β-phenyl-L-phenylalaninamide Tert-butyl (2R,5S)-5-({[(4-fluorobenzyl)carbamoyl]oxy}methyl)-2-[2-(2-{[N-(methoxycarbonyl)-β-phenyl-L-phenylalanyl]amino}pyridin-3-yl)ethyl]morpholine-4-carboxylate in a 1:1 mixture of $CH_2Cl_2$/TFA (0.1 M) was stirred at rt for 1 hr. The reaction mixture was concentrated under reduced pressure and the residue was co-evaporated twice with heptane and triturated in $Et_2O$ to afford the desired product as a TFA salt. Alternatively, the TFA salt, after concentration, could be neutralized with aqueous saturated $NaHCO_3$, extracted with EtOAc, dried over $Na_2SO_4$, filtered and concentrated and then purified by automated $SiO_2$ flash chromatography system using solvent gradient of 0% to 10% MeOH/$CH_2Cl_2$ to afford the desired compound. Alternatively, the free base could be purified by filtration on SCX SPE cartridge made of pTSA-$SiO_2$ eluted first with MeOH to remove non basic impurities and eluted then with 10% $NH_4OH$/MeOH to elute the free base and afford the desired compound after concentration under reduced pressure.

M+1, +ESI=670.1

The following examples (33 to 39) were synthesized from tert-butyl (2R,5S)-5-({[tert-butyl(dimethyl)silyl]oxy}methyl)-2-ethynylmorpholine-4-carboxylate according to the procedures described for the preparation of Example 81 and by using the appropriate reagents.

| Example | Compound name | Characterization data |
|---|---|---|
| 33 | N-(4-{2-[(2R,5S)-5-({[(4-fluorobenzyl)carbamoyl]oxy}methyl)morpholin-2-yl]ethyl}pyridin-3-yl)-Nα-(methoxycarbonyl)-β-phenyl-L-phenylalaninamide | M + 1, +ESI = 670.3 |

-continued

| Example | Compound name | Characterization data |
|---|---|---|
| 34 | Nα-(methoxycarbonyl)-β-phenyl-N-(4-{2-[(2R,5S)-5-({[(2,2,2-trifluoroethyl)carbamoyl]oxy}methyl)morpholin-2-yl]ethyl}pyridin-3-yl)-L-phenylalaninamide | M + 1, +ESI = 644.2 |
| 35 | Nα-(methoxycarbonyl)-N-(2-methoxy-4-{2-[(2R,5S)-5-({[(2,2,2-trifluoroethyl)carbamoyl]oxy}methyl)morpholin-2-yl]ethyl}pyridin-3-yl)-β-phenyl-L-phenylalaninamide | M + 1, +ESI = 674.2 |
| 36 | N-(4-{2-[(2R,5S)-5-({[(4-fluorobenzyl)carbamoyl]oxy}methyl)morpholin-2-yl]ethyl}pyrimidin-5-yl)-Nα-(methoxycarbonyl)-β-phenyl-L-phenylalaninamide | M + 1, +ESI = 670.9 |
| 37 | Nα-(methoxycarbonyl)-β-phenyl-N-(4-{2-[(2R,5S)-5-({[(2,2,2-trifluoroethyl)carbamoyl]oxy}methyl)morpholin-2-yl]ethyl}pyrimidin-5-yl)-L-phenylalaninamide | M + 1, +ESI = 645.3 |
| 38 | N-(4-{2-[(2R,5S)-5-({[(4-fluorobenzyl)carbamoyl]oxy}methyl)morpholin-2-yl]ethyl}-2-oxo-1,2-dihydropyridin-3-yl)-Nα-(methoxycarbonyl)-β-phenyl-L-phenylalaninamide | M + 1, +ESI = 686.2 |
| 39 | Nα-(methoxycarbonyl)-N-(2-oxo-4-{2-[(2R,5S)-5-({[(2,2,2-trifluoroethyl)carbamoyl]oxy}methyl)morpholin-2-yl]ethyl}-1,2-dihydropyridin-3-yl)-β-phenyl-L-phenylalaninamide | M + 1, +ESI = 660.1 |

EXAMPLE 40

N-α-(methoxycarbonyl)-β-phenyl-N-(2-{2-[(2R,5R)-5-{[(phenylcarbamoyl)amino]methyl}morpholin-2-yl]ethyl}phenyl)-L-phenylalaninamide

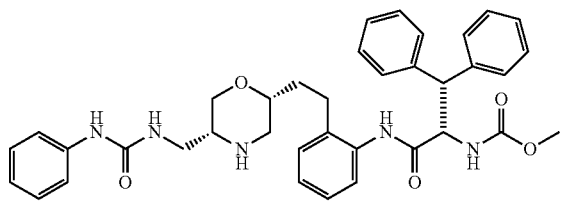 [SMILES: COC(=O)N[C@H](C(=O)Nc1ccccc1CC[C@@H]1CN[C@H](CNC(=O)Nc2ccccc2)CO1)C(c1ccccc1)c1ccccc1]

Step 1: Preparation of tert-butyl (2R,5S)-5-formyl-2-[2-(2-{[N-(methoxycarbonyl)-β-phenyl-L-phenylalanyl]amino}phenyl)ethyl]morpholine-4-carboxylate To a stirred solution of oxalyl chloride (5 eq) in DCM (0.3 M) at −78° C. was added a solution of DMSO (10 eq) in DCM (0.5M). The reaction mixture was stirred at −78° C. for 30 min. A solution of tert-butyl (2R,5R)-5-(hydroxymethyl)-2-[2-(2-{[N-(methoxycarbonyl)-β-phenyl-L-phenylalanyl]amino}phenyl)ethyl]morpholine-4-carboxylate (Example 185, step 10) (1 eq) in $CH_2Cl_2$ (0.2M) was added dropwise and stirred at −40° C. for 1.5 hours. It was then cooled to −78° C. and triethylamine (10 eq)) was added and the reaction mixture was stirred at 0° C. for 1 h. Water was added and the reaction mixture was warmed to rt for 30 min. The mixture was poured into aqueous sodium hydrogen carbonate and the aqueous layer was extracted with $CH_2Cl_2$. The combined organic layers were washed with brine, dried with $MgSO_4$ and concentrated under vacuum to afford the title compound as a yellow gum. The material was used in the subsequent step without further purification.

Step 2: Preparation of tert-butyl (2R,5R)-5-[(benzylamino)methyl]-2-[2-(2-{[N-(methoxycarbonyl)-β-phenyl-L-phenylalanyl]amino}phenyl)ethyl]morpholine-4-carboxylate To a solution of tert-butyl (2R,5S)-5-formyl-2-[2-(2-{[N-(methoxycarbonyl)-b-phenyl-L-phenylalanyl]amino}phenyl)ethyl]morpholine-4-carboxylate (1 eq.) in MeOH (0.05 M) was added benzylamine (7 eq.), magnesium sulfate (1.2 eq.) and acetic acid (7 eq.). The solution was stirred for 30 minutes and sodium cyanoborohydride (2.3 eq.) was added and the reaction mixture was further stirred for 2 hours. The reaction mixture was then quenched by the addition of aqueous sodium bicarbonate and the aqueous layer was extracted with ethyl acetate three times. The combined organic layers were washed with water, dried over $Na_2SO_4$, filtered and concentrated. The residue was purified by automated silica gel flash chromatography system eluted with a gradient 30% to 100% of EtOAc/Hex to afford title compound.

Step 3: Preparation of tert-butyl (2R,5R)-5-(aminomethyl)-2-[2-(2-{[N-(methoxycarbonyl)-β-phenyl-L-phenylalanyl]amino}phenyl)ethyl]morpholine-4-carboxylate To a solution of tert-butyl (2R,5R)-5-[(benzylamino)methyl]-2-[2-(2-{[N-(methoxycarbonyl)-β-phenyl-L-phenylalanyl]amino}phenyl)ethyl]morpholine-4-carboxylate (1 eq.) in 2,2,2-trifluoroethanol (0.17M) was added $Pd(OH)_2$ (0.33 eq.). The reaction mixture was stirred for 16 hrs under one atmosphere of hydrogen. The reaction mixture was filtered on celite and the filtrate was concentrated under reduced pressure. The residue was used as such for the next step.

Step 4: Preparation of tert-butyl (2R,5R)-2-[2-(2-{[N-(methoxycarbonyl)-β-phenyl-L-phenylalanyl]amino}phenyl)ethyl]-5-{[(phenylcarbamoyl)amino]methyl}morpholine-4-carboxylate To a solution of tert-butyl (2R,5R)-5-(aminomethyl)-2-[2-(2-{[N-(methoxycarbonyl)-β-phenyl-L-phenylalanyl]amino}phenyl)ethyl]morpholine-4-carboxylate (1 eq.) in DCM (0.1M) was added phenyl isocyanate (2.2 eq). The reaction mixture was stirred for 16 hrs at room temperature, diluted with $CH_2Cl_2$ and the organic layer was washed with aqueous saturated sodium bicarbonate. The organic layer was dried over $Na_2SO_4$, filtered and concentrated under reduced pressure. The residue was purified by automated silica gel flash chromatography system eluted with a gradient 10% to 100% of EtOAc/Hex to afford title compound.

Step 5: Preparation of N-α-(methoxycarbonyl)-β-phenyl-N-(2-{2-[(2R,5R)-5-{[(phenylcarbamoyl)amino]methyl}morpholin-2-yl]ethyl}phenyl)-L-phenylalaninamide Tert-butyl (2R,5R)-2-[2-(2-{[N-(methoxycarbonyl)-β-phenyl-L-phenylalanyl]amino}phenyl)ethyl]-5-{[(phenylcarbamoyl)amino]methyl}morpholine-4-carboxylate in a 1:1 mixture of $CH_2Cl_2$/TFA (0.1 M) was stirred at rt for 1 hr. The reaction mixture was concentrated under reduced pressure and the residue was co-evaporated twice with heptane and triturated in $Et_2O$ to afford the desired product as a TFA salt. Alternatively, the TFA salt, after concentration, could be neutralized with aqueous saturated $NaHCO_3$, extracted with EtOAc, dried over $Na_2SO_4$, filtered and concentrated and then purified by automated $SiO_2$ flash chromatography system using solvent gradient of 0% to 10% MeOH/$CH_2Cl_2$ to afford the desired compound. Alternatively, the free base could be purified by filtration on SCX SPE cartridge made of pTSA-$SiO_2$ eluted first with MeOH to remove non basic impurities and eluted then with 10% $NH_4OH$/MeOH to elute the free base and afford the desired compound after concentration under reduced pressure.

M+1, +ESI=636.2

The following examples (41 to 43) were synthesized from tert-butyl (2R,5R)-5-(aminomethyl)-2-[2-(2-{[N-(methoxycarbonyl)-β-phenyl-L-phenylalanyl]amino}phenyl)ethyl]morpholine-4-carboxylate according to the procedures described for the preparation of Example 40 and by using the appropriate reagents.

| Example | Compound name | Characterization data |
|---|---|---|
| 41 | methyl N-[(1S)-1-benzhydryl-2-oxo-2-[[2-[2-[(2R,5R)-5-[(pyridazin-3-ylcarbamoyl-amino)methyl]morpholin-2-yl]ethyl]phenyl]amino]ethyl]carbamate | M + 1, +ESI = 638.1 |
| 42 | methyl N-[(1S)-1-benzhydryl-2-oxo-2-[[2-[2-[(2R,5R)-5-[(2-pyridylcarbamoylamino)methyl]morpholin-2-yl]ethyl]phenyl]amino]ethyl]carbamate | M + 1, +ESI = 637.3 |
| 43 | methyl N-[(1S)-1-benzhydryl-2-oxo-2-[[2-[2-[(2R,5R)-5-[(1H-pyrazol-3-ylcarbamoylamino)methyl]morpholin-2-yl]ethyl]phenyl]amino]ethyl]carbamate | M + 1, +ESI = 626.6 |

EXAMPLE 44

Nα-(methoxycarbonyl)-β-phenyl-N-(2-{2-[(2R,5R)-5-{[(phenylsulfonyl)amino]methyl}morpholin-2-yl]ethyl}phenyl)-L-phenylalaninamide

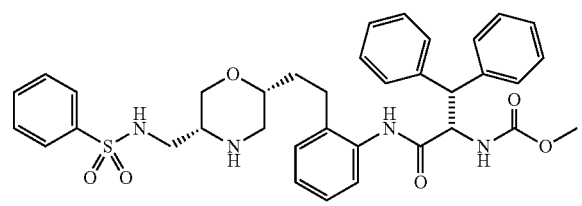 [SMILES: COC(=O)N[C@H](C(=O)Nc1ccccc1CC[C@@H]1CN[C@H](CNS(=O)(=O)c2ccccc2)CO1)C(c1ccccc1)c1ccccc1]

Step 1: Preparation of tert-butyl (2R,5R)-2-[2-(2-{[N-(methoxycarbonyl)-β-phenyl-L-phenylalanyl]amino}phenyl)ethyl]-5-{[(phenylsulfonyl)amino]methyl}morpholine-4-carboxylate To a solution of tert-butyl (2R,5R)-5-(aminomethyl)-2-[2-(2-{[N-(methoxycarbonyl)-β-phenyl-L-phenylalanyl]amino}phenyl)ethyl]morpholine-4-carboxylate (1 eq.) in DCM (0.1M) were added pyridine (3 eq) and benzene sulfonyl chloride (1.3 eq). The reaction mixture was stirred for 4 hrs at room temperature, diluted with CH₂Cl₂ and the organic layer was washed with aqueous saturated sodium bicarbonate. The organic layer was dried over Na₂SO₄, filtered and concentrated under reduced pressure. The residue was purified by automated silica gel flash chromatography system eluted with a gradient 10% to 100% of EtOAc/Hex to afford title compound.

Step 2: Preparation of Nα-(methoxycarbonyl)-β-phenyl-N-(2-{2-[(2R,5R)-5-{[(phenylsulfonyl)amino]methyl}morpholin-2-yl]-ethyl}phenyl)-L-phenylalaninamide Tert-butyl (2R,5R)-2-[2-(2-{[N-(methoxycarbonyl)-β-phenyl-L-phenylalanyl]amino}phenyl)ethyl]-5-{[(phenylsulfonyl)amino]methyl}morpholine-4-carboxylate in a 1:1 mixture of CH₂Cl₂/TFA (0.1 M) was stirred at rt for 1 hr. The reaction mixture was concentrated under reduced pressure and the residue was co-evaporated twice with heptane and triturated in Et₂O to afford the desired product as a TFA salt. Alternatively, the TFA salt, after concentration, could be neutralized with aqueous saturated NaHCO₃, extracted with EtOAc, dried over Na₂SO₄, filtered and concentrated and then purified by automated SiO₂ flash chromatography system using solvent gradient of 0% to 10% MeOH/CH₂Cl₂ to afford the desired compound. Alternatively, the free base could be purified by filtration on SCX SPE cartridge made of pTSA-SiO₂ eluted first with MeOH to remove non basic impurities and eluted then with 10% NH₄OH/MeOH to elute the free base and afford the desired compound after concentration under reduced pressure.

M+1, +ESI=657.4

The following examples (45 to 51) were synthesized from tert-butyl (2R,5R)-5-(aminomethyl)-2-[2-(2-{[N-(methoxycarbonyl)-β-phenyl-L-phenylalanyl]amino}phenyl)ethyl]morpholine-4-carboxylate according to the procedures described for the preparation of Example 44 and by using the appropriate reagents and electrophiles.

| Example | Compound name | Characterization data |
|---|---|---|
| 45 | methyl N-[(1S)-1-benzhydryl-2-oxo-2-[[2-[2-[(2R,5R)-5-[(triazolo[1,5-a]pyridin-6-ylsulfonylamino)methyl]morpholin-2-yl]ethyl]phenyl]amino]ethyl]carbamate | M + 1, +ESI = 698.3 |
| 46 | methyl N- [(1S)-1-benzhydryl-2-oxo-2-[[2-[2-[(2R,5R)-5-[[[6-(trifluoromethyl)-2-pyridyl]sulfonylamino]methyl]morpholin-2-yl]ethyl]phenyl]amino]ethyl]carbamate | M + 1, +ESI = 726.3 |
| 47 | methyl N-[(1S)-1-benzhydryl-2-[[2-[2-[(2R,5R)-5-[(cyclopropylsulfonylamino)methyl]morpholin-2-yl]ethyl]phenyl]amino]-2-oxo-ethyl]carbamate | M + 1, +ESI = 621.3 |
| 48 | methyl N-[(1S)-1-benzhydryl-2-oxo-2-[[2-[2-[(2R,5R)-5-[(2-pyridylsulfonylamino)methyl]morpholin-2-yl]ethyl]phenyl]amino]ethyl]carbamate | M + 1, +ESI = 658.2 |
| 49 | N-(2-{2-[(2R,5R)-5-({[(4-aminophenyl)sulfonyl]amino}methyl)morpholin-2-yl]ethyl}phenyl)-Nα-(methoxycarbonyl)-β-phenyl-L-phenylalaninamide | M + 1, +ESI = 672.2 |
| 50 | N-(2-{2-[(2R,5R)-5-{[(benzylsulfonyl)amino]methyl}morpholin-2-yl]ethyl}phenyl)-Nα-(methoxycarbonyl)-β-phenyl-L-phenylalaninamide | M + 1, +ESI = 671.2 |

| Example | Compound name | Characterization data |
|---|---|---|
| 51 | 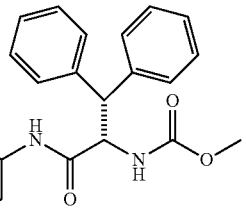 Nα-(methoxycarbonyl)-N-(2-{2-[(2R,5R)-5-{[(phenoxycarbonyl)amino]methyl}morpholin-2-yl]ethyl}phenyl)-β-phenyl-L-phenylalaninamide | M + 1, +ESI = 637.2 |

EXAMPLE 52

Nα-(methoxycarbonyl)-β-phenyl-N-(2-{2-[(2R,5R)-5-{[(phenylcarbonyl)amino]methyl}morpholin-2-yl]ethyl}phenyl)-L-phenylalaninamide

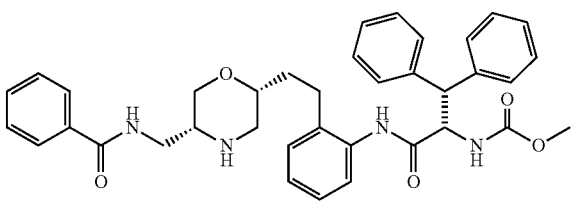 [SMILES: COC(=O)N[C@H](C(=O)Nc1ccccc1CC[C@@H]1CN[C@H](CNC(=O)c2ccccc2)CO1)C(c1ccccc1)c1ccccc1]

Step 1: Preparation of tert-butyl (2R,5R)-2-[2-(2-{[N-(methoxycarbonyl)-β-phenyl-L-phenylalanyl]amino}phenyl)ethyl]-5-{[(phenylcarbonyl)amino]methyl}morpholine-4-carboxylate HATU (1.4 eq) was added to a stirred mixture a solution of tert-butyl (2R,5R)-5-(aminomethyl)-2-[2-(2-{[N-(methoxycarbonyl)-β-phenyl-L-phenylalanyl]amino}phenyl)ethyl]morpholine-4-carboxylate (1 eq), benzoic acid (1.2 eq) and 2,6-lutidine (2 eq) in DMF (0.05 M) and the mixture was stirred at room temperature for 16 hrs. The mixture was diluted in EtOAc, The organic layer was washed with aqueous saturated NH$_4$Cl and brine. The organic layer was dried over Na$_2$SO$_4$, filtered and evaporated. The residue was purified by automated silica gel flash chromatography system eluted with a gradient 10% to 100% of EtOAc/Hex to afford title compound.

Step 2: Preparation of tert-butyl (2R,5R)-2-[2-(2-{[N-(methoxycarbonyl)-β-phenyl-L-phenylalanyl]amino}phenyl)ethyl]-5-{[(phenylcarbonyl)amino]methyl}morpholine-4-carboxylate Tert-butyl (2R,5R)-2-[2-(2-{[N-(methoxycarbonyl)-β-phenyl-L-phenylalanyl]amino}phenyl)ethyl]-5-{[(phenylcarbonyl)amino]methyl}morpholine-4-carboxylate in a 1:1 mixture of CH$_2$Cl$_2$/TFA (0.1 M) was stirred at rt for 1 hr. The reaction mixture was concentrated under reduced pressure and the residue was co-evaporated twice with heptane and triturated in Et$_2$O to afford the desired product as a TFA salt. Alternatively, the TFA salt, after concentration, could be neutralized with aqueous saturated NaHCO$_3$, extracted with EtOAc, dried over Na$_2$SO$_4$, filtered and concentrated and then purified by automated SiO$_2$ flash chromatography system using solvent gradient of 0% to 10% MeOH/CH$_2$Cl$_2$ to afford the desired compound. Alternatively, the free base could be purified by filtration on SCX SPE cartridge made of pTSA-SiO$_2$ eluted first with MeOH to remove non basic impurities and eluted then with 10% NH$_4$OH/MeOH to elute the free base and afford the desired compound after concentration under reduced pressure.

M+1, +ESI=621.4

The following examples (53 to 60) were synthesized from tert-butyl (2R,5R)-5-(aminomethyl)-2-[2-(2-{[N-(methoxycarbonyl)-β-phenyl-L-phenylalanyl]amino}phenyl)ethyl]morpholine-4-carboxylate according to the procedures described for the preparation of Example 52 and by using the appropriate reagents.

| Example | Compound name | Characterization data |
|---|---|---|
| 53 | 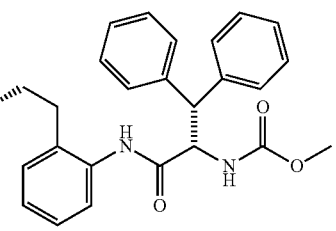 Nα-(methoxycarbonyl)-β-phenyl-N-(2-{2-[(2R,5R)-5-{[(phenylacetyl)amino]methyl}morpholin-2-yl]ethyl}phenyl)-L-phenylalaninamide | M + 1, +ESI = 635.3 |

-continued

| Example | | Compound name | Characterization data |
|---|---|---|---|
| 54 | 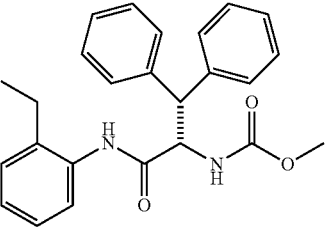 | methyl N-[(1S)-1-benzhydryl-2-oxo-2-[[2-[2-[(2R,5R)-5-[(pyridazine-3-carbonyl-amino)methyl]morpholin-2-yl]ethyl]phenyl]amino]ethyl]carbamate | M + 1, +ESI = 623.3 |
| 55 | 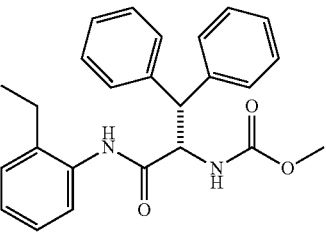 | methyl N-[(1S)-1-benzhydryl-2-[[2-[2-[(2R,5R)-5-[[(2-chloro-benzoyl)amino]methyl]morpholin-2-yl]ethyl]phenyl]amino]-2-oxo-ethyl]carbamate | M + 1, +ESI = 655.3 |
| 56 | 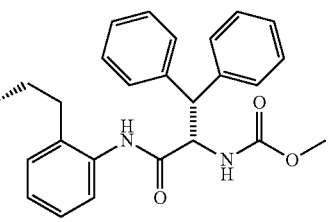 | methyl N-[(1S)-1-benzhydryl-2-[[2-[2-[(2R,5R)-5-[(1H-indole-2-carbonylamino)methyl]morpholin-2-yl]ethyl]phenyl]amino]-2-oxo-ethyl]carbamate | M + 1, +ESI = 661.4 |
| 57 | 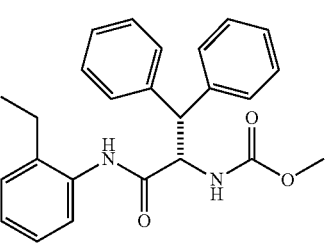 | methyl N-[(1S)-1-benzhydryl-2-[[2-[2-[(2R,5R)-5-[[(2,6-dimethylbenzoyl)amino]methyl]morpholin-2-yl]ethyl]phenyl]amino]-2-oxo-ethyl]carbamate | M + 1, +ESI = 649.3 |
| 58 | 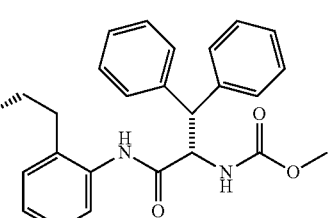 | methyl N-[(1S)-1-benzhydryl-2-[[2-[2-[(2R,5R)-5-[[(3-fluoro-6-oxo-1H-pyridine-2-carbonyl)amino]methyl]morpholin-4-ium-2-yl]ethyl]phenyl]amino]-2-oxo-ethyl]carbamate | M + 1, +ESI = 656.3 |
| 59 | 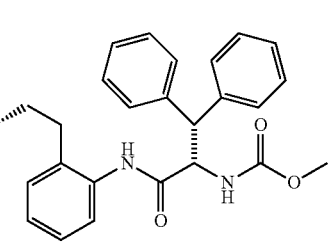 | methyl N-[(1S)-1-benzhydryl-2-oxo-2-[[2-[2-[(2R,5R)-5-[(pyrazolo[1,5-a]pyrimidine-2-carbonylamino)methyl]morpholin-2-yl]ethyl]phenyl]amino]ethyl]carbamate | M + 1, +ESI = 662.2 |

| Example | Compound name | Characterization data |
|---|---|---|
| 60 | methyl N-[(1S)-1-benzhydryl-2-oxo-2-[[2-[2-[(2R,5R)-5-[[[5-(2-pyridyl)-1H-pyrazole-3-carbonyl]amino]methyl]morpholin-2-yl]ethyl]phenyl]amino]ethyl]carbamate | M + 1, +ESI = 688.3 |

EXAMPLE 61

N-(2-{2-[(2R,5R)-5-(hydroxymethyl)morpholin-2-yl]ethyl}phenyl)-Nα-(methoxycarbonyl)-β-phenyl-L-phenylalaninamide

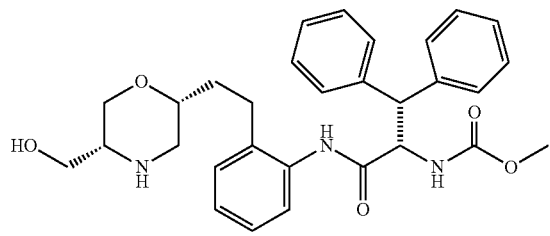 [SMILES: COC(=O)N[C@H](C(=O)Nc1ccccc1CC[C@@H]1CN[C@H](CO)CO1)C(c1ccccc1)c1ccccc1]

Step 1: Preparation of N-(2-{2-[(2R,5R)-5-(hydroxymethyl)morpholin-2-yl]ethyl}-phenyl)-Nα-(methoxycarbonyl)-β-phenyl-L-phenylalaninamide N-(2-{2-[(2R,5R)-5-(hydroxymethyl)morpholin-2-yl]ethyl}phenyl)-Nα-(methoxycarbonyl)-β-phenyl-L-phenylalaninamide was prepared from (2R,5R)-5-Hydroxymethyl-2-{2-[2-((S)-2-methoxycarbonylamino-3,3-diphenyl-propionylamino)-phenyl]-ethyl}-morpholine-4-carboxylic acid tert-butyl ester using procedures described in step 2 of Example 2.
M+1, +ESI=518.2

EXAMPLE 62

Nα-(methoxycarbonyl)-β-phenyl-N-[2-(2-{(2R,5S)-5-[(phenylsulfanyl)methyl]morpholin-2-yl}ethyl)phenyl]-L-phenylalaninamide

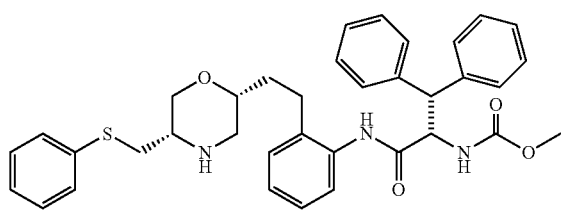 [SMILES: COC(=O)N[C@H](C(=O)Nc1ccccc1CC[C@@H]1CN[C@H](CSc2ccccc2)CO1)C(c1ccccc1)c1ccccc1]

Step 1: Preparation of Nα-(methoxycarbonyl)-β-phenyl-N-[2-(2-{(2R,5S)-5-[(phenylsulfanyl)methyl]morpholin-2-yl}ethyl)phenyl]-L-phenylalaninamide Cyanomethylenetributylphosphorane (2 eq) was added to a stirred mixture of (2R,5R)-5-hydroxymethyl-2-{2-[2-((S)-2-methoxycarbonylamino-3,3-diphenyl-propionylamino)-phenyl]-ethyl}-morpholine-4-carboxylic acid tert-butyl ester (1 eq) and thiophenol (1.5 eq) in toluene (0.04 M). The mixture was stirred at 90° C. for 2 h, cooled to room temperature and evaporated to dryness. The residue was purified by automated silica gel flash chromatography system eluted with a gradient 0% to 100% of EtOAc/Hex to afford tert-butyl (2R,5S)-2-[2-(2-{[N-(methoxycarbonyl)-β-phenyl-L-phenylalanyl]amino}phenyl)ethyl]-5-[(phenylsulfanyl)methyl]morpholine-4-carboxylate which was then treated with TFA following the procedure described in step 2 of Example 2 to afford the title compound.
M+1, +ESI=610.2

EXAMPLE 63

Nα-(methoxycarbonyl)-N-(2-{2-[(2R,5S)-5-(phenoxymethyl)morpholin-2-yl]ethyl}phenyl)-β-phenyl-L-phenylalaninamide

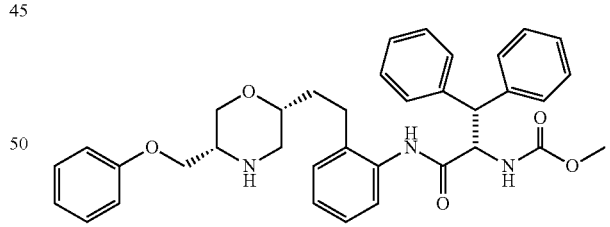

Step 1: Preparation of Nα-(methoxycarbonyl)-N-(2-{2-[(2R,5S)-5-(phenoxymethyl)morpholin-2-yl]ethyl}phenyl)-β-phenyl-L-phenylalaninamide Nα-(methoxycarbonyl)-N-(2-{2-[(2R,5S)-5-(phenoxymethyl)morpholin-2-yl]ethyl}phenyl)-β-phenyl-L-phenylalaninamide was prepared (2R,5R)-5-hydroxymethyl-2-{2-[2-((S)-2-methoxycarbonylamino-3,3-diphenyl-propionylamino)-phenyl]-ethyl}-morpholine-4-carboxylic acid tert-butyl ester using procedures described in step 1 of Example 62.
M+1, +ESI=594.2

EXAMPLE 64

Nα-(methoxycarbonyl)-β-phenyl-N-[2-(2-{(2R,5R)-5-[(4-phenyl-1H-1,2,3-triazol-1-yl)methyl]morpholin-2-yl}ethyl)phenyl]-L-phenylalaninamide

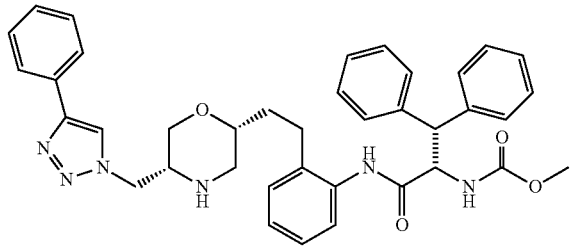 [SMILES: COC(=O)N[C@H](C(=O)Nc1ccccc1CC[C@@H]1CN[C@H](Cn2cc(-c3ccccc3)nn2)CO1)C(c1ccccc1)c1ccccc1]

Step 1: Preparation of tert-butyl (2R,5R)-5-(azidomethyl)-2-[2-(2-{[N-(methoxycarbonyl)-β-phenyl-L-phenylalanyl]amino}phenyl)ethyl]morpholine-4-carboxylate To a solution of tert-butyl (2R,5R)-5-(aminomethyl)-2-[2-(2-{[N-(methoxycarbonyl)-β-phenyl-L-phenylalanyl]amino}phenyl)ethyl]morpholine-4-carboxylate (1 eq.) in $CH_2Cl_2$ (0.4M) was added copper(II) sulfate (0.02 eq.) and sodium bicarbonate (1 eq.) as a solution in water ($NaHCO_3$/$CuSO_4$)) (1M). To that mixture was added triflic azide (3.65 eq.) as a solution in $CH_2Cl_2$ (0.4M). The heterogenous mixture was homogenized by the addition of methanol and the reaction was stirred at room temperature for 30 minutes. Upon completion by LCMS, solvents were evaporated and the evaporation residue was used as such for next step.

Step 2: Preparation of tert-butyl (2R,5R)-2-[2-(2-{[N-(methoxycarbonyl)-β-phenyl-L-phenylalanyl]amino}phenyl)ethyl]-5-[(4-phenyl-1H-1,2,3-triazol-1-yl)methyl]morpholine-4-carboxylate To a solution of tert-butyl (2R,5R)-5-(azidomethyl)-2-[2-(2-{[N-(methoxycarbonyl)-β-phenyl-L-phenylalanyl]amino}phenyl)ethyl]morpholine-4-carboxylate (1 eq.) in tetrahydrofuran (0.033M) were added phenylacetylene (3.9 eq.) and Hunig's base (5 eq.). Nitrogen was then bubbled for 5 minutes through the reaction mixture which was placed in a sealed tube. Copper(I) iodide (1.5 eq.) was added to the reaction mixture and the temperature was raised to 70° C. for 16 hrs. The reaction mixture was evaporated to dryness and the evaporation residue was purified by automated silica gel flash chromatography system eluted with a gradient 0% to 10% of MeOH/$CH_2Cl_2$.

Step 3: Preparation of Nα-(methoxycarbonyl)-β-phenyl-N-[2-(2-{(2R,5R)-5-[(4-phenyl-1H-1,2,3-triazol-1-yl)methyl]morpholin-2-yl}ethyl)phenyl]-L-phenylalaninamide Nα-(methoxycarbonyl)-β-phenyl-N-[2-(2-{(2R,5R)-5-[(4-phenyl-1H-1,2,3-triazol-1-yl)methyl]morpholin-2-yl}ethyl)phenyl]-L-phenylalaninamide was prepared from tert-butyl (2R,5R)-2-[2-(2-{[N-(methoxycarbonyl)-β-phenyl-L-phenylalanyl]amino}phenyl)ethyl]-5-[(4-phenyl-1H-1,2,3-triazol-1-yl)methyl]morpholine-4-carboxylate following the procedure described in step 2 of Example 2 to afford the title compound.

M+1, +ESI=645.3

Example 65

Nα-(methoxycarbonyl)-β-phenyl-N-(2-{2-[(2R,5R)-5-{[4-(trimethylsilyl)-1H-1,2,3-triazol-1-yl]methyl}morpholin-2-yl]ethyl}phenyl)-L-phenylalaninamide

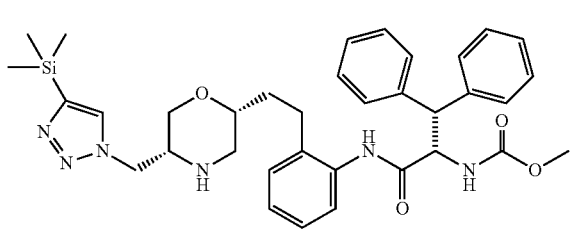

Step 1: Preparation of Nα-(methoxycarbonyl)-β-phenyl-N-(2-{2-[(2R,5R)-5-{[4-(trimethylsilyl)-1H-1,2,3-triazol-1-yl]methyl}morpholin-2-yl]ethyl}phenyl)-L-phenylalaninamide Nα-(methoxycarbonyl)-β-phenyl-N-(2-{2-[(2R,5R)-5-{[4-(trimethylsilyl)-1H-1,2,3-triazol-1-yl]methyl}morpholin-2-yl]ethyl}phenyl)-L-phenylalaninamide was prepared from tert-butyl (2R,5R)-5-(azidomethyl)-2-[2-(2-{[N-(methoxycarbonyl)-β-phenyl-L-phenylalanyl]amino}phenyl)ethyl]morpholine-4-carboxylate by following procedures described in step 2 and 3 of Example 64 and by using the appropriate reagents.

M+1, +ESI=641.2

EXAMPLE 66

Nα-(methoxycarbonyl)-β-phenyl-N-(2-{2-[(2R,5R)-5-(1H-1,2,3-triazol-1-ylmethyl)morpholin-2-yl]ethyl}phenyl)-L-phenylalaninamide

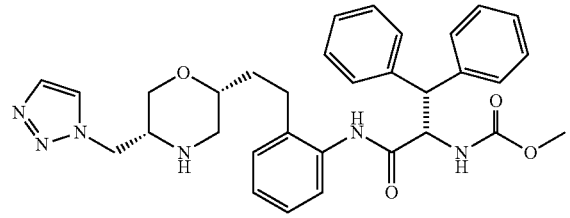 [SMILES: COC(=O)N[C@H](C(=O)Nc1ccccc1CC[C@@H]1CN[C@H](Cn2ccnn2)CO1)C(c1ccccc1)c1ccccc1]

Step 1: Preparation of Nα-(methoxycarbonyl)-β-phenyl-N-(2-{2-[(2R,5R)-5-(1H-1,2,3-triazol-1-ylmethyl)morpholin-2-yl]ethyl}phenyl)-L-phenylalaninamide To a solution of Nα-(methoxycarbonyl)-β-phenyl-N-(2-{2-[(2R,5R)-5-{[4-(trimethylsilyl)-1H-1,2,3-triazol-1-yl]methyl}morpholin-2-yl]ethyl}phenyl)-L-phenylalaninamide (1 eq.) in tetrahydrofuran (0.03M) was added TBAF (2.7 eq.). The reaction mixture was then heated to 50° C. for 16 hrs. The reaction mixture was quenched with aqueous saturated sodium bicarbonate. The aqueous layer was extracted with $CH_2Cl_2$ and the combined organic layers were dried over $Na_2SO_4$, filtered and concentrated. The evaporation residue was purified by automated silica gel flash chromatography system eluted with a gradient 0% to 30% of MeOH/EtOAc.

M+1, +ESI=569.2

EXAMPLE 67 methyl{(1S)-1-(diphenylmethyl)-2-oxo-2-[(2-{2-[(2R,5R)-5-(3-phenylpropyl)morpholin-2-yl]ethyl}phenyl)amino]ethyl}carbamate

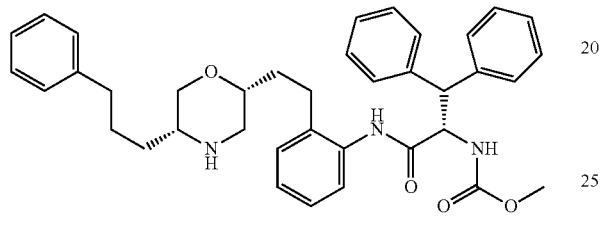

Step 1: Preparation of tert-butyl (2R,5R)-2-[2-(2-{[N-(methoxycarbonyl)-β-phenyl-L-phenylalanyl]amino}phenyl)ethyl]-5-[(1Z)-3-phenylprop-1-en-1-yl]morpholine-4-carboxylate To a cold (0° C.) suspension of phosphonium salt triphenyl (2-phenylethyl)phosphonium iodide (2.5 eq) in THF (0.1M) was added dropwise a solution of 1M lithium bis(trimethylsilyl)amide (3 eq) in THF. The reaction mixture was stirred at that temperature for 30 min then cooled to −78° C. A solution of tert-butyl (2R,5S)-5-formyl-2-[2-(2-{[N-(methoxycarbonyl)-β-phenyl-L-phenylalanyl]amino}phenyl)ethyl]morpholine-4-carboxylate (1 eq) in THF (1M) was added dropwise. The reaction mixture was stirred at that temperature for 30 min then allowed to warm to rt for 30 min, quenched with water and the organic layer was extracted twice with EtOAc. The combined organic layers were washed with brine, dried over $Na_2SO_4$, filtered and concentrated. The residue was purified by automated silica gel flash chromatography system eluted with a gradient 0% to 70% of EtOAc/Hex to afford the desired compound.

Step 2: Preparation of methyl {(1S)-1-(diphenylmethyl)-2-oxo-2-[(2-{2-[(2R,5R)-5-(3-phenylpropyl)morpholin-2-yl]ethyl}phenyl)amino]ethyl}carbamate Methyl {(1S)-1-(diphenylmethyl)-2-oxo-2-[(2-{2-[(2R,5R)-5-(3-phenylpropyl)morpholin-2-yl]ethyl}phenyl)amino]ethyl}carbamate was prepared from tert-butyl (2R,5R)-2-[2-(2-{[N-(methoxycarbonyl)-β-phenyl-L-phenylalanyl]amino}phenyl)ethyl]-5-[(1Z)-3-phenylprop-1-en-1-yl]morpholine-4-carboxylate by following procedures described in steps 7 and 12 of Example 1 and by using the appropriate reagents.

M+1, +ESI=606.3

EXAMPLE 68 dimethyl [(2R,5R)-morpholine-2,5-diylbis{ethane-2,1-diylbenzene-2,1-diylimino[(2S)-1-oxo-3,3-diphenylpropane-1,2-diyl]}]biscarbamate

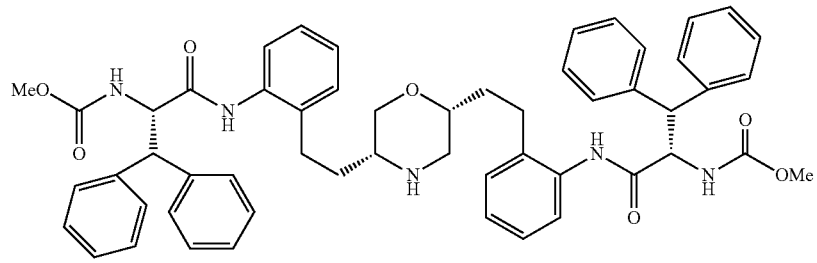 [SMILES: COC(=O)N[C@H](C(=O)Nc1ccccc1CC[C@@H]1CO[C@H](CCc2ccccc2NC(=O)[C@@H](NC(=O)OC)C(c2ccccc2)c2ccccc2)CN1)C(c1ccccc1)c1ccccc1]

Step 1. Preparation of tert-Butyl(2R,5R)-2-{2-[2-({(2S)-2-[(methoxycarbonyl)amino]-3,3-diphenylpropanoyl}amino)phenyl]ethyl}-5-[2-(2-nitrophenyl)vinyl]morpholine-4-carboxylate (2-Nitrobenzyl)triphenylphosphonium bromide monohydrate (1.4 equiv), potassium carbonate (2.0 equiv) and 18-crown-6 (0.1 equiv) were combined in DME (0.16 M vs aldehyde). The mixture was stirred at room temperature for 5 min. tert-Butyl(2R,5S)-5-formyl-2-{2-[2-({(2S)-2-[(methoxycarbonyl)amino]-3,3-diphenylpropanoyl}amino)phenyl]ethyl}morpholine-4-carboxylate (1.0 equiv) was dissolved in DME (0.16 M) and added to the reaction mixture. The reaction mixture was stirred at room temperature for 18 h, filtered over solka floc and concentrated. The crude product was purified using automated silica-gel flash chromatography using a solvent gradient of 0% to 100% of ethyl acetate and hexanes.

Step 2. Preparation of tert-Butyl(2R,5R)-5-[2-(2-aminophenyl)ethyl]-2-{2-[2-({(2S)-2-[(methoxycarbonyl)amino]-3,3-diphenylpropanoyl}amino)phenyl]ethyl}morpholine-4-carboxylate Tert-Butyl(2R,5R)-2-{2-[2-({(2S)-2-[(methoxycarbonyl)amino]-3,3-diphenylpropanoyl}amino)phenyl]ethyl}-5-[2-

(2-nitrophenyl)vinyl]morpholine-4-carboxylate (1.0 equiv) was dissolved in EtOH (0.07 M) in a Parr shaker vessel. Palladium on carbon (12 wt %) was added. The reaction mixture was flushed with nitrogen, and then submitted to 45 psi hydrogen with shaking for 18 h. The crude mixture was flushed with nitrogen, filtered on solka floc and concentrated to yield the desired product.

Step 3. Preparation of tert-Butyl(2R,5R)-2,5-bis {2-[2-({(2S)-2-[(methoxycarbonyl)amino]-3,3-diphenyl propanoyl}amino)phenyl]ethyl}morpholine-4-carboxylate (2S)-2-[(methoxycarbonyl)amino]-3,3-diphenylpropanoic acid (1.2 equiv), HATU (1.4 equiv) and 2,6-lutidine (2.0 equiv) were combined in DMF (0.2 M vs aniline). tert-Butyl(2R,5R)-5-[2-(2-aminophenyl)ethyl]-2-{2-[2-({(2S)-2-[(methoxycarbonyl)amino]-3,3-diphenylpropanoyl}amino)phenyl]ethyl}morpholine-4-carboxylate (1.0 equiv) was dissolved in DMF (0.11 M) and was added to the reaction mixture. The reaction was stirred at room temperature for 18 h and ethyl acetate and saturated sodium bicarbonate were added. Aqueous layer was extracted twice with ethyl acetate and combined organic layers were washed with brine, 10% aqueous lithium chloride, 1N HCl, brine, dried (Na$_2$SO$_4$), filtered and concentrated. The crude product was purified using automated silica-gel flash chromatography using a solvent gradient of 5% to 60% of ethyl acetate and hexanes.

Step 4. Preparation of dimethyl [(2R,5R)-morpholine-2,5-diylbis {ethane-2,1-diylbenzene-2,1-diylimino[(2S)-1-oxo-3,3-diphenylpropane-1,2-diyl]}]biscarbamate Tert-Butyl(2R,5R)-2,5-bis {2-[2-({(2S)-2-[(methoxycarbonyl)amino]-3,3-diphenyl propanoyl}amino)phenyl]ethyl}morpholine-4-carboxylate in a 1:1 mixture of CH$_2$Cl$_2$/TFA (0.1 M) was stirred at rt for 1 hr. The reaction mixture was concentrated under reduced pressure and the residue was co-evaporated twice with heptane and triturated in Et$_2$O to afford the desired product as a TFA salt. Alternatively, the TFA salt, after concentration, could be neutralized with aqueous saturated NaHCO$_3$, extracted with EtOAc, dried over Na$_2$SO$_4$, filtered and concentrated and then purified by automated SiO$_2$ flash chromatography system using solvent gradient of 0% to 10% MeOH/CH$_2$Cl$_2$ to afford the desired compound. Alternatively, the free base could be purified by filtration on SCX SPE cartridge made of pTSA-SiO$_2$ eluted first with MeOH to remove non basic impurities and eluted then with 10% NH$_4$OH/MeOH to elute the free base and afford the desired compound after concentration under reduced pressure.

M+1, +ESI=888.4

The following examples (69 to 72) were synthesized from tert-Butyl(2R,5R)-5-[2-(2-aminophenyl)ethyl]-2-{2-[2-({(2S)-2-[(methoxycarbonyl)amino]-3,3-diphenylpropanoyl}amino)phenyl]ethyl}morpholine-4-carboxylate according to the procedures described for the preparation of Example 68 and by using the appropriate reagents.

| Example | | Compound name | Characterization data |
|---|---|---|---|
| 69 | 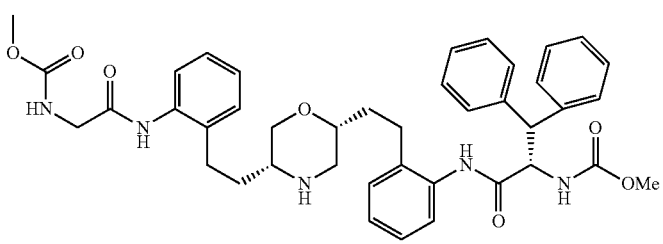 [SMILES: COC(=O)NCC(=O)Nc1ccccc1CC[C@@H]1CO[C@H](CCc2ccccc2NC(=O)[C@@H](NC(=O)OC)C(c2ccccc2)c2ccccc2)CN1] | methyl N-[(1S)-1-benzhydryl-2-[[2-[2-[(2R,5R)-5-[2-[2-[[2-(methoxycarbonylamino)acetyl]amino]phenyl]ethyl]morpholin-2-yl]ethyl]phenyl]amino]-2-oxo-ethyl]carbamate | M + 1, +ESI = 722.2 |
| 70 | 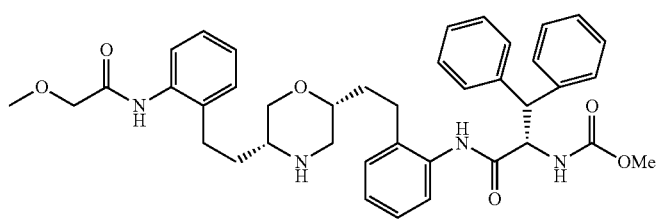 [SMILES: COCC(=O)Nc1ccccc1CC[C@@H]1CO[C@H](CCc2ccccc2NC(=O)[C@@H](NC(=O)OC)C(c2ccccc2)c2ccccc2)CN1] | methyl N-[(1S)-1-benzhydryl-2-[[2-[2-[(2R,5R)-5-[2-[2-[(2-methoxyacetyl)amino]phenyl]ethyl]morpholin-2-yl]ethyl]phenyl]amino]-2-oxo-ethyl]carbamate | M + 1, +ESI = 679.3 |
| 71 | 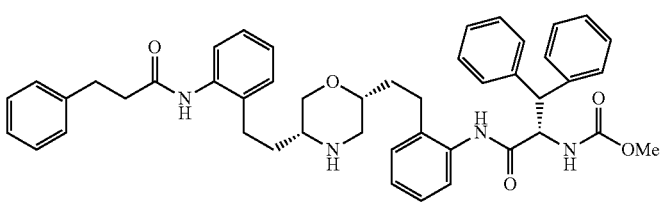 [SMILES: COC(=O)N[C@H](C(=O)Nc1ccccc1CC[C@@H]1CN[C@H](CCc2ccccc2NC(=O)CCc2ccccc2)CO1)C(c1ccccc1)c1ccccc1] | methyl N-[(1S)-1-benzhydryl-2-oxo-2-[[2-[2-[(2R,5R)-5-[2-[2-(3-phenylpropanoylamino)phenyl]ethyl]morpholin-2-yl]ethyl]phenyl]amino]ethyl]carbamate | M + 1, +ESI = 739.4 |

| Example | Compound name | Characterization data |
|---|---|---|
| 72 | methyl N-[(1S)-1-[[2-[2-[(2R,5R)-5-[2-(2-aminophenyl)ethyl]morpholin-2-yl]ethyl]phenyl]carbamoyl]-2,2-diphenylethyl]carbamate | M + 1, +ESI = 607.3 |

EXAMPLE 73

N-(2-{2-[(2R,5R)-5-(2-{2-[(benzylsulfonyl)amino]phenyl}ethyl)morpholin-2-yl]ethyl}phenyl)-Nα-(methoxycarbonyl)-β-phenyl-L-phenylalaninamide

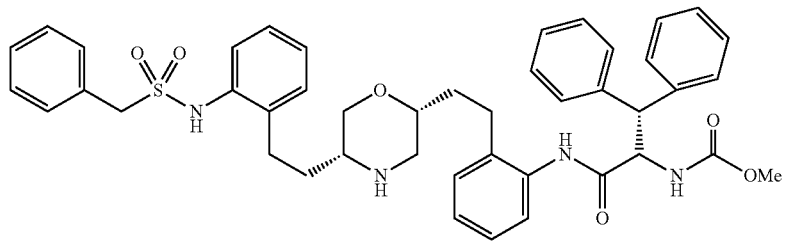

Step 1. Preparation of N-(2-{2-[(2R,5R)-5-(2-{2-[(benzylsulfonyl)amino]phenyl}ethyl)morpholin-2-yl]ethyl}phenyl)-Nα-(methoxycarbonyl)-β-phenyl-L-phenylalaninamide To tert-Butyl(2R,5R)-5-[2-(2-aminophenyl)ethyl]-2-{2-[2-({(2S)-2-[(methoxycarbonyl)amino]-3,3-diphenylpropanoyl}amino)phenyl]ethyl}morpholine-4-carboxylate (1.0 equiv) in CH$_2$Cl$_2$ (0.1 M) were added triethylamine (3 eq) and phenylmethanesulfonyl chloride (1.5 eq). The reaction was stirred at room temperature for 18 h and ethyl acetate and saturated sodium bicarbonate were added. Aqueous layer was extracted twice with ethyl acetate and combined organic layers were washed with brine, dried over Na$_2$SO$_4$, filtered and concentrated. The crude product was purified using automated silica-gel flash chromatography using a solvent gradient of 20% to 100% of ethyl acetate and hexanes to afford tert-butyl (2R,5R)-5-(2-{2-[(benzylsulfonyl)amino]phenyl}ethyl)-2-[2-(2-{[N-(methoxycarbonyl)-β-phenyl-L-phenylalanyl]amino}phenyl)ethyl]morpholine-4-carboxylate which was treated with TFA by following procedure described in step 12 of Example 1 to afford the title compound.

M+1, +ESI=761.2

The following examples (74 to 77) were synthesized from tert-Butyl(2R,5R)-5-[2-(2-aminophenyl)ethyl]-2-{2-[2-({(2S)-2-[(methoxycarbonyl)amino]-3,3-diphenylpropanoyl}amino)phenyl]ethyl}morpholine-4-carboxylate according to the procedures described for the preparation of Example 73 and by using the appropriate reagents.

| Example | Compound name | Characterization data |
|---|---|---|
| 74 | methyl N-[(1S)-1-benzhydryl-2-[[2-[2-[(2R,5R)-5-[2-(2-benzyloxycarbonylaminophenyl)ethyl]morpholin-2-yl]ethyl]phenyl]amino]-2-oxoethyl]carbamate | M + 1, +ESI = 741.2 |

| Example | Compound name | Characterization data |
|---|---|---|
| 75 | methyl N-[(1S)-1-benzhydryl-2-[[2-[2-[(2R,5R)-5-[2-[2-(benzylcarbamoylamino)phenyl]ethyl]morpholin-2-yl]ethyl]phenyl]amino]-2-oxo-ethyl]carbamate | M + 1, +ESI = 740.3 |
| 76 | methyl N-[(1S)-1-benzhydryl-2-[[2-[2-[(2R,5R)-5-[2-[2-(methoxycarbonylamino)phenyl]ethyl]morpholin-2-yl]ethyl]phenyl]amino]-2-oxo-ethyl]carbamate | M + 1, +ESI = 666.3 |
| 77 | methyl N-[(1S)-1-benzhydryl-2-[[2-[2-[(2R,5R)-5-[2-[2-(ethylcarbamoylamino)phenyl]ethyl]morpholin-2-yl]ethyl]phenyl]amino]-2-oxo-ethyl]carbamate | M + 1, +ESI = 679.1 |

EXAMPLE 78

N-(2-{2-fluoro-2-[(2S,5S)-5-({[(4-fluorobenzyl)carbamoyl]oxy}methyl) morpholin-2-yl]ethyl}phenyl)-Nα-(methoxycarbonyl)-β-phenyl-L-phenylalaninamide

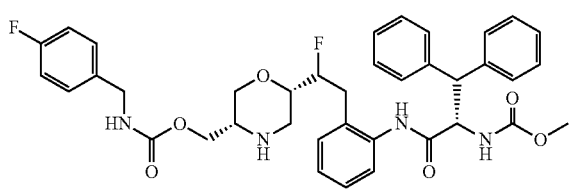 [SMILES: COC(=O)N[C@H](C(=O)Nc1ccccc1CC(F)[C@@H]1CN[C@H](COC(=O)NCc2ccc(F)cc2)CO1)C(c1ccccc1)c1ccccc1]

Step 1. Preparation of tert-butyl (2S,5R)-5-(hydroxymethyl)-2-[1-hydroxy-2-(2-nitrophenyl)ethyl]morpholine-4-carboxylate A freshly prepared solution of mercury(II) trifluoroacetate (2.7 eq.) in water (0.37 M) was added to a solution of tert-butyl (2R,5S)-5-({[tert-butyl(dimethyl)silyl]oxy}methyl)-2-[(Z)-2-(2-nitrophenyl)ethenyl]morpholine-4-carboxylate (1 eq) in THF (0.14 M) and stirred at r.t. for 36 h. Quenched with addition of saturated aqueous NaHCO₃, diluted with DCM and washed with saturated aqueous NaCl, dried over MgSO₄, filtered and concentrated. The yellow foam was dissolved in 2:1 THF:2-Propanol (0.1 M) and treated with sodium borohydride (1.23 eq.); stirred at rt for 60 min, quenched with sat. NaHCO₃, diluted (DCM) washed with brine, dried over MgSO₄ filtered and concentrated. The residue was purified by automated silicagel flash chromatography system eluted with a gradient 0% to 8% MeOH in DCM, to afford title compound as white foam.

Step 2. Preparation of tert-butyl (2S,5S)-5-({[tert-butyl(diphenyl)silyl]oxy}methyl)-2-[1-hydroxy-2-(2-nitrophenyl)ethyl]morpholine-4-carboxylate A solution of intermediate tert-butyl (2S,5R)-5-(hydroxymethyl)-2-[1-hydroxy-2-(2-nitrophenyl)ethyl]morpholine-4-carboxylate and imidazole (3.2 eq.) in dry DMF (0.43 M) was treated with neat TBDPS-Cl (1.1 eq.) and the final solution stirred at room temperature for 48 h, diluted with DCM and heptane (excess) and concentrated. The residue was purified by automated silicagel flash chromatography system eluted with a gradient 10% to 50% EtOAc in hexanes, to afford title compound as white foam.

Step 3. Preparation of tert-butyl (2S,5S)-5-({[tert-butyl(diphenyl)silyl]oxy}methyl)-2-[1-fluoro-2-(2-nitrophenyl)ethyl]morpholine-4-carboxylate A solution of alcohol tert-butyl (2S,5S)-5-({[tert-butyl(diphenyl)silyl]oxy}methyl)-2-[1-hydroxy-2-(2-nitrophenyl)ethyl]morpholine-4-carboxylate (1 eq.) in dry DCM (0.11 M), stirred at 0° C. under N₂ atmosphere was treated with neat DAST (or any other suitable trifluorosulfanyl amine, 17 eq.) and the resulting dark solution further stirred at the same temperature for 2 h, quenched at 0° C. by addition of sat. NaHCO₃, diluted with DCM and washed with sat. NaHCO₃, dried over MgSO₄, filtered and concentrated. The residue was purified by automated silicagel flash chromatography system eluted with 100% DCM, to afford title compound as light yellow oil.

Step 4. Preparation of tert-butyl (2S,5S)-2-[2-(2-aminophenyl)-1-fluoroethyl]-5-({[tert-butyl(diphenyl)silyl]oxy}methyl)morpholine-4-carboxylate A solution of intermediate tert-butyl (2S,5S)-5-({[tert-butyl(diphenyl)silyl]oxy}methyl)-2-[1-fluoro-2-(2-nitrophenyl)ethyl]morpholine-4-carboxylate (1 eq.) in a mixture 5:2:1 THF:MeOH:H$_2$O (0.002 M) was warmed up to +59° C. and treated with solid iron (223 eq.). The mixture was further stirred at the same temperature for 45 min, diluted with DCM, washed with sat. NaHCO$_3$, dried over MgSO$_4$, filtered and concentrated. The product was submitted to the next step without further purification. Light yellow oil.

Step 5. Preparation of N-(2-{2-fluoro-2-[(2S,5S)-5-({[(4-fluorobenzyl)carbamoyl]oxy}methyl) morpholin-2-yl]ethyl}phenyl)-Nα-(methoxycarbonyl)-β-phenyl-L-phenylalaninamide N-(2-{2-fluoro-2-[(2S,5S)-5-({[(4-fluorobenzyl)carbamoyl]oxy}methyl) morpholin-2-yl]ethyl}phenyl)-Nα-(methoxycarbonyl)-β-phenyl-L-phenylalaninamide was prepared from tert-butyl (2S,5S)-2-[2-(2-aminophenyl)-1-fluoroethyl]-5-({[tert-butyl(diphenyl)silyl]oxy}methyl)morpholine-4-carboxylate by following the procedure described in steps 3 to 6 of Example 32.
M+1, +ESI=687.2

EXAMPLE 79

4-Fluoro-β-(4-fluorophenyl)-N-(5-fluoro-4-{2-[(2R,5S)-5-({[(2,2,2-trifluoroethyl)carbamoyl]oxy}methyl)morpholin-2-yl]ethyl}pyridin-3-yl)-L-phenylalaninamide trihydrochloride

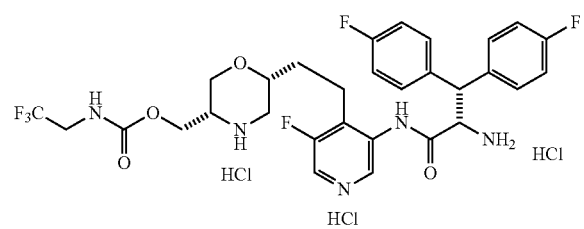

Step 1: N-(5-Fluoropyridin-3-yl)-2,2-dimethylpropanamide

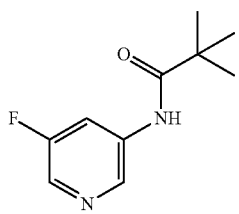

Pivaloyl chloride (18.8 mL, 153 mmol) was added to a solution of 3-amino-5-fluoropyridine (13.2 g, 118 mmol) and TEA (49.2 mL, 353 mmol) in Dichloromethane (235 mL) at 0° C. The reaction was warmed to ambient temperature and stirred for 1 hour. The reaction was quenched with saturated aqueous NaHCO$_3$ and the mixture was extracted with dichloromethane (×3). The combined organic fractions were dried (MgSO$_4$), filtered and the solvent was evaporated under reduced pressure to afford the title compound (22.5 g, 115 mmol, 97% yield) as a light brown solid, MS (ESI): m/z=197.35 (MH+), 100% pure by LCMS.

Step 2: N-(5-Fluoro-4-iodopyridin-3-yl)-2,2-dimethylpropanamide

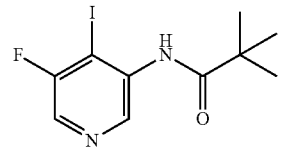

A 2.5M solution of "BuLi (30.6 mL, 76 mmol) in hexanes was added drop-wise to a solution of N-(5-fluoropyridin-3-yl)-2,2-dimethylpropanamide 5.0 g, 25.5 mmol) and TMEDA (11.54 mL, 76 mmol) in THF (127 mL) at −78° C. over 1 hour, while ensuring the internal temperature did not go above −70° C. The resulting solution was stirred at −78° C. for 1 hour. Iodine (19.40 g, 76 mmol) in THF (20 mL) was added drop-wise over 30 min ensuring the internal temperature remained below −70° C. The resulting reaction was stirred for 1 hour at −78° C. The reaction was quenched at −78° C. with water and then warmed to ambient temperature. 10% Aqueous sodium thiosulfate was added until the iodine color dissipated and the mixture was extracted with ethyl acetate (×3). The combined organic fractions were dried (MgSO$_4$), filtered and the solvent was evaporated under reduced pressure to afford the title compound (8.21 g, 25.5 mmol, 100% yield), MS (ESI): m/z=323.26 (MH+), 100% pure by LCMS.

Step 3: 5-Fluoro-4-iodopyridin-3-amine

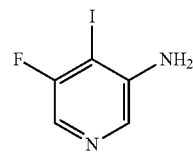

N-(5-Fluoro-4-iodopyridin-3-yl)-2,2-dimethylpropanamide (8.46 g, 26.3 mmol) was heated at reflux in aqueous 3M HCl for 2 hours. The reaction was carefully quenched with aqueous sodium hydroxide (3M) until basic and the mixture was extracted with dichloromethane (×3). The combined organic fractions were dried (MgSO$_4$), filtered and the solvent was evaporated under reduced pressure to afford the title compound (5.16 g, 21.7 mmol, 83% yield) as an off white solid, MS (ESI): m/z=239.18 (MH+), 90% pure by LCMS.

Step 4: tert-butyl (2R,5R)-2-ethynyl-5-(tert-butyldimethylsilyloxy-methyl)morpholine-4-carboxylate

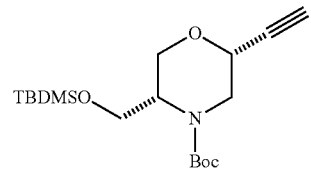 [SMILES: C#C[C@@H]1CN(C(=O)OC(C)(C)C)[C@H](CO[Si](C)(C)C(C)(C)C)CO1]

Dimethyl (1-diazo-2-oxpropyl)phosphonate (3.90 mL, 26.0 mmol) was added to tert-butyl (2S,5S)-5-({[tert-butyl(dimethyl)silyl]oxy}methyl)-2-formylmorpholine-4-carboxylate (Example 1, step 6) (7.78 g, 21.6 mmol) and K$_2$CO$_3$ (5.98 g, 43.3 mmol) in anhydrous MeOH (216 mL) at ambient temperature. The reaction was stirred for 2 hours then filtered and concentrated in vacuo. Saturated aqueous KH$_2$PO$_4$ was added and the mixture was extracted with ethyl acetate (×3). The combined organic fractions were dried (MgSO$_4$), filtered and the solvent was evaporated under reduced pressure. Purification on silica gel (750 g) eluting with a gradient of 0-30% EtOAc/hexanes afforded the title compound (4.60 g, 12.9 mmol, 60% yield) as a colorless oil, MS (ESI): m/z=256.01 (M+H-Boc).

Step 5: tert-Butyl (2R,5S)-2-[(3-amino-5-fluoropyridin-4-yl)ethynyl]-5-({[tert-butyl(dimethyl)silyl]oxy}methyl)morpholine-4-carboxylate

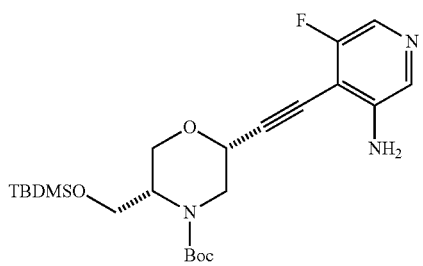 [SMILES: CC(C)(C)OC(=O)N1C[C@@H](C#Cc2c(N)cncc2F)OC[C@H]1CO[Si](C)(C)C(C)(C)C]

tert-Butyl (2R,5R)-2-ethynyl-5-(tert-butyldimethylsilyloxy-methyl)morpholine-4-carboxylate (2.75 g, 7.73 mmol), 5-fluoro-4-iodopyridin-3-amine (1.84 g, 7.73 mmol), bis(triphenylphosphine)palladium(II) chloride (0.380 g, 0.541 mmol), triethylamine (32.3 mL, 232 mmol), and copper(I) iodide (0.147 g, 0.773 mmol) were heated at 70° C. for 2 hours. The reaction was quenched with saturated aqueous KH$_2$PO$_4$ and the mixture was extracted with ethyl acetate (×3). The combined organic fractions were dried (MgSO$_4$), filtered and the solvent was evaporated under reduced pressure. Purification on silica gel (330 g) eluting with a gradient of 0-100% EtOAc/hexanes afforded the title compound (2.20 g, 12.9 mmol, 42% yield) as a viscous oil, MS (ESI): m/z=466.45 (MH+); 68% pure by LCMS, remainder is unreacted 5-fluoro-4-iodopyridin-3-amine, taken onto next reaction as mixture.

Step 6: tert-Butyl (2R,5S)-2-[2-(3-amino-5-fluoropyridin-4-yl)ethyl]-5-({[tert-butyl(dimethyl)silyl]oxy}methyl)morpholine-4-carboxylate

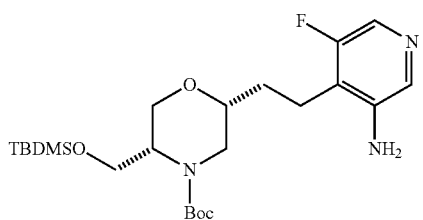 [SMILES: CC(C)(C)OC(=O)N1C[C@@H](CCc2c(N)cncc2F)OC[C@H]1CO[Si](C)(C)C(C)(C)C]

Platinum(IV) oxide (0.536 g, 2.36 mmol) was suspended in nitrogen degassed trifluororoethanol. tert-Butyl (2R,5S)-2-[(3-amino-5-fluoropyridin-4-yl)ethynyl]-5-({[tert-butyl(dimethyl)silyl]oxy}methyl)morpholine-4-carboxylate (2.20 g, 4.72 mmol) (68% pure) was dissolved in nitrogen degassed trifluorethanol (94 mL) and added to the suspension of platinum oxide. The reaction was shaken on the Parr at 50 psi hydrogen for 24 hr. The reaction was degassed with nitrogen, filtered through celite and the solvent removed in vacuo. Purification on silica gel (330 g) eluting with a gradient of 0-100% EtOAc/hexanes afforded the title compound (1.52 g, 3.24 mmol, 69% yield) as a white solid, MS (ESI): m/z=470.51 (MH+); 100% pure by LCMS Step 7: tert-Butyl (2R,5R)-2-[2-(3-{[N-(tert-butoxycarbonyl)-4-fluoro-β-(4-fluorophenyl)-L-phenylalanyl]amino}-5-fluoropyridin-4-yl)ethyl]-5-(hydroxymethyl)morpholine-4-carboxylate

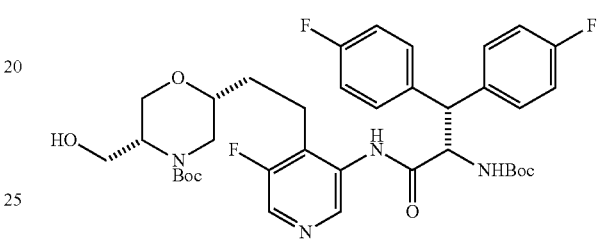

POCl$_3$ (0.579 mL, 6.21 mmol) was added to a solution of tert-Butyl (2R,5S)-2-[2-(3-amino-5-fluoropyridin-4-yl)ethyl]-5-({[tert-butyl(dimethyl)silyl]oxy}methyl)morpholine-4-carboxylate (2.65 g, 5.64 mmol) and N-(tert-butoxycarbonyl)-4-fluoro-β-(4-fluorophenyl)-L-phenylalanine [Patterson, D. E., et al. Org. Proc. Res. Dev. 2009, 13, 900-906.] (2.13 g, 5.64 mmol) in pyridine (28 mL) at −15° C. The reaction stirred for 30 min then warmed to 0° C. and stirred for 3 hours. The reaction was quenched with saturated aqueous KH$_2$PO$_4$, then brine and the mixture was extracted with ethyl acetate (×3). The combined organic fractions were dried (MgSO$_4$), filtered and the solvent was evaporated under reduced pressure to afford a brown viscous oil. The resulting oil was dissolved in THF (28 mL) and a 1M solution of TBAF (11.3 mL, 11.3 mmol) in THF was added and the reaction stirred at ambient temperature overnight. The reaction was quenched with saturated aqueous KH$_2$PO$_4$ and the mixture was extracted with ethyl acetate (×3). The combined organic fractions were dried (MgSO$_4$), filtered and the solvent was evaporated under reduced pressure. Purification on silica gel (330 g) eluting with a gradient of 0-100% CHCl$_3$ to 70:20:10 CHCl$_3$/EtOAc/MeOH afforded the title compound (2.07 g, 2.90 mmol, 51% yield) as a white solid, MS (ESI): m/z=715.48 (MH+); 100% pure by LCMS.

Step 8: tert-Butyl (2R,5S)-2-[2-(3-{[N-(tert-butoxycarbonyl)-4-fluoro-β-(4-fluorophenyl)-L-phenylalanyl]amino}-5-fluoropyridin-4-yl)ethyl]-5-({[(2,2,2-trifluoroethyl)carbamoyl]oxy}methyl)morpholine-4-carboxylate

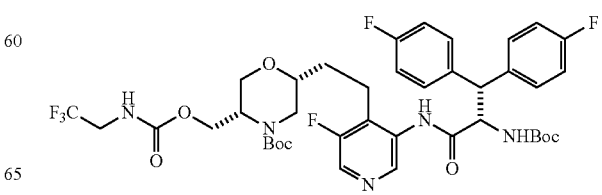

tert-Butyl (2R,5R)-2-[2-(3-{[N-(tert-butoxycarbonyl)-4-fluoro-β-(4-fluorophenyl)-L-phenylalanyl]amino}-5-fluoropyridin-4-yl)ethyl]-5-(hydroxymethyl)morpholine-4-carboxylate (1.50 g, 2.10 mmol) and CDI (0.425 g, 2.62 mmol) were heated at 60° C. in Pyridine (21 mL) for 30 min. 2,2,2-Trifluoroethylamine (3.29 mL, 42.0 mmol) was added and the reaction heated at 60° C. for 24 hours, A further aliquot of 2,2,2-Trifluoroethylamine (1.65 mL, 21.0 mmol) was added and the reaction heated at 60° C. for a further 24 hours. The reaction was quenched with saturated aqueous $KH_2PO_4$ then brine and the mixture was extracted with ethyl acetate (×3). The combined organic fractions were dried ($MgSO_4$), filtered and the solvent was evaporated under reduced pressure. Purification on silica gel (220 g) eluting with a gradient of 0-100% EtOAc/hexanes afforded the title compound (1.29 g, 1.54 mmol, 73% yield) as a white solid, MS (ESI): m/z=840.46 (MH+); 100% pure by LCMS.

Step 9: 4-Fluoro-β-(4-fluorophenyl)-N-(5-fluoro-4-{2-[(2R,5S)-5-({[(2,2,2-trifluoroethyl)carbamoyl]oxy}methyl)morpholin-2-yl]ethyl}pyridin-3-yl)-L-phenylalaninamide trihydrochloride

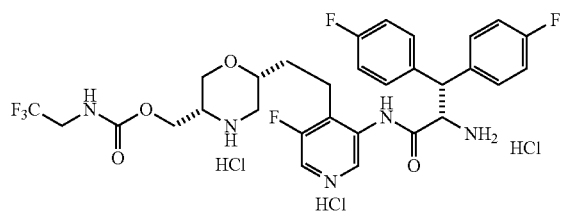 [SMILES: N[C@H](C(=O)Nc1cncc(F)c1CC[C@@H]1CN[C@H](COC(=O)NCC(F)(F)F)CO1)C(c1ccc(F)cc1)c1ccc(F)cc1 ; Cl ; Cl ; Cl]

4M HCl (3.54 mL, 14.17 mmol) in dioxane was added to a solution of tert-Butyl (2R,5S)-2-[2-(3-{[N-(tert-butoxycarbonyl)-4-fluoro-β-(4-fluorophenyl)-L-phenylalanyl]amino}-5-fluoropyridin-4-yl)ethyl]-5-({[(2,2,2-trifluoroethyl)carbamoyl]oxy}methyl)morpholine-4-carboxylate (1.19 g, 1.42 mmol) in Dioxane (14 mL) at ambient temperature and the reaction stirred for 4 hours. The solvent was removed in vacuo and ether was added to the residue. The title compound was filtered off as a white solid (1.00 g, 1.34 mmol, 94% yield), MS (ESI): m/z=640.40 (MH+); 100% pure by LCMS.

EXAMPLE 80

4-Fluoro-β-(4-fluorophenyl)-N-(3-fluoro-2-{2-[(2R,5S)-5-({[(2,2,2-trifluoroethyl)carbamoyl]oxy}methyl)morpholin-2-yl]ethyl}phenyl)-L-phenylalaninamide dihydrochloride

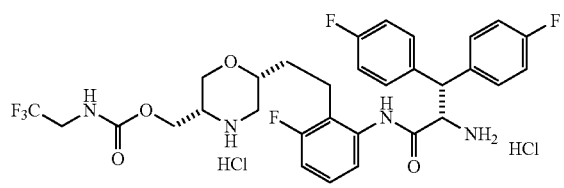 [SMILES: N[C@H](C(=O)Nc1cccc(F)c1CC[C@@H]1CN[C@H](COC(=O)NCC(F)(F)F)CO1)C(c1ccc(F)cc1)c1ccc(F)cc1 ; Cl ; Cl]

Step 1: (2-Fluoro-6-nitrobenzyl)(triphenyl)phosphonium bromide

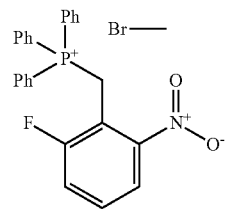

Triphenylphosphine (31.2 g, 119 mmol) was added to a solution of 2-(bromomethyl)-1-fluoro-3-nitrobenzene (27.9 g, 119 mmol) in Acetonitrile (445 mL) (degassed with nitrogen) and the reaction stirred at ambient temperature for 10 min then heated to 85° C. for 2 hrs. The solvent was evaporated under reduced pressure to afford the title compound (59.1 g, 119 mmol, 100% yield) as a yellow powder, MS (ESI): m/z=416.2 (MH+); 100% pure by LCMS.

Step 2: tert-Butyl (2R,5S)-5-({[tert-butyl(dimethyl)silyl]oxy}methyl)-2-[(E/Z)-2-(2-fluoro-6-nitrophenyl)ethenyl]morpholine-4-carboxylate

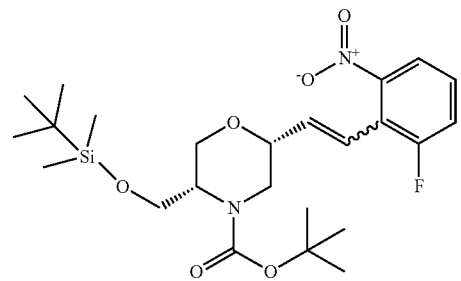

A solution of (2-Fluoro-6-nitrobenzyl)(triphenyl)phosphonium bromide, 18-crown-6 (0.388 g, 1.469 mmol) and potassium carbonate (4.06 g, 29.4 mmol) were stirred in DME (100 mL) at ambient temperature for 10 min to afford a deep purple solution. tert-Butyl (2S,5S)-5-({[tert-butyl(dimethyl)silyl]oxy}methyl)-2-formylmorpholine-4-carboxylate (Example 1, Step 6) (5.28 g, 14.69 mmol) in DME (50 mL) was added and the deep purple solution stirred overnight to afford a light brown suspension. The reaction was filtered through celite, rinsing with ether and concentrated under vacuum. Purification on silica gel (330 g) eluting with a gradient of 0-40% EtOAc/hexanes afforded the title compound (6.39 g, 12.9 mmol, 88% yield) as a thick gum, MS (ESI): m/z=497.5 (MH+); LCMS shows mixture of E & Z olefin.

Step 3: tert-Butyl (2R,5S)-2-[2-(2-amino-6-fluorophenyl)ethyl]-5-({[tert-butyl(dimethyl)silyl]oxy}methyl)morpholine-4-carboxylate

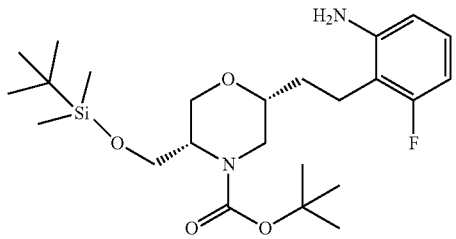 [SMILES: CC(C)(C)OC(=O)N1C[C@@H](CCc2c(N)cccc2F)OC[C@H]1CO[Si](C)(C)C(C)(C)C]

A solution of tert-Butyl (2R,5S)-5-({[tert-butyl(dimethyl)silyl]oxy}methyl)-2-[(E/Z)-2-(2-fluoro-6-nitrophenyl)ethenyl]morpholine-4-carboxylate (6.39 g, 12.9 mmol) in Trifluoroethanol was added to a suspension of nitrogen degassed Pearlman's Catalyst (1.81 g, 2.57 mmol) in Trifluoroethanol (Total Trifluoroethanol (52 mL)). The reaction was shaken at 50 psi hydrogen pressure on a Parr for 24 hours. The reaction was degassed with nitrogen and filtered through celite, rinsing with Ethyl Acetate, and the solvent removed in vacuo. Purification on silica gel (330 g) eluting with a gradient of 0-50% EtOAc/hexanes afforded the title compound (4.86 g, 10.4 mmol, 81% yield) as a white solid, MS (ESI): m/z=469.6 (MH+); 100% pure by LCMS.

Step 4: 4-Morpholinecarboxylic acid, 2-[2-[2-[[(2S)-2-[[(1,1-dimethylethoxy)carbonyl]amino]-3,3-bis(4-fluorophenyl)-1-oxopropyl]amino]-6-fluorophenyl]ethyl]-5-(hydroxymethyl)-1,1-dimethylethyl ester, (2R,5R)

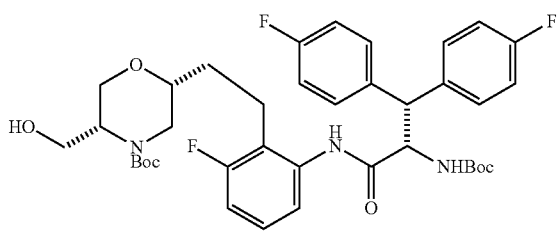 [SMILES: CC(C)(C)OC(=O)N[C@H](C(=O)Nc1cccc(F)c1CC[C@@H]1CN(C(=O)OC(C)(C)C)[C@H](CO)CO1)C(c1ccc(F)cc1)c1ccc(F)cc1]

POCl$_3$ (1.094 mL, 11.74 mmol) was added to a solution of tert-Butyl (2R,5S)-2-[2-(2-amino-6-fluorophenyl)ethyl]-5-({[tert-butyl(dimethyl)silyl]oxy}methyl)morpholine-4-carboxylate (5.00 g, 10.7 mmol) and N-(tert-butoxycarbonyl)-4-fluoro-β-(4-fluorophenyl)-L-phenylalanine (4.03 g, 10.7 mmol) in Pyridine (53 mL) at −15° C. and the reaction stirred for 30 min then warmed to 0° C. and stirred for 1.5 hours. The reaction was quenched with saturated aqueous KH$_2$PO$_4$ (saturated) and the mixture was extracted with ethyl acetate (×3). The combined organic fractions were dried (MgSO$_4$), filtered and the solvent was evaporated under reduced pressure to afford a viscous brown oil. The resulting oil was dissolved in THF (53 mL) and a 1M solution of TBAF (32.0 mL, 32.0 mmol) was added and the reaction stirred at ambient temperature for 4 hours. The reaction was quenched with saturated aqueous KH$_2$PO$_4$ and the mixture was extracted with ethyl acetate (×3). The combined organic fractions were dried (MgSO$_4$), filtered and the solvent was evaporated under reduced pressure. Purification on silica gel (750 g) eluting with a gradient of 0-100% EtOAc/hexanes afforded the title compound (4.40 g, 6.16 mmol, 58% yield) as a white solid, MS (ESI): m/z=714.6 (MH+); 100% pure by LCMS.

Step 5: tert-Butyl (2R,5S)-2-[2-(2-{[N-(tert-butoxycarbonyl)-4-fluoro-β-(4-fluorophenyl)-L-phenylalanyl]amino}-6-fluorophenyl)ethyl]-5-({[(2,2,2-trifluoroethyl)carbamoyl]oxy}methyl)morpholine-4-carboxylate

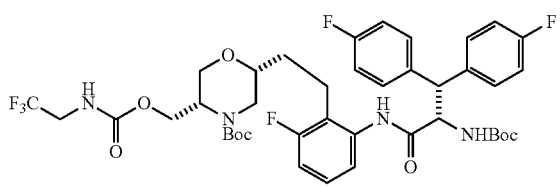 [SMILES: CC(C)(C)OC(=O)N[C@H](C(=O)Nc1cccc(F)c1CC[C@@H]1CN(C(=O)OC(C)(C)C)[C@H](COC(=O)NCC(F)(F)F)CO1)C(c1ccc(F)cc1)c1ccc(F)cc1]

4-Morpholinecarboxylic acid, 2-[2-[2-[[(2S)-2-[[(1,1-dimethylethoxy)carbonyl]amino]-3,3-bis(4-fluorophenyl)-1-oxopropyl]amino]-6-fluorophenyl]ethyl]-5-(hydroxymethyl)-1,1-dimethylethyl ester, (2R,5R)-(7.15 g, 10.0 mmol) and CDI (3.25 g, 20.0 mmol) were heated at 60° C. in Pyridine (100 mL) for 30 min, then 2,2,2-Trifluoroethylamine (23.6 mL, 301 mmol) was added and the reaction heated at 60° C. for 20 hours. Another aliquot of 2,2,2-Trifluoroethylamine (7.86 mL, 100 mmol) was added and the reaction heated at 60° C. for 24 hours. The reaction was quenched with aqueous KH$_2$PO$_4$ then brine and the mixture was extracted with ethyl acetate (×3). The combined organic fractions were dried (MgSO$_4$), filtered and the solvent was evaporated under reduced pressure. Purification on silica gel (750 g) eluting with a gradient of 0-100% EtOAc/hexanes afforded the title compound (7.46 g, 8.89 mmol, 89% yield) as a white solid, MS (ESI): m/z=839.6 (MH+); 100% pure by LCMS.

Step 6: 4-Fluoro-β-(4-fluorophenyl)-N-(3-fluoro-2-{2-[(2R,5S)-5-({[(2,2,2-trifluoroethyl)carbamoyl]oxy}methyl)morpholin-2-yl]ethyl}phenyl)-L-phenylalaninamide dihydrochloride

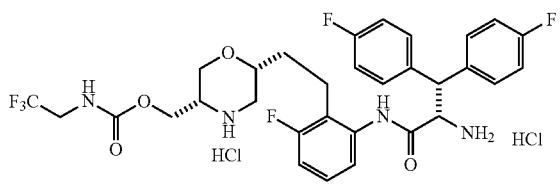 [SMILES: N[C@H](C(=O)Nc1cccc(F)c1CC[C@@H]1CN[C@H](COC(=O)NCC(F)(F)F)CO1)C(c1ccc(F)cc1)c1ccc(F)cc1 ; Cl ; Cl]

4M HCl (44.5 mL, 178 mmol) in dioxane was added to a solution of tert-Butyl (2R,5S)-2-[2-(2-{[N-(tert-butoxycarbonyl)-4-fluoro-β-(4-fluorophenyl)-L-phenylalanyl]amino}-6-fluorophenyl)ethyl]-5-({[(2,2,2-trifluoroethyl)carbamoyl]oxy}methyl)morpholine-4-carboxylate (7.46 g, 8.89 mmol) in Dioxane (89 mL) at 0° C. and then the reaction was stirred at rt for 4 hours. The solvent was removed in vacuo and ether was added to the residue to afford a white ppt. The ppt was triturated with ether (×3) and the residing white solid dried under high vacuum to afford the title compound (5.84 g, 8.21 mmol, 92% yield) as a white powder, MS (ESI): m/z=639.5 (MH+); 100% pure by LCMS.

EXAMPLE 81

((3S,6R)-6-(2-(3-(3,3-bis(4-fluorophenyl)propana-mido)-5-fluoropyridin-4-yl)ethyl)morpholin-3-yl)methyl ((6-chloropyridin-2-yl)methyl)carbamate

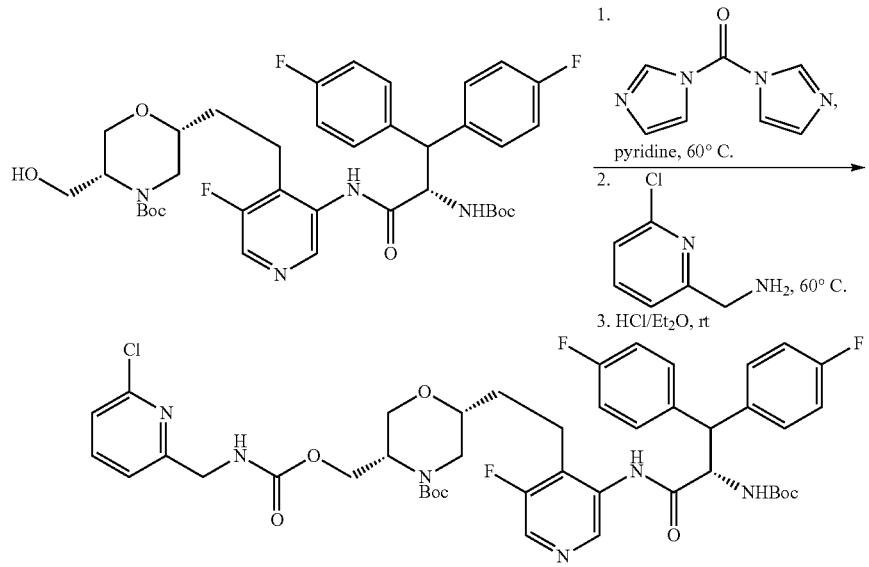

Example 81

To a mixture of tert-Butyl (2R,5R)-2-[2-(3-{[N-(tert-bu-toxycarbonyl)-4-fluoro-β-(4-fluorophenyl)-L-phenylalanyl]amino}-5-fluoropyridin-4-yl)ethyl]-5-(hydroxymethyl)morpholine-4-carboxylate (Example 149, Step 7) (677 mg, 0.95 mmol) and carbonyldiimidazole (154 mg, 0.95 mmol) was added dry pyridine (22.5 mL). The resulting solution was heated at 60° C. and stirred for 2 h. This solution was then distributed in 0.5 mL (0.021 mmol) aliquots to 45 2-dram sample vials, each containing a diverse amine (0.042 mmol); among them (6-chloropyridin-2-yl)methanamine. The resulting mixtures were stirred at 60° C. for 3 h. Solvent was removed under stream of $N_2$ gas. The residues were diluted with 4 N HCl/diethyl ether (1 mL) and stirred at room temperature for 16 h. Solvent was removed under stream of $N_2$ gas, and the residues were diluted with DMSO and purified by mass-guided reversed-phase HPLC (10-90% $CH_3CN$:0.1% $NH_4OH/H_2O$). HRMS (ES) 683.2353 (M+H). found, 683.2355 required.

EXAMPLE 82

((3S,6S)-6-((2-((S)-2-amino-3,3-bis(4-fluorophenyl)propanamido)-6-fluorophenoxy)methyl)morpholin-3-yl)methyl (2,2,2-trifluoroethyl)carbamate

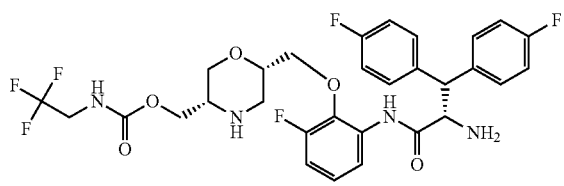 [SMILES: N[C@H](C(=O)Nc1cccc(F)c1OC[C@@H]1CN[C@H](COC(=O)NCC(F)(F)F)CO1)C(c1ccc(F)cc1)c1ccc(F)cc1]

Step 1: tert-butyl (2S,5S)-5-({[tert-butyl(dimethyl)silyl]oxy}methyl)-2-[(2-fluoro-6-nitrophenoxy)methyl]morpholine-4-carboxylate

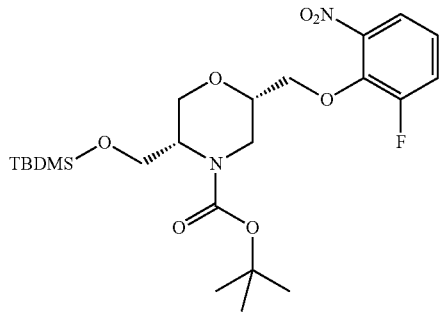

To a stirring solution of sodium hydride (0.257 g, 6.43 mmol) (pre-washed in hexanes) in DMF (15.30 mL) at 0° C., tert-butyl (2S,5S)-5-({[tert-butyl(dimethyl)silyl]oxy}methyl)-2-(hydroxymethyl)morpholine-4-carboxylate (Example 1, Step 5) (1.66 g, 4.59 mmol) in DMF (2 mL) was added dropwise. The resulting mixture was stirred at 0° C. for 1 hour. At this point, 1,2-difluoro-3-nitrobenzene (0.494 mL, 4.50 mmol) in 0.5 mL of DMF was added dropwise and the final solution was slowly warmed toward room temperature and stirred for 1 hour. Complete by LC/MS at this time. The contents were quenched by adding saturated aqueous sodium bicarbonate and then extracted between water and EtOAc (3×75 mL). The organic layer was dried over $MgSO_4$, filtered and concentrated. Purification on silica gel (120 g) eluting with a gradient of 0-60% EtOAc/hexanes afforded the title compound (1.68 g, 3.36 mmol, 73% yield) as a yellow oil, MS (ESI): m/z=401.11 (M+H-boc).

Step 2: tert-butyl (2S,5S)-2-[(2-amino-6-fluorophenoxy)methyl]-5-({[tert-butyl(dimethyl)silyl]oxy}methyl)morpholine-4-carboxylate

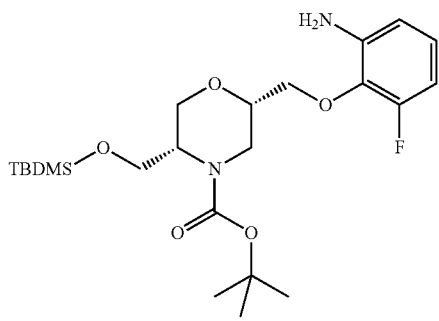

Dissolved tert-butyl (2S,5S)-5-({[tert-butyl(dimethyl)silyl]oxy}methyl)-2-[(2-fluoro-6-nitrophenoxy)methyl]morpholine-4-carboxylate (1.68 g, 3.36 mmol) in ethyl acetate (11.19 mL) and to this solution, carefully added 10% Pd/C (0.714 g, 0.671 mmol). A hydrogen filled balloon was attached and the contents were evacuated and backfilled with H₂ several times. Stirred at room temperature for 4 hours. Complete at this time by LC/MS. The solids were filtered off through a pad of celite and washed with ethyl acetate and ethanol. The contents were concentrated and then purified on silica gel (40 g) eluting with a gradient of 0-90% EtOAc/hexanes afforded the title compound (1.57 g, 3.34 mmol, 100% yield) as a yellow oil, MS (ESI): m/z=371.14 (M+H-boc); 100% pure by LC/MS.

Step 3: tert-butyl (2S,5S)-2-[(2-{[N-(tert-butoxycarbonyl)-4-fluoro-β-(4-fluorophenyl)-L-phenylalanyl]amino}-6-fluorophenoxy)methyl]-5-({[tert-butyl(dimethyl)silyl]oxy}methyl)morpholine-4-carboxylate

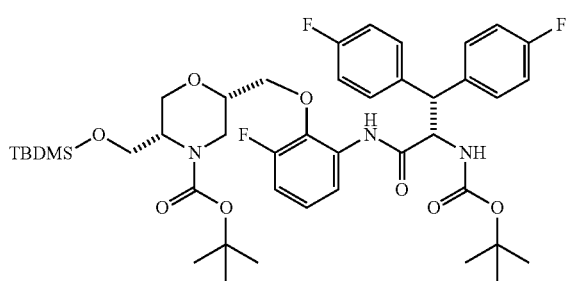

Phosphorus (V) oxychloride (118 μl, 1.262 mmol) was added to a solution of tert-butyl (2S,5S)-2-[(2-amino-6-fluorophenoxy)methyl]-5-({[tert-butyl(dimethyl)silyl]oxy}methyl)morpholine-4-carboxylate (540 mg, 1.147 mmol) and N-(tert-butoxycarbonyl)-4-fluoro-β-(4-fluorophenyl)-L-phenylalanine (433 mg, 1.147 mmol) in pyridine (5.74 mL) at −15° C. The reaction was stirred for 30 minutes then warmed to 0° C. and stirred for another 1.5 hours. LC/MS at this time only shows pyridine and desired product. The reaction was quenched with a saturated aqueous solution of KH₂PO₄ and the mixture was extracted with ethyl acetate (3×50 mL). The combined organic fractions were dried over MgSO₄, filtered and the solvent was evaporated under reduced pressure to afford the title compound (977 mg, 1.106 mmol, 96% yield) as an off-white foam, MS (ESI): m/z=730.51 (M+H-boc). 94% pure by LC/MS. The material was taken on crude to the next step.

Step 4: tert-butyl (2S,5R)-2-[(2-{[N-(tert-butoxycarbonyl)-4-fluoro-β-(4-fluorophenyl)-L-phenylalanyl]amino}-6-fluorophenoxy)methyl]-5-(hydroxymethyl)morpholine-4-carboxylate

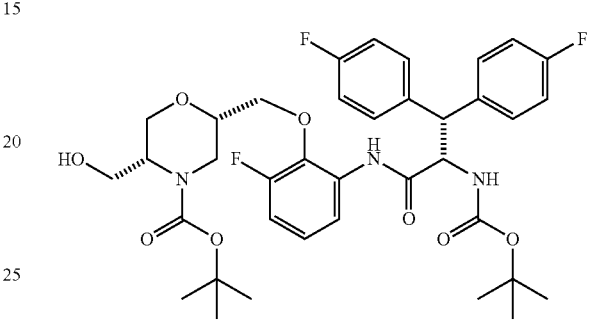

1M TBAF (1766 μl, 1.766 mmol) in THF was added to a solution of tert-butyl (2S,5S)-2-[(2-{[N-(tert-butoxycarbonyl)-4-fluoro-β-(4-fluorophenyl)-L-phenylalanyl]amino}-6-fluorophenoxy)methyl]-5-({[tert-butyl(dimethyl)silyl]oxy}methyl)morpholine-4-carboxylate (977 mg, 1.177 mmol) in THF (5.89 mL) at room temperature and the reaction stirred at room temperature until completion (6 hours). The reaction was quenched with a saturated aqueous solution of KH₂PO₄ and the mixture was extracted with ethyl acetate (3×50 mL). The combined organic fractions were dried over MgSO₄, filtered and the solvent was evaporated under reduced pressure. The crude material was then purified on silica gel (120 g), eluting with a gradient of 0-100% a 7:2:1 CHCl₃/EtOAc/MeOH blend in CHCl₃ to afford the title compound (439 mg, 0.589 mmol, 50% yield) as a white foam, MS (ESI): m/z=616.4 (M+H-boc); 96% pure by LC/MS.

Step 6: tert-butyl (2S,5S)-2-[(2-{[N-(tert-butoxycarbonyl)-4-fluoro-β-(4-fluorophenyl)-L-phenylalanyl]amino}-6-fluorophenoxy)methyl]-5-[({[(2,2,2-trifluoroethyl)amino]carbonyl}oxy)methyl]morpholine-4-carboxylate

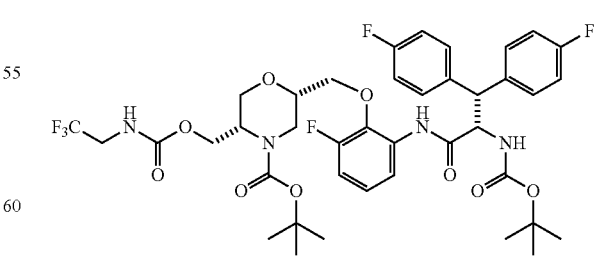

tert-butyl (2S,5R)-2-[(2-{[N-(tert-butoxycarbonyl)-4-fluoro-β-(4-fluorophenyl)-L-phenylalanyl]amino}-6-fluorophenoxy)methyl]-5-(hydroxymethyl)morpholine-4-carboxylate (350 mg, 0.489 mmol) and CDI (159 mg, 0.978 mmol) in pyridine (4.89 mL) were heated to 60° C. for 30 min, LC/MS shows formation of desired intermediate. 2,2,2-trifluoroethylamine (1153 µl, 14.67 mmol) was then added and the reaction heated at 60° C. overnight (18 hours). LCMS shows complete conversion the next morning. The solvent was removed in vacuo and the residue was purified on silica gel (120 g), eluting with a gradient of 10-100% EtOAc/hexanes to afford the title compound (310 mg, 0.361 mmol, 74% yield) as a white foam, MS (ESI): m/z=841.4 (M+H); 98% pure by LC/MS.

Step 7: ((3S,6S)-6-((2-((S)-2-amino-3,3-bis(4-fluorophenyl)propanamido)-6-fluorophenoxy)methyl)morpholin-3-yl)methyl (2,2,2-trifluoroethyl)carbamate

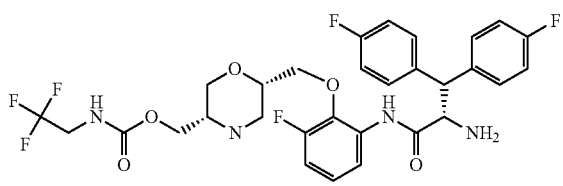 [SMILES: N[C@H](C(=O)Nc1cccc(F)c1OC[C@@H]1CN[C@H](COC(=O)NCC(F)(F)F)CO1)C(c1ccc(F)cc1)c1ccc(F)cc1]

4M HCl (922 µl, 3.69 mmol) in dioxane was added to a solution of tert-butyl (2S,5S)-2-[(2-{[N-(tert-butoxycarbonyl)-4-fluoro-β-(4-fluorophenyl)-L-phenylalanyl]amino}-6-fluorophenoxy)methyl]-5-[({[(2,2,2-trifluoroethyl)amino]carbonyl}oxy)methyl]morpholine-4-carboxylate (310 mg, 0.369 ml) at room temperature and the reaction stirred until complete by LC/MS (8 hrs). The solvent was removed in vacuo and ether was added to the residue. The desired product was filtered off to afford the title compound (253 mg, 0.355 mmol, 96% yield) as a white solid, MS (ESI): m/z=641.4 (M+H); 100% pure by LC/MS.

EXAMPLE 83

2S-Amino-3,3-di-(4-fluorophenyl)-N-(5-fluoro-4-(2-((2R,5R)-5-(2,2,2-trifluoroethoxycarbonylaminomethyl)morpholine-2-yl)ethyl)pyridin-3-yl)propanamide

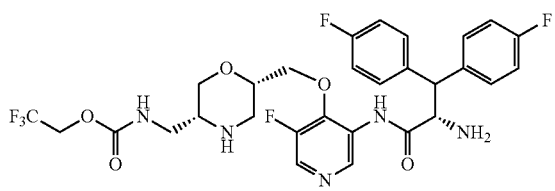 [SMILES: N[C@H](C(=O)Nc1cncc(F)c1OC[C@@H]1CN[C@H](CNC(=O)OCC(F)(F)F)CO1)C(c1ccc(F)cc1)c1ccc(F)cc1]

Step 1. (2S)-tert-butyloxycarbonylamino-3,3-di-(4-fluorophenyl)-N-(5-fluoro-4-(2-((2R,5R)-4-tert-butyloxycarbonyl-5-(carbaldehyde)morpholine-2-yl)ethyl)pyridin-3-yl)propanamide

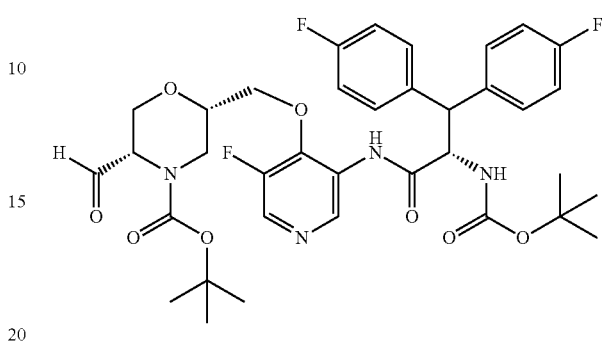

To a solution of DMSO (0.226 mL, 3.19 mmol) in DCM (14.18 mL) at −78° C. was added oxallyl chloride (0.261 mL, 2.98 mmol). The mixture was stirred at −78° C. for 15 min and then to it was added (2S)-tert-butyloxycarbonylamino-3,3-di-(4-fluorophenyl)-N-(5-fluoro-4-(2-((2R,5R)-4-tert-butyloxycarbonyl-5-(hydroxymethyl)morpholine-2-yl)ethyl)pyridin-3-yl)propanamide (Example 79, step 7) (1.52 g, 2.127 mmol) in DCM (3 mL). The mixture was stirred at −78° C. for 30 min. To the resulting mixture was added triethylamine (1.186 mL, 8.51 mmol) dropwise. The mixture was warmed to 0° C. over 1 h then quenched with brine and extracted with DCM. The combined organic extracts were dried (Na2SO4), filtered and concentrated to afford the title compound which was used in the next step without further purification.

Step 2. (2S)-tert-butyloxycarbonylamino-3,3-di-(4-fluorophenyl)-N-(5-fluoro-4-(2-((2R,5R)-4-tert-butyloxycarbonyl-5-(benzylaminomethyl)morpholine-2-yl)ethyl)pyridin-3-yl)propanamide

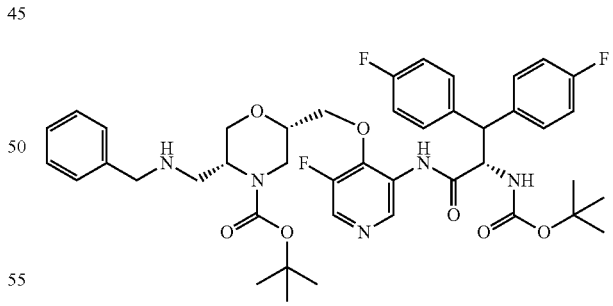

To a solution of the product from the previous step (1.516 g, 2.127 mmol) in CHCl3 (10.64 mL) at ambient temperature was added benzylamine (0.256 mL, 2.340 mmol).

The mixture was stirred for 10 min and then sodium triacetoxyborohydride (0.902 g, 4.25 mmol) was added. The mixture was stirred at ambient temperature for 1 h, then quenched with water and extracted with DCM. The combined organic extracts were dried (Na2SO4), filtered and concentrated. Purification by silica gel chromatography (0-4% MeOH/

DCM) on a 40 g silica gel column afforded the title compound as a beige solid. LCMS: RT=1.98 min, M+H=804.3 (3.75 min gradient).

Step 3. (2S)-tert-butyloxycarbonylamino-3,3-di-(4-fluorophenyl)-N-(5-fluoro-4-(2-((2R,5R)-4-tert-butyloxycarbonyl-5-(aminomethyl)morpholine-2-yl)ethyl)pyridin-3-yl)propanamide

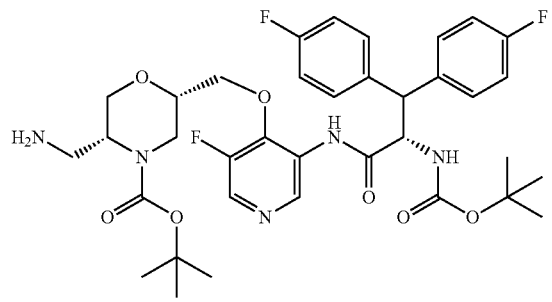 [SMILES: CC(C)(C)OC(=O)N[C@H](C(=O)Nc1cncc(F)c1OC[C@@H]1CN(C(=O)OC(C)(C)C)[C@H](CN)CO1)C(c1ccc(F)cc1)c1ccc(F)cc1]

A solution of the product from the previous step (1.12 g, 1.393 mmol) in MeOH (13.93 mL) was bubbled with a stream of N2 for 5 min. Palladium hydroxide on carbon (0.978 g, 1.393 mmol) was then added and the mixture was hydrogenated with an H2 balloon at ambient temperature for 7 h. The catalyst was removed by filtration through celite and the filtrate was concentrated to afford the title compound as a beige solid. LCMS: RT=1.85 min, M+H=714.2 (3.75 min gradient).

Step 4. (2S)-tert-butyloxycarbonylamino-3,3-di-(4-fluorophenyl)-N-(5-fluoro-4-(2-((2R,5R)-4-tert-butyloxycarbonyl-5-(2,2,2-trifluoroethoxycarbonylaminomethyl)-morpholine-2-yl)ethyl)pyridin-3-yl)propanamide

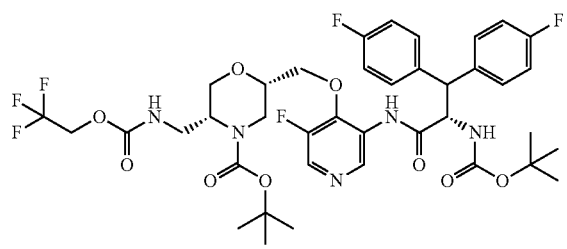 [SMILES: CC(C)(C)OC(=O)N[C@H](C(=O)Nc1cncc(F)c1OC[C@@H]1CN(C(=O)OC(C)(C)C)[C@H](CNC(=O)OCC(F)(F)F)CO1)C(c1ccc(F)cc1)c1ccc(F)cc1]

To a solution of the product from the previous step (40 mg, 0.056 mmol) in pyridine (280 μl) at ambient temperature was added CDI (18.17 mg, 0.112 mmol). The mixture was heated to 65° C. for 1 h. Acyl imidazole formed by LCMS. To the resulting solution was added 2,2,2-trifluoroethanol (40.3 μl, 0.560 mmol). The mixture was heated at 90° C. for 3 h then concentrated. The crude product was purified by isco silica gel chromatography (15-100% Ethyl acetate/Hexane) on a 12 g silica gel column to afford the title compound as a white solid.

LCMS: RT=2.56 min, M+H=840.3 (3.75 min gradient).

Step 5. (2S)-Amino-3,3-di-(4-fluorophenyl)-N-(5-fluoro-4-(2-((2R,5R)-5-(2,2,2-trifluoroethoxycarbonylaminomethyl)morpholine-2-yl)ethyl)pyridin-3-yl)propanamide

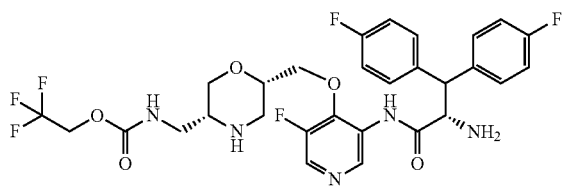 [SMILES: N[C@H](C(=O)Nc1cncc(F)c1OC[C@@H]1CN[C@H](CNC(=O)OCC(F)(F)F)CO1)C(c1ccc(F)cc1)c1ccc(F)cc1]

A solution of the product from the previous step (33.4 mg, 0.040 mmol) in ethyl acetate (795 μl) at 0° C. was saturated with HCl gas over 2 min. The mixture was warmed to ambient temperature and stirred for 10 min. The solvent was removed in vacuo to give the HCl salt of the title compound as a solid. LCMS: RT=1.12 min, M+H=640.1 (3.75 min gradient).

The following compounds could be prepared using procedures used for Example 83.

| Example | Structure | IUPAC Name | Mass [M + H]+ |
|---|---|---|---|
| 84 | 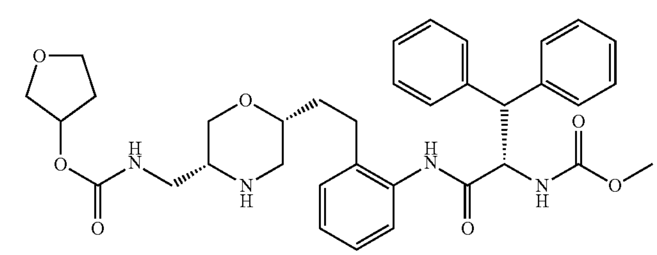 [SMILES: COC(=O)N[C@H](C(=O)Nc1ccccc1CC[C@@H]1CN[C@H](CNC(=O)OC2CCOC2)CO1)C(c1ccccc1)c1ccccc1] | Nα-(methoxycarbonyl)-β-phenyl-N-(2-{2-[(2R,5R)-5-({[(tetrahydrofuran-3-yloxy)carbonyl]amino}methyl)morpholin-2-yl]ethyl}phenyl)-L-phenylalaninamide | 631.3 |

-continued

| Example | Structure | IUPAC Name | Mass [M + H]+ |
|---|---|---|---|
| 85 | 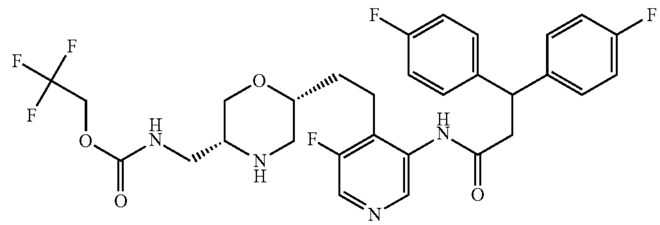 [SMILES: O=C(CC(c1ccc(F)cc1)c1ccc(F)cc1)Nc1cncc(F)c1CC[C@@H]1CN[C@H](CNC(=O)OCC(F)(F)F)CO1] | 2,2,2-trifluoroethyl ({(3R,6R)-6-[2-(3-{[3,3-bis(4-fluorophenyl)propanoyl]amino}-5-fluoropyridin-4-yl)ethyl]morpholin-3-yl}methyl)carbamate | 625.2 |
| 86 | 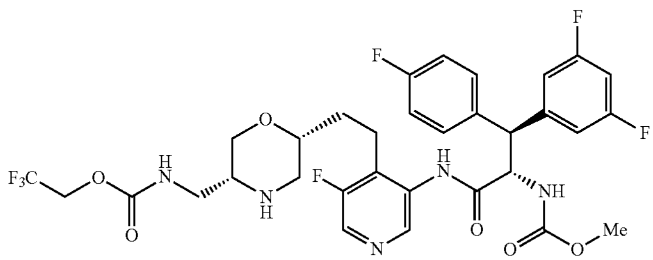 [SMILES: COC(=O)N[C@H](C(=O)Nc1cncc(F)c1CC[C@@H]1CN[C@H](CNC(=O)OCC(F)(F)F)CO1)[C@@H](c1ccc(F)cc1)c1cc(F)cc(F)c1] | (2S,3S)-2-Methoxycarbonylamino-3-(4-Fluorophenyl)-3-(3,5-difluorophenyl)-N-(5-fluoro-4-(2-((2R,5R)-5-(2,2,2-trifluoroethoxycarbonylaminomethyl)morpholine-2-yl)ethyl)pyridin-3-yl)propanamide | |
| 87 | 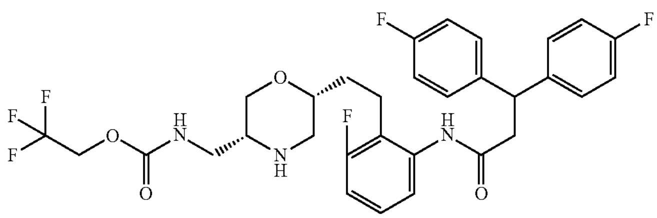 [SMILES: O=C(CC(c1ccc(F)cc1)c1ccc(F)cc1)Nc1cccc(F)c1CC[C@@H]1CN[C@H](CNC(=O)OCC(F)(F)F)CO1] | 2,2,2-trifluoroethyl ({(3R,6R)-6-[2-(2-{[3,3-bis(4-fluorophenyl)propanoyl]amino}-6-fluorophenyl)ethyl]morpholin-3-yl}methyl)carbamate | 624.2 |
| 88 | 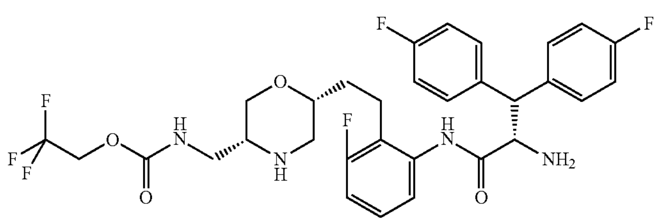 [SMILES: N[C@H](C(=O)Nc1cccc(F)c1CC[C@@H]1CN[C@H](CNC(=O)OCC(F)(F)F)CO1)C(c1ccc(F)cc1)c1ccc(F)cc1] | 4-fluoro-β-(4-fluorophenyl)-N-(3-fluoro-2-{2-[(2R,5R)-5-({[(2,2,2-trifluoroethoxy)carbonyl]amino}methyl)morpholin-2-yl]ethyl}phenyl)-L-phenylalaninamide | 639.2 |

EXAMPLE 89

(3S)-3-(4-Fluorophenyl)-3-(3,5-difluorophenyl)-N-(5-fluoro-4-(2-((2R,5R)-5-(2,2,2-trifluoroethylaminocarbonyloxymethyl)morpholine-2-yl)ethyl)pyridin-3-yl)propanamide

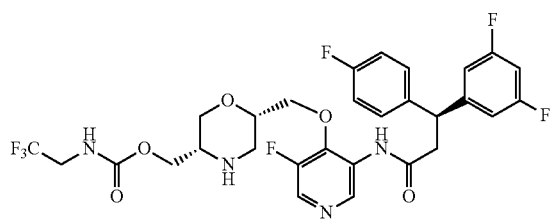 [SMILES: O=C(C[C@@H](c1ccc(F)cc1)c1cc(F)cc(F)c1)Nc1cncc(F)c1OC[C@@H]1CN[C@H](COC(=O)NCC(F)(F)F)CO1]

Step 1. tert-Butyl (2R,5R)-2-ethynyl-5-(hydroxymethyl)morpholine-4-carboxylate

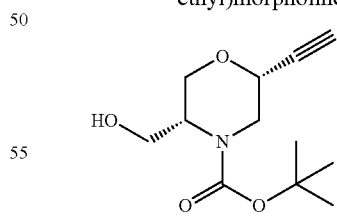

To a solution of tert-butyl (2R,5R)-2-ethynyl-5-(tert-butyldimethylsilyloxy-methyl)morpholine-4-carboxylate (Example 79, step 4) (2.0 g, 5.7 mmol) in 20 mL of THF was added tetrabutylammonium fluoride (1.0 M in THF, 15 mL, 15 mmol). The solution was stirred at ambient temperature for 1 h and then diluted with EtOAc, washed with aqueous NH4Cl, and brine. The solution was dried (MgSO4), filtered, and the solvent was removed in vacuo. The residue was chro- Step 2. tert-Butyl (2R,5R)-2-ethynyl-5-(2,2,2-trifluoroethylaminocarbonyloxymethyl)morpholine-4-carboxylate

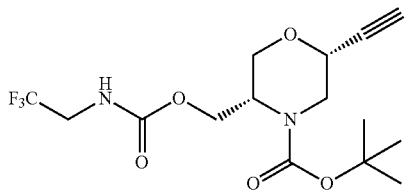 [SMILES: C#C[C@@H]1CN(C(=O)OC(C)(C)C)[C@H](COC(=O)NCC(F)(F)F)CO1]

To a solution of tert-Butyl (2R,5R)-2-ethynyl-5-(hydroxymethyl)morpholine-4-carboxylate (0.51 g, 2.1 mmol) in 6 mL of pyridine was added carbonyldiimidazole (0.45 g, 2.8 mmol). The mixture was stirred at ambient temperature for 3 h. Trifluoroethylamine (4.1 mL, 53 mmol) was added, the vessel was sealed and heated to 50° C. for 24 h. The pyridine was removed in vacuo and the residue was dissolved in EtOAc and washed with water and brine. The EtOAc solution was dried (MgSO4), filtered, and the solvent was removed in vacuo. The residue was chromatographed on a 40 g SiO2 column using a gradient elution of 0-50% EtOAc in hexanes. Fractions containing product were combined and removal of solvents in vacuo gave a solid.

Step 3. tert-Butyl (2R,5R)-2-(3-amino-5-fluoropyridin-4-yl)ethynyl-5-(2,2,2-trifluoroethylaminocarbonyloxymethyl)morpholine-4-carboxylate

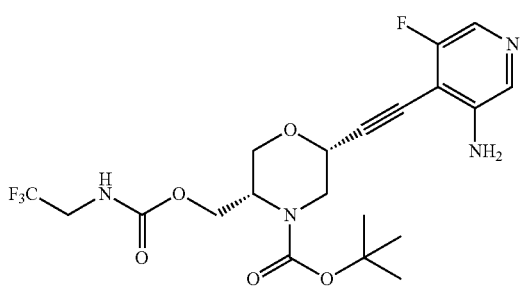 [SMILES: CC(C)(C)OC(=O)N1C[C@@H](C#Cc2c(N)cncc2F)OC[C@H]1COC(=O)NCC(F)(F)F]

A solution of tert-butyl (2R,5R)-2-ethynyl-5-(2,2,2-trifluoroethylaminocarbonyloxymethyl)morpholine-4-carboxylate (3.5 g, 9.6 mmol), 3-amino-5-fluoro-4-iodopyridine (2.5 g, 10.5 mmol), and triethylamine (40 mL, 290 mmol) in acetonitrile (50 mL) was purged with nitrogen gas for 2 min. To the solution was added CuI (180 mg, 0.96 mmol) and bis(triphenylphosphine)palladium(II) chloride (0.47 g, 0.67 mmol). The mixture was stirred and heated in an oil bath at 70° C. for 3 h. The mixture was cooled to ambient temperature and the solvents were removed in vacuo. The residue was partitioned between EtOAc and water. The water layer was removed and the organic phase was washed with water and brine, then dried (MgSO4), filtered, and the solvent was removed in vacuo. The residue was chromatographed on a 330 g SiO2 column eluting with a gradient of 0-7% MeOH in CHCl3 over 30 min. Fractions containing product were combined and the solvents were evaporated to give a gum. LC MS: RT=1.08 min, M+H=477 (2 min gradient)

Step 4. tert-Butyl (2R,5R)-2-(2-(3-amino-5-fluoropyridin-4-yl)ethyl)-5-(2,2,2-trifluoroethylaminocarbonyloxymethyl)morpholine-4-carboxylate

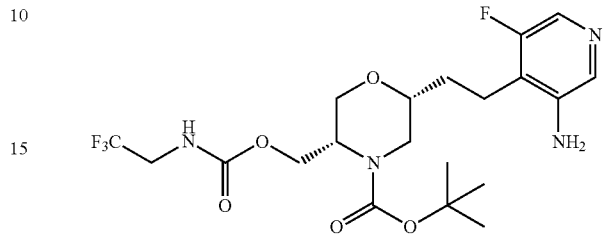

A solution of tert-butyl (2R,5R)-2-(3-amino-5-fluoropyridin-4-yl)ethynyl-5-(2,2,2-trifluoroethylaminocarbonyloxymethyl)morpholine-4-carboxylate (3.7 g, 7.8 mmol) in 50 mL of trifluoroethanol was purged with nitrogen gas for 2 min. To the solution was added PtO2 (700 mg) and the mixture was shaken on a Parr apparatus under 50 psi of hydrogen as for 48 h. LCMS analysis indicated conversion of the alkyne to the alkene. The catalyst was removed by filtration and the solvent was removed in vacuo. The residue was dissolved in 30 mL of MeOH. The solution was purged with nitrogen gas for 2 min. To the solution was added 10% palladium on carbon (700 mg) and the mixture was shaken on a Parr apparatus under 50 psi of hydrogen gas for 48 h. LCMS indicated partial conversion of the alkene to the desired product. The catalyst was removed by filtration and the solvent was removed in vacuo. The residue was dissolved in 30 mL of MeOH. The solution was purged with nitrogen gas for 2 min. To the solution was added 10% palladium on carbon (700 mg) and the mixture was shaken on a Parr apparatus under 50 psi of hydrogen gas for 48 h. LCMS indicated complete conversion to the desired product. The catalyst was removed by filtration and the solvent was removed in vacuo to give a gum. LC MS: RT=0.98 min, M+H=481 (2 min gradient)

Step 5. (4R)-3-[(2E)-3-(3,5-Difluorophenyl)prop-2-enoyl]-4-phenyl-1,3-oxazolidin-2-one

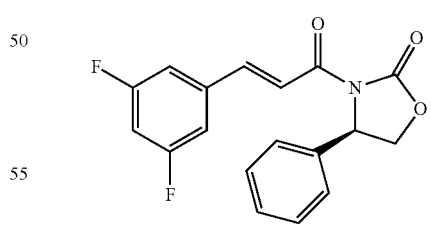

To a slurry of 3,5-difluorocinammic acid (6.3 g, 34 mmol) in CH2Cl2 (130 mL) was added thionyl chloride (6.2 mL, 85 mmol). The mixture was heated to reflux under a nitrogen atmosphere for 5 h, at which time all solids had dissolved. The solvents were removed in vacuo to give the acid chloride as a solid. A solution of (4R)-4-phenyl-1,3-oxazolidin-2-one (5.6 g, 34 mmol) in THF (100 mL) under an atmosphere of nitrogen was cooled to −10° C. in an ice-acetone bath. To the stirred solution was added nBuLi (13.6 mL of a 2.5 M solution in hexane, 34 mmol) dropwise over a period of 10 min. To this solution was added a solution of the acid chloride in 40 mL of THF dropwise over 10 min. The resulting solution was stirred at 0° C. in an ice-water bath for 1 h. The reaction was quenched with the addition of aqueous NaHCO3, and the mixture was extracted three times with EtOAc. The combined organic extracts were washed with water and brine, then dried (MgSO4), filtered, and the solvent was removed in vacuo. The residue was chromatographed on a 330 g SiO2 column using a gradient elution of 0-50% EtOAc:A, where A=1:1 hexanes: CHCl3. Fractions containing product were combined and the solvents were removed in vacuo to give a solid.

Step 6. (4R)-3-[(3S)-3-(3,5-Difluorophenyl)-3-(4-fluorophenyl)propanoyl]-4-phenyl-1,3-oxazolidin-2-one

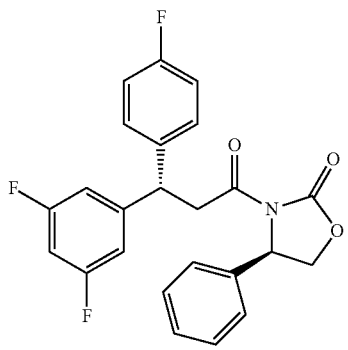 [SMILES: O=C(C[C@@H](c1ccc(F)cc1)c1cc(F)cc(F)c1)N1C(=O)OC[C@H]1c1ccccc1]

A solution of 4-fluorophenylmagnesium bromide (29 mL of a 2.0 M solution in THF, 58 mmol) and copper(I) bromide-dimethylsulfide complex (12 g, 59 mmol) in THF (100 mL) under an atmosphere of nitrogen was cooled to −40° C. in a dry ice-acetonitrile bath. To the stirred solution was added a solution of (4R)-3-[(2E)-3-(3,5-difluorophenyl)prop-2-enoyl]-4-phenyl-1,3-oxazolidin-2-one (7.7 g, 23 mmol) in 100 mL of THF dropwise over 15 min. The resulting mixture was stirred at −40° C. for 1.5 h, then the cooling bath was removed and the stirred mixture was allowed to warm to ambient temperature. The reaction was quenched by the addition of aqueous NH4Cl solution. The resulting mixture was stirred for 15 min then extracted with two portions of EtOAc. The combined organic phases were washed with water and brine, then dried (MgSO4), filtered, and the solvents were removed in vacuo. The residue was chromatographed on a 330 g SiO2 column using a gradient elution of 0-50% EtOAc: A, where A=1:1 hexanes:CHCl3. Fractions containing product were combined and the solvents were removed in vacuo to give a solid.

Step 7. (3S)-3-(3,5-Difluorophenyl)-3-(4-fluorophenyl)propanoic acid

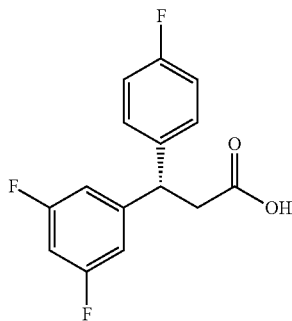 [SMILES: O=C(O)C[C@@H](c1ccc(F)cc1)c1cc(F)cc(F)c1]

A solution of (4R)-3-[(3S)-3-(3,5-difluorophenyl)-3-(4-fluorophenyl)propanoyl]-4-phenyl-1,3-oxazolidin-2-one (7.3 g, 17 mmol) in 90 mL of THF and 30 mL of water was cooled to 0° C. in an ice-water bath. To the solution was added hydrogen peroxide (7.0 mL of a 30% solution in water, 69 mmol) and LiOH (0.83 gg, 35 mmol). After 45 min, a solution of sodium sulfite (8.7 g, 69 mmol) in 30 mL of water was added, followed by 170 mL of a 0.5 M solution of aqueous NaHCO3 (86 mmol). The stirred mixture was warmed to ambient temperature and most of the THF was removed in vacuo. The aqueous mixture was extracted with two portions of CH2Cl2 to remove the chiral auxiliary. The aqueous phase was then acidified to pH 1 with the addition of 6 N HCl and extracted with two portions of EtOAc. The combined EtOAc layers were dried (MgSO4), filtered, and the solvent was removed in vacuo to give a solid.

Step 8. (3S)-3-(4-Fluorophenyl)-3-(3,5-difluorophenyl)-N-(5-fluoro-4-(2-((2R,5R)-4-(tert-butyloxycarbonyl)-5-(2,2,2-trifluoroethylaminocarbonyloxymethyl)-morpholine-2-yl)ethyl)pyridin-3-yl)propanamide

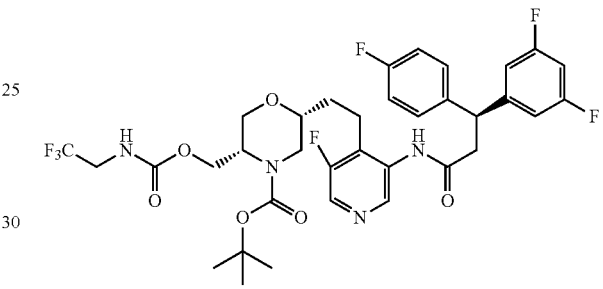

A solution of tert-butyl (2R,5R)-2-(2-(3-amino-5-fluoropyridin-4-yl)ethyl)-5-(2,2,2-trifluoroethylaminocarbonyloxymethyl)morpholine-4-carboxylate (75 mg, 0.16 mmol) and (3S)-3-(3,5-difluorophenyl)-3-(4-fluorophenyl)propanoic acid (44 mg, 0.16 mmol) in pyridine (1.0 mL) was cooled to −10° C. in an ice-acetone bath. To the stirred solution was added POCl3 (0.016 mL, 0.17 mmol) and the mixture was stirred for 30 min. The reaction was quenched by the addition of aqueous NaHCO3 solution and the resulting mixture was extracted with two portions of EtOAc. The combined EtOAc layers were dried (MgSO4), filtered, and the solvents were removed in vacuo. The residue was chromatographed on a 12 g SiO2 column using a gradient elution of 0-70% EtOAc in hexanes. Fractions containing product were combined and the solvents were removed in vacuo to give a gum. LC MS: RT=1.41 min, M+H=743 (2 min gradient)

Step 9. (3S)-3-(4-Fluorophenyl)-3-(3,5-difluorophenyl)-N-(5-fluoro-4-(2-((2R,5R)-5-(2,2,2-trifluoroethylaminocarbonyloxymethyl)morpholine-2-yl)ethyl)pyridin-3-yl)propanamide

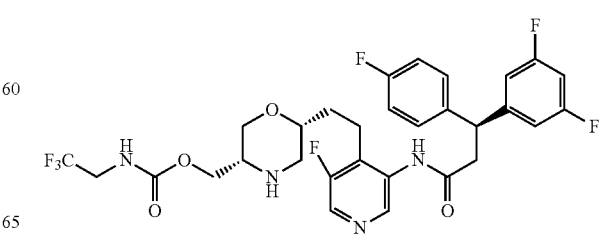

3S-3-(4-Fluorophenyl)-3-(3,5-difluorophenyl)-N-(5-fluoro-4-(2-((2R,5R)-4-(tert-butyloxycarbonyl)-5-(2,2,2-trifluoroethylaminocarbonyloxymethyl)morpholine-2-yl)ethyl)pyridin-3-yl)propanamide (43 mg, 0.058 mmol) was dissolved in 0.5 mL of 4.0 M HCl in dioxane. The solution was stirred at ambient temperature for 30 min then the solvent and excess HCl were removed in vacuo to give the HCl salt of the title compound as a solid. LC MS: RT=1.08 min, M+H=643 (2 min gradient), hi-res MS calc'd 643.2150, found 643.2136.

EXAMPLE 90

(2S,3S)-2-Amino-3-(4-fluorophenyl)-3-(3,5-difluorophenyl)-N-(5-fluoro-4-(2-((2R,5R)-5-(2,2,2-trifluoroethylaminocarbonyloxymethyl)morpholine-2-yl)ethyl)pyridin-3-yl)propanamide

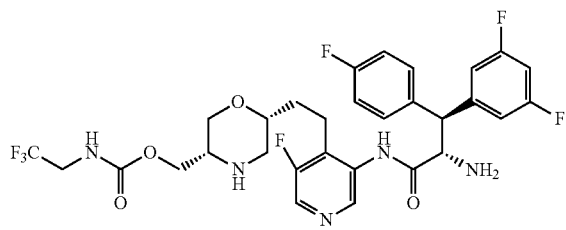 [SMILES: N[C@H](C(=O)Nc1cncc(F)c1CC[C@@H]1CN[C@H](COC(=O)NCC(F)(F)F)CO1)[C@@H](c1ccc(F)cc1)c1cc(F)cc(F)c1]

Step 1. (4S)-3-[(3S)-3-(3,5-Difluorophenyl)-3-(4-fluorophenyl)propanoyl]-4-phenyl-1,3-oxazolidin-2-one

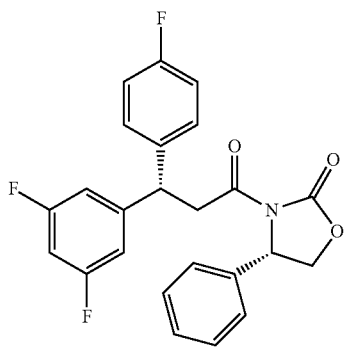 [SMILES: O=C(C[C@@H](c1ccc(F)cc1)c1cc(F)cc(F)c1)N1C(=O)OC[C@@H]1c1ccccc1]

To a solution of (3S)-3-(3,5-difluorophenyl)-3-(4-fluorophenyl)propanoic acid (Example 89, step 7) (3.0 g, 11 mmol) in CH2Cl2 (70 mL) was added thionyl chloride (2.0 mL, 27 mmol). The mixture was heated to reflux under a nitrogen atmosphere for 1 h. The solvents were removed in vacuo to give the acid chloride as a gum. A solution of (4S)-4-phenyl-1,3-oxazolidin-2-one (1.7 g, 11 mmol) in THF (60 mL) under an atmosphere of nitrogen was cooled to −10° C. in an ice-acetone bath. To the stirred solution was added nBuLi (4.3 mL of a 2.5 M solution in hexane, 11 mmol) dropwise over a period of 5 min. To this solution was added a solution of the acid chloride in 20 mL of THF dropwise over 5 min. The resulting solution was stirred at 0° C. in an ice-water bath for 1 h. The reaction was quenched with the addition of aqueous NaHCO3, and the mixture was extracted three times with EtOAc. The combined organic extracts were washed with water and brine, then dried (MgSO4), filtered, and the solvent was removed in vacuo. The residue was chromatographed on a 120 g SiO2 column using a gradient elution of 0-50% EtOAc:A, where A=1:1 hexanes:CHCl3. Fractions containing product were combined and the solvents were removed in vacuo to give a solid.

Step 2. (4S)-3-[(2S,3S)-2-Azido-3-(3,5-difluorophenyl)-3-(4-fluorophenyl)propanoyl]-4-phenyl-1,3-oxazolidin-2-one

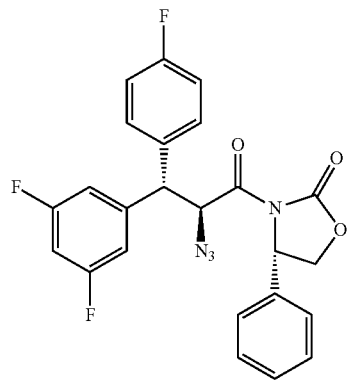 [SMILES: [N-]=[N+]=N[C@H](C(=O)N1C(=O)OC[C@@H]1c1ccccc1)[C@@H](c1ccc(F)cc1)c1cc(F)cc(F)c1]

10 mL of THF under an atmosphere of nitrogen was cooled to −78° C. in a dry ice-acetone bath and to the stirred solution was added sodium hexamethyldisilazide (9.1 mL of a 1.0 M solution in THF, 9.1 mmol). A solution of (4S)-3-[(3S)-3-(3,5-difluorophenyl)-3-(4-fluorophenyl)propanoyl]-4-phenyl-1,3-oxazolidin-2-one (3.5 g, 8.2 mmol) in 20 mL of THF under nitrogen atmosphere was cooled to −78° C. in a dry ice-acetone bath and added via cannula to the cold sodium hexamethyldisilazide solution. The resulting mixture was stirred at −78° C. for 30 min when trisyl azide (3.3 g, 11 mmol) was added as a solid. The solids dissolved and the cold solution was stirred for 2 min. To the cold solution was added HOAc (2.8 mL, 49 mmol) and solid tetramethylammonium acetate (4.4 g, 33 mmol). The cooling bath was removed and the mixture was stirred at ambient temperature for 4 h. The reaction was diluted with EtOAc and washed with brine. The aqueous phase was extracted with EtOAc, and the combined EtOAc layers were washed with aqueous NaHCO3 and brine, then dried (MgSO4), filtered, and the solvents were removed in vacuo. The residue was chromatographed on a 120 g SiO2 column using a gradient elution of 0-40% EtOAc in hexanes. Fractions containing product were combined and the solvents were removed in vacuo to give a solid.

Step 3. (2S,3S)-2-Azido-3-(3,5-difluorophenyl)-3-(4-fluorophenyl)propanoic acid

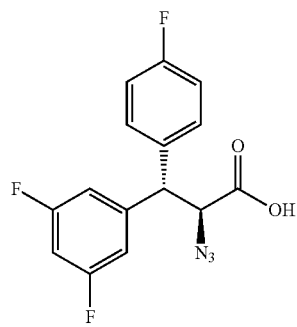 [SMILES: [N-]=[N+]=N[C@H](C(=O)O)[C@@H](c1ccc(F)cc1)c1cc(F)cc(F)c1]

A solution of (4S)-3-[(2S,3S)-2-azido-3-(3,5-difluorophenyl)-3-(4-fluorophenyl)propanoyl]-4-phenyl-1,3-oxazolidin-2-one (3.1 g, 6.7 mmol) in 45 mL of THF and 15 mL of water was cooled to 0° C. in an ice-water bath. To the stirred solution was added hydrogen peroxide (2.7 mL of a 30% solution in water, 27 mmol) and LiOH (0.32 g, 13 mmol), and the mixture was stirred at 0° C. for 45 min. The reaction was quenched by the addition of a solution of sodium sulfite (3.4 g, 27 mmol) in 20 mL of water, followed by 67 mL of a 0.5 M solution of aqueous NaHCO3 (33 mmol). The stirred mixture was warmed to ambient temperature and most of the THF was removed in vacuo. The aqueous mixture was extracted with two portions of CH2Cl2 to remove the chiral auxiliary. The aqueous phase was then acidified to pH 1 with the addition of 6 N HCl and extracted with two portions of EtOAc. The combined EtOAc layers were dried (MgSO4), filtered, and the solvent was removed in vacuo to give a gum.

Step 4. (2S,3S)-2-Azido-3-(4-fluorophenyl)-3-(3,5-difluorophenyl)-N-(5-fluoro-4-(2-((2R,5R)-4-(tert-butyloxycarbonyl)-5-(2,2,2-trifluoroethylaminocarbonyloxymethyl)morpholine-2-yl)ethyl)pyridin-3-yl)propanamide

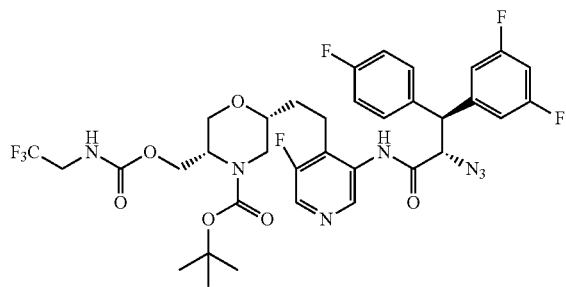 [SMILES: CC(C)(C)OC(=O)N1C[C@@H](CCc2c(F)cncc2NC(=O)[C@@H](N=[N+]=[N-])[C@@H](c2ccc(F)cc2)c2cc(F)cc(F)c2)OC[C@H]1COC(=O)NCC(F)(F)F]

A solution of tert-butyl (2R,5R)-2-(2-(3-amino-5-fluoropyridin-4-yl)ethyl)-5-(2,2,2-trifluoroethylaminocarbonyloxymethyl)morpholine-4-carboxylate (Example 89, step 4) (64 mg, 0.13 mmol) and (2S,3S)-2-azido-3-(3,5-difluorophenyl)-3-(4-fluorophenyl)propanoic acid (43 mg, 0.13 mmol) in pyridine (0.5 mL) was cooled to −10° C. in an ice-acetone bath. To the stirred solution was added POCl3 (0.014 mL, 0.15 mmol) and the mixture was stirred for 30 min. The reaction was quenched by the addition of aqueous NaHCO3 solution and the resulting mixture was extracted with two portions of EtOAc. The combined EtOAc layers were dried (MgSO4), filtered, and the solvents were removed in vacuo. The residue was chromatographed on a 12 g SiO2 column using a gradient elution of 0-80% EtOAc in hexanes. Fractions containing product were combined and the solvents were removed in vacuo to give a gum. LC MS: RT=1.48 min, M+H=784 (2 min gradient)

Step 5. (2S,3S)-2-Amino-3-(4-fluorophenyl)-3-(3,5-difluorophenyl)-N-(5-fluoro-4-(2-((2R,5R)-4-(tert-butyloxycarbonyl)-5-(2,2,2-trifluoroethylaminocarbonyloxymethyl)morpholine-2-yl)ethyl)pyridin-3-yl)propanamide

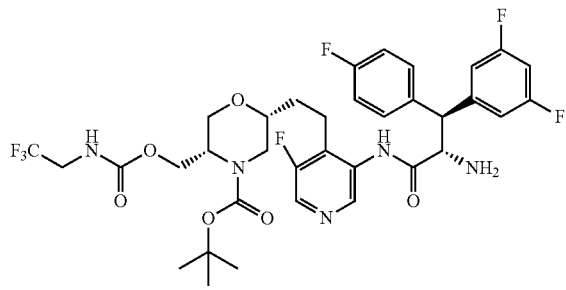 [SMILES: CC(C)(C)OC(=O)N1C[C@@H](CCc2c(F)cncc2NC(=O)[C@@H](N)[C@@H](c2ccc(F)cc2)c2cc(F)cc(F)c2)OC[C@H]1COC(=O)NCC(F)(F)F]

A solution of (2S,3S)-2-azido-3-(4-fluorophenyl)-3-(3,5-difluorophenyl)-N-(5-fluoro-4-(2-((2R,5R)-4-(tert-butyloxycarbonyl)-5-(2,2,2-trifluoroethylaminocarbonyloxymethyl)morpholine-2-yl)ethyl)pyridin-3-yl)propanamide (36 mg, 0.046 mmol) in 1 mL of MeOH was purged with nitrogen gas for 1 min. To the solution was added 10% palladium on carbon (18 mg) and the mixture was stirred under 1 atmosphere of hydrogen gas for 4 h. The catalyst was removed by filtration and the filtrate solvents were removed in vacuo to give a gum. LC MS: RT=1.20 min, M+H=758 (2 min gradient)

Step 6. (2S,3S)-2-Amino-3-(4-fluorophenyl)-3-(3,5-difluorophenyl)-N-(5-fluoro-4-(2-((2R,5R)-5-(2,2,2-trifluoroethylaminocarbonyloxymethyl)morpholine-2-yl)ethyl)pyridin-3-yl)propanamide

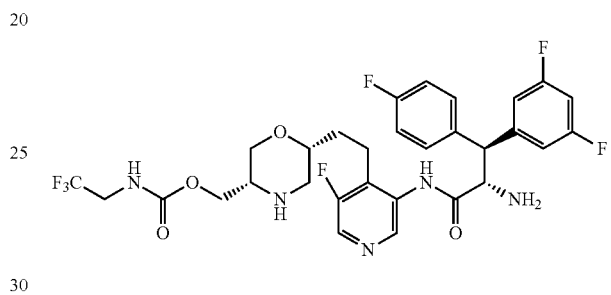

(2S,3S)-2-Amino-3-(4-fluorophenyl)-3-(3,5-difluorophenyl)-N-(5-fluoro-4-(2-((2R,5R)-4-(tert-butyloxycarbonyl)-5-(2,2,2-trifluoroethylaminocarbonyloxymethyl)morpholine-2-yl)ethyl)pyridin-3-yl)propanamide (27 mg, 0.036 mmol) was dissolved in 0.5 mL of 4.0 M HCl in dioxane. The solution was stirred at ambient temperature for 45 min then the solvent and excess HCl were removed in vacuo to give the HCl salt of the title compound as a solid. LC MS: RT=0.9 min, M+H=658 (2 min gradient), hi-res MS calc'd 658.2259. found 658.2257.

EXAMPLE 91

(2S,3S)-2-(Methoxycarbonylamino)-3-(4-fluorophenyl)-3-(3,5-difluorophenyl)-N-(5-fluoro-4-(2-((2R,5R)-5-(2,2,2-trifluoroethylaminocarbonyloxymethyl)morpholine-2-yl)ethyl)pyridin-3-yl)propanamide

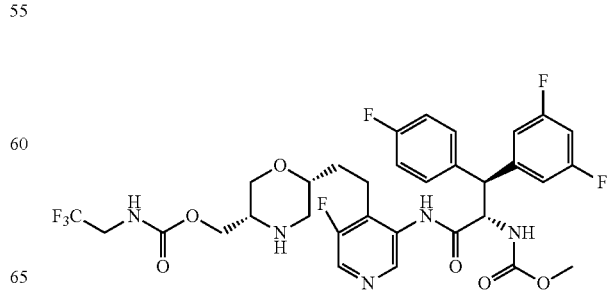

Step 1. (2S,3S)-2-(Methoxycarbonylamino)-3-(4-fluorophenyl)-3-(3,5-difluorophenyl)-N-(5-fluoro-4-(2-((2R,5R)-4-(tert-butyloxycarbonyl)-5-(2,2,2-trifluoroethylaminocarbonyloxymethyl)morpholine-2-yl)ethyl)pyridin-3-yl)propanamide

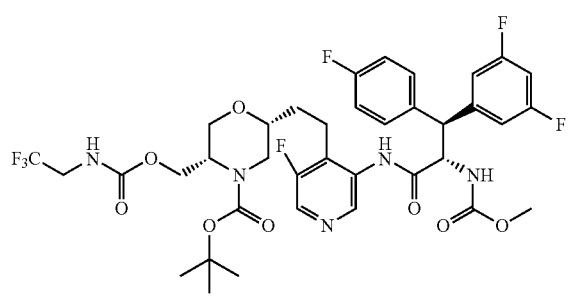 [SMILES: COC(=O)N[C@H](C(=O)Nc1cncc(F)c1CC[C@@H]1CN(C(=O)OC(C)(C)C)[C@H](COC(=O)NCC(F)(F)F)CO1)[C@@H](c1ccc(F)cc1)c1cc(F)cc(F)c1]

To a stirred solution of (2S,3S)-2-amino-3-(4-fluorophenyl)-3-(3,5-difluorophenyl)-N-(5-fluoro-4-(2-((2R,5R)-4-(tert-butyloxycarbonyl)-5-(2,2,2-trifluoroethylaminocarbonyloxymethyl)morpholine-2-yl)ethyl)pyridin-3-yl)propanamide (Example 90, step 5) (64 mg, 0.084 mmol) in 1 mL of CH2Cl2 was added triethylamine (0.047 mL, 0.34 mmol) and methyl chloroformate (0.013 mL, 0.17 mmol). The mixture was stirred at ambient temperature for 1 h, then diluted with CH2Cl2 and washed with aqueous NaHCO3 and brine. The organic phase was dried (MgSO4), filtered, and the solvents were removed in vacuo. The residue was chromatographed on a 12 g SiO2 column using a gradient elution of 0-100% EtOc in hexanes. Fractions containing product were combined and the solvents were removed in vacuo to give a gum. LC MS: RT=1.38 min, M+H=816 (2 min gradient)

Step 2. (2S,3S)-2-(Methoxycarbonylamino)-3-(4-fluorophenyl)-3-(3,5-difluorophenyl)-N-(5-fluoro-4-(2-((2R,5R)-5-(2,2,2-trifluoroethylaminocarbonyloxymethyl)morpholine-2-yl)ethyl)pyridin-3-yl)propanamide

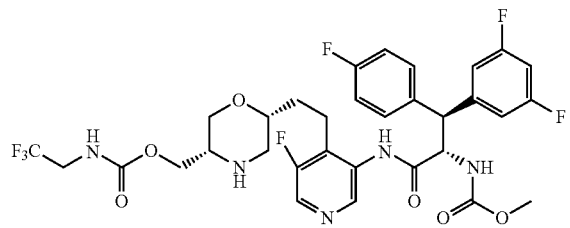 [SMILES: COC(=O)N[C@H](C(=O)Nc1cncc(F)c1CC[C@@H]1CN[C@H](COC(=O)NCC(F)(F)F)CO1)[C@@H](c1ccc(F)cc1)c1cc(F)cc(F)c1]

(2S,3S)-2-(Methoxycarbonylamino)-3-(4-fluorophenyl)-3-(3,5-difluorophenyl)-N-(5-fluoro-4-(2-((2R,5R)-4-(tert-butyloxycarbonyl)-5-(2,2,2-trifluoroethylaminocarbonyloxymethyl)morpholine-2-yl)ethyl)pyridin-3-yl)propanamide (57 mg, 0.070 mmol) was dissolved in 1.0 mL of 4.0 M HCL in dioxane. The solution was stirred at ambient temperature for 1 h. The solvent and excess HCl were removed in vacuo. The residue was purified by preparative reverse phase HPLC on a C18 column using a gradient elution of 5-95% CH3CN in water containing 0.1% TFA. Fractions containing product were combined and lyophilized to give the TFA salt of the title compound as a solid. LC MS: RT=1.08 min, M+H=716 (2 min gradient), hi-res MS calc'd 716.2314. found 716.2295.

EXAMPLE 92

(2S,3R)-2-Amino-3-(4-fluorophenyl)-3-(4-fluorophenyl)-N-(5-fluoro-4-(2-((2R,5R)-5-(2,2,2-trifluoroethylaminocarbonyloxymethyl)morpholine-2-yl)ethyl)pyridin-3-yl)propanamide

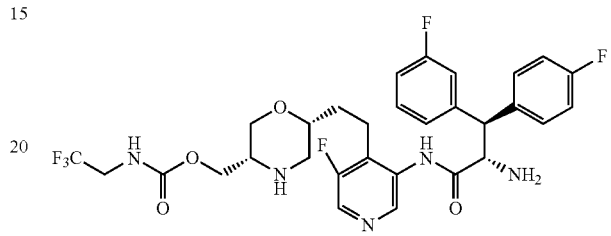

Step 1. ((4S)-3-[(2E)-3-(3-fluorophenyl)prop-2-enoyl]-4-phenyl-1,3-oxazolidin-2-one

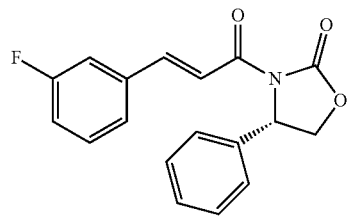 [SMILES: O=C(/C=C/c1cccc(F)c1)N1C(=O)OC[C@@H]1c1ccccc1]

To a slurry of 3-fluorocinammic acid (2.0 g, 12 mmol) in dichloromethane (25 mL) was added thionyl chloride (1.8 mL, 24 mmol). The mixture was heated to reflux under a nitrogen atmosphere for 6 h. The solvents were removed in vacuo to give the acid chloride as a solid. A solution of (4S)-4-phenyl-1,3-oxazolidin-2-one (2.0 g, 12 mmol) in THF (20 mL) under an atmosphere of nitrogen was cooled to −10° C. in an ice-acetone bath. To the stirred solution was added nBuLi (4.8 mL of a 2.5 M solution in hexane, 12 mmol) dropwise over a period of 10 min. To this cold solution was added a solution of the acid chloride in 15 mL of THF dropwise over 10 min. The resulting solution was stirred at 0° C. in an ice-water bath for 1 h. The reaction was quenched with the addition of aqueous NaHCO3, and the mixture was extracted three times with EtOAc. The combined organic extracts were washed with water and brine, then dried (MgSO4), filtered, and the solvent was removed in vacuo. The residue was chromatographed on a 80 g silica gel column using a gradient elution of 0-50% EtOAc:A, where A=1:1 hexanes:CHCl3. Fractions containing product were combined and the solvents were removed in vacuo to give the title compound as a solid.

Step 2. (4S)-3-[(3R)-3-(4-fluorophenyl)-3-(4-fluorophenyl)propanoyl]-4-phenyl-1,3-oxazolidin-2-one

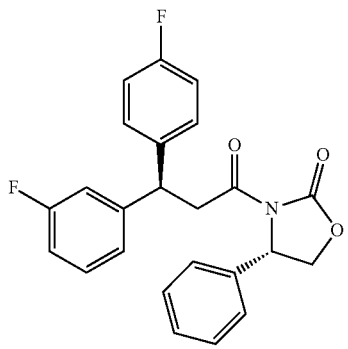 [SMILES: O=C(C[C@H](c1ccc(F)cc1)c1cccc(F)c1)N1C(=O)OC[C@@H]1c1ccccc1]

A solution of 4-fluorophenylmagnesium bromide (12 mL of a 1.0 M solution in THF, 12 mmol) and copper(I) bromide-dimethylsulfide complex (2.4 g, 59 mmol) in THF (20 mL) under an atmosphere of nitrogen was cooled to −40° C. in a dry ice-acetonitrile bath. To the stirred cold solution was added a solution of the product from step 1 (1.5 g, 4.8 mmol) in 10 mL of THF dropwise over 10 min. The resulting mixture was stirred at −40° C. for 1.5 h, then the cooling bath was removed and the stirred mixture was allowed to warm to ambient temperature over 1 h. The reaction was quenched by the addition of aqueous $NH_4Cl$ solution. The resulting mixture was stirred for 15 min then extracted with two portions of EtOAc. The combined EtOAc extracts were washed with water and brine, then dried ($MgSO_4$), filtered, and the solvents were removed in vacuo. The residue was chromatographed on an 80 g silica gel column using a gradient elution of 0-50% EtOAc:hexanes. Fractions containing product were combined and the solvents were removed in vacuo to give the title compound as a solid.

Step 3. (4S)-3-[(2S,3R)-2-azido-3-(3-fluorophenyl)-3-(4-fluorophenyl)propanoyl]-4-phenyl-1,3-oxazolidin-2-one

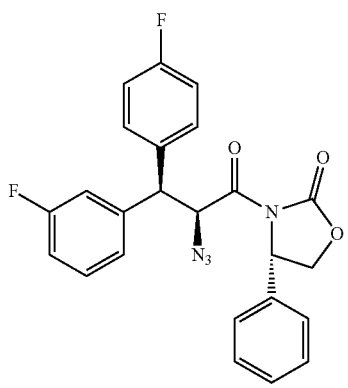 [SMILES: [N-]=[N+]=N[C@H](C(=O)N1C(=O)OC[C@@H]1c1ccccc1)[C@H](c1ccc(F)cc1)c1cccc(F)c1]

5 mL of THF under an atmosphere of nitrogen was cooled to −78° C. in a dry ice-acetone bath and to the stirred solution was added sodium hexamethyldisilazide (5.5 mL of a 1.0 M solution in THF, 5.5 mmol). A solution of the product from step 2 (1.5 g, 3.7 mmol) in 8 mL of THF under nitrogen atmosphere was cooled to −78° C. in a dry ice-acetone bath and added via cannula to the cold sodium hexamethyldisilazide solution. The resulting mixture was stirred at −78° C. for 30 min when trisyl azide (1.5 g, 4.8 mmol) was added as a solid. The solids dissolved and the cold solution was stirred for 2 min. To the cold solution was added HOAc (1.3 mL, 22 mmol) and solid tetramethylammonium acetate (2.0 g, 15 mmol). The cooling bath was removed and the mixture was stirred at ambient temperature for 4 h. The reaction was diluted with EtOAc and washed with brine. The aqueous phase was extracted with EtOAc, and the combined EtOAc layers were washed with aqueous $NaHCO_3$ and brine, then dried ($MgSO_4$), filtered, and the solvents were removed in vacuo. The residue was chromatographed on an 80 g silica gel column using a gradient elution of 0-50% EtOAc in hexanes. Fractions containing product were combined and the solvents were removed in vacuo to give the title compound as a solid.

Step 4. (2S,3R)-2-azido-3-(3-fluorophenyl)-3-(4-fluorophenyl)propanoic acid

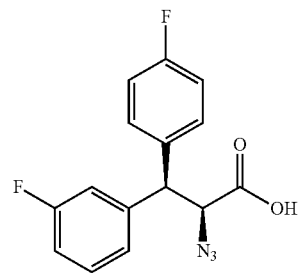 [SMILES: [N-]=[N+]=N[C@H](C(=O)O)[C@H](c1ccc(F)cc1)c1cccc(F)c1]

A solution of the product from step 3 (0.7 g, 1.6 mmol) in 15 mL of THF and 5 mL of water was cooled to 0° C. in an ice-water bath. To the stirred solution was added hydrogen peroxide (0.7 mL of a 30% solution in water, 7 mmol) and LiOH (75 mg, 3.1 mmol), and the mixture was stirred at 0° C. for 45 min. The reaction was quenched by the addition of a solution of sodium sulfite (0.8 g, 7 mmol) in 5 mL of water, followed by a 0.5 M solution of aqueous $NaHCO_3$ (16 mL, 8 mmol). The stirred mixture was warmed to ambient temperature and most of the THF was removed in vacuo. The aqueous mixture was extracted with two portions of dichloromethane to remove the chiral auxiliary. The aqueous phase was acidified to pH 1 with the addition of 6 N HCl and extracted with two portions of EtOAc. The combined EtOAc layers were dried ($MgSO_4$), filtered, and the solvent was removed in vacuo to give the title compound as a gum.

Step 5. (2S,3R)-2-Amino-3-(3-fluorophenyl)-3-(4-fluorophenyl)-N-(5-fluoro-4-(2-((2R,5R)-5-(2,2,2-trifluoroethylaminocarbonyloxymethyl)morpholine-2-yl)ethyl)pyridin-3-yl)propanamide

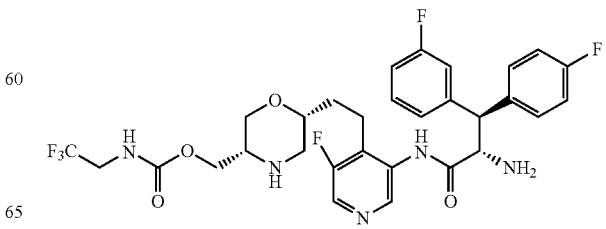

The title compound was prepared from the product of Step 4 using the procedures described in Example 90, steps 4 and 5 and Example 91, step 2 to give the TFA salt of the title compound as a solid. LCMS: RT=0.88 min (2 min gradient); high-resolution MS M+H calc'd 640.2353. found 623.2050.

EXAMPLE 93

(2S,3S)-2-Amino-3-(3-chlorophenyl)-3-(4-fluorophenyl)-N-(5-fluoro-4-(2-((2R,5R)-5-(2,2,2-trifluoroethylaminocarbonyloxymethyl)morpholine-2-yl)ethyl)pyridin-3-yl)propanamide

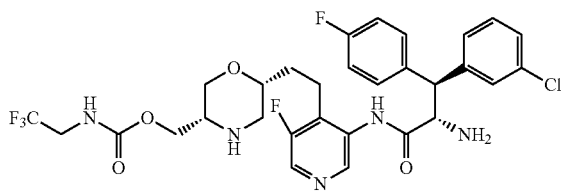 [SMILES: N[C@H](C(=O)Nc1cncc(F)c1CC[C@@H]1CN[C@H](COC(=O)NCC(F)(F)F)CO1)[C@@H](c1ccc(F)cc1)c1cccc(Cl)c1]

Step 1. (2S,3S)-2-Azido-3-(3-chlorophenyl)-3-(4-fluorophenyl)propanoic acid

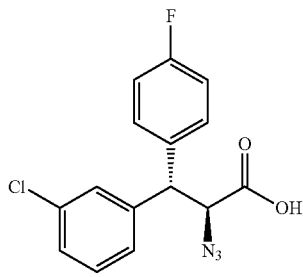 [SMILES: [N-]=[N+]=N[C@H](C(=O)O)[C@@H](c1ccc(F)cc1)c1cccc(Cl)c1]

The title compound was prepared from 3-chlorocinnamic acid using the procedures described for Example 90, step 3.

Step 2. (2S,3S)-2-Azido-3-(3-chlorophenyl)-3-(4-fluorophenyl)-N-(5-fluoro-4-(2-((2R,5R)-4-(tert-butyloxycarbonyl)-5-(2,2,2-trifluoroethylaminocarbonyloxymethyl)morpholine-2-yl)ethyl)pyridin-3-yl)propanamide

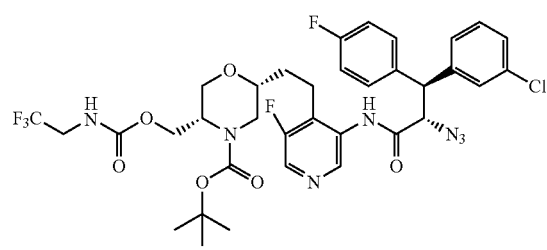 [SMILES: CC(C)(C)OC(=O)N1C[C@@H](CCc2c(F)cncc2NC(=O)[C@@H](N=[N+]=[N-])[C@@H](c2ccc(F)cc2)c2cccc(Cl)c2)OC[C@H]1COC(=O)NCC(F)(F)F]

The title compound was prepared from the product of Step 1 using the procedure described for Example 90, step 4. LCMS: RT=1.51 min, M+H=782.5 (2 min gradient).

Step 3. (2S,3S)-2-Amino-3-(3-chlorophenyl)-3-(4-fluorophenyl)-N-(5-fluoro-4-(2-((2R,5R)-4-(tert-butyloxycarbonyl)-5-(2,2,2-trifluoroethylaminocarbonyloxymethyl)morpholine-2-yl)ethyl)pyridin-3-yl)propanamide

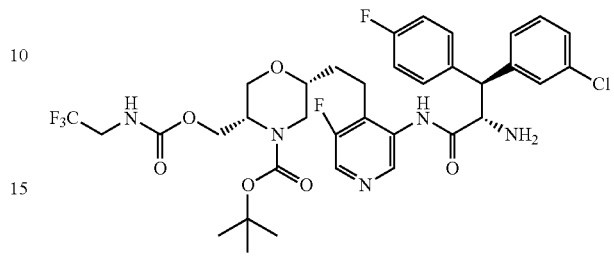

The product from Step 2 (255 mg, 0.33 mmol) was dissolved in 3 mL THF and to the stirred solution was added triphenylphosphine (128 mg, 0.49 mmol) and water (0.3 mL). The mixture was heated to reflux for 24 h. The solvents were removed in vacuo and the residue was purified on a 12 g silica gel column eluting with a gradient of 0-30% EtOAc:hexanes. Fractions containing product were combined and the solvents were removed in vacuo to give a dense gum. LCMS: RT=1.23 min, M+H=756.5 (2 min gradient).

Step 4. (2S,3S)-2-Amino-3-(3-chlorophenyl)-3-(4-fluorophenyl)-N-(5-fluoro-4-(2-((2R,5R)-5-(2,2,2-trifluoroethylaminocarbonyloxymethyl)morpholine-2-yl)ethyl)pyridin-3-yl)propanamide

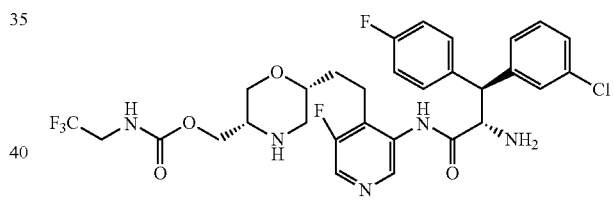

The title compound was prepared from the product of Step 3 using the procedure described for Example 91, step 2. The TFA salt of the title compound was obtained as a solid. LCMS: RT=0.96 min (2 min gradient); high-resolution MS M+H calc'd 656.2058. found 656.2053.

EXAMPLE 94

(βR)-4-Chloro-3-fluoro-β-(3-fluorophenyl)-N-(5-fluoro-4-{2-[(2R,5S)-5-({[(2,2,2-trifluoroethyl)carbamoyl]oxy}methyl)morpholin-2-yl]ethyl}pyridin-3-yl)-L-phenylalaninamide

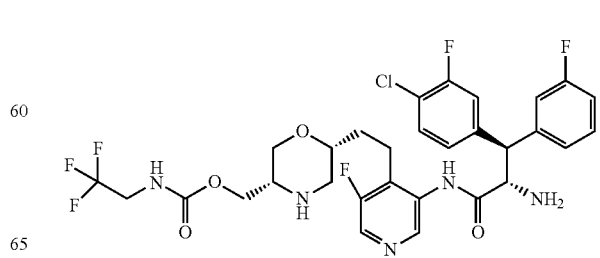

95

Step 1. (2S,3R)-2-Azido-3-(4-chloro-3-fluorophenyl)-3-(3-fluorophenyl)propanoic acid

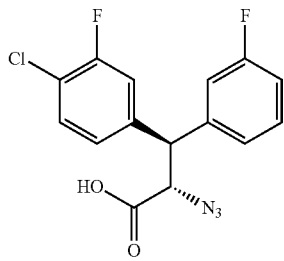 [SMILES: [N-]=[N+]=N[C@H](C(=O)O)[C@H](c1cccc(F)c1)c1ccc(Cl)c(F)c1]

The title compound was prepared from 4-chloro-3-fluorocinnamic acid and 3-fluorophenylmagnesium bromide using the procedures given in Steps 1-4 of Example 92.

Step 2. (βR)-4-Chloro-3-fluoro-β-(3-fluorophenyl)-N-(5-fluoro-4-{2-[(2R,5S)-5-({[(2,2,2-trifluoroethyl)carbamoyl]oxy}methyl)morpholin-2-yl]ethyl}pyridin-3-yl)-L-phenylalaninamide The title compound was prepared from the product of step 1 using the procedures given in steps 2-4 of Example 93. MS (ES) m/z=674 (M+H)$^+$.

96

Step 1. (2S,3R)-2-Azido-3-(4-chlorophenyl)-3-phenylpropanoic acid

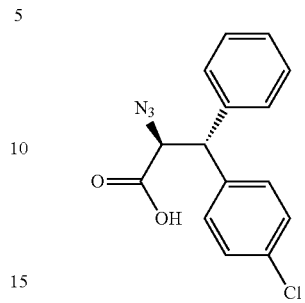

The title compound was prepared from 4-chlorocinnamic acid and phenylmagnesium bromide using the procedures given in steps 1-4 of Example 92.

Step 2. (βR)-β-(4-Chlorophenyl)-N-(5-fluoro-4-{2-[(2R,5S)-5-({[(2,2,2-trifluoroethyl)carbamoyl]oxy}methyl)morpholin-2-yl]ethyl}pyridin-3-yl)-L-phenylalaninamide The title compound was prepared from the product of step 1 using the procedures given in steps 2-4 of Example 93. MS (ES) m/z=638 (M+H)$^+$.

EXAMPLE 95

(βR)-β-(4-Chlorophenyl)-N-(5-fluoro-4-{2-[(2R,5S)-5-({[(2,2,2-trifluoroethyl)carbamoyl]oxy}methyl)morpholin-2-yl]ethyl}pyridin-3-yl)-L-phenylalaninamide

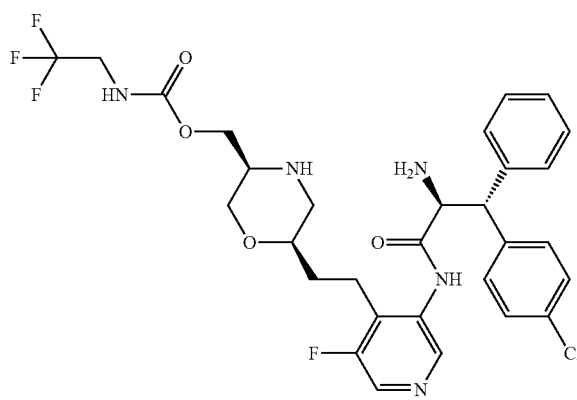

EXAMPLE 96

(βR)-4-Fluoro-N-(5-fluoro-4-{2-[(2R,5S)-5-({[(2,2,2-trifluoroethyl)carbamoyl]oxy}methyl)morpholin-2-yl]ethyl}pyridin-3-yl)-β-naphthalen-2-yl-L-phenylalaninamide

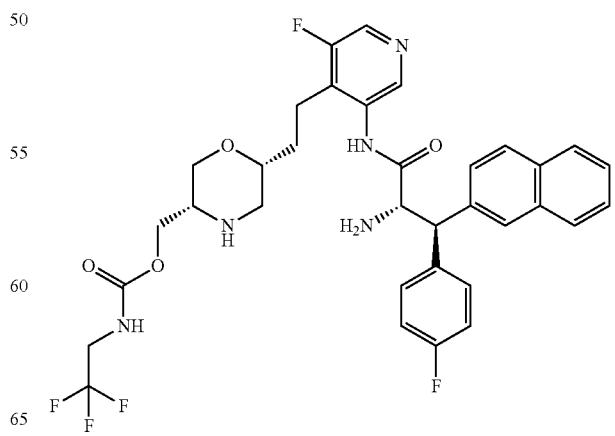

Step 1. (2S,3R)-2-Azido-3-(4-fluorophenyl)-3-(naphthalen-2-yl)propanoic acid

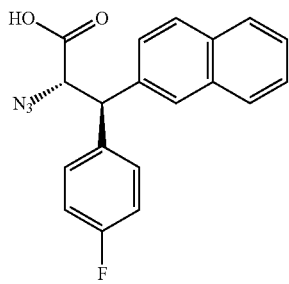 [SMILES: [N-]=[N+]=N[C@H](C(=O)O)[C@H](c1ccc(F)cc1)c1ccc2ccccc2c1]

The title compound was prepared from 3-(2-naphthyl)propenoic acid and 4-fluorophenylmagnesium bromide using the procedures given in steps 1-4 of Example 92.

Step 2. (βR)-4-Fluoro-N-(5-fluoro-4-{2-[(2R,5S)-5-({[(2,2,2-trifluoroethyl)carbamoyl]oxy}methyl)morpholin-2-yl]ethyl}pyridin-3-yl)-β-naphthalen-2-yl-L-phenylalaninamide The title compound was prepared from the product of step 1 using the procedures given in steps 2-4 of Example 93. MS (ES) m/z=672 (M+H)+.

EXAMPLE 97

(βS)-β-(4-Chlorophenyl)-3,5-difluoro-N-(5-fluoro-4-{2-[(2R,5S)-5-({[(2,2,2-trifluoroethyl)carbamoyl]oxy}methyl)morpholin-2-yl]ethyl}pyridin-3-yl)-L-phenylalaninamide

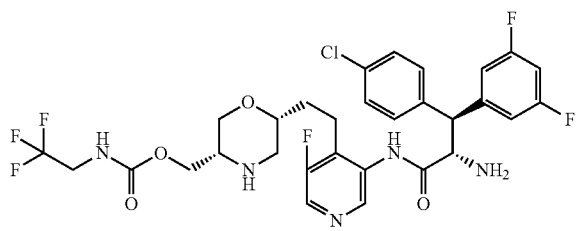 [SMILES: N[C@H](C(=O)Nc1cncc(F)c1CC[C@@H]1CN[C@H](COC(=O)NCC(F)(F)F)CO1)[C@@H](c1ccc(Cl)cc1)c1cc(F)cc(F)c1]

Step 1. (2S,3S)-2-Azido-3-(4-chlorophenyl)-3-(3,5-difluorophenyl)propanoic acid

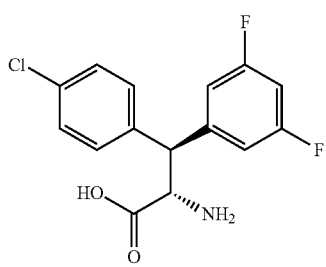 [SMILES: N[C@H](C(=O)O)[C@@H](c1ccc(Cl)cc1)c1cc(F)cc(F)c1]

The title compound was prepared from 4-chlorocinnamic acid and 3,5-difluorophenylmagnesium bromide using the procedures given in steps 1-4 of Example 92.

Step 2. (2R,5S)-tert-butyl 2-(2-(3-((2S,3S)-2-azido-3-(4-chlorophenyl)-3-(3,5-difluorophenyl)propanamido)-5-fluoropyridin-4-yl)ethyl)-5-((((2,2,2-trifluoroethyl)carbamoyl)oxy)methyl)morpholine-4-carboxylate

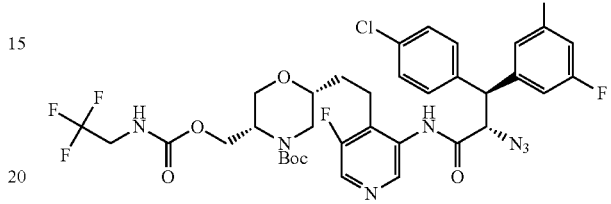

The product from step 1 (105 mg, 0.31 mmol) and the product from step 4 of Example 89 (150 mg, 0.31 mmol) were dissolved in pyridine (1 mL) and the stirred solution was cooled to −10° C. in an ice/acetone bath. To the cold solution was added POCl3 dropwise (0.035 mL, 0.38 mmol). The mixture was stirred at −10° C. for 30 min. The reaction was quenched by the addition of saturated aqueous NaHCO3 solution (1 mL) and the mixture was allowed to warm to ambient temperature. The mixture was diluted with water (10 mL) and extracted with dichloromethane (3×10 mL). The combined dichloromethane phases were dried (Na2SO4), filtered, and the filtrate solvents were removed in vacuo. The residue was purified on a 12 g silica gel column using a gradient elution of 0-70% EtOAc:hexanes. Fractions containing product were combined and the solvents were removed in vacuo to give the title compound as a gum. (M+H)+=800.6.

Step 3. (2R,5S)-tert-butyl 2-(2-(3-((2S,3S)-2-amino-3-(4-chlorophenyl)-3-(3,5-difluorophenyl)propanamido)-5-fluoropyridin-4-yl)ethyl)-5-((((2,2,2-trifluoroethyl)carbamoyl)oxy)methyl)morpholine-4-carboxylate

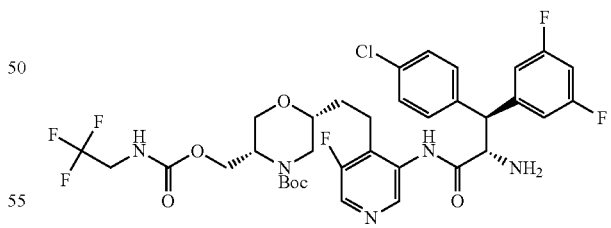

The product from step 2 (150 mg, 0.19 mmol) and triphenylphosphine (74 mg, 0.28 mmol) were dissolved in THF (4 mL) and to the solution was added water (1 mL). The mixture was heated to reflux under a nitrogen atmosphere for 12 h. The mixture was cooled to ambient temperature and the solvents were removed in vacuo. The residue was purified on a 12 g silica gel column eluting with a gradient of 0-10% methanol:chloroform. Fractions containing product were combined and the solvents were removed in vacuo to give the title compound as a gum. (M+H)+=774.7.

Step 4. (βS)-β-(4-Chlorophenyl)-3,5-difluoro-N-(5-fluoro-4-{2-[(2R,5S)-5-({[(2,2,2-trifluoroethyl)carbamoyl]oxy}methyl)morpholin-2-yl]ethyl}pyridin-3-yl)-L-phenylalaninamide The product from step 3 (60 mg, 0.078 mmol) was dissolved in a solution of 4M HCl in dioxane (1 mL, 4 mmol) and the solution was stirred at ambient temperature for 1 h. The solvent was removed under reduced pressure and the residue was dried in vacuo for 12 h to give an HCl salt of the title compound as a solid. LCMS: RT=0.95 min (2 min gradient), MS (ES) m/z=674.6 (M+H)$^+$.

EXAMPLE 98

(βS)-β-(4-Chlorophenyl)-N-(5-fluoro-4-{2-[(2R,5S)-5-({[(2,2,2-trifluoroethyl)carbamoyl]oxy}methyl)morpholin-2-yl]ethyl}pyridin-3-yl)-3-(trifluoromethoxy)-L-phenylalaninamide

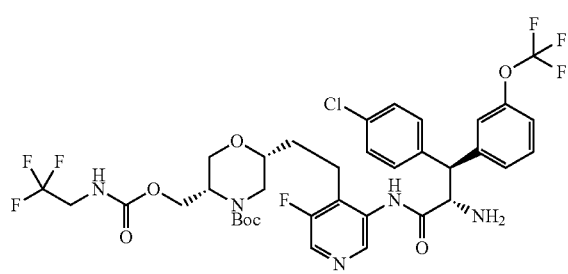 [SMILES: CC(C)(C)OC(=O)N1C[C@@H](CCc2c(F)cncc2NC(=O)[C@@H](N)[C@@H](c2ccc(Cl)cc2)c2cccc(OC(F)(F)F)c2)OC[C@H]1COC(=O)NCC(F)(F)F]

Step 1. (2S,3S)-2-Azido-3-(4-chlorophenyl)-3-(3-(trifluoromethoxy)phenyl)propanoic acid

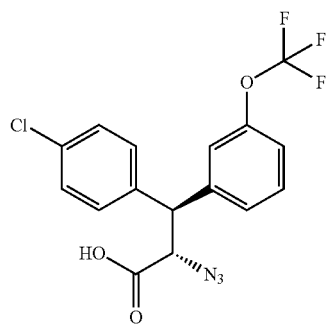 [SMILES: [N-]=[N+]=N[C@H](C(=O)O)[C@@H](c1ccc(Cl)cc1)c1cccc(OC(F)(F)F)c1]

The title compound was prepared from (4S)-4-phenyl-1,3-oxazolidin-2-one, 4-chlorobenzaldehyde, and 3-trifluoromethoxyphenylmagnesium bromide using the procedures given in steps 1-3 of Example 100 and steps 2-4 of Example 92.

Step 2. (βS)-β-(4-Chlorophenyl)-N-(5-fluoro-4-{2-[(2R,5S)-5-({[(2,2,2-trifluoroethyl)carbamoyl]oxy}methyl)morpholin-2-yl]ethyl}pyridin-3-yl)-3-(trifluoromethoxy)-L-phenylalaninamide The title compound was prepared from the product of step 1 using the procedures given in steps 2-4 of Example 93. MS (ES) m/z=722 (M+H)$^+$.

EXAMPLE 99

(βR)-β-(3,4-Difluorophenyl)-3-fluoro-N-(3-fluoro-2-{2-[(2R,5S)-5-({[(2,2,2-trifluoroethyl)carbamoyl]oxy}methyl)morpholin-2-yl]ethyl}phenyl)-L-phenylalaninamide

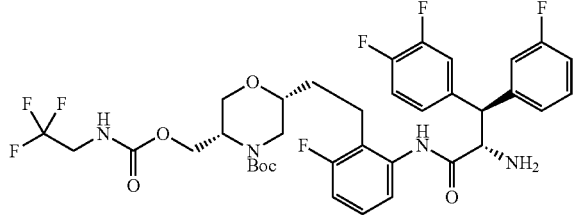 [SMILES: CC(C)(C)OC(=O)N1C[C@@H](CCc2c(F)cccc2NC(=O)[C@@H](N)[C@H](c2cccc(F)c2)c2ccc(F)c(F)c2)OC[C@H]1COC(=O)NCC(F)(F)F]

Step 1. (2S,3R)-2-Azido-3-(3,4-difluorophenyl)-3-(3-fluorophenyl)propanoic acid

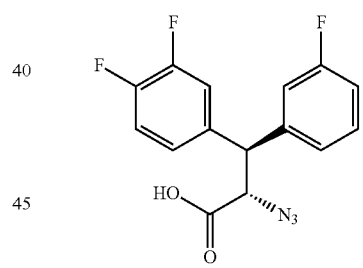

The title compound was prepared from (4S)-4-phenyl-1,3-oxazolidin-2-one, 3,4-difluorobenzaldehyde, and 3-fluorophenylmagnesium bromide using the procedures given in steps 1-3 of Example 100 and steps 2-4 of Example 92.

Step 2. (2R,5R)-tert-butyl 2-(2-fluoro-6-nitrostyryl)-5-(hydroxymethyl)morpholine-4-carboxylate

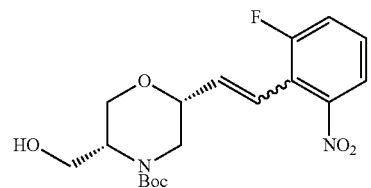 [SMILES: CC(C)(C)OC(=O)N1C[C@@H](C=Cc2c(F)cccc2[N+](=O)[O-])OC[C@H]1CO]

To a solution of the product from step 2 of Example 80 (6.79 g, 13.67 mmol) in MeOH (120 mL) was added 1N HCl (41.0 mL, 41.0 mmol) dropwise over a period of 5 min.

The mixture was stirred for 2 h at ambient temperature. To the solution was added 1N NaOH (41.0 mL, 41.0 mmol) dropwise over 10 min and the methanol was removed in vacuo. To the mixture was added water (150 mL) and ethyl acetate (50 mL). The layers were separated and the aqueous phase was extracted with two more 100 mL portions of ethyl acetate. The combined organic extracts were dried over Na$_2$SO$_4$, filtered, and concentrated in vacuo to give the title compound as a yellow oil. (M+H)$^+$=383.4.

Step 3. (2R,5S)-tert-butyl 2-(2-fluoro-6-nitrostyryl)-5-((((2,2,2-trifluoroethyl)carbamoyl)oxy)methyl)morpholine-4-carboxylate

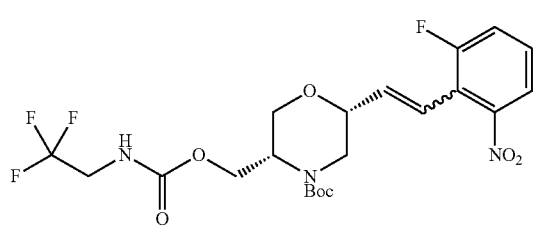 [SMILES: CC(C)(C)OC(=O)N1C[C@@H](C=Cc2c(F)cccc2[N+](=O)[O-])OC[C@H]1COC(=O)NCC(F)(F)F]

A mixture of the product from step 2 (5.2 g, 13.60 mmol) and carbonyl-1,1-diimidazole (8.82 g, 54.4 mmol) in anhydrous pyridine (30 mL) was stirred for 18 h at ambient temperature. To the slurry was added 2,2,2-trifluoroethylamine (26.7 mL, 340 mmol) and the mixture was stirred at ambient temperature for 72 h. The mixture was diluted with water (150 mL) and extracted with three 75 mL portions of EtOAc. The combined organic extracts were dried over Na$_2$SO$_4$, filtered, and evaporated in vacuo. The residue was purified on an 80 g silica gel column using a gradient elution of 20-50% EtOAc:hexane over 40 min. The fractions containing product were combined and evaporated in vacuo to give the title compound as a pale yellow solid. (M+H-tBu)$^+$=452.4.6.

Step 4. (2R,5S)-tert-butyl 2-(2-amino-6-fluorophenethyl)-5-((((2,2,2-trifluoroethyl)carbamoyl)oxy)methyl)morpholine-4-carboxylate

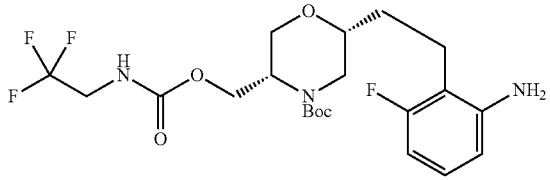 [SMILES: CC(C)(C)OC(=O)N1C[C@@H](CCc2c(N)cccc2F)OC[C@H]1COC(=O)NCC(F)(F)F]

A solution of the product from step 3 (6.9 g, 13.60 mmol) in trifluoroethanol (54 mL) was degassed with a stream of nitrogen. To the solution was added Pd(OH)$_2$ (1.910 g, 2.72 mmol) and the mixture was shaken under an atmosphere of hydrogen gas at 49 psi for 20 h. The catalyst was removed by filtration under nitrogen through a pad of Celite, and the filtercake was washed with ethanol. The filtrate solvents were removed in vacuo and the residue was purified on a 120 g silica gel column using a gradient elution of 0-70% EtOAc:hexane over 40 min. The title compound was obtained as a pale yellow oil. (M+H)$^+$=480.5.

Step 5. (2R,5S)-tert-butyl 2-(2-((2S,3R)-2-azido-3-(3,4-difluorophenyl)-3-(3-fluorophenyl)propanamido)-6-fluorophenethyl)-5-((((2,2,2-trifluoroethyl)carbamoyl)oxy)methyl)morpholine-4-carboxylate

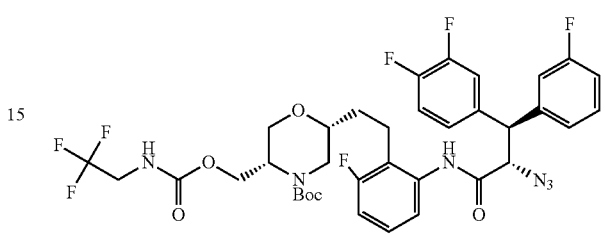

The product from step 1 (134 mg, 0.42 mmol) and the product from step 4 (200 mg, 0.42 mmol) were dissolved in pyridine (4 mL) and the stirred solution was cooled to –10° C. in an ice/acetone bath. To the cold solution was added POCl$_3$ dropwise (0.04 mL, 0.46 mmol). The mixture was stirred at –10° C. for 30 min. The reaction was quenched by the addition of saturated aqueous NaHCO$_3$ solution (5 mL) and the mixture was allowed to warm to ambient temperature. The mixture was diluted with water (20 mL) and extracted with dichloromethane (3×15 mL). The combined dichloromethane phases were dried (Na$_2$SO$_4$), filtered, and the filtrate solvents were removed in vacuo. The residue was purified on a 12 g silica gel column using a gradient elution of 0-100% EtOAc:hexanes. Fractions containing product were combined and the solvents were removed in vacuo to give the title compound as a gum. (M+H-Boc)$^+$=683.

Step 6. (2R,5S)-tert-butyl 2-(2-((2S,3R)-2-amino-3-(3,4-difluorophenyl)-3-(3-fluorophenyl)propanamido)-6-fluorophenethyl)-5-((((2,2,2-trifluoroethyl)carbamoyl)oxy)methyl)morpholine-4-carboxylate

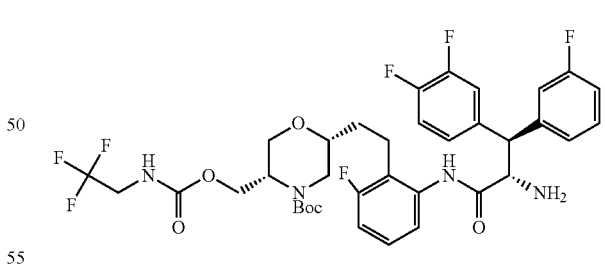

A solution of the product from step 5 (160 mg, 0.20 mmol) in EtOAc (4.50 mL) was de-gassed with a stream of nitrogen for 10 min. To the solution was added 10% palladium on charcoal (20 mg), and the mixture was stirred under an atmosphere of hydrogen gas at 1 atm pressure for 16 h. The catalyst was removed by filtration through a Celite pad, and the filter cake was washed with EtOAc (100 mL). The filtrate solvents were removed under reduced pressure. The residue was purified on a 12 g C-80 column using CH$_3$CN in H$_2$O. Fractions containing product were combined and lyophilized to provide the title compound as an off-white solid. (M+H)$^+$=757.

Step 7. (βR)-β-(3,4-Difluorophenyl)-3-fluoro-N-(3-fluoro-2-{2-[(2R,5S)-5-({[(2,2,2-trifluoroethyl)carbamoyl]oxy}methyl)morpholin-2-yl]ethyl}phenyl)-L-phenylalaninamide To a solution of the product from step 6 (50 mg, 0.06 mmol) in CH$_2$Cl$_2$ (2.0 mL) was added trifluoroacetic acid (1.0 mL) and the reaction mixture was stirred at ambient temperature for 2 h. The solvents were removed under reduced pressure and the residue was purified by HPLC on a C18 column using a gradient of 10-90% acetonitrile/water as the mobile phase. Fractions containing product were combined and lyophilized to provide the TFA salt of the title compound as white solid. MS (ES) m/z=657 (M+H)$^+$.

EXAMPLE 100

{(3S,6R)-6-[2-(2-{[(3R)-3-(1,3-Benzodioxol-5-yl)-3-(4-chlorophenyl)-L-alanyl]amino}-6-fluorophenyl)ethyl]morpholin-3-yl}methyl (2,2,2-trifluoroethyl) carbamate

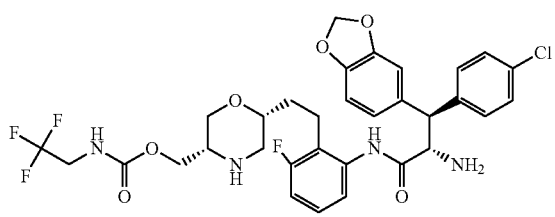 [SMILES: N[C@H](C(=O)Nc1cccc(F)c1CC[C@@H]1CN[C@H](COC(=O)NCC(F)(F)F)CO1)[C@H](c1ccc(Cl)cc1)c1ccc2c(c1)OCO2]

Step 1. (R)-3-(2-Bromoacetyl)-4-phenyloxazolidin-2-one

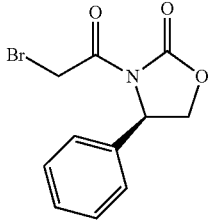 [SMILES: O=C(CBr)N1C(=O)OC[C@H]1c1ccccc1]

A solution of (4R)-4-phenyl-1,3-oxazolidin-2-one (100 g, 613 mmol) in THF (2 L) under a nitrogen atmosphere was cooled to −78° C. in dry ice-acetone bath. To the stirred solution was added n-BuLi (337 mL, 2 M solution in cyclohexane, 675 mmol) dropwise over a period of 30 min, followed by the addition of 2-bromoacetyl bromide (123.7 g, 613 mmol) over 15 min. The resulting solution was stirred at 25° C. for 2 h. The reaction was quenched with aqueous NH$_4$Cl (500 mL), and the mixture was extracted three times with EtOAc (3×1 L). The combined organic extracts were washed with water (500 mL) and brine (500 mL), dried (MgSO$_4$), filtered, and the solvent was removed under reduced pressure to give the title compound as a brown solid. The crude product was used directly in the next step.

Step 2. (R)-Dimethyl [2-oxo-2-(2-oxo-4-phenyloxazolidin-3-yl)ethyl]phosphonate

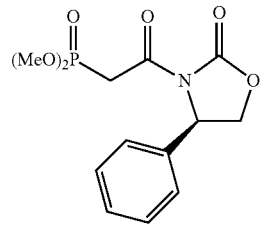

A solution of (R)-3-(2-bromoacetyl)-4-phenyloxazolidin-2-one (175 g, 616 mmol) and trimethyl phosphite (83.3 g, 671 mmol) in toluene (870 mL) was heated to reflux for 16 h. The reaction mixture was cooled to ambient temperature and the solvent was concentrated under reduced pressure to give a brown colored gum, which was triturated with 1:1 CH$_2$Cl$_2$ and hexanes (250 mL) to provide a brown solid. The solid was collected by filtration under reduced pressure and washed with CH$_2$Cl$_2$ (50 mL) to provide the product (98.8 g) as light brown solid.

Step 3. (R,E)-3-(3-(4-chlorophenyl)acryloyl)-4-phenyloxazolidin-2-one

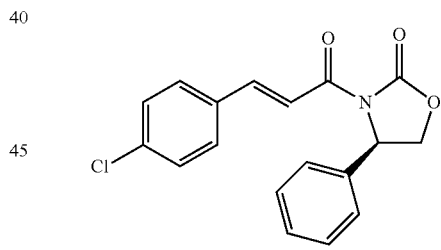

A solution of (R)-dimethyl 2-oxo-2-(2-oxo-4-phenyloxazolidin-3-yl)ethylphosphonate (60.7 g, 177.8 mmol) in dry THF (275 ml) under an atmosphere of N$_2$ was cooled to 0° C. in an ice-water bath. Potassium tert-butoxide (23.9 g, 213.4 mmol, 1.0 M solution in THF) was added over a period of 45 min in a dropwise manner and the reaction mixture stirred at 0° C. for 30 min. A solution of 4-chlorobenzaldehyde (25.0 g, 177.84 mmol) in dry THF (100 ml) was added over a period of 20 min and the reaction mixture was stirred at ambient temperature for 16 h. The reaction mixture was cooled to 0° C. and quenched with saturated solution of ammonium chloride (250 mL) and diluted with EtOAc (1.5 L). The biphasic system was stirred at ambient temperature for 10 min and the layers were separated. The organic layer was washed with brine (250 mL), dried (Na$_2$SO$_4$), filtered and concentrated under reduced pressure. The residue was purified by SiO$_2$ column using a gradient elution of 0-25% EtOAc in hexanes.

Fractions containing product were combined and the solvents were removed in vacuo to provide the product (43.0 g, 74%) as a pale yellow solid.

Step 4. (2S,3R)-2-Azido-3-(benzo[d][1,3]dioxol-5-yl)-3-(4-chlorophenyl)propanoic acid

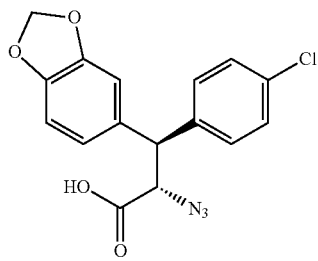 [SMILES: [N-]=[N+]=N[C@H](C(=O)O)[C@H](c1ccc(Cl)cc1)c1ccc2c(c1)OCO2]

The title compound was prepared from the product of step 3 and 1,3-benzodioxol-5-ylmagnesium bromide using the procedures given in steps 6 and 7 of Example 89 and steps 1-3 of Example 90.

Step 5. {(3S,6R)-6-[2-(2-{[(3R)-3-(1,3-Benzodioxol-5-yl)-3-(4-chlorophenyl)-L-alanyl]amino}-6-fluorophenyl)ethyl]morpholin-3-yl}methyl (2,2,2-trifluoroethyl)carbamate The title compound was prepared from the product of step 1 and the product of step 4 of Example 99 using the procedures given in steps 2-4 of Example 93. MS (ES) m/z=681 (M+H)+.

EXAMPLE 101

{(3S,6R)-6-[2-(2-{[(βS)-4-Chloro-β-(quinolin-4-yl)-L-phenylalanyl]amino}-6-fluorophenyl)ethyl]morpholin-3-yl}methyl (2,2,2-trifluoroethyl)carbamate

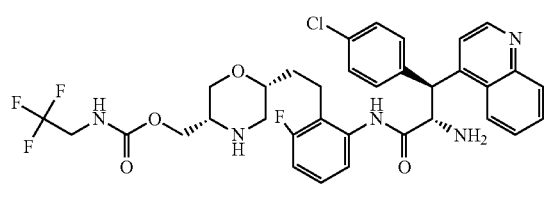 [SMILES: N[C@H](C(=O)Nc1cccc(F)c1CC[C@@H]1CN[C@H](COC(=O)NCC(F)(F)F)CO1)[C@@H](c1ccc(Cl)cc1)c1ccnc2ccccc12]

Step 1. (2S,3S)-2-azido-3-(4-chlorophenyl)-3-(quinolin-4-yl)propanoic acid

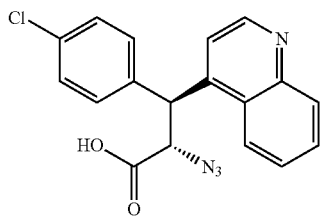 [SMILES: [N-]=[N+]=N[C@H](C(=O)O)[C@@H](c1ccc(Cl)cc1)c1ccnc2ccccc12]

The title compound was prepared from the product of step 2 of Example 100, quinoline-4-carbaldehyde, and 4-chlorophenylmagnesium bromide using the procedures given in steps 3 and 4 of Example 100.

Step 2. {(3S,6R)-6-[2-(2-{[(βS)-4-Chloro-β-(quinolin-4-yl)-L-phenylalanyl]amino}-6-fluorophenyl)ethyl]morpholin-3-yl}methyl (2,2,2-trifluoroethyl) carbamate The title compound was prepared from the product of step 1 and the product of step 4 of Example 99 using the procedures given in steps 2-4 of Example 93. MS (ES) m/z=688 (M+H)+.

EXAMPLE 102

(βR)-β-(4-Cyanophenyl)-3,4-difluoro-N-(3-fluoro-2-{2-[(2R,5S)-5-({[(2,2,2-trifluoroethyl)carbamoyl]oxy}methyl)morpholin-2-yl]ethyl}phenyl)-L-phenylalaninamide

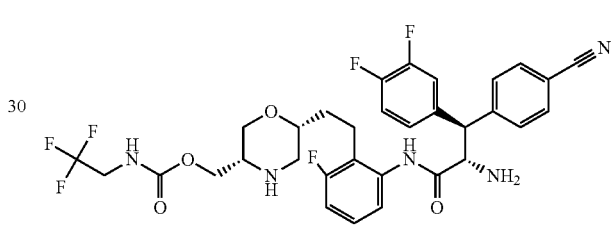

Step 1. (2S,3R)-2-Azido-3-(4-cyanophenyl)-3-(3,4-difluorophenyl)propanoic acid

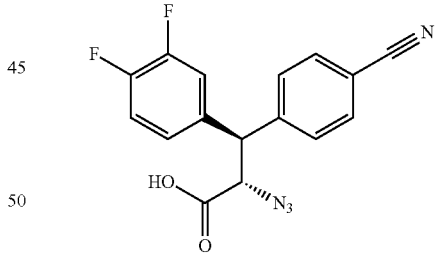

The title compound was prepared from 4-cyanocinammic acid and 3,4-difluorophenylmagnesium bromide using the procedures given in steps 5-7 of Example 89 and steps 1-3 of Example 90.

Step 2. (βR)-β-(4-Cyanophenyl)-3,4-difluoro-N-(3-fluoro-2-{2-[(2R,5S)-5-({[(2,2,2-trifluoroethyl)carbamoyl]oxy}methyl)morpholin-2-yl]ethyl}phenyl)-L-phenylalaninamide The title compound was prepared from the product of step 1 and the product of step 4 of Example 99 using the procedures given in steps 2-4 of Example 93. MS (ES) m/z=664 (M+H)+.

EXAMPLE 103

(βS)-4-Chloro-β-(3-fluorophenyl)-N-(5-fluoro-4-{2-[(2R,5S)-5-({[(2,2,2-trifluoroethyl)carbamoyl]oxy}methyl)morpholin-2-yl]ethyl}pyridin-3-yl)-Nα-(methoxycarbonyl)-L-phenylalaninamide

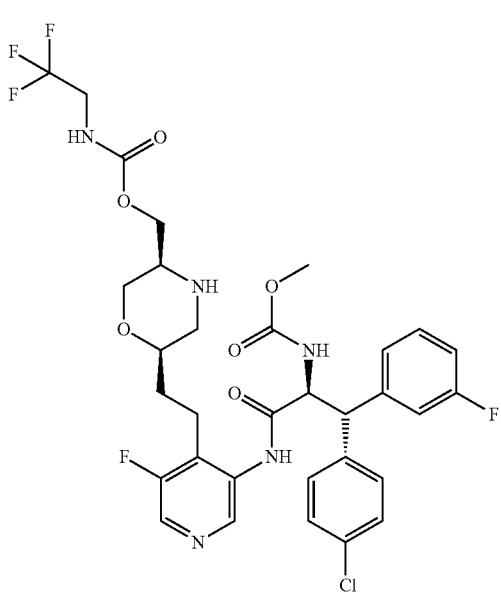

Step 1. (2S,3S)-2-Azido-3-(4-chlorophenyl)-3-(3-fluorophenyl)propanoic acid

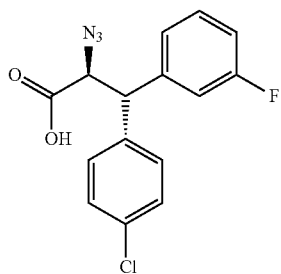

The title compound was prepared from 4-chlorocinammic acid and 3-fluorophenylmagnesium bromide using the procedures given in steps 1-4 of Example 92.

Step 2. (βS)-4-Chloro-β-(3-fluorophenyl)-N-(5-fluoro-4-{2-[(2R,5S)-5-({[(2,2,2-trifluoroethyl)carbamoyl]oxy}methyl)morpholin-2-yl]ethyl}pyridin-3-yl)-Nα-(methoxycarbonyl)-L-phenylalaninamide The title compound was prepared from the product of step 1 using the procedures given in steps 2 and 3 of Example 93 and steps 1 and 2 of Example 91. MS (ES) m/z=714 (M+H)⁺.

EXAMPLE 104

(βS)-β-1,3-Benzodioxol-5-yl-4-chloro-N-(5-fluoro-4-{2-[(2R,5S)-5-({[(2,2,2-trifluoroethyl)carbamoyl]oxy}methyl)morpholin-2-yl]ethyl}pyridin-3-yl)-Nα-(methoxycarbonyl)-L-phenylalaninamide

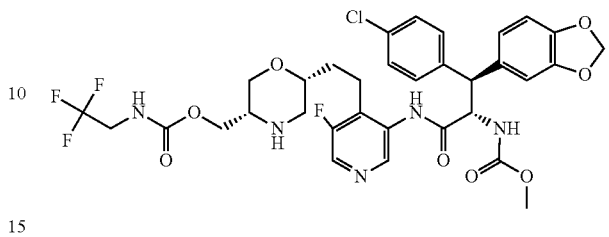

Step 1. (2S,3S)-2-Azido-3-(benzo[d][1,3]dioxol-5-yl)-3-(4-chlorophenyl)propanoic acid

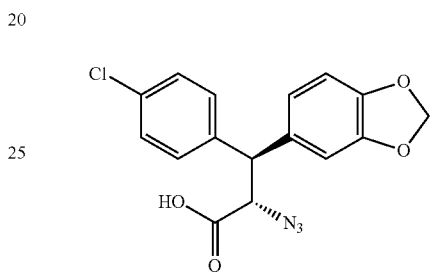

The title compound was prepared from (4S)-4-phenyl-1,3-oxazolidin-2-one, 4-chlorobenzaldehyde, and 1,3-benzodioxol-5-ylmagnesium bromide using the procedures given in steps 1-3 of Example 100 and steps 2-4 of Example 92.

Step 2. (2R,5S)-tert-butyl 2-(2-(3-((2S,3S)-2-azido-3-(benzo[d][1,3]dioxol-5-yl)-3-(4-chlorophenyl)propanamido)-5-fluoropyridin-4-yl)ethyl)-5-((((2,2,2-trifluoroethyl)carbamoyl)oxy)methyl)morpholine-4-carboxylate

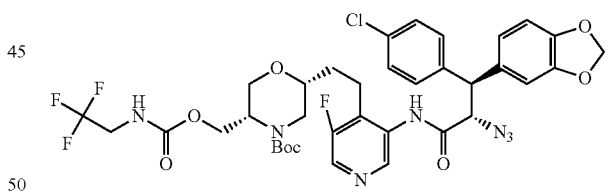

The product from step 1 (55 mg, 0.16 mmol) and the product from step 4 of Example 89 (76 mg, 0.16 mmol) were dissolved in pyridine (2 mL) and the stirred solution was cooled to −10° C. in an ice/acetone bath. To the cold solution was added POCl₃ (0.02 mL, 0.19 mmol). The mixture was stirred at −10° C. for 30 min. The reaction was quenched by the addition of saturated aqueous NaHCO₃ solution (2 mL) and the mixture was allowed to warm to ambient temperature. The mixture was diluted with water (mL) and extracted with dichloromethane (3×10 mL). The combined dichloromethane phases were dried (Na₂SO₄), filtered, and the filtrate solvents were removed in vacuo. The residue was purified on a 12 g silica gel column using a gradient elution of 0-100% EtOAc:hexanes. Fractions containing product were combined and the solvents were removed in vacuo to give the title compound as a gum. (M+H)⁺=808.

Step 3. (2R,5S)-tert-butyl 2-(2-(3-((2S,3S)-2-amino-3-(benzo[d][1,3]dioxol-5-yl)-3-(4-chlorophenyl)propanamido)-5-fluoropyridin-4-yl)ethyl)-5-((((2,2,2-trifluoroethyl)carbamoyl)oxy)methyl)morpholine-4-carboxylate

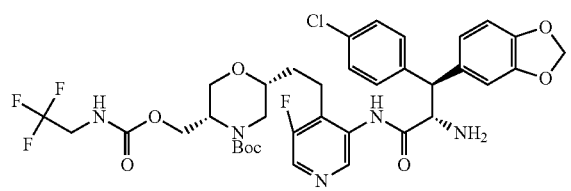 [SMILES: CC(C)(C)OC(=O)N1C[C@@H](CCc2c(F)cncc2NC(=O)[C@@H](N=[N+]=[N-])[C@@H](c2ccc(Cl)cc2)c2ccc3c(c2)OCO3)OC[C@H]1COC(=O)NCC(F)(F)F]

To a solution of the product from step 2 (80 mg, 0.102 mmol) in EtOAc (8 mL) and water (2 mL), was added trimethylphosphine (0.5 mL, 1M solution in THF, 0.5 mmol). The reaction mixture was stirred at ambient temperature for 2 h, then diluted with water (20 mL) and extracted with EtOAc (25 mL×3). The combined organic extracts were washed with brine (25 mL), dried (Na$_2$SO$_4$), filtered, and concentrated under reduced pressure to provide the title compound as colorless oil. This material was used in the next step without any additional purification. (M+H-Boc)$^+$=682.

Step 4. (2R,5S)-tert-butyl 2-(2-(3-((2S,3S)-3-(benzo[d][1,3]dioxol-5-yl)-3-(4-chlorophenyl)-2-((methoxycarbonyl)amino)propanamido)-5-fluoropyridin-4-yl)ethyl)-5-((((2,2,2-trifluoroethyl)carbamoyl)oxy)methyl)morpholine-4-carboxylate

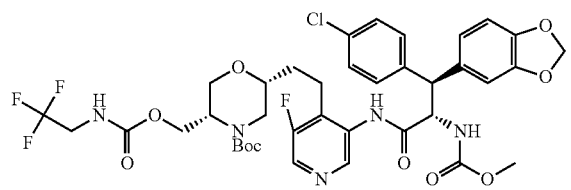 [SMILES: COC(=O)N[C@H](C(=O)Nc1cncc(F)c1CC[C@@H]1CN(C(=O)OC(C)(C)C)[C@H](COC(=O)NCC(F)(F)F)CO1)[C@@H](c1ccc(Cl)cc1)c1ccc2c(c1)OCO2]

To a stirred solution of the product from step 3 (50 mg, 0.06 mmol) in dichloromethane (2 mL) was added triethylamine (0.02 mL, 0.13 mmol) and methyl chloroformate (0.006 mL, 0.07 mmol). The mixture was stirred at ambient temperature for 6 h, then diluted with dichloromethane (10 mL) and washed with aqueous NaHCO$_3$ and brine. The organic phase was dried (MgSO$_4$), filtered, and the solvents were removed in vacuo. The residue was chromatographed on a 12 g SiO2 column using a gradient elution of 0-100% EtOc in hexanes. Fractions containing product were combined and the solvents were removed in vacuo to give the title compound as a gum. (M+H)$^+$=840.

Step 5. (βS)-β-1,3-Benzodioxol-5-yl-4-chloro-N-(5-fluoro-4-{2-[(2R,5S)-5-({[(2,2,2-trifluoroethyl)carbamoyl]oxy}methyl)morpholin-2-yl]ethyl}pyridin-3-yl)-Nα-(methoxycarbonyl)-L-phenylalaninamide To a solution of the product from step 4 (55 mg, 0.06 mmol) in CH$_2$Cl$_2$ (2.0 mL) was added trifluoroacetic acid (0.5 mL) and the reaction mixture was stirred at ambient temperature for 2 h. The solvents were removed under reduced pressure and the residue was purified by HPLC on a C18 column using a gradient of 10-90% acetonitrile/water as the mobile phase. Fractions containing product were combined and lyophilized to provide the TFA salt of the title compound as white solid. MS (ES) m/z=740 (M+H)$^+$.

EXAMPLE 105

(βS)-β-(4-Chlorophenyl)-3,5-difluoro-N-(5-fluoro-4-{2-[(2R,5S)-5-({[(2,2,2-trifluoroethyl)carbamoyl]oxy}methyl)morpholin-2-yl]ethyl}pyridin-3-yl)-Nα-(methoxycarbonyl)-L-phenylalaninamide

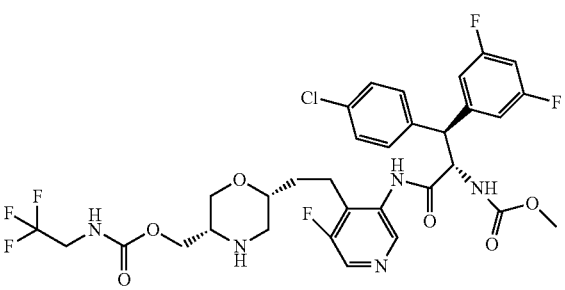 [SMILES: COC(=O)N[C@H](C(=O)Nc1cncc(F)c1CC[C@@H]1CN[C@H](COC(=O)NCC(F)(F)F)CO1)[C@@H](c1ccc(Cl)cc1)c1cc(F)cc(F)c1]

The title compound was prepared from (2S,3S)-2-azido-3-(4-chlorophenyl)-3-(3,5-difluorophenyl)propanoic acid (Example 1003, step 1) using the procedures given in steps 2 and 3 of Example 93 and steps 1 and 2 of Example 91. MS (ES) m/z=732.7 (M+H)$^+$.

Example 106

(βS)-β-(4-Chlorophenyl)-N-(5-fluoro-4-{2-[(2R,5S)-5-({[(2,2,2-trifluoroethyl)carbamoyl]oxy}methyl)morpholin-2-yl]ethyl}pyridin-3-yl)-Nα-(methoxycarbonyl)-3-(trifluoromethoxy)-L-phenylalaninamide

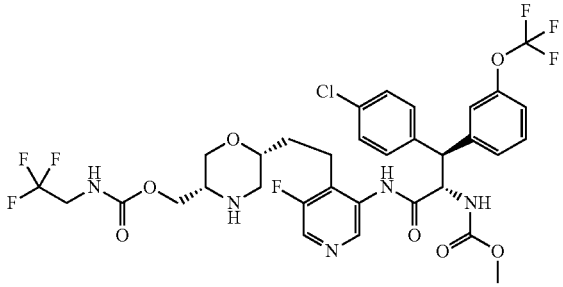 [SMILES: COC(=O)N[C@H](C(=O)Nc1cncc(F)c1CC[C@@H]1CN[C@H](COC(=O)NCC(F)(F)F)CO1)[C@@H](c1ccc(Cl)cc1)c1cccc(OC(F)(F)F)c1]

The title compound was prepared from (2S,3S)-2-azido-3-(4-chlorophenyl)-3-(3-(trifluoromethoxy)phenyl)propanoic acid (Example 1004, step 1) using the procedures given in steps 2 and 3 of Example 93 and steps 1 and 2 of Example 91. MS (ES) m/z=780 (M+H)$^+$.

EXAMPLE 107

(βR)-β-(4-Chlorophenyl)-N-(5-fluoro-4-{2-[(2R,5S)-5-({[(2,2,2-trifluoroethyl)carbamoyl]oxy}methyl)morpholin-2-yl]ethyl}pyridin-3-yl)-Nα-(methoxycarbonyl)-L-phenylalaninamide

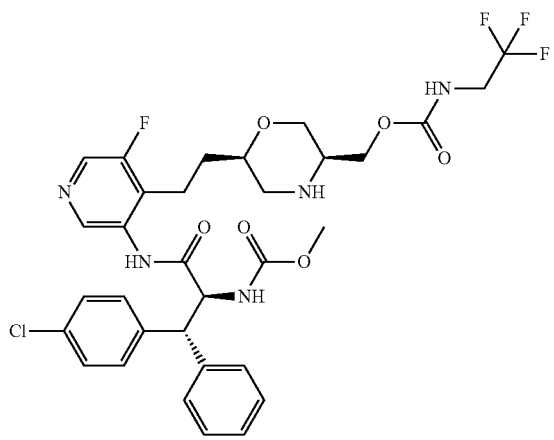 [SMILES: COC(=O)N[C@H](C(=O)Nc1cncc(F)c1CC[C@@H]1CN[C@H](COC(=O)NCC(F)(F)F)CO1)[C@H](c1ccccc1)c1ccc(Cl)cc1]

The title compound was prepared from (2S,3R)-2-azido-3-(4-chlorophenyl)-3-phenylpropanoic acid (Example 1001, step 1) using the procedures given in steps 2 and 3 of Example 93 and steps 1 and 2 of Example 91. MS (ES) m/z=696 (M+H)+.

EXAMPLE 108

4-Chloro-β-(4-chlorophenyl)-N-(3-fluoro-2-{2-[(2R,5S)-5-({[(2,2,2-trifluoroethyl)carbamoyl]oxy}methyl)morpholin-2-yl]ethyl}phenyl)-Nα-(methoxycarbonyl)-L-phenylalaninamide

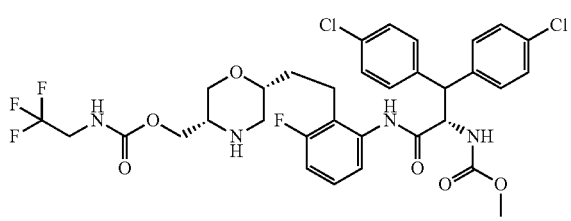 [SMILES: COC(=O)N[C@H](C(=O)Nc1cccc(F)c1CC[C@@H]1CN[C@H](COC(=O)NCC(F)(F)F)CO1)C(c1ccc(Cl)cc1)c1ccc(Cl)cc1]

Step 1.
(S)-2-Azido-3,3-bis(4-chlorophenyl)propanoic acid

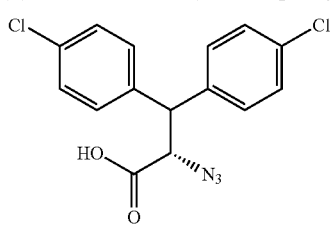 [SMILES: [N-]=[N+]=N[C@H](C(=O)O)C(c1ccc(Cl)cc1)c1ccc(Cl)cc1]

The title compound was prepared from 4-chlorophenylmagnesium bromide using the procedures (4S)-4-phenyl-1,3-oxazolidin-2-one, 4-chlorobenzaldehyde, and 3-trifluoromethoxyphenylmagnesium bromide using the procedures given in steps 1-3 of Example 100 and steps 2-4 of Example 92.

Step 2. 4-Chloro-β-(4-chlorophenyl)-N-(3-fluoro-2-{2-[(2R,5S)-5-({[(2,2,2-trifluoroethyl)carbamoyl]oxy}methyl)morpholin-2-yl]ethyl}phenyl)-Nα-(methoxycarbonyl)-L-phenylalaninamide The title compound was prepared from the product of step 1 and the product of step 4 of Example 99 using the procedures given in steps 2 and 3 of Example 93 and steps 1 and 2 of Example 91. MS (ES) m/z=729 (M+H)+.

EXAMPLE 109

(βR)-3-Chloro-N-(3-fluoro-2-{2-[(2R,5S)-5-({[(2,2,2-trifluoroethyl)carbamoyl]oxy}methyl)morpholin-2-yl]ethyl}phenyl)-Nα-(methoxycarbonyl)-O-methyl-β-phenyl-L-tyrosinamide

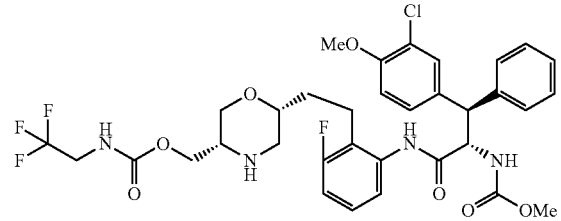 [SMILES: COC(=O)N[C@H](C(=O)Nc1cccc(F)c1CC[C@@H]1CN[C@H](COC(=O)NCC(F)(F)F)CO1)[C@H](c1ccccc1)c1ccc(OC)c(Cl)c1]

Step 1. (2S,3R)-2-Azido-3-(3-chloro-4-methoxyphenyl)-3-phenylpropanoic acid

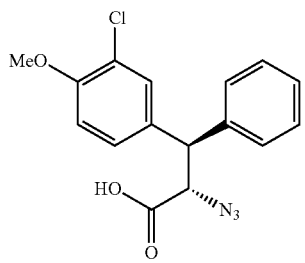 [SMILES: COc1ccc([C@@H](c2ccccc2)[C@H](N=[N+]=[N-])C(=O)O)cc1Cl]

The title compound was prepared from 4-methoxy-3-chlorocinammic acid and phenylmagnesium bromide using the procedures given in steps 1-4 of Example 92.

Step 2. (2R,5S)-tert-butyl 2-(2-((2S,3R)-2-azido-3-(3-chloro-4-methoxyphenyl)-3-phenylpropanamido)-6-fluorophenethyl)-5-((((2,2,2-trifluoroethyl)carbamoyl)oxy)methyl)morpholine-4-carboxylate

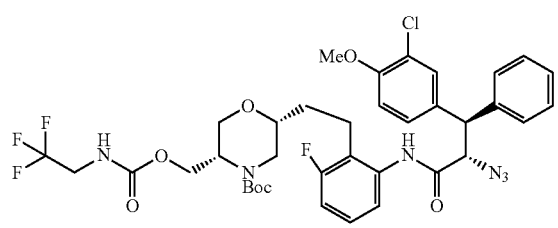 [SMILES: COc1ccc([C@@H](c2ccccc2)[C@H](N=[N+]=[N-])C(=O)Nc2cccc(F)c2CC[C@@H]2CN(C(=O)OC(C)(C)C)[C@H](COC(=O)NCC(F)(F)F)CO2)cc1Cl]

The product from step 1 (151 mg, 0.45 mmol) and the product from step 4 of Example 99 (200 mg, 0.42 mmol) were dissolved in pyridine (5 mL) and the stirred solution was cooled to −10° C. in an ice/acetone bath. To the cold solution was added POCl$_3$ dropwise (0.04 mL, 0.45 mmol). The mixture was stirred at −10° C. for 30 min. The reaction was quenched by the addition of saturated aqueous NaHCO$_3$ solution (5 mL) and the mixture was allowed to warm to ambient temperature. The mixture was diluted with water (20 mL) and extracted with dichloromethane (3×15 mL). The combined dichloromethane extracts were dried (Na$_2$SO$_4$), filtered, and the filtrate solvents were removed in vacuo. The residue was purified on a 12 g silica gel column using a gradient elution of 0-100% EtOAc:hexanes. Fractions containing product were combined and the solvents were removed in vacuo to give the title compound as a gum. (M+H−N$_2$)$^+$=764.

Step 3. (2R,5S)-tert-butyl 2-(2-((2S,3R)-2-amino-3-(3-chloro-4-methoxyphenyl)-3-phenylpropanamido)-6-fluorophenethyl)-5-((((2,2,2-trifluoroethyl)carbamoyl)oxy)methyl)morpholine-4-carboxylate

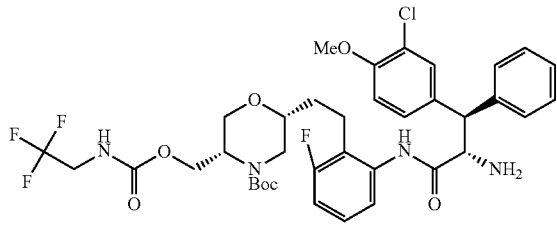 [SMILES: COc1ccc([C@@H](c2ccccc2)[C@H](N)C(=O)Nc2cccc(F)c2CC[C@@H]2CN(C(=O)OC(C)(C)C)[C@H](COC(=O)NCC(F)(F)F)CO2)cc1Cl]

To a solution of the product from step 2 (160 mg, 0.20 mmol) in EtOAc (8 mL) and water (2 mL), was added trimethylphosphine (1.0 mL, 1M solution in THF, 1.0 mmol). The reaction mixture was stirred at ambient temperature for 2 h, then diluted with water (20 mL) and extracted with EtOAc (25 mL×3). The combined organic extracts were washed with brine (25 mL), dried (Na$_2$SO$_4$), filtered and concentrated under reduced pressure to provide the title compound as colorless oil. (M+H)$^+$=767.

Step 4. (2R,5S)-tert-butyl 2-(2-((2S,3R)-3-(3-chloro-4-methoxyphenyl)-2-((methoxycarbonyl)amino)-3-phenylpropanamido)-6-fluorophenethyl)-5-((((2,2,2-trifluoroethyl)carbamoyl)oxy)methyl)morpholine-4-carboxylate

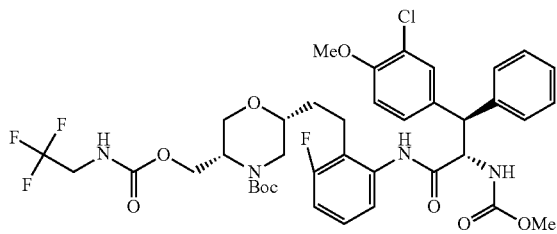 [SMILES: COC(=O)N[C@H](C(=O)Nc1cccc(F)c1CC[C@@H]1CN(C(=O)OC(C)(C)C)[C@H](COC(=O)NCC(F)(F)F)CO1)[C@H](c1ccccc1)c1ccc(OC)c(Cl)c1]

To a stirred solution of the product from step 3 (80 mg, 0.1 mmol) in dichloromethane (2 mL) was added triethylamine (0.02 mL, 0.16 mmol) and methyl chloroformate (0.01 mL, 0.12 mmol). The mixture was stirred at ambient temperature for 6 h, then diluted with dichloromethane (10 mL) and washed with aqueous NaHCO3 and brine. The organic phase was dried (MgSO4), filtered, and the solvents were removed in vacuo. The residue was chromatographed on a 12 g SiO2 column using a gradient elution of 0-100% EtOc in hexanes. Fractions containing product were combined and the solvents were removed in vacuo to give the title compound as a gum. (M+H)$^+$=825.

Step 5. (βR)-3-Chloro-N-(3-fluoro-2-{2-[(2R,5S)-5-({[(2,2,2-trifluoroethyl)carbamoyl]oxy}methyl)morpholin-2-yl]ethyl}phenyl)-Nα-(methoxycarbonyl)-O-methyl-β-phenyl-L-tyrosinamide To a solution of the product from step 4 (70 mg, 0.085 mmol) in CH$_2$Cl$_2$ (2.0 mL) was added trifluoroacetic acid (1.0 mL) and the reaction mixture was stirred at ambient temperature for 2 h. The solvents were removed under reduced pressure and the residue was purified by HPLC on a C18 column using a gradient of 10-90% acetonitrile/water as the mobile phase. Fractions containing product were combined and lyophilized to provide the TFA salt of the title compound as white solid. MS (ES) m/z=725 (M+H)$^+$.

EXAMPLE 110

(βS)-β-1,3-Benzodioxol-5-yl-4-chloro-N-(3-fluoro-2-{2-[(2R,5S)-5-({[(2,2,2-trifluoroethyl)carbamoyl]oxy}methyl)morpholin-2-yl]ethyl}phenyl)-Nα-(methoxycarbonyl)-L-phenylalaninamide

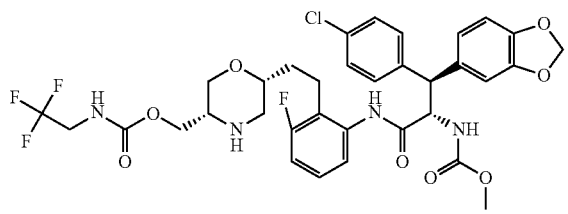 [SMILES: COC(=O)N[C@H](C(=O)Nc1cccc(F)c1CC[C@@H]1CN[C@H](COC(=O)NCC(F)(F)F)CO1)[C@@H](c1ccc(Cl)cc1)c1ccc2c(c1)OCO2]

The title compound was prepared from (2S,3S)-2-azido-3-(benzo[d][1,3]dioxol-5-yl)-3-(4-chlorophenyl)propanoic acid (Example 1010, step 1) and the product of step 4 of Example 99 using the procedures given in steps 2 and 3 of Example 93 and steps 1 and 2 of Example 91. MS (ES) m/z=739 (M+H)$^+$.

EXAMPLE 111

(βS)-4-Fluoro-N-(3-fluoro-2-{2-[(2R,5S)-5-({[(2,2,2-trifluoroethyl)carbamoyl]oxy}methyl)morpholin-2-yl]ethyl}phenyl)-Nα-(methoxycarbonyl)-β-[2-(trifluoromethoxy)phenyl]-L-phenylalaninamide

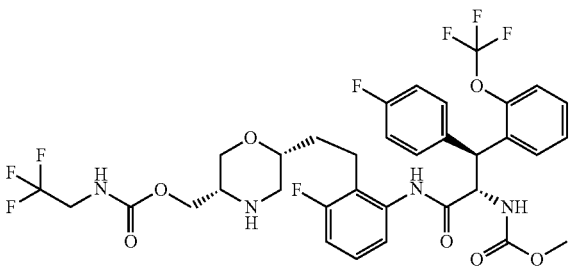 [SMILES: COC(=O)N[C@H](C(=O)Nc1cccc(F)c1CC[C@@H]1CN[C@H](COC(=O)NCC(F)(F)F)CO1)[C@@H](c1ccc(F)cc1)c1ccccc1OC(F)(F)F]

Step 1. (2S,3S)-2-Azido-3-(4-fluorophenyl)-3-(2-(trifluoromethoxy)phenyl)propanoic acid

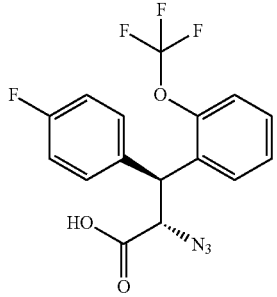 [SMILES: [N-]=[N+]=N[C@H](C(=O)O)[C@@H](c1ccc(F)cc1)c1ccccc1OC(F)(F)F]

The title compound was prepared from 4-fluorocinammic acid and 2-trifluoromethoxy-phenylmagnesium bromide using the procedures given in steps 1-4 of Example 92.

Step 2. (βS)-4-Fluoro-N-(3-fluoro-2-{2-[(2R,5S)-5-({[(2,2,2-trifluoroethyl)carbamoyl]oxy}methyl)morpholin-2-yl]ethyl}phenyl)-Nα-(methoxycarbonyl)-β-[2-(trifluoromethoxy)phenyl]-L-phenylalaninamide The title compound was prepared from the product of step 1 and the product of step 4 of Example 99 using the procedures given in steps 2 and 3 of Example 93 and steps 1 and 2 of Example 91. MS (ES) m/z=763 (M+H)+.

EXAMPLE 112

(βR)-4-Fluoro-N-(3-fluoro-2-{2-[(2R,5S)-5-({[(2,2,2-trifluoroethyl)carbamoyl]oxy}methyl)morpholin-2-yl]ethyl}phenyl)-Nα-(methoxycarbonyl)-β-pyridin-4-yl-L-phenylalaninamide

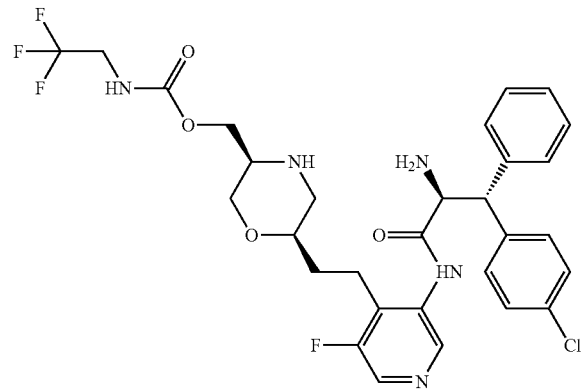 [SMILES: N[C@H](C(=O)Nc1cncc(F)c1CC[C@@H]1CN[C@H](COC(=O)NCC(F)(F)F)CO1)[C@H](c1ccccc1)c1ccc(Cl)cc1]

Step 1. (2S,3R)-2-azido-3-(4-fluorophenyl)-3-(pyridin-4-yl)propanoic acid

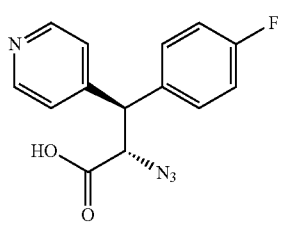 [SMILES: [N-]=[N+]=N[C@H](C(=O)O)[C@@H](c1ccncc1)c1ccc(F)cc1]

The title compound was prepared from 3-(4-pyridyl)propenoic acid and 4-fluorophenylmagnesium bromide using the procedures given in steps 1-4 of Example 92.

Step 2. (βR)-4-Fluoro-N-(3-fluoro-2-{2-[(2R,5S)-5-({[(2,2,2-trifluoroethyl)carbamoyl]oxy}methyl)morpholin-2-yl]ethyl}phenyl)-Nα-(methoxycarbonyl)-β-pyridin-4-yl-L-phenylalaninamide The title compound was prepared from the product of step 1 and the product of step 4 of Example 99 using the procedures given in steps 2 and 3 of Example 93 and steps 1 and 2 of Example 91. MS (ES) m/z=680 (M+H)+.

EXAMPLE 113

[(3S,6R)-6-{2-[2-Fluoro-6-({(3R)-3-(3-fluorophenyl)-3-[4-(methylsulfonyl)phenyl]propanoyl}amino)phenyl]ethyl}morpholin-3-yl]methyl (2,2,2-trifluoroethyl)carbamate

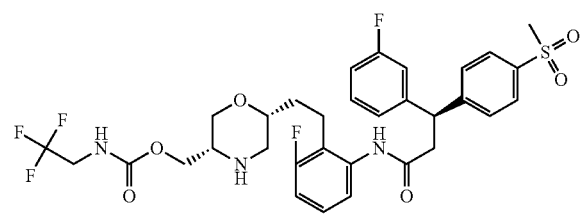 [SMILES: CS(=O)(=O)c1ccc([C@@H](CC(=O)Nc2cccc(F)c2CC[C@@H]2CN[C@H](COC(=O)NCC(F)(F)F)CO2)c2cccc(F)c2)cc1]

Step 1. (R)-3-(3-Fluorophenyl)-3-(4-(methylsulfonyl)phenyl)propanoic acid

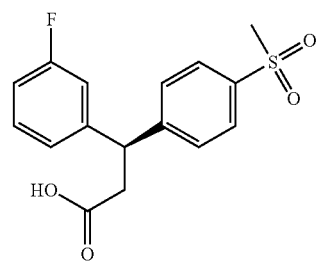 [SMILES: CS(=O)(=O)c1ccc([C@@H](CC(=O)O)c2cccc(F)c2)cc1]

The title compound was prepared from 4-methylsulfonyl-cinammic acid and 3-fluorophenylmagnesium bromide using the procedures given in steps 5-7 of Example 89.

Step 2. (2R,5S)-tert-butyl 2-(2-fluoro-6-((R)-3-(3-fluorophenyl)-3-(4-(methylsulfonyl)phenyl)propanamido)phenethyl)-5-((((2,2,2-trifluoroethyl)carbamoyl)oxy)methyl)morpholine-4-carboxylate

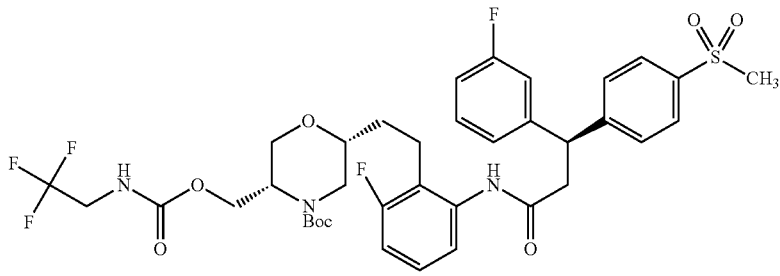 [SMILES: CC(C)(C)OC(=O)N1C[C@@H](CCc2c(F)cccc2NC(=O)C[C@H](c2ccc(S(C)(=O)=O)cc2)c2cccc(F)c2)OC[C@H]1COC(=O)NCC(F)(F)F]

The product from step 1 (34 mg, 0.1 mmol) and the product from step 4 of Example 99 (50 mg, 0.1 mmol) were dissolved in pyridine (1 mL) and the stirred solution was cooled to −10° C. in an ice/acetone bath. To the cold solution was added POCl₃ (0.01 mL, 0.12 mmol). The mixture was stirred at −10° C. for 30 min. The reaction was quenched by the addition of saturated aqueous NaHCO₃ solution (1 mL) and the mixture was allowed to warm to ambient temperature. The mixture was diluted with water (10 mL) and extracted with dichloromethane (3×10 mL). The combined dichloromethane phases were dried (Na₂SO₄), filtered, and the filtrate solvents were removed in vacuo. The residue was purified on a 12 g silica gel column using a gradient elution of 0-100% EtOAc: hexanes. Fractions containing product were combined and the solvents were removed in vacuo to give the title compound as a gum. (M+H−Boc)⁺=684.

Step 3. [(3S,6R)-6-{2-[2-Fluoro-6-({(3R)-3-(3-fluorophenyl)-3-[4-(methylsulfonyl)phenyl]propanoyl}amino)phenyl]ethyl}morpholin-3-yl]methyl (2,2,2-trifluoroethyl)carbamate To a solution of the product from step 2 (49 mg, 0.06 mmol) in CH₂Cl₂ (2.0 mL) was added trifluoroacetic acid (0.5 mL) and the reaction mixture was stirred at ambient temperature for 2 h. The solvents were removed under reduced pressure and the residue was purified by HPLC on a C18 column using a gradient of 10-90% acetonitrile/water as the mobile phase. Fractions containing product were combined and lyophilized to provide the TFA salt of the title compound as white solid. MS (ES) m/z=684 (M+H)⁺.

EXAMPLE 114

{(3S,6R)-6-[2-(3-{[(3S)-3-(4-Chlorophenyl)-3-(2,3-dihydro-1-benzofuran-5-yl)propanoyl]amino}-5-fluoropyridin-4-yl)ethyl]morpholin-3-yl}methyl (2,2,2-trifluoroethyl)carbamate Step 1. (S)-3-(4-Chlorophenyl)-3-(2,3-dihydrobenzofuran-5-yl)propanoic acid

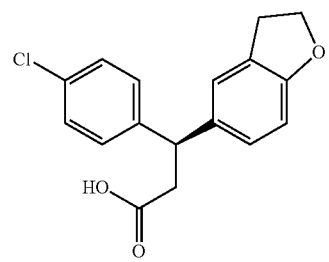

The title compound was prepared from 2,3-dihydrobenzofuran-5-carboxaldehyde and 4-chlorophenylmagnesium bromide using the procedures given in steps 1-3 of Example 100 and steps 6 and 7 of Example 89.

Step 2. {(3S,6R)-6-[2-(3-{[(3S)-3-(4-Chlorophenyl)-3-(2,3-dihydro-1-benzofuran-5-yl)propanoyl]amino}-5-fluoropyridin-4-yl)ethyl]morpholin-3-yl}methyl (2,2,2-trifluoroethyl)carbamate The title compound was prepared from the product of step 1 using the procedures given in steps 8 and 9 of Example 89. MS (ES) m/z=665 (M+H)⁺.

EXAMPLE 115

{(3S,6R)-6-[2-(3-{[(3R)-3-(4-Cyanophenyl)-3-(3,4-difluorophenyl)propanoyl]amino}-5-fluoropyridin-4-yl)ethyl]morpholin-3-yl}methyl (2,2,2-trifluoroethyl)carbamate

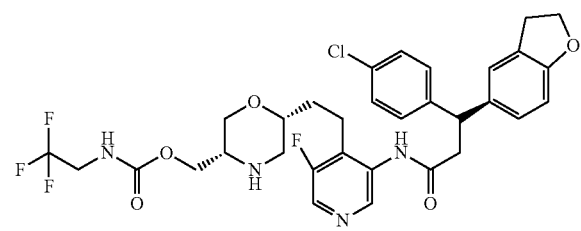

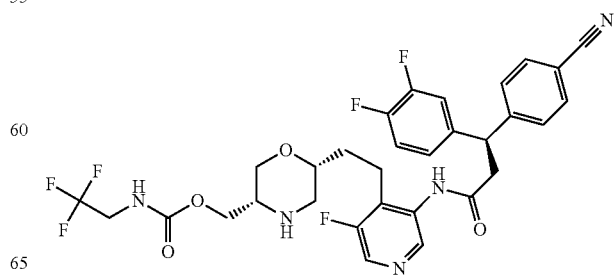

Step 1. (R)-3-(4-Cyanophenyl)-3-(3,4-difluorophenyl)propanoic acid

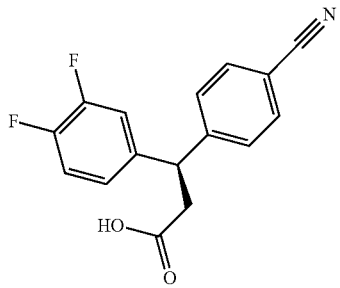 [SMILES: N#Cc1ccc([C@@H](CC(=O)O)c2ccc(F)c(F)c2)cc1]

The title compound was prepared from 4-cyanocinammic acid and 3,4-difluorophenylmagnesium bromide using the procedures given in steps 5-7 of Example 89.

Step 2. (2R,5S)-tert-butyl 2-(2-(3-((R)-3-(4-cyanophenyl)-3-(3,4-difluorophenyl)propanamido)-5-fluoropyridin-4-yl)ethyl)-5-((((2,2,2-trifluoroethyl)carbamoyl)oxy)methyl)morpholine-4-carboxylate

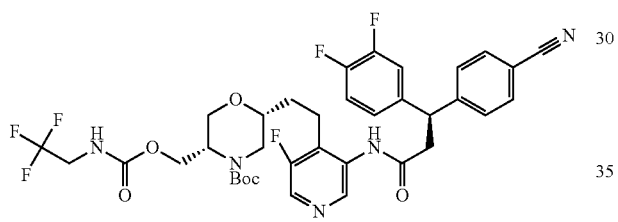

The product from step 1 (50 mg, 0.16 mmol) and the product from step 4 of Example 89 (78 mg, 0.16 mmol) were dissolved in pyridine (1 mL) and the stirred solution was cooled to −10° C. in an ice/acetone bath. To the cold solution was added POCl₃ dropwise (0.02 mL, 0.18 mmol). The mixture was stirred at −10° C. for 30 min. The reaction was quenched by the addition of saturated aqueous NaHCO₃ solution (1 mL) and the mixture was allowed to warm to ambient temperature. The mixture was diluted with water (10 mL) and extracted with dichloromethane (3×10 mL). The combined dichloromethane phases were dried (Na₂SO₄), filtered, and the filtrate solvents were removed in vacuo. The residue was purified on a 12 g silica gel column using a gradient elution of 0-100% EtOAc:hexanes. Fractions containing product were combined and the solvents were removed in vacuo to give the title compound as a gum. (M+H−Boc)⁺=650.

Step 3. {(3S,6R)-6-[2-(3-{[(3R)-3-(4-Cyanophenyl)-3-(3,4-difluorophenyl)propanoyl]amino}-5-fluoropyridin-4-yl)ethyl]morpholin-3-yl}methyl (2,2,2-trifluoroethyl)carbamate To a solution of the product from step 2 (60 mg, 0.08 mmol) in CH₂Cl₂ (2.0 mL) was added trifluoroacetic acid (0.5 mL) and the reaction mixture was stirred at ambient temperature for 2 h. The solvents were removed under reduced pressure and the residue was purified by HPLC on a C18 column using a gradient of 10-90% acetonitrile/water as the mobile phase.

Fractions containing product were combined and lyophilized to provide the TFA salt of the title compound as white solid. MS (ES) m/z=650 (M+H)⁺.

EXAMPLE 116

N-[2-(2-{(2R,5S)-5-[(Carbamoyloxy)methyl]morpholin-2-yl}ethyl)-3-fluorophenyl]-4-fluoro-β-(4-fluorophenyl)-L-phenylalaninamide

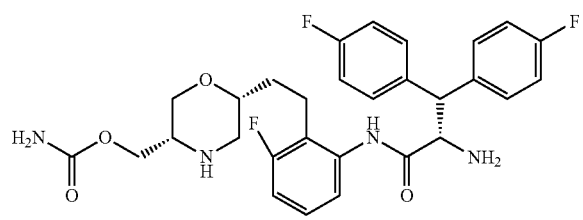 [SMILES: NC(=O)OC[C@@H]1CO[C@H](CCc2c(F)cccc2NC(=O)[C@@H](N)C(c2ccc(F)cc2)c2ccc(F)cc2)CN1]

The title compound was prepared from N-(tert-butoxycarbonyl)-4-fluoro-β-(4-fluorophenyl)-L-phenylalanine and (2R,5S)-tert-butyl 2-[(2-amino-6-fluorophenethyl)-5-((carbamoyloxy)methyl]morpholine-4-carboxylate (Example 118, step 2) using the procedures given in steps 2-4 of Example 93. MS (ES) m/z=557.5 (M+H)⁺.

Example 117

(βS)—N-[2-({(2S,5S)-5-[(Carbamoyloxy)methyl]morpholin-2-yl}methoxy)-3-fluorophenyl]-4-fluoro-β-(3-fluorophenyl)-Nα-(methoxycarbonyl)-L-phenylalaninamide

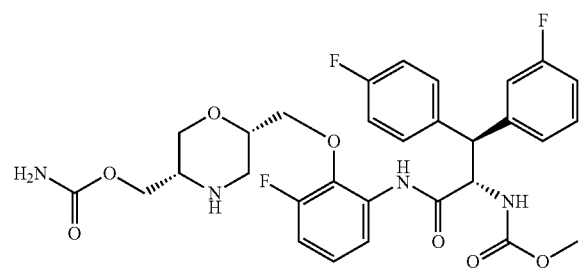 [SMILES: COC(=O)N[C@H](C(=O)Nc1cccc(F)c1OC[C@@H]1CN[C@H](COC(N)=O)CO1)[C@@H](c1ccc(F)cc1)c1cccc(F)c1]

Step 1. (2S,3S)-2-Azido-3-(3-fluorophenyl)-3-(4-fluorophenyl)propanoic acid

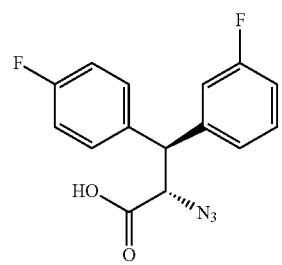 [SMILES: [N-]=[N+]=N[C@H](C(=O)O)[C@@H](c1ccc(F)cc1)c1cccc(F)c1]

The title compound was prepared from 4-fluorocinammic acid and 3-fluorophenylmagnesium bromide using the procedures given in steps 1-4 of Example 92.

Step 2. (2S,5S)-tert-butyl 5-{[(tert-butyldimethylsilyl)oxy]methyl}-2-[(2-fluoro-6-nitrophenoxy)methyl]morpholine-4-carboxylate

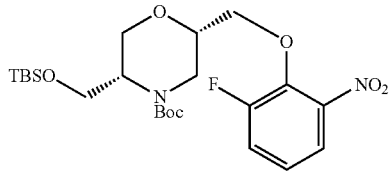 [SMILES: CC(C)(C)OC(=O)N1C[C@@H](COc2c(F)cccc2[N+](=O)[O-])OC[C@H]1CO[Si](C)(C)C(C)(C)C]

To a solution of (2S,5S)-tert-butyl 5-{[(tert-butyldimethylsilyl)oxy]methyl}-2-(hydroxymethyl)morpholine-4-carboxylate (7.2 g, 19.9 mmol) and 2,4-di-fluoronitrobenzene (6.34 g, 39.8 mmol) in anhydrous toluene (100 mL) under a nitrogen atmosphere, was added potassium carbonate (5.5 g, 39.8 mmol) and potassium hydroxide (2.4 g, 39.8 mmol). The reaction mixture was heated at reflux with vigorous stirring for 16 h. The reaction was cooled to ambient temperature and the solids were removed by filtration under reduced pressure. The filtrate solvent was concentrated to afford an oil. The oil was purified on a 120 g SiO₂ column using a gradient elution of 0-30% EtOAc in hexanes. Fractions containing product were combined and the solvents were removed in vacuo to provide the product (8.0 g) as a light yellow solid. LC MS: RT=4.52 min, (M-Boc)+H=401 (6 min gradient).

Step 3. (2S,5R)-tert-butyl 2-[(2-fluoro-6-nitrophenoxy)methyl]-5-(hydroxymethyl)morpholine-4-carboxylate

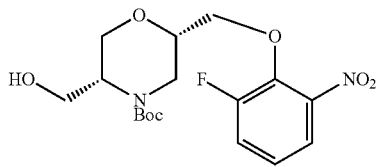 [SMILES: CC(C)(C)OC(=O)N1C[C@@H](COc2c(F)cccc2[N+](=O)[O-])OC[C@H]1CO]

To a solution of the product from step 2 (2.4 g, 4.8 mmol) in anhydrous THF (50 mL) under a nitrogen atmosphere was added a solution of tetra-n-butyl ammonium fluoride (1.0 M in THF, 9.6 mL) and the reaction mixture was stirred at ambient temperature for 2 h. The reaction mixture was diluted with EtOAc (200 mL) and washed with saturated solution of ammonium chloride (50 mL), brine (100 mL), dried (Na₂SO₄) and concentrated under reduced pressure. The residue was purified on a 40 g SiO₂ column using a gradient elution of 20-50% EtOAc in hexanes. Fractions containing product were combined and the solvents were removed in vacuo to provide the product (1.6 g) as a yellow oil. LC MS: RT=3.66 min, M+H=387 (6 min gradient).

Step 4. (2S,5S)-tert-butyl 5-[(carbamoyloxy)methyl]-2-[(2-fluoro-6-nitrophenoxy)methyl]morpholine-4-carboxylate

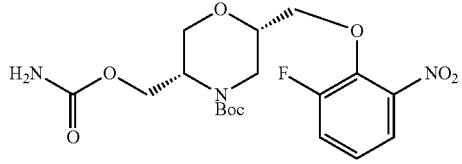

To a solution of the product from step 3 (1.6 g, 4.1 mmol) in pyridine (12 mL) was added carbonyl diimidazole (2.0 g, 12.3 mmol) and the mixture was heated in a sealed tube at 60° C. for 2 h. The reaction mixture was cooled to ambient temperature and NH₃ gas was bubbled into the solution for 5 min, and the mixture was heated in a sealed tube at 60° C. for 16 h. The reaction was cooled to ambient temperature and the solvent was concentrated under reduced pressure. The residue was purified on a 24 g SiO₂ column using a gradient elution of 20-70% EtOAc in hexanes. Fractions containing product were combined and the solvents were removed under reduced pressure to provide the product (1.4 g) as a colorless oil. LC MS: RT=3.60 min, M+H=430 (6 min gradient).

Step 5. (2S,5S)-tert-butyl 2-[(2-amino-6-fluorophenoxy)methyl]-5-[(carbamoyloxy)methyl]morpholine-4-carboxylate

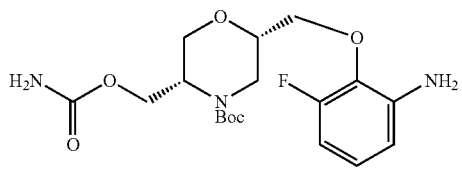 [SMILES: CC(C)(C)OC(=O)N1C[C@@H](COc2c(F)cccc2[N+](=O)[O-])OC[C@H]1COC(N)=O]

A solution of the product from step 4 (1.4 g, 3.3 mmol) was dissolved in ethyl acetate (50 mL) and the solution was degassed with a stream of nitrogen for 10 min. To the degassed solution was added 5% palladium on charcoal (400 mg), and the mixture was stirred under a hydrogen atmosphere at ambient pressure for 16 h. The catalyst was removed by filtration through a celite pad, and the filter cake was washed with CH₂Cl₂ (200 mL). The filtrate solvents were removed under reduced pressure. The residue was purified on a 12 g SiO₂ column using 20-50% EtOAc in hexanes to provide the product (700 mg) as a white solid. LC MS: RT=3.49 min, M+H=400 (6 min gradient).

Step 6. (βS)—N-[2-({(2S,5S)-5-[(Carbamoyloxy)methyl]morpholin-2-yl}methoxy)-3-fluorophenyl]-4-fluoro-β-(3-fluorophenyl)-Nα-(methoxycarbonyl)-L-phenylalaninamide The title compound was prepared from the product of step 1 and the product of step 5 using the procedures given in steps 2-4 of Example 93. MS (ES) m/z=617 (M+H)⁺.

EXAMPLE 118

(βS)—N-[2-(2-{(2R,5S)-5-[(Carbamoyloxy)methyl]morpholin-2-yl}ethyl)-3-fluorophenyl]-4-fluoro-β-(3-fluorophenyl)-Nα-(methoxycarbonyl)-L-phenylalaninamide

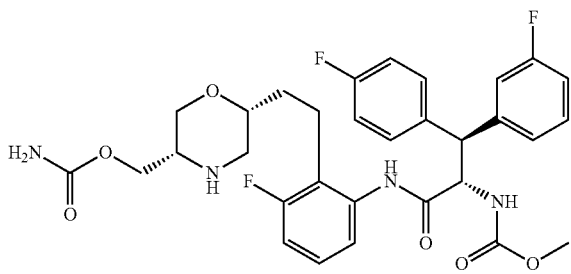 [SMILES: COC(=O)N[C@H](C(=O)Nc1cccc(F)c1CC[C@@H]1CN[C@H](COC(N)=O)CO1)[C@@H](c1ccc(F)cc1)c1cccc(F)c1]

Step 1. (2R,5S)-tert-butyl 5-[(carbamoyloxy)methyl)-2-((E)-2-fluoro-6-nitrostyryl]morpholine-4-carboxylate

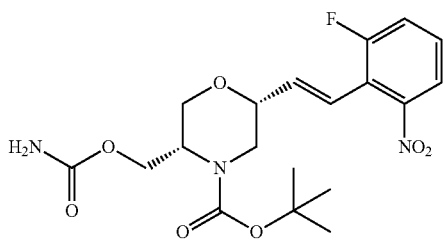 [SMILES: CC(C)(C)OC(=O)N1C[C@@H](/C=C/c2c(F)cccc2[N+](=O)[O-])OC[C@H]1COC(N)=O]

To a solution of (2R,5R)-tert-butyl 2-[(E)-2-fluoro-6-nitrostyryl)-5-(hydroxymethyl)]morpholine-4-carboxylate (5 g, 13 mmol) from step 2 of Example 99 in pyridine (15 mL) was added carbonyl diimidazole (8.4 g, 52 mmol) and the mixture was heated in sealed tube at 60° C. for 2 h. The reaction mixture was cooled to ambient temperature, then purged with NH₃ gas for 5 min and heated in a sealed tube at 60° C. for 16 h. The mixture was cooled to ambient temperature and the solvent was concentrated under reduced pressure. The residue was purified on an 80 g SiO$_2$ column using gradient elution of 0-50% EtOAc in hexanes. Fractions containing product were combined and the solvents were removed under reduced pressure to give the product (5.50 g,) a pale yellow gum.

Step 2. (2R,5S)-tert-butyl 2-[(2-amino-6-fluorophenethyl)-5-((carbamoyloxy)methyl)]morpholine-4-carboxylate

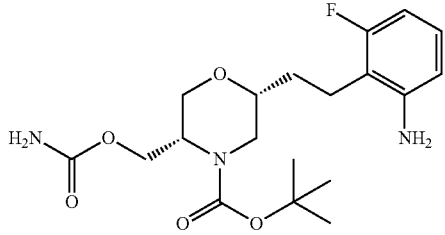 [SMILES: CC(C)(C)OC(=O)N1C[C@@H](CCc2c(N)cccc2F)OC[C@H]1COC(N)=O]

A solution of the product from step 1 (5.5 g, 12.9 mmol) in EtOAc (50 mL) was de-gassed under a nitrogen atmosphere for 5 min. To the degassed solution was added 5% palladium on carbon (1.3 g) under a nitrogen atmosphere. The mixture was stirred under an atmosphere of hydrogen gas at ambient pressure for 16 h. The catalyst was removed by filtration through a celite pad and the filter cake was washed with EtOAc (100 mL). The filtrate solvent was removed under reduced pressure to give the product (4.80 g,) as an off-white solid. LC MS: RT=2.37 min, M+H=398 (5 min gradient).

Step 3. (βS)—N-[2-(2-{(2R,5S)-5-[(Carbamoyloxy)methyl]morpholin-2-yl}ethyl)-3-fluorophenyl]-4-fluoro-β-(3-fluorophenyl)-Nα-(methoxycarbonyl)-L-phenylalaninamide The title compound was prepared from (2S,3S)-2-azido-3-(3-fluorophenyl)-3-(4-fluorophenyl)propanoic acid (Example 117, step 1) and the product from step 2 using the procedures given in steps 2 and 3 of Example 93 and steps 1 and 2 of Example 91. MS (ES) m/z=615 (M+H)⁺.

EXAMPLE 119

N-[4-(2-{(2R,5S)-5-[(Carbamoyloxy)methyl]morpholin-2-yl}ethyl)-5-fluoropyridin-3-yl]-4-fluoro-β-(4-fluorophenyl)-L-phenylalaninamide

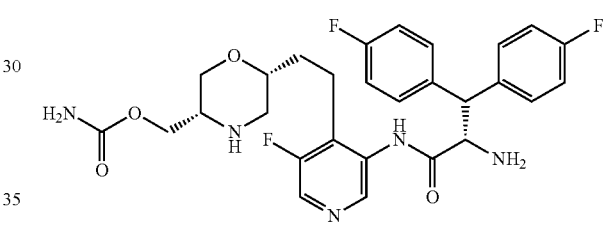

The title compound was prepared from tert-Butyl (2R,5R)-2-[2-(3-{[N-(tert-butoxycarbonyl)-4-fluoro-β-(4-fluorophenyl)-L-phenylalanyl]amino}-5-fluoropyridin-4-yl)ethyl]-5-(hydroxymethyl)morpholine-4-carboxylate (Example 79, step 7) using the procedures given in Example 118, step 1 and Example 90, step 6. MS (ES) m/z=558.5 (M+H)⁺.

EXAMPLE 120

(βS)—N-[2-(2-{(2R,5S)-5-[(Carbamoyloxy)methyl]morpholin-2-yl}ethyl)-3-fluorophenyl]-4-fluoro-β-(3-fluorophenyl)-L-phenylalaninamide

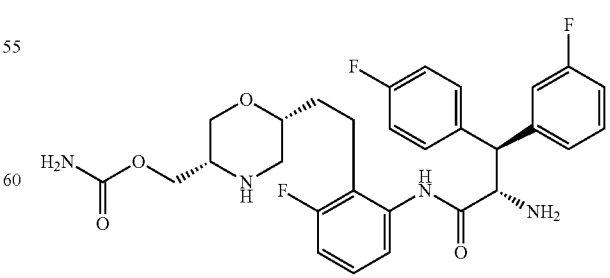

The title compound was prepared from (2S,3S)-2-azido-3-(3-fluorophenyl)-3-(4-fluorophenyl)propanoic acid (Example 117, step 1) and the product from step 2 of Example 118 using the procedures given in steps 2-4 of Example 93. MS (ES) m/z=557 (M+H)⁺.

EXAMPLE 121

4-Fluoro-N-(3-fluoro-2-{2-[(2R,5S)-5-({[(2-hydroxy-2-methylpropyl)carbamoyl]oxy}methyl)morpholin-2-yl]ethyl}phenyl)-β-(4-fluorophenyl)-Nα-(methoxycarbonyl)-L-phenylalaninamide

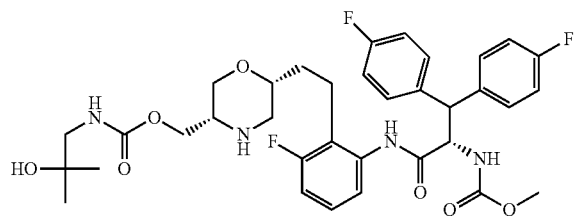 [SMILES: COC(=O)N[C@H](C(=O)Nc1cccc(F)c1CC[C@@H]1CN[C@H](COC(=O)NCC(C)(C)O)CO1)C(c1ccc(F)cc1)c1ccc(F)cc1]

The title compound was prepared from tert-butyl (2R,5R)-2-[2-(3-{[N-(tert-butoxycarbonyl)-4-fluoro-β-(4-fluorophenyl)-L-phenylalanyl]amino}-5-fluoropyridin-4-yl)ethyl]-5-(hydroxymethyl)morpholine-4-carboxylate (Example 79, step 7) and 1-amino-2-methylpropan-2-ol using the procedures described for Example 81 and step 2 of Example 91. MS (ES) m/z=687.4 (M+H)⁺.

EXAMPLE 122

4-Fluoro-β-(4-fluorophenyl)-N-(3-fluoro-2-{2-[(2R,5S)-5-({[(3S)-tetrahydro-2H-pyran-3-ylcarbamoyl]oxy}methyl)morpholin-2-yl]ethyl}phenyl)-L-phenylalaninamide

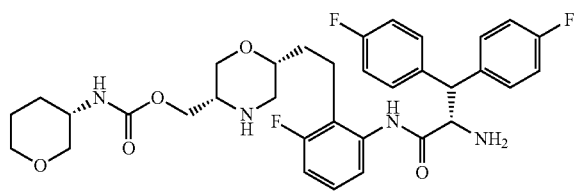 [SMILES: N[C@H](C(=O)Nc1cccc(F)c1CC[C@@H]1CN[C@H](COC(=O)N[C@H]2CCCOC2)CO1)C(c1ccc(F)cc1)c1ccc(F)cc1]

The title compound was prepared from tert-butyl (2R,5R)-2-[2-(3-{[N-(tert-butoxycarbonyl)-4-fluoro-β-(4-fluorophenyl)-L-phenylalanyl]amino}-5-fluoropyridin-4-yl)ethyl]-5-(hydroxymethyl)morpholine-4-carboxylate (Example 79, step 7) and (S)-tetrahydro-2H-pyran-3-amine using the procedures described for Example 81. MS (ES) m/z=641.4 (M+H)⁺.

EXAMPLE 123

4-Fluoro-N-[5-fluoro-4-(2-{(2R,5S)-5-[({[(2-methyltetrahydrofuran-2-yl)methyl]carbamoyl}oxy)methyl]morpholin-2-yl}ethyl)pyridin-3-yl]-β-(4-fluorophenyl)-L-phenylalaninamide

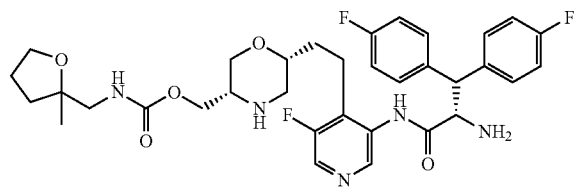 [SMILES: CC1(CNC(=O)OC[C@@H]2CO[C@H](CCc3c(F)cncc3NC(=O)[C@@H](N)C(c3ccc(F)cc3)c3ccc(F)cc3)CN2)CCCO1]

The title compound was prepared from tert-butyl (2R,5R)-2-[2-(3-{[N-(tert-butoxycarbonyl)-4-fluoro-β-(4-fluorophenyl)-L-phenylalanyl]amino}-5-fluoropyridin-4-yl)ethyl]-5-(hydroxymethyl)morpholine-4-carboxylate (Example 79, step 7) and (2-methyltetrahydrofuran-2-yl)methanamine using the procedures described for Example 81.

EXAMPLE 124

(βR)-4-Chloro-3-fluoro-β-(3-fluorophenyl)-N-(3-fluoro-2-{2-[(2R,5S)-5-({[(3R)-tetrahydro-2H-pyran-3-ylcarbamoyl]oxy}methyl)morpholin-2-yl]ethyl}phenyl)-Nα-(methoxycarbonyl)-L-phenylalaninamide

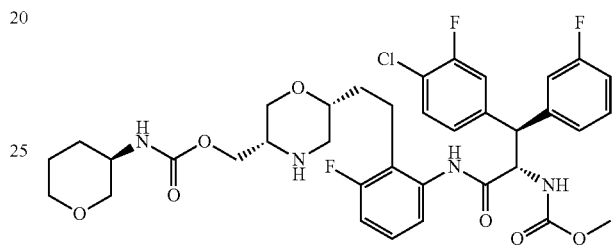

The title compound was prepared from (2S,3R)-2-azido-3-(4-chloro-3-fluorophenyl)-3-(3-fluorophenyl)propanoic acid (Example 94, step 1) using the procedures described for Example 150, steps 4 and Example 151 using (R)-tetrahydro-2H-pyran-3-amine and Example 91, step 2. MS (ES) m/z=733.5 (M+H)⁺.

EXAMPLE 125

(βS)-β-(3,5-Difluorophenyl)-4-fluoro-N-(5-fluoro-4-{2-[(2R,5S)-5-({[(3R)-tetrahydro-2H-pyran-3-ylcarbamoyl]oxy}methyl)morpholin-2-yl]ethyl}pyridin-3-yl)-Nα-(methoxycarbonyl)-D-phenylalaninamide

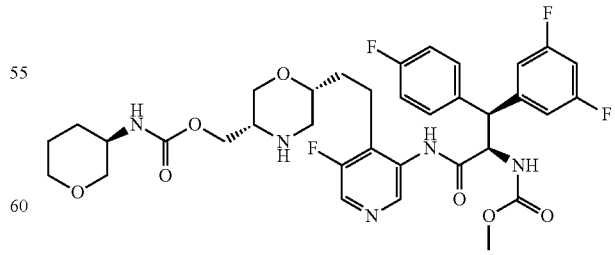

The title compound was prepared from (2R,3S)-2-azido-3-(3,5-difluorophenyl)-3-(4-fluorophenyl)propanoic acid (Example 90, step 3) using the procedures described for Example 124. MS (ES) m/z=718.5 (M+H)⁺.

EXAMPLE 126

4-Fluoro-N-[3-fluoro-2-(2-{(2R,5S)-5-[({[(5-meth-ylisoxazol-3-yl)methyl]carbamoyl}oxy)methyl]mor-pholin-2-yl}ethyl)phenyl]-β-(4-fluorophenyl)-Nα-(methoxycarbonyl)-L-phenylalaninamide

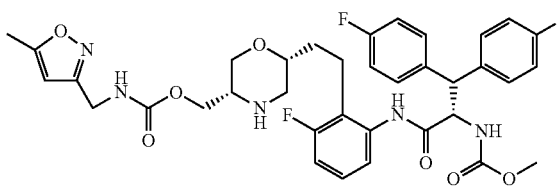

The title compound was prepared from tert-butyl (2R,5R)-2-[2-(3-{[N-(tert-butoxycarbonyl)-4-fluoro-β-(4-fluorophenyl)-L-phenylalanyl]amino}-5-fluoropyridin-4-yl)ethyl]-5-(hydroxymethyl)morpholine-4-carboxylate (Example 79, step 7) and (5-methylisoxazol-3-yl)methanamine using the procedures described for Example 81 and step 2 of Example 91. MS (ES) m/z=710.5 (M+H)⁺.

EXAMPLE 127

(βR)-4-Fluoro-N-(5-fluoro-4-{2-[(2R,5S)-5-({[(2,2,2-trifluoroethyl)carbamoyl]oxy}methyl)morpholin-2-yl]ethyl}pyridin-3-yl)-β-(tetrahydro-2H-pyran-4-yl)-L-phenylalaninamide

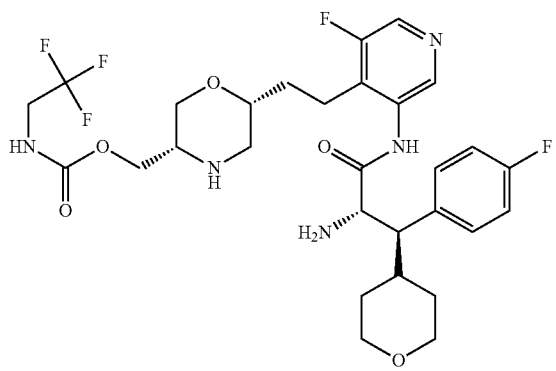 [SMILES: N[C@H](C(=O)Nc1cncc(F)c1CC[C@@H]1CN[C@H](COC(=O)NCC(F)(F)F)CO1)[C@@H](c1ccc(F)cc1)C1CCOCC1]

Step 1. (2S,3R)-2-Azido-3-(4-fluorophenyl)-3-(tetrahydro-2H-pyran-4-yl)propanoic acid

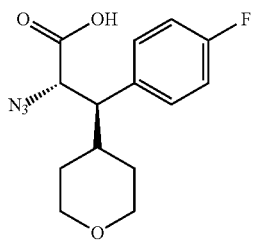 [SMILES: [N-]=[N+]=N[C@H](C(=O)O)[C@@H](c1ccc(F)cc1)C1CCOCC1]

The title compound was prepared from tetrahydropyran-4-carboxaldehyde and 4-fluorophenylmagnesium bromide using the procedures given in steps 1-3 of Example 100, steps 6 and 7 of Example 89, and steps 1-3 of Example 90.

Step 2. (βR)-4-Fluoro-N-(5-fluoro-4-{2-[(2R,5S)-5-({[(2,2,2-trifluoroethyl)carbamoyl]oxy}methyl)morpholin-2-yl]ethyl}pyridin-3-yl)-β-(tetrahydro-2H-pyran-4-yl)-L-phenylalaninamide The title compound was prepared from the product of step 1 and the product of step 4 of Example 89 using the procedures given in steps 2-4 of Example 93. MS (ES) m/z=630 (M+H)⁺.

EXAMPLE 128

(βR)-4-Fluoro-N-(3-fluoro-2-{2-[(2R,5S)-5-({[(2,2,2-trifluoroethyl)carbamoyl]oxy}methyl)morpholin-2-yl]ethyl}phenyl)-β-(tetrahydro-2H-pyran-4-yl)-L-phenylalaninamide

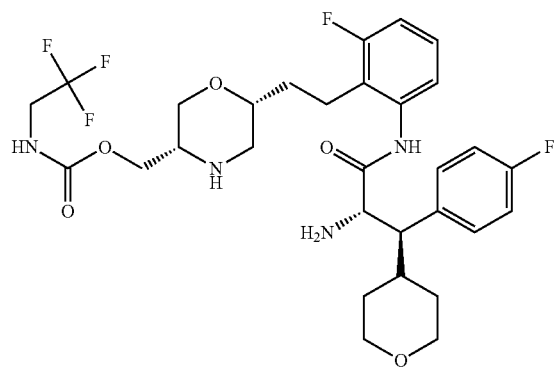 [SMILES: N[C@H](C(=O)Nc1cccc(F)c1CC[C@@H]1CN[C@H](COC(=O)NCC(F)(F)F)CO1)[C@@H](c1ccc(F)cc1)C1CCOCC1]

The title compound was prepared from (2S,3R)-2-azido-3-(4-fluorophenyl)-3-(tetrahydro-2H-pyran-4-yl)propanoic acid (Example 1033, step 1) and the product of step 4 of Example 99 using the procedures given in steps 2-4 of Example 93. MS (ES) m/z=629 (M+H)⁺.

EXAMPLE 129

(βR)-4-Chloro-3-fluoro-N-(3-fluoro-2-{2-[(2R,5S)-5-({[(2,2,2-trifluoroethyl)carbamoyl]oxy}methyl)morpholin-2-yl]ethyl}phenyl)-Nα-(methoxycarbonyl)-β-(tetrahydro-2H-pyran-4-yl)-L-phenylalaninamide

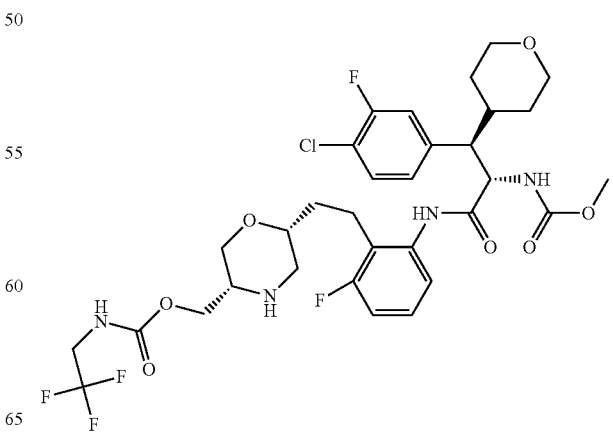

Step 1. (2S,3R)-2-Azido-3-(4-chloro-3-fluorophe-nyl)-3-(tetrahydro-2H-pyran-4-yl)propanoic acid

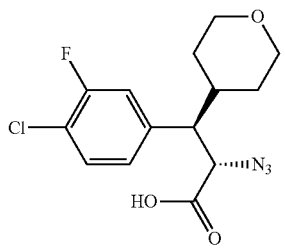 [SMILES: [N-]=[N+]=N[C@H](C(=O)O)[C@@H](c1ccc(Cl)c(F)c1)C1CCOCC1]

The title compound was prepared from tetrahydropyran-4-carboxaldehyde and 4-chloro-3-fluorophenylmagnesium bromide using the procedures given in steps 1-3 of Example 100, steps 6 and 7 of Example 89, and steps 1-3 of Example 90.

Step 2. (βR)-4-Chloro-3-fluoro-N-(3-fluoro-2-{2-[(2R,5S)-5-({[(2,2,2-trifluoroethyl)carbamoyl]oxy}methyl)morpholin-2-yl]ethyl}phenyl)-Nα-(methoxycarbonyl)-β-(tetrahydro-2H-pyran-4-yl)-L-phenylalaninamide The title compound was prepared from the product of step 1 and the product of step 4 of Example 99 using the procedures given in steps 2 and 3 of Example 93 and steps 1 and 2 of Example 91. MS (ES) m/z=721 (M+H)⁺.

EXAMPLE 130

(βR)-4-Fluoro-N-(3-fluoro-2-{2-[(2R,5S)-5-({[(2,2,2-trifluoroethyl)carbamoyl]oxy}methyl)morpholin-2-yl]ethyl}phenyl)-Nα-(methoxycarbonyl)-β-(tetrahydro-2H-pyran-4-yl)-L-phenylalaninamide

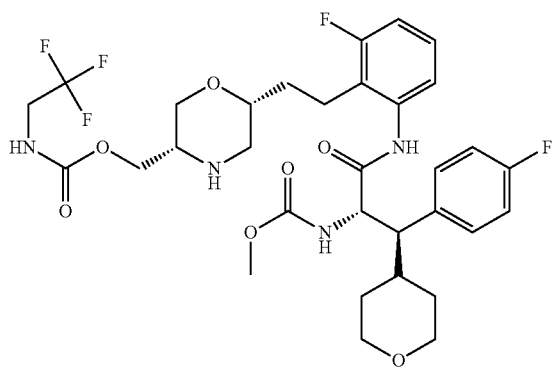 [SMILES: COC(=O)N[C@H](C(=O)Nc1cccc(F)c1CC[C@@H]1CN[C@H](COC(=O)NCC(F)(F)F)CO1)[C@@H](c1ccc(F)cc1)C1CCOCC1]

The title compound was prepared from (2S,3R)-2-azido-3-(4-fluorophenyl)-3-(tetrahydro-2H-pyran-4-yl)propanoic acid (Example 127, step 1) using the procedures given in step 2 of Example 129. MS (ES) m/z=687 (M+H)⁺.

EXAMPLE 131

(βR)-4-Chloro-3-fluoro-N-(3-fluoro-2-{2-[(2R,5S)-5-({[(2,2,2-trifluoroethyl)carbamoyl]oxy}methyl)morpholin-2-yl]ethyl}phenyl)-β-(tetrahydro-2H-pyran-4-yl)-L-phenylalaninamide

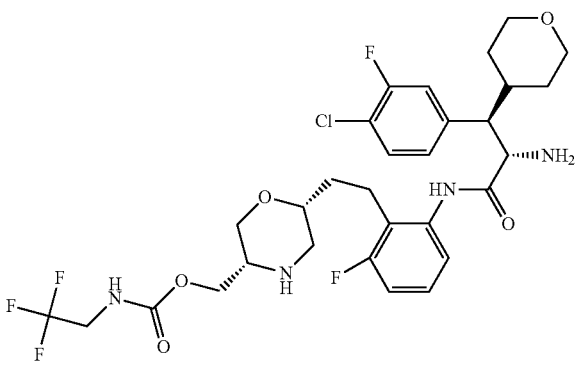 [SMILES: N[C@H](C(=O)Nc1cccc(F)c1CC[C@@H]1CN[C@H](COC(=O)NCC(F)(F)F)CO1)[C@@H](c1ccc(Cl)c(F)c1)C1CCOCC1]

The title compound was prepared from (2S,3R)-2-azido-3-(4-chloro-3-fluorophenyl)-3-(tetrahydro-2H-pyran-4-yl)propanoic acid (Example 1035, step 1) using the procedures and the product of step 4 of Example 99 using the procedures given in steps 2-4 of Example 93. MS (ES) m/z=663 (M+H)⁺.

EXAMPLE 132

(βS)-4-Chloro-3-fluoro-β-(5-fluoropyridin-3-yl)-N-(3-fluoro-2-{2-[(2R,5S)-5-({[(2,2,2-trifluoroethyl)carbamoyl]oxy}methyl)morpholin-2-yl]ethyl}phenyl)-Nα-(methoxycarbonyl)-L-phenylalaninamide

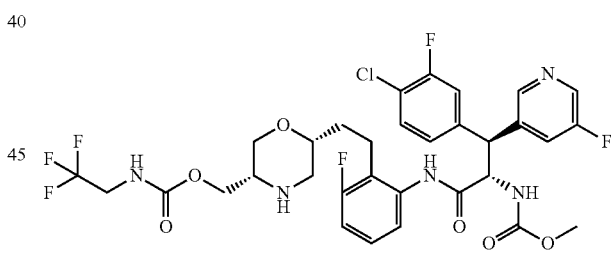

Step 1. (2S,3S)-2-Azido-3-(4-chloro-3-fluorophe-nyl)-3-(5-fluoropyridin-3-yl)propanoic acid

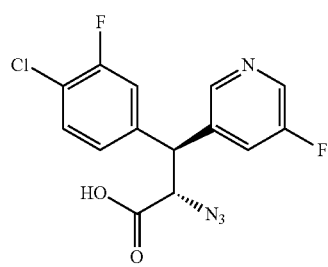 [SMILES: [N-]=[N+]=N[C@H](C(=O)O)[C@H](c1cncc(F)c1)c1ccc(Cl)c(F)c1]

The title compound was prepared from 5-fluoropyridine-3-carboxaldehyde and 4-chloro-3-fluorophenylmagnesium bromide using the procedures given in steps 3 and 4 of Example 100.

Step 2. (βS)-4-Chloro-3-fluoro-β-(5-fluoropyridin-3-yl)-N-(3-fluoro-2-{2-[(2R,5S)-5-({[(2,2,2-trifluoroethyl)carbamoyl]oxy}methyl)morpholin-2-yl]ethyl}phenyl)-Nα-(methoxycarbonyl)-L-phenylalaninamide The title compound was prepared from the product of step 1 and the product of step 4 of Example 99 using the procedures given in steps 2 and 3 of Example 93 and steps 1 and 2 of Example 91. MS (ES) m/z=732 (M+H)+.

EXAMPLE 133

[(3S,6R)-6-{2-[3-Fluoro-5-({(3S)-3-(4-fluorophenyl)-3-[6-(trifluoromethyl)pyridin-3-yl]propanoyl}amino)pyridin-4-yl]ethyl}morpholin-3-yl]methyl (2,2,2-trifluoroethyl)carbamate

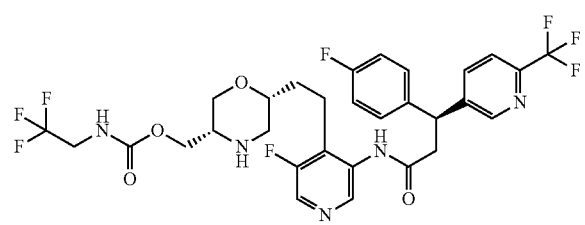 [SMILES: O=C(C[C@@H](c1ccc(F)cc1)c1ccc(C(F)(F)F)nc1)Nc1cncc(F)c1CC[C@@H]1CN[C@H](COC(=O)NCC(F)(F)F)CO1]

Step 1. (S)-3-(4-Fluorophenyl)-3-(6-(trifluoromethyl)pyridin-3-yl)propanoic acid

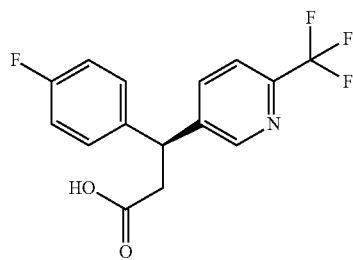 [SMILES: O=C(O)C[C@@H](c1ccc(F)cc1)c1ccc(C(F)(F)F)nc1]

The title compound was prepared from 2-trifluoromethylpyridine-5-carboxaldehyde and 4-fluorophenylmagnesium bromide using the procedures given in step 3 of Example 100 and steps 6 and 7 of Example 89.

Step 2. [(3S,6R)-6-{2-[3-Fluoro-5-({(3S)-3-(4-fluorophenyl)-3-[6-(6-(trifluoromethyl)pyridin-3-yl]propanoyl}amino)pyridin-4-yl]ethyl}morpholin-3-yl]methyl (2,2,2-trifluoroethyl)carbamate The title compound was prepared from the product of step y using the procedures given in steps 8 and 9 of Example 89. MS (ES) m/z=676 (M+H)+.

EXAMPLE 134

(βS)-4-Chloro-β-(3-fluoropyridin-4-yl)-N-(3-fluoro-2-{2-[(2R,5S)-5-({[(2,2,2-trifluoroethyl)carbamoyl]oxy}methyl)morpholin-2-yl]ethyl}phenyl)-Nα-(methoxycarbonyl)-L-phenylalaninamide

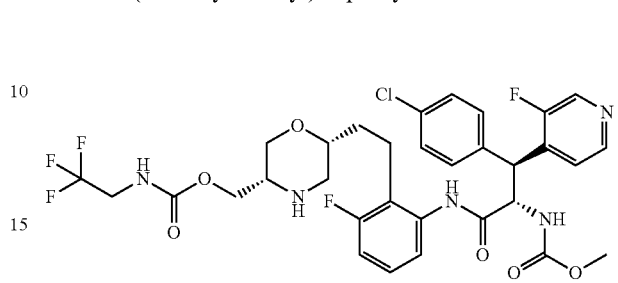

Step 1. (2S,3S)-2-Azido-3-(4-chlorophenyl)-3-(3-fluoropyridin-4-yl)propanoic acid

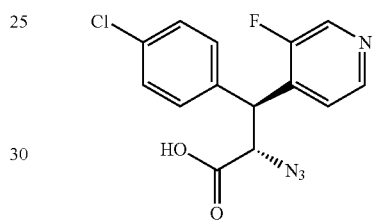

The title compound was prepared from 3-fluoropyridine-4-carboxaldehyde and 4-chlorophenylmagnesium bromide using the procedures given in step 3 and 4 of Example 100.

Step 2. (βS)-4-Chloro-β-(3-fluoropyridin-4-yl)-N-(3-fluoro-2-{2-[(2R,5S)-5-({[(2,2,2-trifluoroethyl)carbamoyl]oxy}methyl)morpholin-2-yl]ethyl}phenyl)-Nα-(methoxycarbonyl)-L-phenylalaninamide The title compound was prepared from the product of step 1 and the product of step 4 from Example 99 using the procedures given in steps 2 and 3 of Example 93 and steps 1 and 2 of Example 91. MS (ES) m/z=714 (M+H)+.

EXAMPLE 135

(βS)-3,4-Difluoro-β-(5-fluoropyridin-3-yl)-N-(5-fluoro-4-{2-[(2R,5S)-5-({[(2,2,2-trifluoroethyl)carbamoyl]oxy}methyl)morpholin-2-yl]ethyl}pyridin-3-yl)-Nα-(methoxycarbonyl)-L-phenylalaninamide

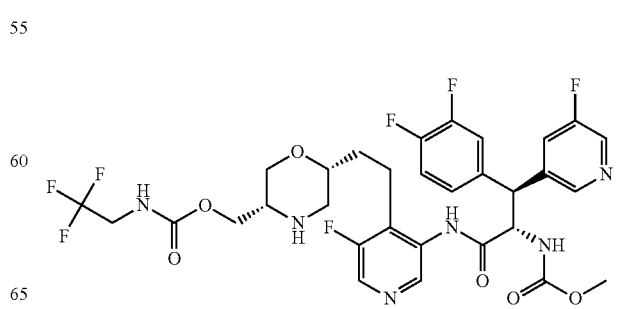

133

Step 1. (2S,3S)-2-Azido-3-(3,4-difluorophenyl)-3-(5-fluoropyridin-3-yl)propanoic acid

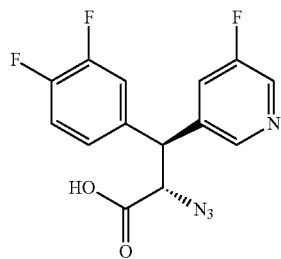 [SMILES: [N-]=[N+]=N[C@H](C(=O)O)[C@H](c1cncc(F)c1)c1ccc(F)c(F)c1]

The title compound was prepared from 3-fluoropyridine-5-carboxaldehyde and 3,4-difluorophenylmagnesium bromide using the procedures given in step 3 and 4 of Example 100.

Step 2. (βS)-3,4-Difluoro-β-(5-fluoropyridin-3-yl)-N-(5-fluoro-4-{2-[(2R,5S)-5-({[(2,2,2-trifluoroethyl)carbamoyl]oxy}methyl)morpholin-2-yl]ethyl}pyridin-3-yl)-Nα-(methoxycarbonyl)-L-phenylalaninamide The title compound was prepared from the product of step 1 using the procedures given in steps 2 and 3 of Example 93 and steps 1 and 2 of Example 91. MS (ES) m/z=717 (M+H)⁺.

EXAMPLE 136

(βS)-4-Chloro-β-(3-fluoropyridin-4-yl)-N-(3-fluoro-2-{2-[(2R,5S)-5-({[(2,2,2-trifluoroethyl)carbamoyl]oxy}methyl)morpholin-2-yl]ethyl}phenyl)-L-phenylalaninamide

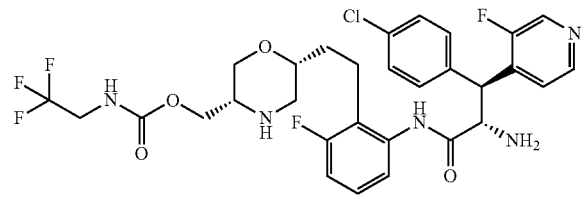 [SMILES: N[C@H](C(=O)Nc1cccc(F)c1CC[C@@H]1CN[C@H](COC(=O)NCC(F)(F)F)CO1)[C@@H](c1ccc(Cl)cc1)c1ccncc1F]

The title compound was prepared from (2S,3S)-2-azido-3-(4-chlorophenyl)-3-(3-fluoropyridin-4-yl)propanoic acid (Example 1040, step 1) and the product from step 4 of Example 99 using the procedures given in steps 2-4 of Example 93. MS (ES) m/z=656 (M+H)⁺.

Example 137

(βS)-4-Chloro-β-(5-fluoropyridin-3-yl)-N-(3-fluoro-2-{2-[(2R,5S)-5-({[(2,2,2-trifluoroethyl)carbamoyl]oxy}methyl)morpholin-2-yl]ethyl}phenyl)-Nα-(methoxycarbonyl)-L-phenylalaninamide

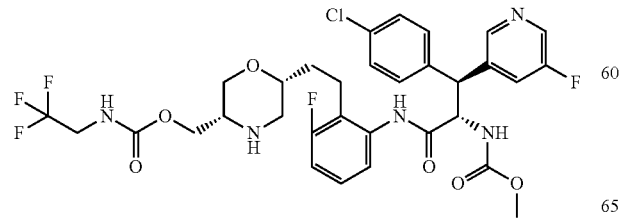

134

Step 1. (2S,3S)-2-Azido-3-(4-chlorophenyl)-3-(5-fluoropyridin-3-yl)propanoic acid

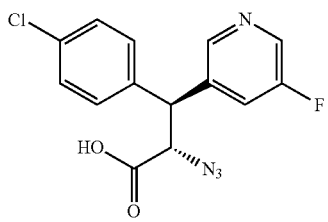 [SMILES: [N-]=[N+]=N[C@H](C(=O)O)[C@@H](c1ccc(Cl)cc1)c1cncc(F)c1]

The title compound was prepared from 3-fluoropyridine-5-carboxaldehyde and 4-chlorophenylmagnesium bromide using the procedures given in steps 3 and 4 of Example 100.

Step 2. (βS)-4-Chloro-β-(5-fluoropyridin-3-yl)-N-(3-fluoro-2-{2-[(2R,5S)-5-({[(2,2,2-trifluoroethyl)carbamoyl]oxy}methyl)morpholin-2-yl]ethyl}phenyl)-Nα-(methoxycarbonyl)-L-phenylalaninamide The title compound was prepared from the product of step 1 and the product of step 4 of Example 99 using the procedures given in steps 2 and 3 of Example 93 and steps 1 and 2 of Example 91. MS (ES) m/z=714 (M+H)⁺.

EXAMPLE 138

{(3S,6R)-6-[2-(2-Fluoro-6-{[(3S)-3-(4-fluorophenyl)-3-(3-fluoropyridin-4-yl)propanoyl]amino}phenyl)ethyl]morpholin-3-yl}methyl (2,2,2-trifluoroethyl)carbamate

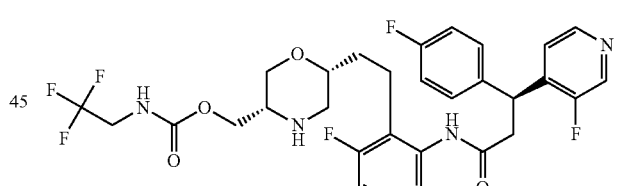

Step 1. (S)-3-(4-Fluorophenyl)-3-(3-fluoropyridin-4-yl)propanoic acid

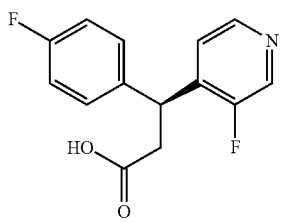 [SMILES: O=C(O)C[C@@H](c1ccc(F)cc1)c1ccncc1F]

The title compound was prepared from 3-fluoropyridine-4-carboxaldehyde and 4-fluorophenylmagnesium bromide using the procedures given in step 3 of Example 100 and steps 6 and 7 of Example 89.

Step 2. {(3S,6R)-6-[2-(2-Fluoro-6-{[(3S)-3-(4-fluorophenyl)-3-(3-fluoropyridin-4-yl)propanoyl]amino}phenyl)ethyl]morpholin-3-yl}methyl (2,2,2-trifluoroethyl)carbamate The title compound was prepared from the product of step 1 and the product of step 4 of Example 99 using the procedures given in steps 8 and 9 of Example 89. MS (ES) m/z=625.5 (M+H)⁺.

EXAMPLE 139

[(3S,6R)-6-{2-[2-Fluoro-6-({(3S)-3-(4-fluorophenyl)-3-[5-(trifluoromethyl)pyridin-3-yl]propanoyl}amino)phenyl]ethyl}morpholin-3-yl]methyl (2,2,2-trifluoroethyl)carbamate

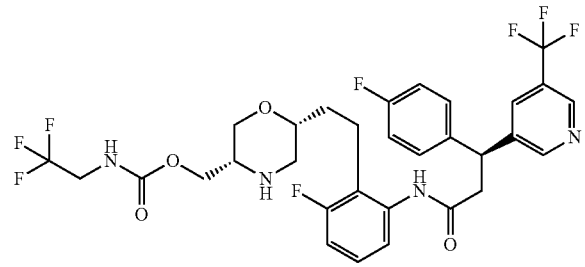 [SMILES: O=C(C[C@@H](c1ccc(F)cc1)c1cncc(C(F)(F)F)c1)Nc1cccc(F)c1CC[C@@H]1CN[C@H](COC(=O)NCC(F)(F)F)CO1]

Step 1. (S)-3-(4-Fluorophenyl)-3-(5-(trifluoromethyl)pyridin-3-yl)propanoic acid

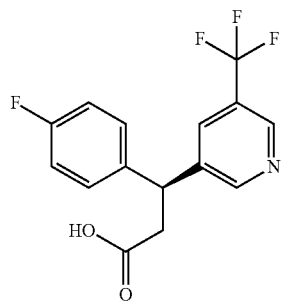 [SMILES: O=C(O)C[C@@H](c1ccc(F)cc1)c1cncc(C(F)(F)F)c1]

The title compound was prepared from 3-trifluoromethylpyridine-5-carboxaldehyde and 4-fluorophenylmagnesium bromide using the procedures using the procedures given in step 3 of Example 100 and steps 6 and 7 of Example 89.

Step 2. [(3S,6R)-6-{2-[2-Fluoro-6-({(3S)-3-(4-fluorophenyl)-3-[5-(trifluoromethyl)pyridin-3-yl]propanoyl}amino)phenyl]ethyl}morpholin-3-yl]methyl (2,2,2-trifluoroethyl)carbamate The title compound was prepared from the product of step 1 and the product of step 4 of Example 99 using the procedures given in steps 8 and 9 of Example 89. MS (ES) m/z=675 (M+H)⁺.

EXAMPLE 140

4-Fluoro-β-(4-fluorophenyl)-N-(5-fluoro-4-{2-[(2R,5S)-5-({[(2,2,2-trifluoroethyl)carbamoyl]oxy}methyl)morpholin-2-yl]ethyl}pyridin-3-yl)-Nα-[(2-methylpropoxy)carbonyl]-L-phenylalaninamide

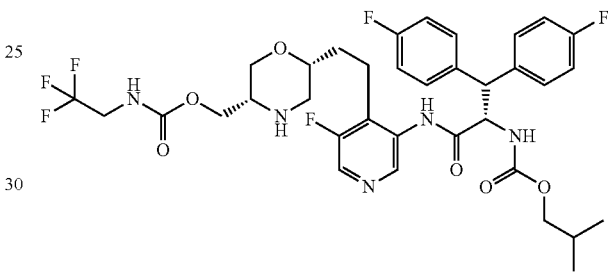

Step 1: 4-Morpholinecarboxylic acid, 2-[2-[3-[[(2S)-2-amino-3,3-bis(4-fluorophenyl)-1-oxopropyl]amino]-5-fluoro-4-pyridinyl]ethyl]-5-[[[[(2,2,2-trifluoroethyl)amino]carbonyl]oxy]methyl]-1,1-dimethylethyl ester, (2R,5S)—

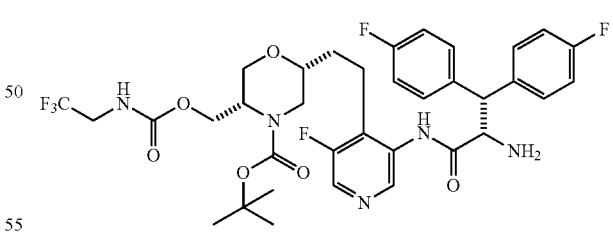

Boc₂O (51 μl, 0.220 mmol) was added to a solution of 4-fluoro-β-(4-fluorophenyl)-N-(5-fluoro-4-{2-[(2R,5S)-5-({[(2,2,2-trifluoroethyl)carbamoyl]oxy}methyl)morpholin-2-yl]ethyl}pyridin-3-yl)-L-phenylalaninamide trihydrochloride (Example 79) (157 mg, 0.210 mmol) and triethylamine (146 μL, 1.05 mmol) in dichloromethane (1 mL) and the reaction stirred for 30 min at RT. The reaction was directly loaded onto a 12 g silica column and eluted with a gradient of 0-100% CHCl₃ to 70:20:10 CHCl₃/EtOAc/MeOH to afford the title compound (110 mg, 0.149 mmol) as a white solid.

Step 2. tert-Butyl (2R,5S)-2-{2-[3-fluoro-5-({4-fluoro-β-(4-fluorophenyl)-N-[(2-methylpropoxy)carbonyl]-L-phenylalanyl}amino)pyridin-4-yl]ethyl}-5-({[(2,2,2-trifluoroethyl)carbamoyl]oxy}methyl)morpholine-4-carboxylate

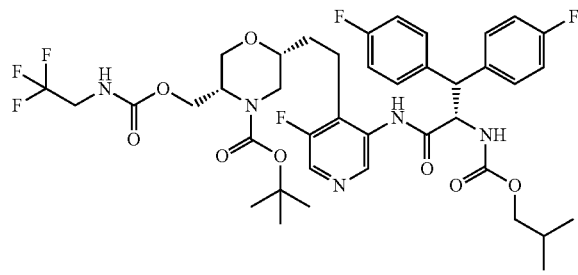 [SMILES: CC(C)COC(=O)N[C@H](C(=O)Nc1cncc(F)c1CC[C@@H]1CN(C(=O)OC(C)(C)C)[C@H](COC(=O)NCC(F)(F)F)CO1)C(c1ccc(F)cc1)c1ccc(F)cc1]

Isobutylchloroformate (3.7 μL, 0.028 mmol) was added to a solution of the product of step 1 (20 mg, 0.027 mmol) and triethylamine (19 μL, 0.135 mmol) in dichloromethane (1 mL) and the reaction stirred for 2.5 hours at RT. The reaction was directly loaded onto a 4 g silica column and eluted with a gradient of 0-100% Hexanes to EtOAc to the title compound (14 mg, 0.013 mmol) as a white solid.

Step 3. 4-fluoro-β-(4-fluorophenyl)-N-(5-fluoro-4-{2-[(2R,5S)-5-({[(2,2,2-trifluoroethyl)carbamoyl]oxy}methyl)morpholin-2-yl]ethyl}pyridin-3-yl)-Nα-[(2-methylpropoxy)carbonyl]-L-phenylalaninamide 4M HCl in Dioxane (0.2 mL) was added directly to the product from step 2 (14 mg, 0.016 mmol) and the reaction stirred at RT for 1 hour. The solvent was removed in vacuo and the residue was dissolved in MeOH and loaded onto a 400 mg Porapak cartridge (preconditioned with 5 mL of MeOH). The cartridge was washed with 100 mL of MeOH, then the desired product was eluted with 10 mL of 2M NH₃ in MeOH. The solvent was removed in vacuo to afford 4-fluoro-β-(4-fluorophenyl)-N-(5-fluoro-4-{2-[(2R,5S)-5-({[(2,2,2-trifluoroethyl)carbamoyl]oxy}methyl)morpholin-2-yl]ethyl}pyridin-3-yl)-Nα-[(2-methylpropoxy)carbonyl]-L-phenylalaninamide (10 mg, 0.014 mmol) as a tan solid, LC MS: RT=1.94 min, M+H=740.4 (4 min gradient).

EXAMPLE 141

4-Fluoro-β-(4-fluorophenyl)-N-(5-fluoro-4-{2-[(2R,5S)-5-({[(2,2,2-trifluoroethyl)carbamoyl]oxy}methyl)morpholin-2-yl]ethyl}pyridin-3-yl)-Nα-[(2,2,2-trifluoroethoxy)carbonyl]-L-phenylalaninamide

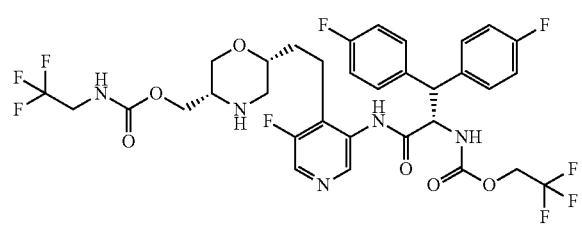 [SMILES: O=C(NCC(F)(F)F)OC[C@@H]1CO[C@H](CCc2c(F)cncc2NC(=O)[C@@H](NC(=O)OCC(F)(F)F)C(c2ccc(F)cc2)c2ccc(F)cc2)CN1]

The title compound was prepared using the procedures described for Example 140, steps 1-3, using trifluoroethyl chloroformate in step 2. MS (ES) m/z=766.5 (M+H)⁺.

EXAMPLE 142

4-Fluoro-β-(4-fluorophenyl)-N-(3-fluoro-2-{2-[(2R,5S)-5-({[(2,2,2-trifluoroethyl)carbamoyl]oxy}methyl)morpholin-2-yl]ethyl}phenyl)-Nα-[(1-methylcyclopropyl)carbonyl]-L-phenylalaninamide

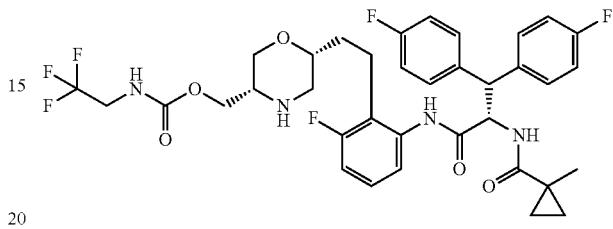

The title compound was prepared using the procedures described for Example 140, steps 1-3, using 1-methylcyclopropanecarboxylic acid and EDC in step 2. MS (ES) m/z=721.4 (M+H)⁺.

EXAMPLE 143

N-({(3R,6R)-6-[2-(3-{[3,3-Bis(4-fluorophenyl)propanoyl]amino}-5-fluoropyridin-4-yl)ethyl]morpholin-3-yl}methyl)-3,3,3-trifluoropropanamide

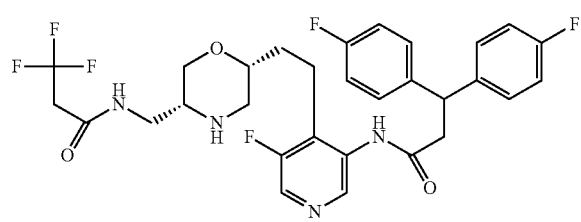 [SMILES: O=C(CC(F)(F)F)NC[C@@H]1CO[C@H](CCc2c(F)cncc2NC(=O)CC(c2ccc(F)cc2)c2ccc(F)cc2)CN1]

The title compound was prepared using the procedures described for Example 85 using 3,3,3-trifluoropropanoic acid. MS (ES) m/z=609.1 (M+H)⁺.

EXAMPLE 144

N-({(3R,6R)-6-[2-(2-{[3,3-Bis(4-fluorophenyl)propanoyl]amino}-6-fluorophenyl)ethyl]morpholin-3-yl}methyl)-3,3,3-trifluoropropanamide

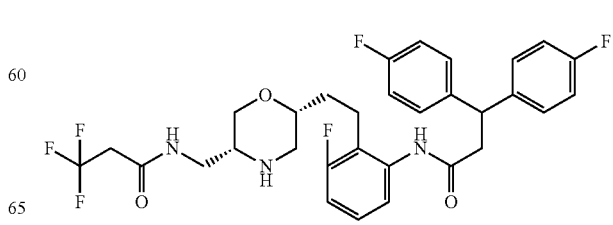

The title compound was prepared using the procedures described for Example 87 using 3,3,3-trifluoropropanoic acid. MS (ES) m/z=608.1 (M+H)⁺.

EXAMPLE 145

(βS)-β-(3,5-Difluorophenyl)-N-(3,6-difluoro-2-{2-[(2R,5S)-5-({[(2,2,2-trifluoroethyl)carbamoyl]oxy}methyl)morpholin-2-yl]ethyl}phenyl)-4-fluoro-Nα-(methoxycarbonyl)-L-phenylalaninamide

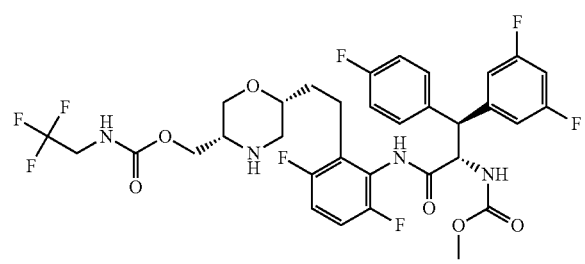 [SMILES: COC(=O)N[C@H](C(=O)Nc1c(F)ccc(F)c1CC[C@@H]1CN[C@H](COC(=O)NCC(F)(F)F)CO1)[C@@H](c1ccc(F)cc1)c1cc(F)cc(F)c1]

Step 1. Di-tert-butyl (2,5-difluorophenyl)imidodicarbonate

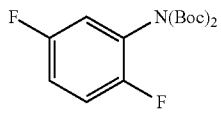

To a solution of 2,5-difluoroaniline (0.56 g, 4.30 mmol) in THF (14.3 mL) was added DMAP (0.053 g, 0.430 mmol) and Boc₂O (2.5 mL, 10.8 mmol). The contents were refluxed under nitrogen at 75° C. for 1 h, at which point LC/MS indicates that the reaction is complete. The solvent was evaporated to give di-tert-butyl (2,5-difluorophenyl)imidodicarbonate (1.48 g, 3.48 mmol) as a brown foam and taken on to the next step crude. MS (ESI): m/z=218.2 (M+H-[t-Bu]₂).

Step 2. tert-Butyl (2,5-difluorophenyl)carbamate

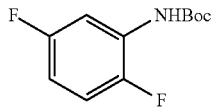

Di-tert-butyl (2,5-difluorophenyl)imidodicarbonate (1.48 g, 4.49 mmol) was dissolved in DCM (15.0 mL) at rt. TFA (0.48 mL, 6.28 mmol) was added to the reaction and the contents were stirred for 1 h. LC/MS at this time shows that starting material has been consumed. The solution was then washed with saturated aqueous sodium bicarbonate. The organics were dried over MgSO₄ filtered and concentrated. The crude product was purified on silica gel, eluting with 0-50% EtOAc in hexanes over 32 minutes to afford the title compound (758 mg, 2.88 mmol) as a pale yellow oil. MS (ESI): m/z=174.2 (M+H-[t-Bu]).

Step 3. tert-Butyl (3,6-difluoro-2-iodophenyl)carbamate

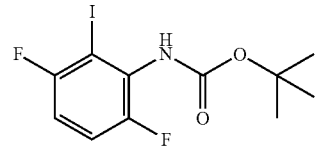 [SMILES: CC(C)(C)OC(=O)Nc1c(F)ccc(F)c1I]

nBuLi (5.67 mL, 14.2 mmol) was added to a solution of tert-butyl (2,5-difluorophenyl)carbamate (1.08 g, 4.73 mmol) and TMEDA (2.14 mL, 14.2 mmol) in THF (21.6 mL) at −78° C. over 20 minutes, ensuring the internal temperature remained below −70° C. The resulting solution was stirred at −78° C. for 1 h. Iodine (3.60 g, 14.2 mmol) in THF (10 mL) was added dropwise over 30 min, also ensuring the internal temperature remained below −70° C. The resulting reaction was stirred for 1 h at −78° C., The reaction was quenched at −78° C. with water and the reaction warmed to room temperature. 10% Sodium thiosulfate was added until the iodine color dissipated and the mixture was then extracted with ethyl acetate (3×50 mL). The combined organic fractions were dried (MgSO₄), filtered and concentrated. The crude material was purified on silica gel, eluting 0-60% EtOAc in hexanes over 28 minutes to afford tert-butyl (3,6-difluoro-2-iodophenyl)carbamate (1.14 g, 3.20 mmol) as a white crystalline solid. MS (ESI): m/z=300.2 (M+H-[t-Bu]).

Step 4. 3,6-Difluoro-2-iodoaniline

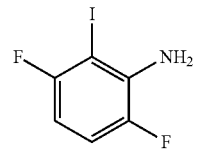

4M HCl (7.60 mL, 30.4 mmol) in dioxane was added to a solution of tert-butyl (3,6-difluoro-2-iodophenyl)carbamate (1.08 g, 3.04 mmol) in THF (7.60 ml) at room temperature and then stirred overnight. The solvent was removed in vacuo, and then the contents were partitioned between DCM (3×50 mL) and sat'd aqueous sodium bicarbonate. The organics were dried over MgSO₄, filtered and concentrated. The crude material was purified on silica gel, eluting 0-50% EtOAc in hexanes over 16 minutes to afford 3,6-difluoro-2-iodoaniline (373 mg, 1.46 mmol) as a tan oil. MS (ESI): m/z=256.2 (M+H-Boc).

Step 5. (βS)-β-(3,5-Difluorophenyl)-N-(3,6-difluoro-2-{2-[(2R,5S)-5-({[(2,2,2-trifluoroethyl)carbamoyl]oxy}methyl)morpholin-2-yl]ethyl}phenyl)-4-fluoro-Nα-(methoxycarbonyl)-L-phenylalaninamide The title compound was prepared from the product of step 4 using the procedures described in Example 130. MS (ES) m/z=733.5 (M+H)⁺.

TABLE 1

The following examples can be prepared using the procedures described above.

| Example | Structure | IUPAC Name | Mass [M + H]+ |
|---|---|---|---|
| 146 | 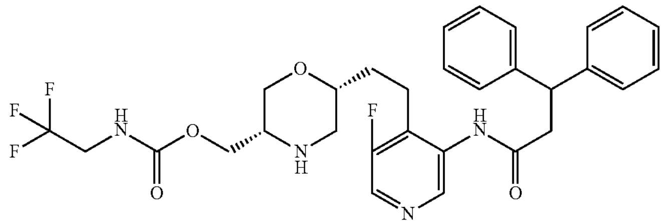 [SMILES: O=C(CC(c1ccccc1)c1ccccc1)Nc1cncc(F)c1CC[C@@H]1CN[C@H](COC(=O)NCC(F)(F)F)CO1] | [(3S,6R)-6-(2-{3-[(3,3-diphenylpropanoyl)amino]-5-fluoropyridin-4-yl}ethyl)morpholin-3-yl]methyl (2,2,2-trifluoroethyl)carbamate | 589.2 |
| 147 | 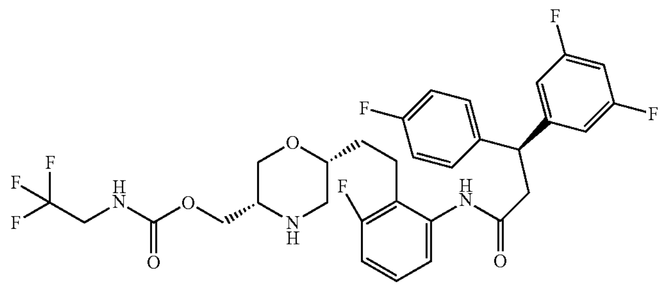 [SMILES: O=C(C[C@@H](c1ccc(F)cc1)c1cc(F)cc(F)c1)Nc1cccc(F)c1CC[C@@H]1CN[C@H](COC(=O)NCC(F)(F)F)CO1] | {(3S,6R)-6-[2-(2-{[(3S)-3-(3,5-difluorophenyl)-3-(4-fluorophenyl)propanoyl]amino}-6-fluorophenyl)ethyl]morpholin-3-yl}methyl (2,2,2-trifluoroethyl)carbamate | 642.2 |
| 148 | 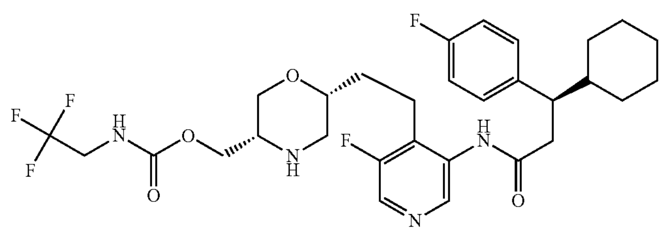 [SMILES: O=C(C[C@@H](c1ccc(F)cc1)C1CCCCC1)Nc1cncc(F)c1CC[C@@H]1CN[C@H](COC(=O)NCC(F)(F)F)CO1] | {(3S,6R)-6-[2-(3-{[(3R)-3-cyclohexyl-3-(4-fluorophenyl)propanoyl]amino}-5-fluoropyridin-4-yl)ethyl]morpholin-3-yl}methyl (2,2,2-trifluoroethyl)carbamate | 613.3 |
| 149 | 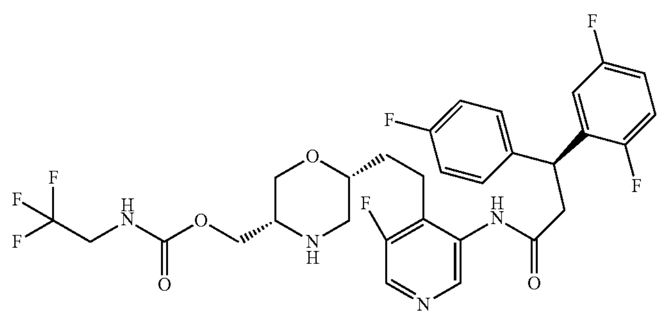 [SMILES: O=C(C[C@@H](c1ccc(F)cc1)c1cc(F)ccc1F)Nc1cncc(F)c1CC[C@@H]1CN[C@H](COC(=O)NCC(F)(F)F)CO1] | {(3S,6R)-6-[2-(3-{[(3S)-3-(2,5-difluorophenyl)-3-(4-fluorophenyl)propanoyl]amino}-5-fluoropyridin-4-yl)ethyl]morpholin-3-yl}methyl (2,2,2-trifluoroethyl)carbamate | 643.2 |
| 150 | 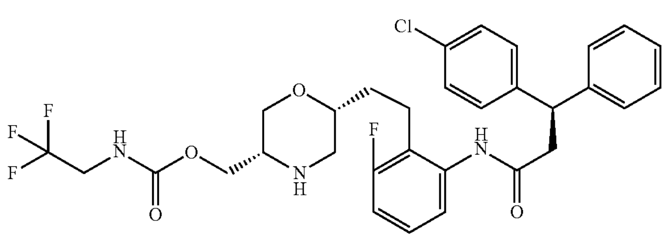 [SMILES: O=C(C[C@H](c1ccccc1)c1ccc(Cl)cc1)Nc1cccc(F)c1CC[C@@H]1CN[C@H](COC(=O)NCC(F)(F)F)CO1] | {(3S,6R)-6-[2-(2-{[(3R)-3-(4-chlorophenyl)-3-phenylpropanoyl]amino}-6-fluorophenyl)ethyl]morpholin-3-yl}methyl (2,2,2-trifluoroethyl)carbamate | 622.2 |
| 151 | 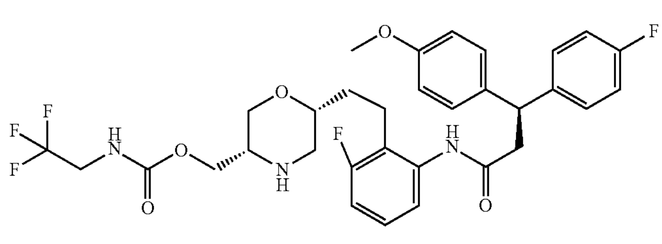 [SMILES: COc1ccc([C@H](CC(=O)Nc2cccc(F)c2CC[C@@H]2CN[C@H](COC(=O)NCC(F)(F)F)CO2)c2ccc(F)cc2)cc1] | {(3S,6R)-6-[2-(2-fluoro-6-{[(3S)-3-(4-fluorophenyl)-3-(4-methoxyphenyl)propanoyl]amino}phenyl)ethyl]morpholin-3-yl}methyl (2,2,2-trifluoroethyl)carbamate | 636.2 |

TABLE 1-continued

The following examples can be prepared using the procedures described above.

| Example | Structure | IUPAC Name | Mass [M + H]+ |
|---------|-----------|------------|---------------|
| 152 | 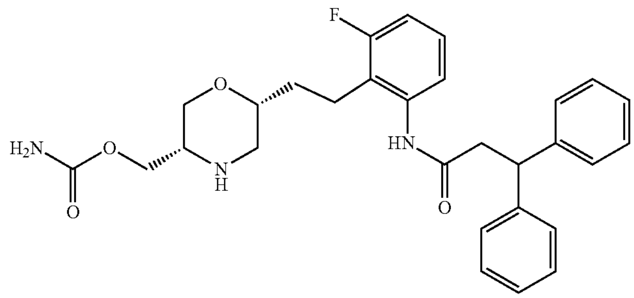 [SMILES: NC(=O)OC[C@@H]1CO[C@H](CCc2c(F)cccc2NC(=O)CC(c2ccccc2)c2ccccc2)CN1] | [(3S,6R)-6-(2-{2-[(3,3-diphenylpropanoyl)amino]-6-fluorophenyl}ethyl)morpholin-3-yl]methyl carbamate | 506.2 |
| 153 | 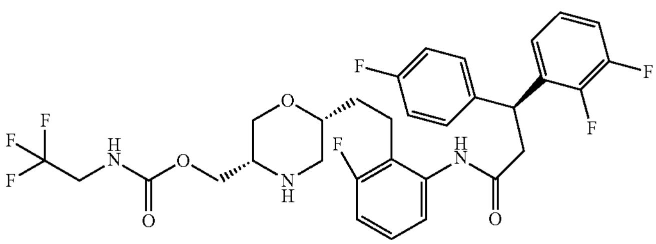 [SMILES: O=C(C[C@@H](c1ccc(F)cc1)c1cccc(F)c1F)Nc1cccc(F)c1CC[C@@H]1CN[C@H](COC(=O)NCC(F)(F)F)CO1] | {(3S,6R)-6-[2-(2-{[(3S)-3-(2,3-difluorophenyl)-3-(4-fluorophenyl)propanoyl]amino}-6-fluorophenyl)ethyl]morpholin-3-yl}methyl (2,2,2-trifluoroethyl)carbamate | 642.2 |
| 154 | 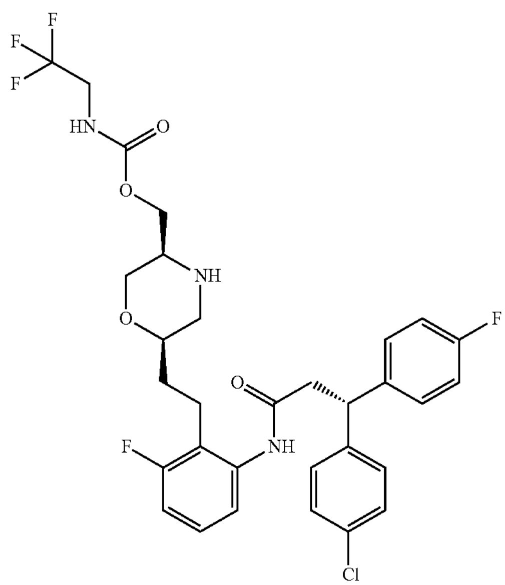 [SMILES: O=C(C[C@H](c1ccc(F)cc1)c1ccc(Cl)cc1)Nc1cccc(F)c1CC[C@@H]1CN[C@H](COC(=O)NCC(F)(F)F)CO1] | {(3S,6R)-6-[2-(2-{[(3R)-3-(4-chlorophenyl)-3-(4-fluorophenyl)propanoyl]amino}-6-fluorophenyl)ethyl]morpholin-3-yl}methyl (2,2,2-trifluoroethyl)carbamate | 640.2 |
| 155 | 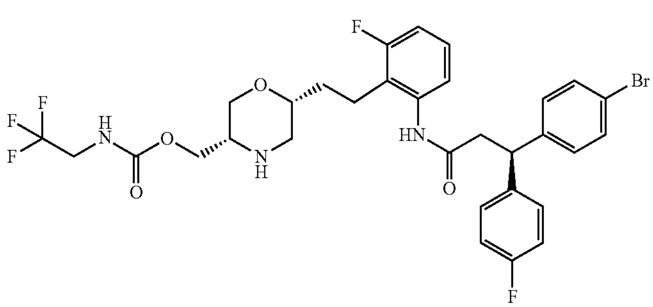 [SMILES: O=C(C[C@H](c1ccc(F)cc1)c1ccc(Br)cc1)Nc1cccc(F)c1CC[C@@H]1CN[C@H](COC(=O)NCC(F)(F)F)CO1] | {(3S,6R)-6-[2-(2-{[(3R)-3-(4-bromophenyl)-3-(4-fluorophenyl)propanoyl]amino}-6-fluorophenyl)ethyl]morpholin-3-yl}methyl (2,2,2-trifluoroethyl)carbamate | 684.1 |

TABLE 1-continued

The following examples can be prepared using the procedures described above.

| Example | Structure | IUPAC Name | Mass [M + H]+ |
|---------|-----------|------------|---------------|
| 156 | 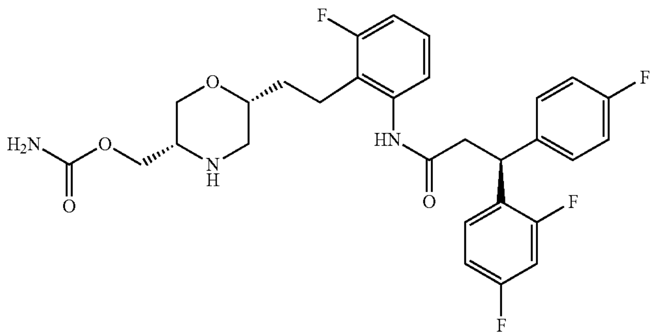 [SMILES: NC(=O)OC[C@@H]1CO[C@H](CCc2c(F)cccc2NC(=O)C[C@@H](c2ccc(F)cc2)c2ccc(F)cc2F)CN1] | {(3S,6R)-6-[2-(2-{[(3S)-3-(2,4-difluorophenyl)-3-(4-fluorophenyl)propanoyl]amino}-6-fluorophenyl)ethyl]morpholin-3-yl}methyl carbamate | 560.2 |
| 157 | 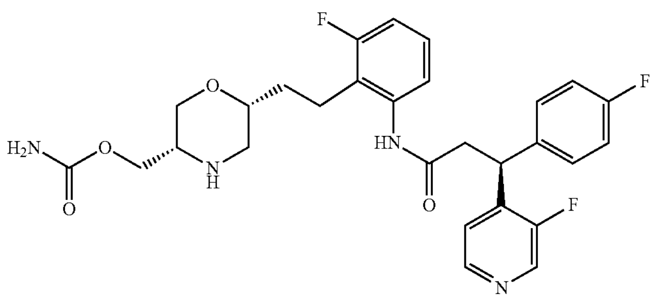 [SMILES: NC(=O)OC[C@@H]1CO[C@H](CCc2c(F)cccc2NC(=O)C[C@@H](c2ccc(F)cc2)c2ccncc2F)CN1] | {(3S,6R)-6-[2-(2-fluoro-6-{[(3S)-3-(4-fluorophenyl)-3-(3-fluoropyridin-4-yl)propanoyl]amino}phenyl)ethyl]morpholin-3-yl}methyl carbamate | 543.2 |
| 158 | 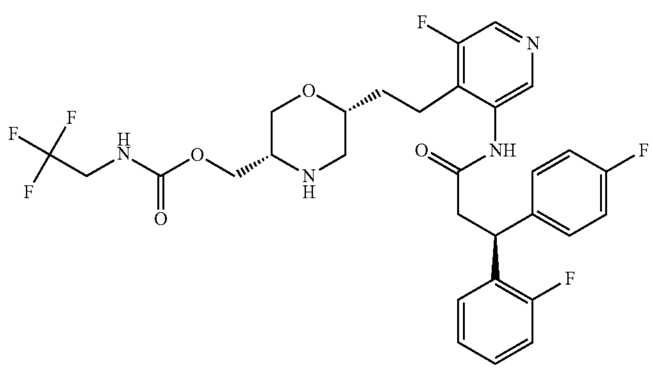 [SMILES: O=C(C[C@@H](c1ccc(F)cc1)c1ccccc1F)Nc1cncc(F)c1CC[C@@H]1CN[C@H](COC(=O)NCC(F)(F)F)CO1] | {(3S,6R)-6-[2-(3-fluoro-5-{[(3S)-3-(2-fluorophenyl)-3-(4-fluorophenyl)propanoyl]amino}pyridin-4-yl)ethyl]morpholin-3-yl}methyl (2,2,2-trifluoroethyl)carbamate | 625.2 |
| 159 | 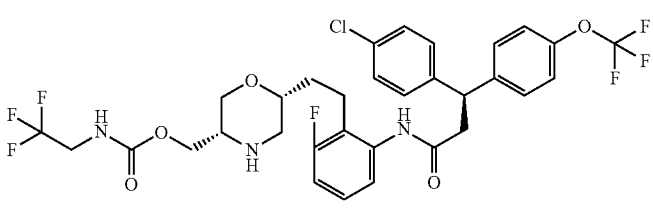 [SMILES: O=C(C[C@@H](c1ccc(Cl)cc1)c1ccc(OC(F)(F)F)cc1)Nc1cccc(F)c1CC[C@@H]1CN[C@H](COC(=O)NCC(F)(F)F)CO1] | [(3S,6R)-6-{2-[2-fluoro-6-({(3R)-3-(4-fluorophenyl)-3-[4-(trifluoromethoxy)phenyl]propanoyl}amino)phenyl]ethyl}morpholin-3-yl]methyl (2,2,2-trifluoroethyl)carbamate | 690.2 |
| 160 | 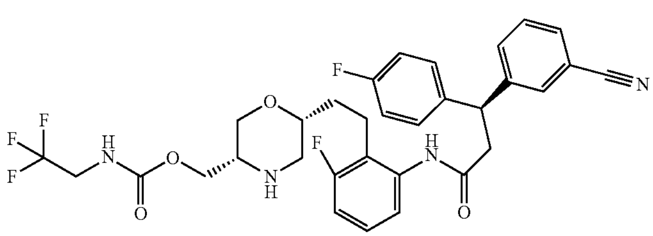 [SMILES: N#Cc1cccc([C@@H](CC(=O)Nc2cccc(F)c2CC[C@@H]2CN[C@H](COC(=O)NCC(F)(F)F)CO2)c2ccc(F)cc2)c1] | {(3S,6R)-6-[2-(2-{[(3S)-3-(3-cyanophenyl)-3-(4-fluorophenyl)propanoyl]amino}-6-fluorophenyl)ethyl]morpholin-3-yl}methyl (2,2,2-trifluoroethyl)carbamate | 631.2 |

TABLE 1-continued

The following examples can be prepared using the procedures described above.

| Example | Structure | IUPAC Name | Mass [M + H]+ |
|---|---|---|---|
| 161 | 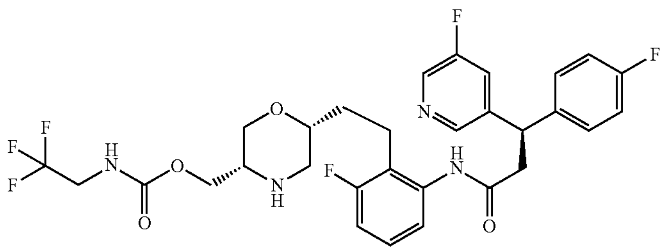 [SMILES: O=C(C[C@H](c1ccc(F)cc1)c1cncc(F)c1)Nc1cccc(F)c1CC[C@@H]1CN[C@H](COC(=O)NCC(F)(F)F)CO1] | {(3S,6R)-6-[2-(2-fluoro-6-{[(3R)-3-(4-fluorophenyl)-3-(5-fluoropyridin-3-yl)propanoyl]amino}phenyl)ethyl]morpholin-3-yl}methyl (2,2,2-trifluoroethyl)carbamate | 625.2 |
| 162 | 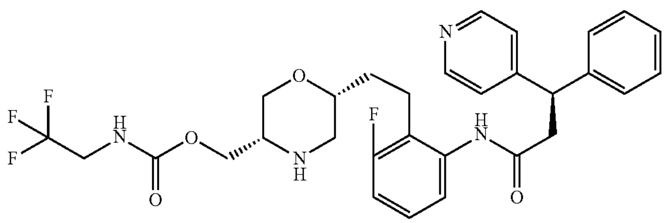 [SMILES: O=C(C[C@H](c1ccccc1)c1ccncc1)Nc1cccc(F)c1CC[C@@H]1CN[C@H](COC(=O)NCC(F)(F)F)CO1] | {(3S,6R)-6-[2-(2-fluoro-6-{[(3R)-3-phenyl-3-pyridin-4-ylpropanoyl]amino}phenyl)ethyl]morpholin-3-yl}methyl (2,2,2-trifluoroethyl)carbamate | 589.2 |
| 163 | 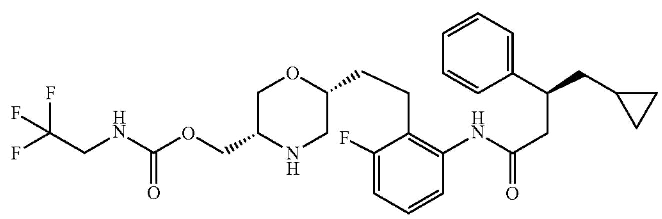 [SMILES: O=C(C[C@H](CC1CC1)c1ccccc1)Nc1cccc(F)c1CC[C@@H]1CN[C@H](COC(=O)NCC(F)(F)F)CO1] | {(3S,6R)-6-[2-(2-{[(3S)-4-cyclopropyl-3-phenyl-butanoyl]amino}-6-fluoro-phenyl)ethyl]morpholin-3-yl}methyl (2,2,2-trifluoroethyl)carbamate | 566.3 |
| 164 | 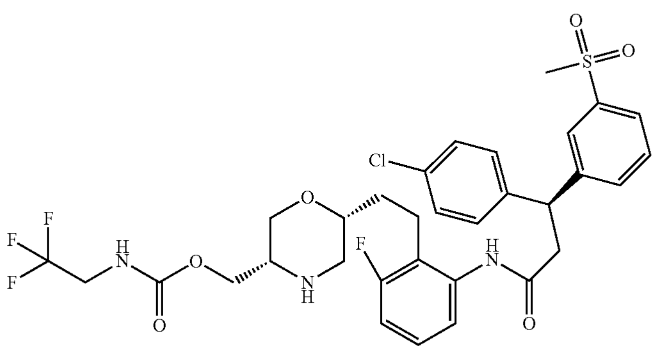 [SMILES: CS(=O)(=O)c1cccc([C@@H](CC(=O)Nc2cccc(F)c2CC[C@@H]2CN[C@H](COC(=O)NCC(F)(F)F)CO2)c2ccc(Cl)cc2)c1] | [(3S,6R)-6-{2-[2-({(3S)-3-(4-chlorophenyl)-3-[3-(methylsulfonyl)phenyl]propanoyl}amino)-6-fluorophenyl]ethyl}morpholin-3-yl]methyl (2,2,2-trifluoroethyl)carbamate | 700.2 |
| 165 | 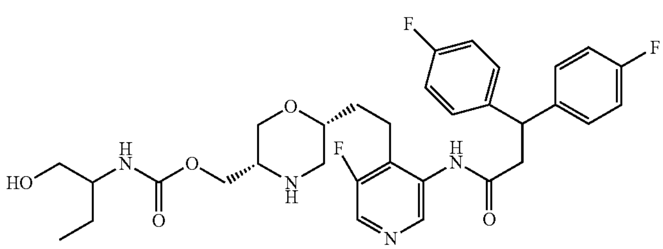 [SMILES: CCC(CO)NC(=O)OC[C@@H]1CO[C@H](CCc2c(F)cncc2NC(=O)CC(c2ccc(F)cc2)c2ccc(F)cc2)CN1] | {(3S,6R)-6-[2-(3-{[3,3-bis(4-fluorophenyl)propanoyl]amino}-5-fluoropyridin-4-yl)ethyl]morpholin-3-yl}methyl [1-(hydroxymethyl)propyl]carbamate | 615.3 |
| 166 | 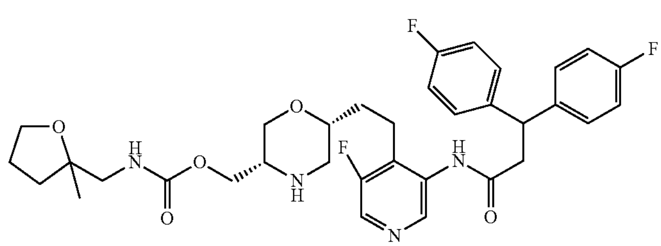 [SMILES: CC1(CNC(=O)OC[C@@H]2CO[C@H](CCc3c(F)cncc3NC(=O)CC(c3ccc(F)cc3)c3ccc(F)cc3)CN2)CCCO1] | {(3S,6R)-6-[2-(3-{[3,3-bis(4-fluorophenyl)propanoyl]amino}-5-fluoropyridin-4-yl)ethyl]morpholin-3-yl}methyl [(2-methyltetrahydrofuran-2-yl)methyl]carbamate | 641.3 |

TABLE 1-continued

The following examples can be prepared using the procedures described above.

| Example | Structure | IUPAC Name | Mass [M + H]+ |
|---|---|---|---|
| 167 | 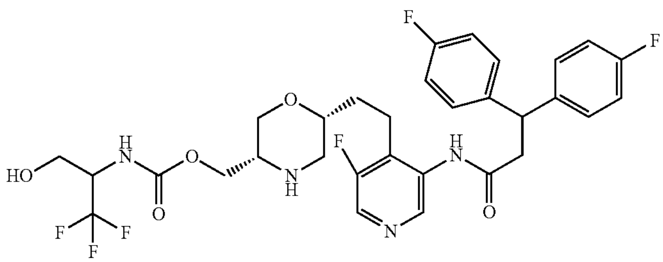 [SMILES: O=C(CC(c1ccc(F)cc1)c1ccc(F)cc1)Nc1cncc(F)c1CC[C@@H]1CN[C@H](COC(=O)NC(CO)C(F)(F)F)CO1] | {(3S,6R)-6-[2-(3-{[3,3-bis(4-fluoro-phenyl)propanoyl]amino}-5-fluoropyridin-4-yl)ethyl]morpholin-3-yl}methyl [2,2,2-trifluoro-1-(hydroxymethyl)ethyl]carbamate | 655.2 |
| 168 | 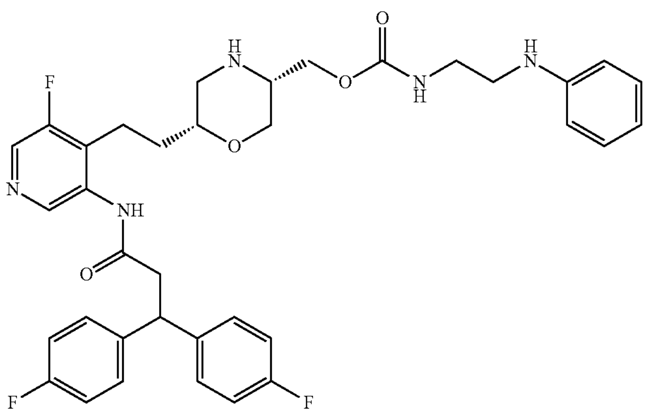 [SMILES: O=C(CC(c1ccc(F)cc1)c1ccc(F)cc1)Nc1cncc(F)c1CC[C@@H]1CN[C@H](COC(=O)NCCNc2ccccc2)CO1] | {(3S,6R)-6-[2-(3-{[3,3-bis(4-fluorophenyl)propanoyl]amino}-5-fluoropyridin-4-yl)ethyl]morpholin-3-yl}methyl [2-(phenyl-amino)ethyl]carbamate | 662.3 |
| 169 | 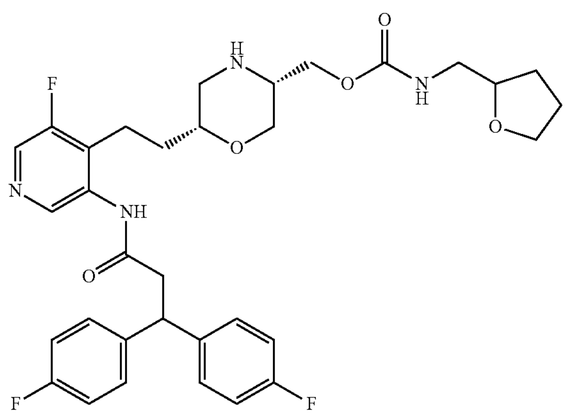 [SMILES: O=C(CC(c1ccc(F)cc1)c1ccc(F)cc1)Nc1cncc(F)c1CC[C@@H]1CN[C@H](COC(=O)NCC2CCCO2)CO1] | {(3S,6R)-6-[2-(3-{[3,3-bis(4-fluoro-phenyl)propanoyl]amino}-5-fluoropyridin-4-yl)ethyl]morpholin-3-yl}methyl (tetrahydrofuran-2-ylmethyl)carbamate | 627.3 |
| 170 | 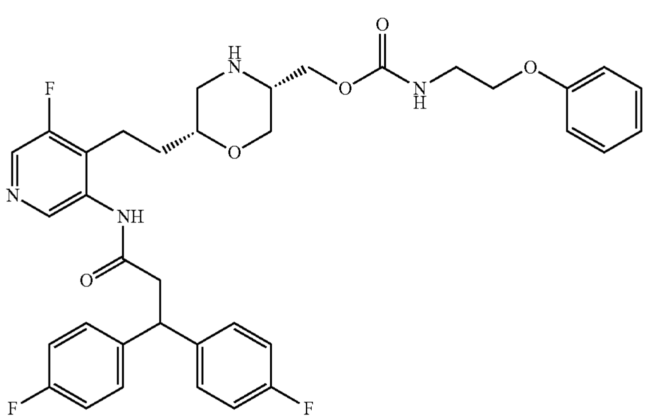 [SMILES: O=C(CC(c1ccc(F)cc1)c1ccc(F)cc1)Nc1cncc(F)c1CC[C@@H]1CN[C@H](COC(=O)NCCOc2ccccc2)CO1] | {(3S,6R)-6-[2-(3-{[3,3-bis(4-fluoro-phenyl)propanoyl]amino}-5-fluoropyridin-4-yl)ethyl]morpholin-3-yl}methyl (2-phenoxyethyl)carbamate | 663.3 |

TABLE 1-continued

The following examples can be prepared using the procedures described above.

| Example | Structure | IUPAC Name | Mass [M + H]+ |
|---|---|---|---|
| 171 | 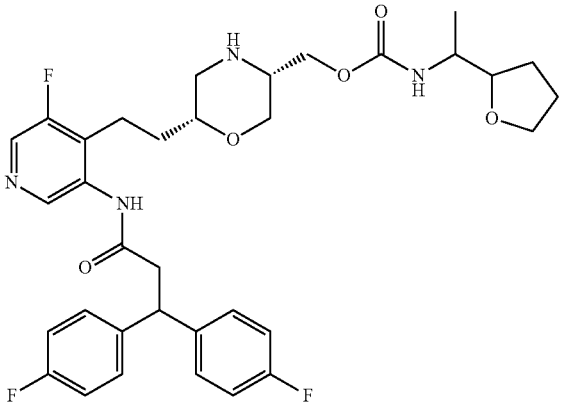 [SMILES: CC(NC(=O)OC[C@@H]1CO[C@H](CCc2c(F)cncc2NC(=O)CC(c2ccc(F)cc2)c2ccc(F)cc2)CN1)C1CCCO1] | {(3S,6R)-6-[2-(3-{[3,3-bis(4-fluoro-phenyl)propanoyl]amino}-5-fluoropyridin-4-yl)ethyl]morpholin-3-yl}methyl [1-(tetrahydrofuran-2-yl)ethyl]carbamate | 641.3 |
| 172 | 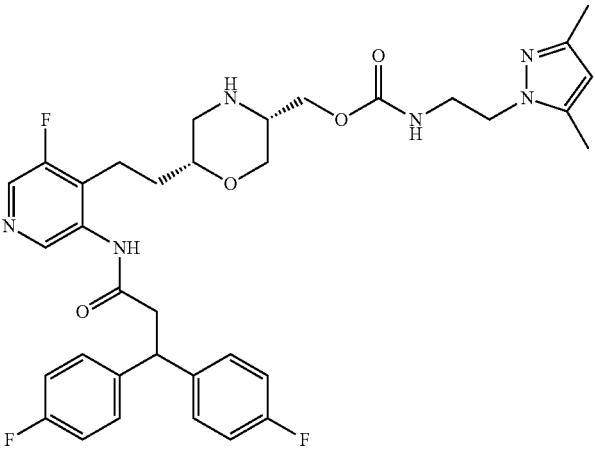 [SMILES: Cc1cc(C)n(CCNC(=O)OC[C@@H]2CO[C@H](CCc3c(F)cncc3NC(=O)CC(c3ccc(F)cc3)c3ccc(F)cc3)CN2)n1] | {(3S,6R)-6-[2-(3-{[3,3-bis(4-fluoro-phenyl)propanoyl]amino}-5-fluoropyridin-4-yl)ethyl]morpholin-3-yl}methyl [2-(3,5-dimethyl-1H-pyrazol-1-yl)ethyl]carbamate | 665.3 |
| 173 | 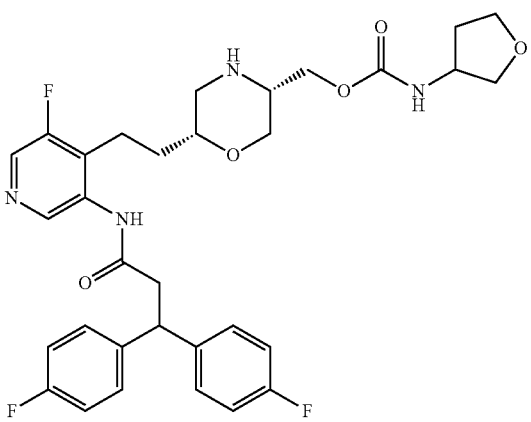 [SMILES: O=C(CC(c1ccc(F)cc1)c1ccc(F)cc1)Nc1cncc(F)c1CC[C@@H]1CN[C@H](COC(=O)NC2CCOC2)CO1] | {(3S,6R)-6-[2-(3-{[3,3-bis(4-fluoro-phenyl)propanoyl]amino}-5-fluoropyridin-4-yl)ethyl]morpholin-3-yl}methyl tetrahydrofuran-3-ylcarbamate | 613.3 |

TABLE 1-continued

The following examples can be prepared using the procedures described above.

| Example | Structure | IUPAC Name | Mass [M + H]+ |
|---|---|---|---|
| 174 | 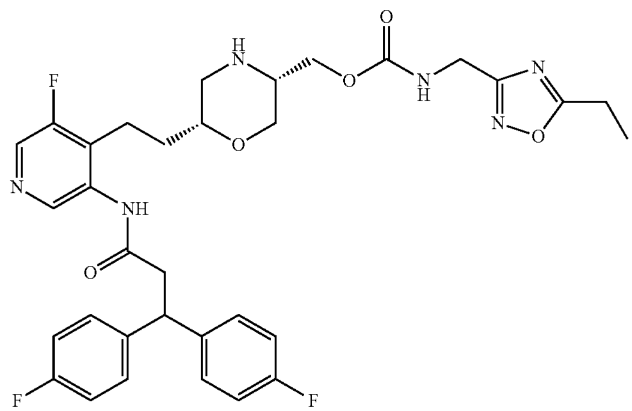 [SMILES: CCc1nc(CNC(=O)OC[C@@H]2CO[C@H](CCc3c(F)cncc3NC(=O)CC(c3ccc(F)cc3)c3ccc(F)cc3)CN2)no1] | {(3S,6R)-6-[2-(3-{[3,3-bis(4-fluoro-phenyl)propanoyl]amino}-5-fluoropyridin-4-yl)ethyl]morpholin-3-yl}methyl [(5-ethyl-1,2,4-oxadiazol-3-yl)methyl]carbamate | 653.3 |
| 175 | 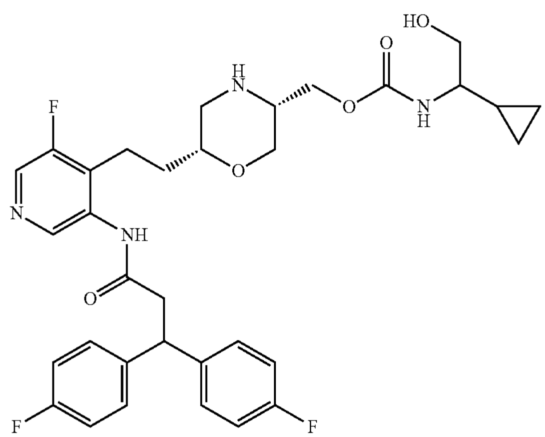 [SMILES: O=C(CC(c1ccc(F)cc1)c1ccc(F)cc1)Nc1cncc(F)c1CC[C@@H]1CN[C@H](COC(=O)NC(CO)C2CC2)CO1] | {(3S,6R)-6-[2-(3-{[3,3-bis(4-fluoro-phenyl)propanoyl]amino}-5-fluoropyridin-4-yl)ethyl]morpholin-3-yl}methyl (1-cyclopropyl-2-hydroxyethyl)carbamate | 627.3 |
| 176 | 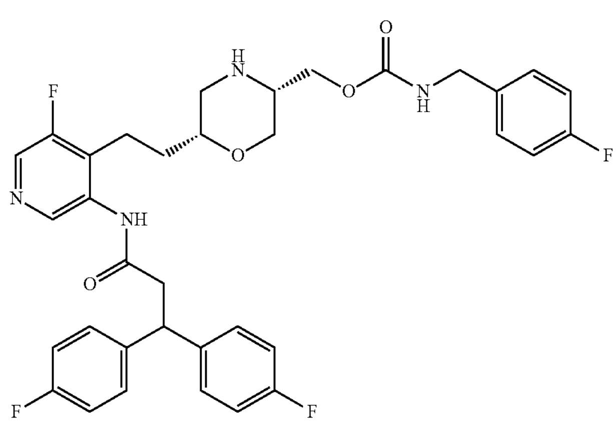 [SMILES: O=C(CC(c1ccc(F)cc1)c1ccc(F)cc1)Nc1cncc(F)c1CC[C@@H]1CN[C@H](COC(=O)NCc2ccc(F)cc2)CO1] | {(3S,6R)-6-[2-(3-{[3,3-bis(4-fluoro-phenyl)propanoyl]amino}-5-fluoropyridin-4-yl)ethyl]morpholin-3-yl}methyl (4-fluorobenzyl)carbamate | 651.3 |

TABLE 1-continued

The following examples can be prepared using the procedures described above.

| Example | Structure | IUPAC Name | Mass [M + H]+ |
|---|---|---|---|
| 177 | 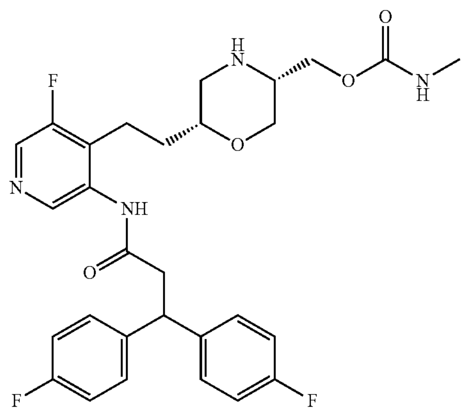 [SMILES: CNC(=O)OC[C@@H]1CO[C@H](CCc2c(F)cncc2NC(=O)CC(c2ccc(F)cc2)c2ccc(F)cc2)CN1] | {(3S,6R)-6-[2-(3-{[3,3-bis(4-fluoro-phenyl)propanoyl]amino}-5-fluoropyridin-4-yl)ethyl]morpholin-3-yl}methyl methylcarbamate | 557.2 |
| 178 | 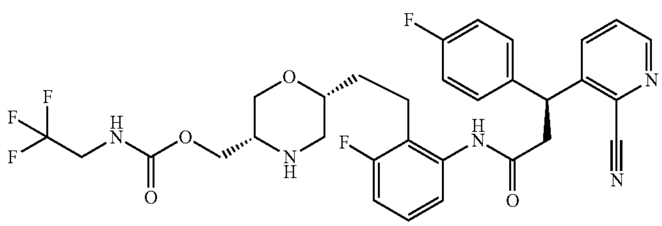 [SMILES: N#Cc1ncccc1[C@@H](CC(=O)Nc1cccc(F)c1CC[C@@H]1CN[C@H](COC(=O)NCC(F)(F)F)CO1)c1ccc(F)cc1] | {(3S,6R)-6-[2-(2-{[(3S)-3-(2-cyanopyridin-3-yl)-3-(4-fluorophenyl)propanoyl]amino}-6-fluoro-phenyl)ethyl]morpholin-3-yl}methyl (2,2,2-trifluoroethyl)carbamate | 632.2 |
| 179 | 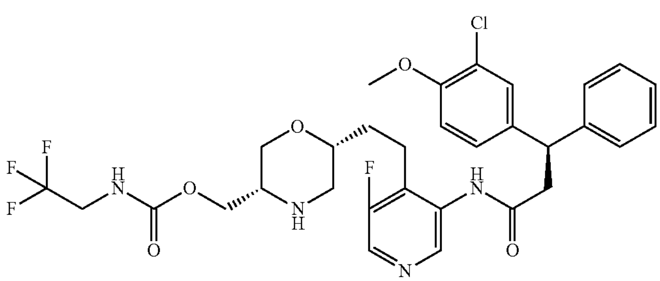 [SMILES: COc1ccc([C@H](CC(=O)Nc2cncc(F)c2CC[C@@H]2CN[C@H](COC(=O)NCC(F)(F)F)CO2)c2ccccc2)cc1Cl] | {(3S,6R)-6-[2-(3-{[(3R)-3-(3-chloro-4-methoxyphenyl)-3-phenylpropanoyl]amino}-5-fluoropyridin-4-yl)ethyl]morpholin-3-yl}methyl (2,2,2-trifluoroethyl)carbamate | 653.2 |
| 180 | 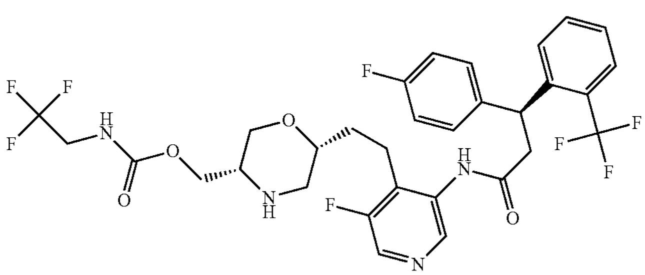 [SMILES: O=C(C[C@@H](c1ccc(F)cc1)c1ccccc1C(F)(F)F)Nc1cncc(F)c1CC[C@@H]1CN[C@H](COC(=O)NCC(F)(F)F)CO1] | [(3S,6R)-6-{2-[3-fluoro-5-({(3S)-3-(4-fluorophenyl)-3-[2-(trifluoro-methyl)phenyl]propanoyl}amino)pyridin-4-yl]ethyl}morpholin-3-yl]methyl (2,2,2-trifluoroethyl)carbamate | 675.2 |
| 181 | 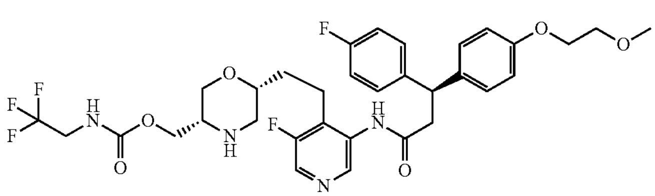 [SMILES: COCCOc1ccc([C@@H](CC(=O)Nc2cncc(F)c2CC[C@@H]2CN[C@H](COC(=O)NCC(F)(F)F)CO2)c2ccc(F)cc2)cc1] | [(3S,6R)-6-{2-[3-fluoro-5-({(3R)-3-(4-fluorophenyl)-3-[4-(2-methoxy-ethoxy)phenyl]propanoyl}amino)pyridin-4-yl]ethyl}morpholin-3-yl]methyl (2,2,2-trifluoroethyl)carbamate | 681.3 |

TABLE 1-continued

The following examples can be prepared using the procedures described above.

| Example | Structure | IUPAC Name | Mass [M + H]+ |
|---|---|---|---|
| 182 | 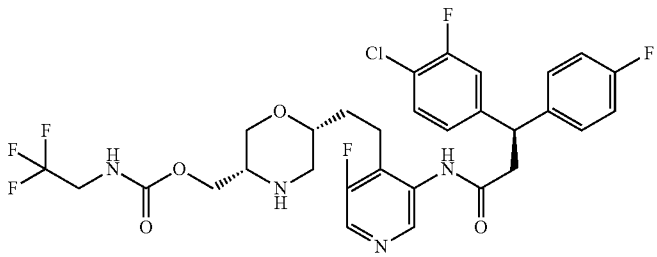 [SMILES: O=C(C[C@H](c1ccc(F)cc1)c1ccc(Cl)c(F)c1)Nc1cncc(F)c1CC[C@@H]1CN[C@H](COC(=O)NCC(F)(F)F)CO1] | {(3S,6R)-6-[2-(3-{[(3R)-3-(4-chloro-3-fluorophenyl)-3-(4-fluoro-phenyl)propanoyl]amino}-5-fluoropyridin-4-yl)ethyl]morpholin-3-yl}methyl (2,2,2-trifluoroethyl)carbamate | 659.2 |
| 183 | 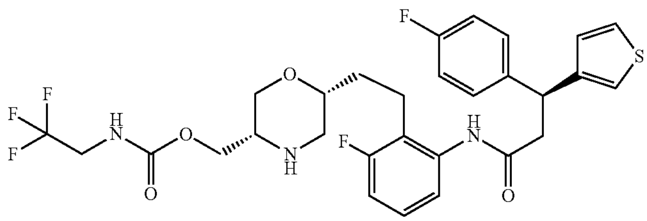 [SMILES: O=C(C[C@@H](c1ccc(F)cc1)c1ccsc1)Nc1cccc(F)c1CC[C@@H]1CN[C@H](COC(=O)NCC(F)(F)F)CO1] | {(3S,6R)-6-[2-(2-fluoro-6-{[(3S)-3-(4-fluorophenyl)-3-thiophen-3-ylpropanoyl]amino}phenyl)ethyl]morpholin-3-yl}methyl (2,2,2-trifluoroethyl)carbamate | 612.2 |
| 184 | 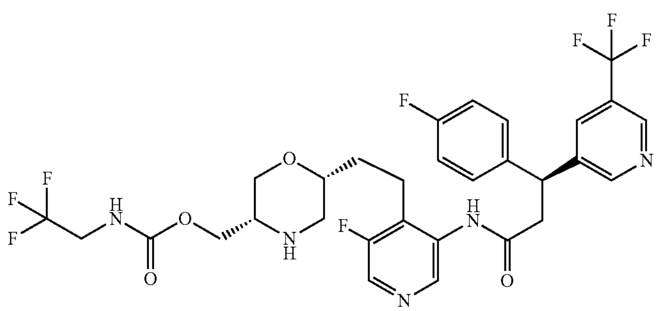 [SMILES: O=C(C[C@@H](c1ccc(F)cc1)c1cncc(C(F)(F)F)c1)Nc1cncc(F)c1CC[C@@H]1CN[C@H](COC(=O)NCC(F)(F)F)CO1] | [(3S,6R)-6-{2-[3-fluoro-5-({(3S)-3-(4-fluorophenyl)-3-[5-(trifluoromethyl)pyridin-3-yl]propanoyl}amino)pyridin-4-yl]ethyl}morpholin-3-yl]methyl (2,2,2-trifluoroethyl)carbamate | 676.2 |
| 185 | 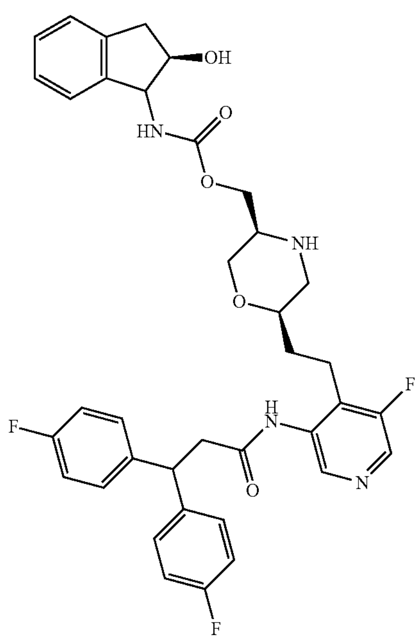 [SMILES: O=C(CC(c1ccc(F)cc1)c1ccc(F)cc1)Nc1cncc(F)c1CC[C@@H]1CN[C@H](COC(=O)NC2c3ccccc3C[C@H]2O)CO1] | {(3S,6R)-6-[2-(3-{[3,3-bis(4-fluoro-phenyl)propanoyl]amino}-5-fluoropyridin-4-yl)ethyl]morpholin-3-yl}methyl [(2R)-2-hydroxy-2,3-dihydro-1H-inden-1-yl]carbamate | 675.3 |

TABLE 1-continued

The following examples can be prepared using the procedures described above.

| Example | Structure | IUPAC Name | Mass [M + H]+ |
|---|---|---|---|
| 186 | 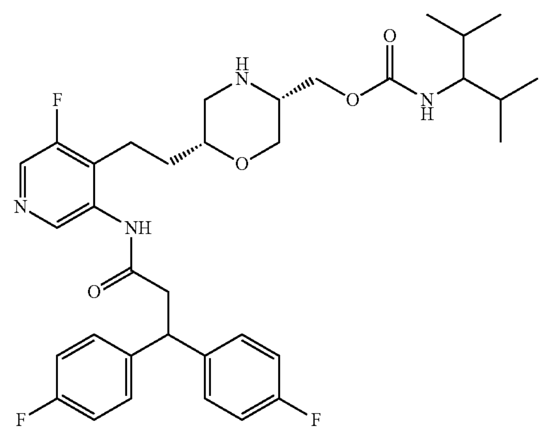 [SMILES: CC(C)C(NC(=O)OC[C@@H]1CO[C@H](CCc2c(F)cncc2NC(=O)CC(c2ccc(F)cc2)c2ccc(F)cc2)CN1)C(C)C] | {(3S,6R)-6-[2-(3-{[3,3-bis(4-fluoro-phenyl)propanoyl]amino}-5-fluoropyridin-4-yl)ethyl]morpholin-3-yl}methyl [2-methyl-1-(1-methylethyl)propyl]carbamate | 641.3 |
| 187 | 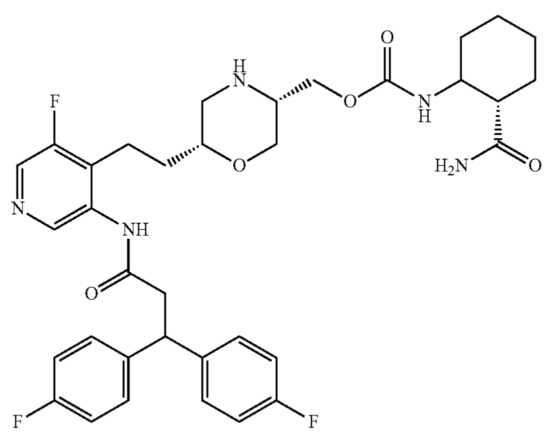 [SMILES: NC(=O)[C@H]1CCCCC1NC(=O)OC[C@@H]1CO[C@H](CCc2c(F)cncc2NC(=O)CC(c2ccc(F)cc2)c2ccc(F)cc2)CN1] | {(3S,6R)-6-[2-(3-{[3,3-bis(4-fluoro-phenyl)propanoyl]amino}-5-fluoropyridin-4-yl)ethyl]morpholin-3-yl}methyl [(2S)-2-carbamoylcyclohexyl]carbamate | 668.3 |
| 188 | 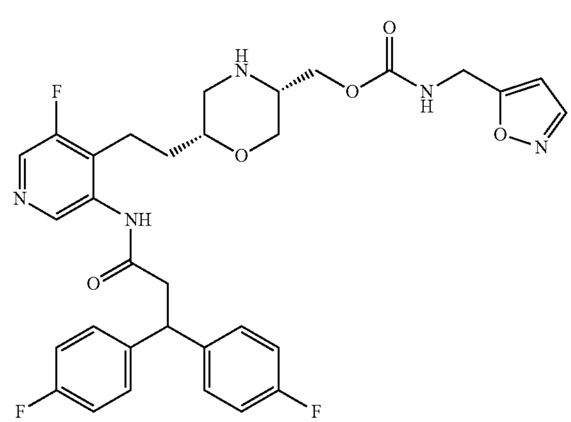 [SMILES: O=C(CC(c1ccc(F)cc1)c1ccc(F)cc1)Nc1cncc(F)c1CC[C@@H]1CN[C@H](COC(=O)NCc2ccno2)CO1] | {(3S,6R)-6-[2-(3-{[3,3-bis(4-fluoro-phenyl)propanoyl]amino}-5-fluoropyridin-4-yl)ethyl]morpholin-3-yl}methyl (isoxazol-5-ylmethyl)carbamate | 624.2 |

TABLE 2

The following examples can be prepared using the procedures described above.

| Example | Structure | IUPAC Name | Mass [M + H]+ |
|---------|-----------|------------|---------------|
| 189 | 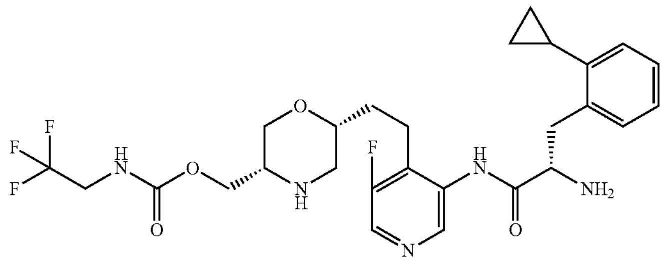 [SMILES: N[C@@H](Cc1ccccc1C1CC1)C(=O)Nc1cncc(F)c1CC[C@@H]1CN[C@H](COC(=O)NCC(F)(F)F)CO1] | 2-cyclopropyl-N-(5-fluoro-4-{2-[(2R,5S)-5-({[(2,2,2-trifluoroethyl)carbamoyl]oxy}methyl)morpholin-2-yl]ethyl}pyridin-3-yl)-L-phenylalaninamide | 568.3 |
| 190 | 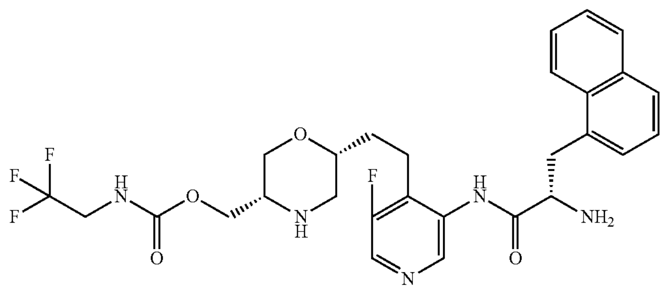 [SMILES: N[C@@H](Cc1cccc2ccccc12)C(=O)Nc1cncc(F)c1CC[C@@H]1CN[C@H](COC(=O)NCC(F)(F)F)CO1] | {(3S,6R)-6-[2-(3-{[(2S)-2-amino-3-naphthalen-1-ylpropanoyl]amino}-5-fluoropyridin-4-yl)ethyl]morpholin-3-yl}methyl (2,2,2-trifluoroethyl)carbamate (non-preferred name) | 578.2 |
| 191 | 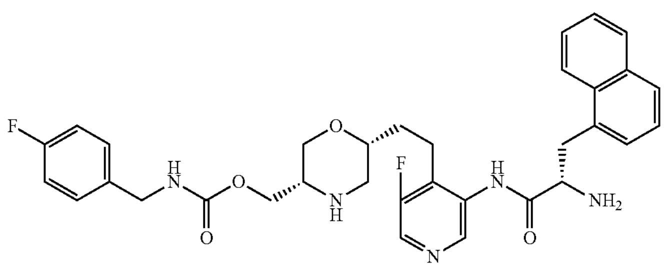 [SMILES: N[C@@H](Cc1cccc2ccccc12)C(=O)Nc1cncc(F)c1CC[C@@H]1CN[C@H](COC(=O)NCc2ccc(F)cc2)CO1] | {(3S,6R)-6-[2-(3-{[(2S)-2-amino-3-naphthalen-1-ylpropanoyl]amino}-5-fluoropyridin-4-yl)ethyl]morpholin-3-yl}methyl (4-fluorobenzyl)carbamate (non-preferred name) | 604.3 |
| 192 | 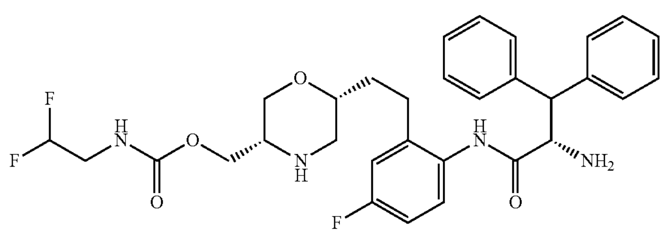 [SMILES: N[C@H](C(=O)Nc1ccc(F)cc1CC[C@@H]1CN[C@H](COC(=O)NCC(F)F)CO1)C(c1ccccc1)c1ccccc1] | N-(2-{2-[(2R,5S)-5-({[(2,2-difluoroethyl)carbamoyl]oxy}methyl)morpholin-2-yl]ethyl}-4-fluorophenyl)-β-phenyl-L-phenylalaninamide | 585.3 |
| 193 | 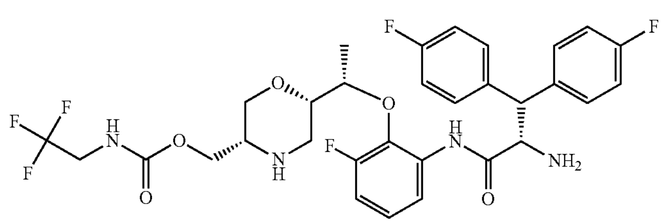 [SMILES: C[C@H](Oc1c(F)cccc1NC(=O)[C@@H](N)C(c1ccc(F)cc1)c1ccc(F)cc1)[C@@H]1CN[C@H](COC(=O)NCC(F)(F)F)CO1] | 4-fluoro-β-(4-fluorophenyl)-N-(3-fluoro-2-{(1S)-1-[(2S,5S)-5-({[(2,2,2-trifluoroethyl)carbamoyl]oxy}methyl)morpholin-2-yl]ethoxy}phenyl)-L-phenylalaninamide | 655.2 |

TABLE 2-continued

The following examples can be prepared using the procedures described above.

| Example | Structure | IUPAC Name | Mass [M + H]+ |
|---|---|---|---|
| 194 | 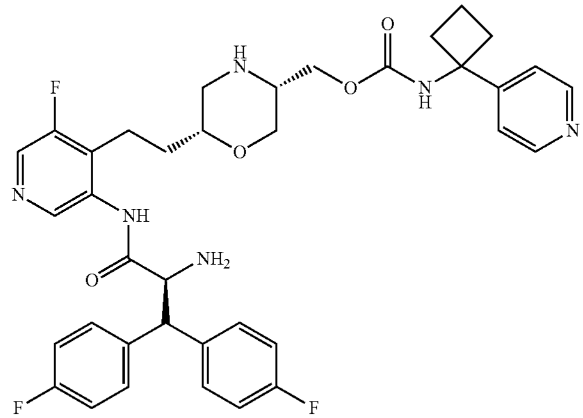 [SMILES: N[C@H](C(=O)Nc1cncc(F)c1CC[C@@H]1CN[C@H](COC(=O)NC2(c3ccncc3)CCC2)CO1)C(c1ccc(F)cc1)c1ccc(F)cc1] | 4-fluoro-β-(4-fluorophenyl)-N-(5-fluoro-4-{2-[(2R,5S)-5-({[(1-pyridin-4-ylcyclobutyl)carbamoyl]oxy}methyl)morpholin-2-yl]ethyl}pyridin-3-yl)-L-phenylalaninamide | 689.3 |
| 195 | 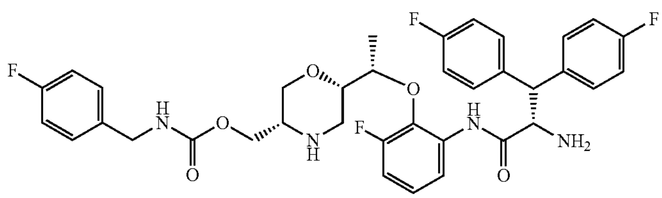 [SMILES: C[C@H](Oc1c(F)cccc1NC(=O)[C@@H](N)C(c1ccc(F)cc1)c1ccc(F)cc1)[C@@H]1CN[C@H](COC(=O)NCc2ccc(F)cc2)CO1] | 4-fluoro-N-(3-fluoro-2-{(1S)-1-[(2S,5S)-5-({[(4-fluorobenzyl)carbamoyl]oxy}methyl)morpholin-2-yl]ethoxy}phenyl)-β-(4-fluorophenyl)-L-phenylalaninamide | 681.3 |
| 196 | 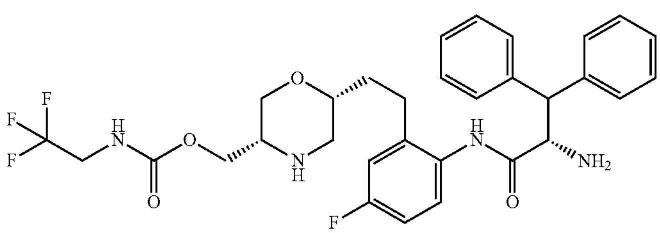 [SMILES: N[C@H](C(=O)Nc1ccc(F)cc1CC[C@@H]1CN[C@H](COC(=O)NCC(F)(F)F)CO1)C(c1ccccc1)c1ccccc1] | N-(4-fluoro-2-{2-[(2R,5S)-5-({[(2,2,2-trifluoroethyl)carbamoyl]oxy}methyl)morpholin-2-yl]ethyl}phenyl)-β-phenyl-L-phenylalaninamide | 603.3 |
| 197 | 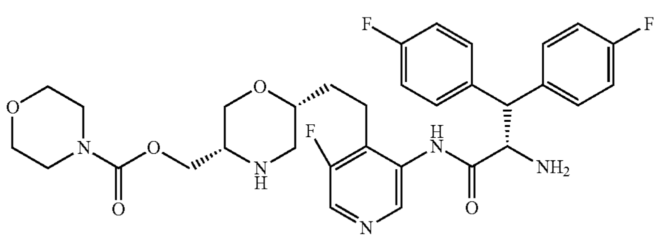 [SMILES: N[C@H](C(=O)Nc1cncc(F)c1CC[C@@H]1CN[C@H](COC(=O)N2CCOCC2)CO1)C(c1ccc(F)cc1)c1ccc(F)cc1] | {(3S,6R)-6-[2-(3-fluoro-5-{[4-fluoro-β-(4-fluorophenyl)-L-phenylalanyl]amino}pyridin-4-yl)ethyl]morpholin-3-yl}methyl morpholine-4-carboxylate | 628.3 |
| 198 | 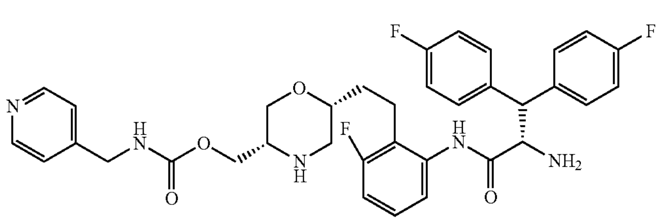 [SMILES: N[C@H](C(=O)Nc1cccc(F)c1CC[C@@H]1CN[C@H](COC(=O)NCc2ccncc2)CO1)C(c1ccc(F)cc1)c1ccc(F)cc1] | 4-fluoro-β-(4-fluorophenyl)-N-(3-fluoro-2-{2-[(2R,5S)-5-({[(pyridin-4-ylmethyl)carbamoyl]oxy}methyl)morpholin-2-yl]ethyl}phenyl)-L-phenylalaninamide | 648.3 |

TABLE 2-continued

The following examples can be prepared using the procedures described above.

| Example | Structure | IUPAC Name | Mass [M + H]+ |
|---|---|---|---|
| 199 | 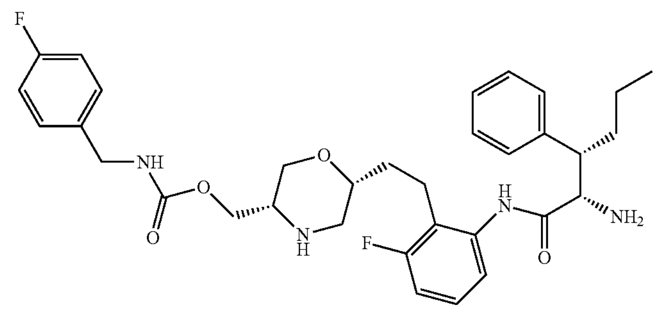 [SMILES: CCC[C@@H](c1ccccc1)[C@H](N)C(=O)Nc1cccc(F)c1CC[C@@H]1CN[C@H](COC(=O)NCc2ccc(F)cc2)CO1] | (βS)-N-(3-fluoro-2-{2-[(2R,5S)-5-({[(4-fluorobenzyl)carbamoyl]oxy}methyl)morpholin-2-yl]ethyl}phenyl)-β-propyl-L-phenylalaninamide | 595.3 |
| 200 | 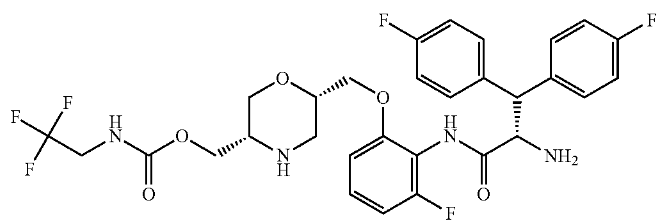 [SMILES: N[C@H](C(=O)Nc1c(F)cccc1OC[C@@H]1CN[C@H](COC(=O)NCC(F)(F)F)CO1)C(c1ccc(F)cc1)c1ccc(F)cc1] | 4-fluoro-β-(4-fluorophenyl)-N-(2-fluoro-6-{[(2S,5S)-5-({[(2,2,2-trifluoroethyl)carbamoyl]oxy}methyl)morpholin-2-yl]methoxy}phenyl)-L-phenylalaninamide | 641.2 |
| 201 | 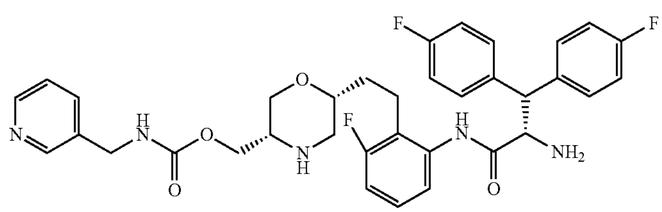 [SMILES: N[C@H](C(=O)Nc1cccc(F)c1CC[C@@H]1CN[C@H](COC(=O)NCc2cccnc2)CO1)C(c1ccc(F)cc1)c1ccc(F)cc1] | 4-fluoro-β-(4-fluorophenyl)-N-(3-fluoro-2-{2-[(2R,5S)-5-({[(pyridin-3-ylmethyl)carbamoyl]oxy}methyl)morpholin-2-yl]ethyl}phenyl)-L-phenylalaninamide | 648.3 |
| 202 | 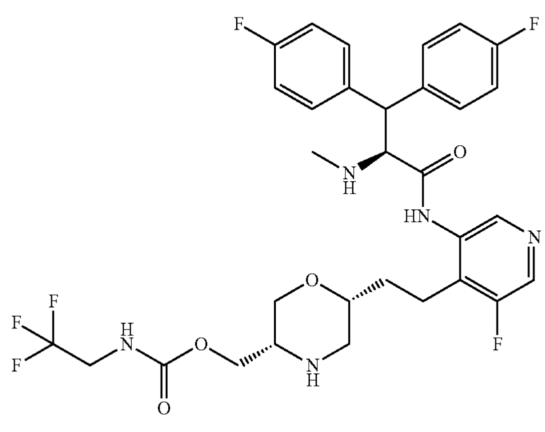 [SMILES: CN[C@H](C(=O)Nc1cncc(F)c1CC[C@@H]1CN[C@H](COC(=O)NCC(F)(F)F)CO1)C(c1ccc(F)cc1)c1ccc(F)cc1] | 4-fluoro-β-(4-fluorophenyl)-N-(5-fluoro-4-{2-[(2R,5S)-5-({[(2,2,2-trifluoroethyl)carbamoyl]oxy}methyl)morpholin-2-yl]ethyl}pyridin-3-yl)-Nα-methyl-L-phenylalaninamide | 654.3 |
| 203 | 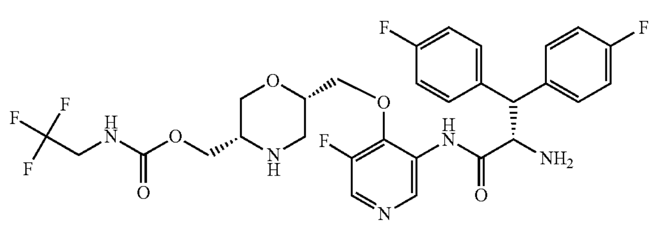 [SMILES: N[C@H](C(=O)Nc1cncc(F)c1OC[C@@H]1CN[C@H](COC(=O)NCC(F)(F)F)CO1)C(c1ccc(F)cc1)c1ccc(F)cc1] | 4-fluoro-β-(4-fluorophenyl)-N-(5-fluoro-4-{[(2S,5S)-5-({[(2,2,2-trifluoroethyl)carbamoyl]oxy}methyl)morpholin-2-yl]methoxy}pyridin-3-yl)-L-phenylalaninamide | 642.2 |

TABLE 2-continued

The following examples can be prepared using the procedures described above.

| Example | Structure | IUPAC Name | Mass [M + H]+ |
|---|---|---|---|
| 204 | 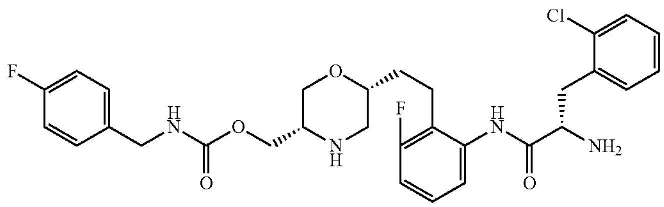 [SMILES: N[C@@H](Cc1ccccc1Cl)C(=O)Nc1cccc(F)c1CC[C@@H]1CN[C@H](COC(=O)NCc2ccc(F)cc2)CO1] | 2-chloro-N-(3-fluoro-2-{2-[(2R,5S)-5-({[(4-fluorobenzyl)carbamoyl]oxy}methyl)morpholin-2-yl]ethyl}phenyl)-L-phenylalaninamide | 587.2 |
| 205 | 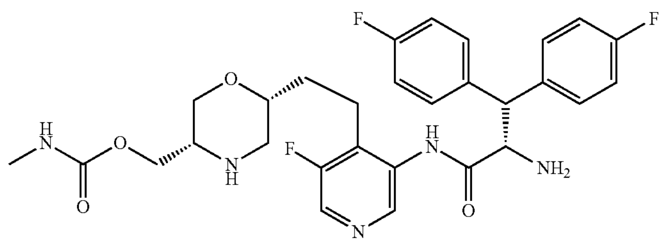 [SMILES: CNC(=O)OC[C@@H]1CO[C@H](CCc2c(F)cncc2NC(=O)[C@@H](N)C(c2ccc(F)cc2)c2ccc(F)cc2)CN1] | 4-fluoro-N-(5-fluoro-4-{2-[(2R,5S)-5-{[(methylcarbamoyl)oxy]methyl}morpholin-2-yl]ethyl}pyridin-3-yl)-β-(4-fluorophenyl)-L-phenylalaninamide | 572.2 |
| 206 | 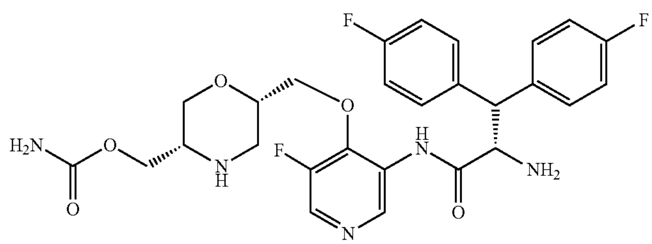 [SMILES: NC(=O)OC[C@@H]1CO[C@H](COc2c(F)cncc2NC(=O)[C@@H](N)C(c2ccc(F)cc2)c2ccc(F)cc2)CN1] | N-[4-({(2S,5S)-5-[(carbamoyloxy)methyl]morpholin-2-yl}methoxy)-5-fluoropyridin-3-yl]-4-fluoro-β-(4-fluorophenyl)-L-phenylalaninamide | 560.2 |
| 207 | 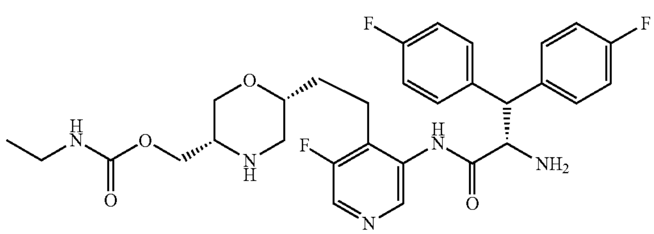 [SMILES: CCNC(=O)OC[C@@H]1CO[C@H](CCc2c(F)cncc2NC(=O)[C@@H](N)C(c2ccc(F)cc2)c2ccc(F)cc2)CN1] | N-(4-{2-[(2R,5S)-5-{[(ethylcarbamoyl)oxy]methyl}morpholin-2-yl]ethyl}-5-fluoropyridin-3-yl)-4-fluoro-β-(4-fluorophenyl)-L-phenylalaninamide | 586.3 |
| 208 | 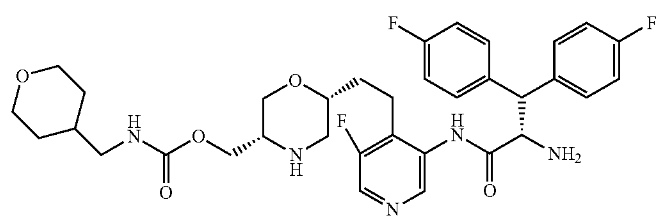 [SMILES: N[C@H](C(=O)Nc1cncc(F)c1CC[C@@H]1CN[C@H](COC(=O)NCC2CCOCC2)CO1)C(c1ccc(F)cc1)c1ccc(F)cc1] | 4-fluoro-β-(4-fluorophenyl)-N-(5-fluoro-4-{2-[(2R,5S)-5-({[(tetrahydro-2H-pyran-4-ylmethyl)carbamoyl]oxy}methyl)morpholin-2-yl]ethyl}pyridin-3-yl)-L-phenylalaninamide | 656.3 |
| 209 | 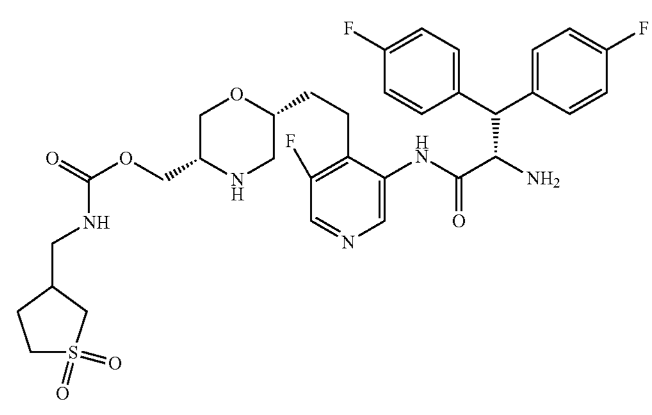 [SMILES: N[C@H](C(=O)Nc1cncc(F)c1CC[C@@H]1CN[C@H](COC(=O)NCC2CCS(=O)(=O)C2)CO1)C(c1ccc(F)cc1)c1ccc(F)cc1] | N-[4-(2-{(2R,5S)-5-[({[(1,1-dioxidotetrahydrothiophen-3-yl)methyl]carbamoyl}oxy)methyl]morpholin-2-yl}ethyl)-5-fluoropyridin-3-yl]-4-fluoro-β-(4-fluorophenyl)-L-phenylalaninamide | 690.3 |

TABLE 2-continued

The following examples can be prepared using the procedures described above.

| Example | Structure | IUPAC Name | Mass [M + H]+ |
|---|---|---|---|
| 210 | 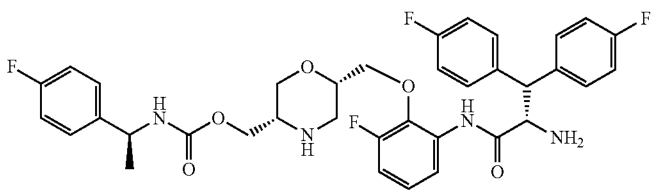 [SMILES: C[C@H](NC(=O)OC[C@@H]1CO[C@H](COc2c(F)cccc2NC(=O)[C@@H](N)C(c2ccc(F)cc2)c2ccc(F)cc2)CN1)c1ccc(F)cc1] | 4-fluoro-N-[3-fluoro-2-({(2S,5S)-5-[({[(1S)-1-(4-fluorophenyl)ethyl]carbamoyl}oxy)methyl]morpholin-2-yl}methoxy)phenyl]-β-(4-fluorophenyl)-L-phenylalaninamide | 681.3 |
| 211 | 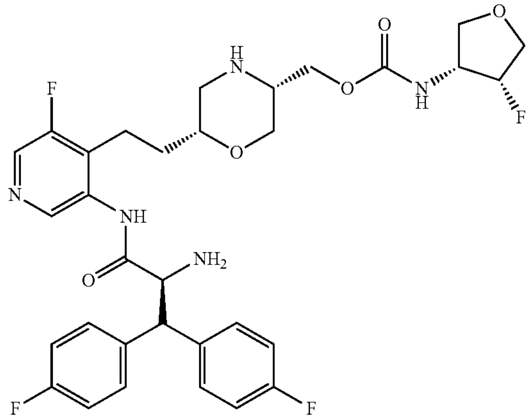 [SMILES: N[C@H](C(=O)Nc1cncc(F)c1CC[C@@H]1CN[C@H](COC(=O)N[C@@H]2COC[C@@H]2F)CO1)C(c1ccc(F)cc1)c1ccc(F)cc1] | 4-fluoro-N-[5-fluoro-4-(2-{(2R,5S)-5-[({[(3R,4R)-4-fluorotetrahydrofuran-3-yl]carbamoyl}oxy)methyl]morpholin-2-yl}ethyl)pyridin-3-yl]-p-(4-fluorophenyl)-L-phenylalaninamide | 646.3 |
| 212 | 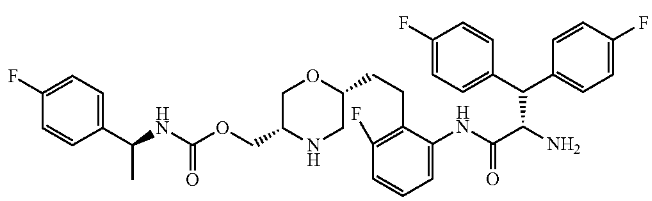 [SMILES: C[C@H](NC(=O)OC[C@@H]1CO[C@H](CCc2c(F)cccc2NC(=O)[C@@H](N)C(c2ccc(F)cc2)c2ccc(F)cc2)CN1)c1ccc(F)cc1] | 4-fluoro-N-[3-fluoro-2-(2-{(2R,5S)-5-[({[(1S)-1-(4-fluorophenyl)ethyl]carbamoyl}oxy)methyl]morpholin-2-yl}ethyl)phenyl]-β-(4-fluorophenyl)-L-phenylalaninamide | 679.3 |
| 213 | 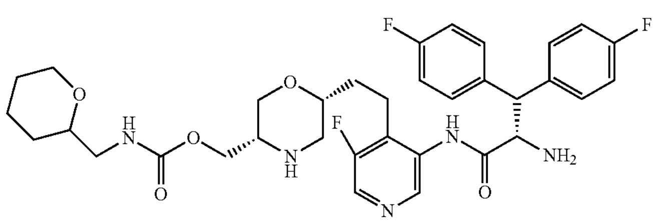 [SMILES: N[C@H](C(=O)Nc1cncc(F)c1CC[C@@H]1CN[C@H](COC(=O)NCC2CCCCO2)CO1)C(c1ccc(F)cc1)c1ccc(F)cc1] | 4-fluoro-β-(4-fluorophenyl)-N-(5-fluoro-4-{2-[(2R,5S)-5-({[(tetrahydro-2H-pyran-2-ylmethyl)carbamoyl]oxy}methyl)morpholin-2-yl]ethyl}pyridin-3-yl)-L-phenylalaninamide | 656.3 |
| 214 | 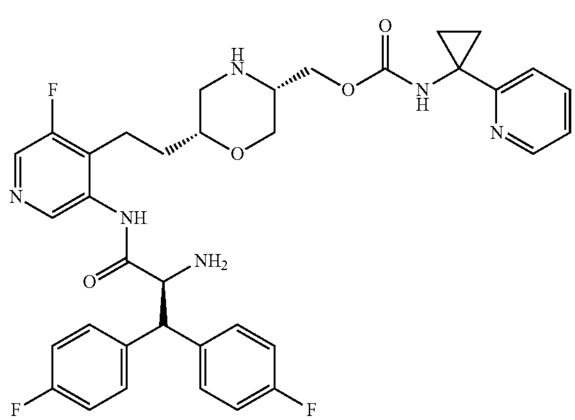 [SMILES: N[C@H](C(=O)Nc1cncc(F)c1CC[C@@H]1CN[C@H](COC(=O)NC2(c3ccccn3)CC2)CO1)C(c1ccc(F)cc1)c1ccc(F)cc1] | 4-fluoro-β-(4-fluorophenyl)-N-(5-fluoro-4-{2-[(2R,5S)-5-({[(1-pyridin-2-ylcyclopropyl)carbamoyl]oxy}methyl)morpholin-2-yl]ethyl}pyridin-3-yl)-L-phenylalaninamide | 675.3 |

TABLE 2-continued

The following examples can be prepared using the procedures described above.

| Example | Structure | IUPAC Name | Mass [M + H]+ |
|---|---|---|---|
| 215 | 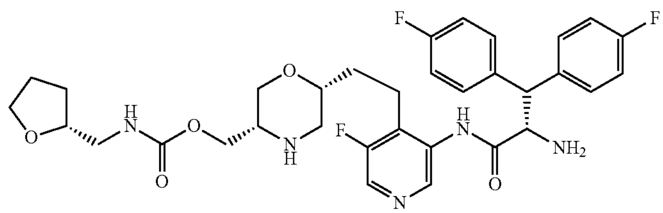 [SMILES: N[C@H](C(=O)Nc1cncc(F)c1CC[C@@H]1CN[C@H](COC(=O)NC[C@H]2CCCO2)CO1)C(c1ccc(F)cc1)c1ccc(F)cc1] | 4-fluoro-β-(4-fluorophenyl)-N-[5-fluoro-4-(2-{(2R,5S)-5-[({[(2R)-tetrahydrofuran-2-ylmethyl]carbamoyl}oxy)methyl]morpholin-2-yl}ethyl)pyridin-3-yl]-L-phenylalaninamide | 642.3 |
| 216 | 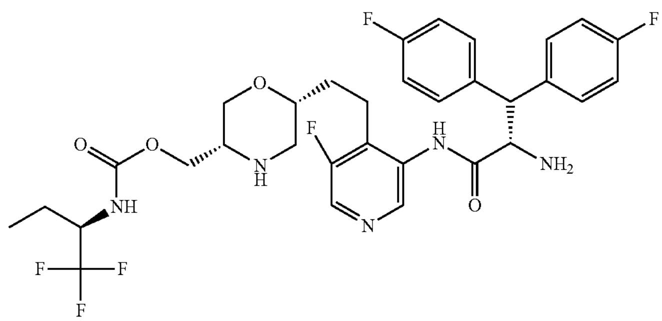 [SMILES: CC[C@@H](NC(=O)OC[C@@H]1CO[C@H](CCc2c(F)cncc2NC(=O)[C@@H](N)C(c2ccc(F)cc2)c2ccc(F)cc2)CN1)C(F)(F)F] | 4-fluoro-(3-(4-fluorophenyl)-N-[5-fluoro-4-(2-{(2R,5S)-5-[({[(1R)-1-(trifluoromethyl)propyl]carbamoyl}oxy)methyl]morpholin-2-yl}ethyl)pyridin-3-yl]-L-phenylalaninamide | 668.3 |
| 217 | 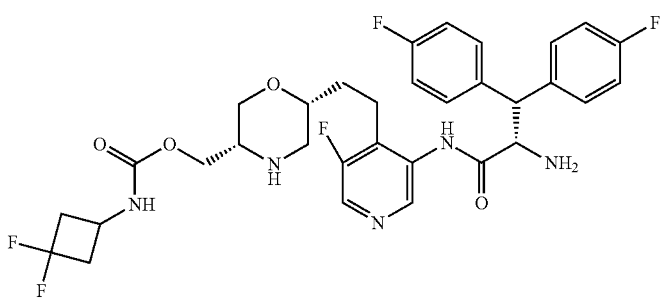 [SMILES: N[C@H](C(=O)Nc1cncc(F)c1CC[C@@H]1CN[C@H](COC(=O)NC2CC(F)(F)C2)CO1)C(c1ccc(F)cc1)c1ccc(F)cc1] | N-(4-{2-[(2R,5S)-5-({[(3,3-difluorocyclobutyl)carbamoyl]oxy}methyl)morpholin-2-yl]ethyl}-5-fluoropyridin-3-yl)-4-fluoro-β-(4-fluorophenyl)-L-phenylalaninamide | 648.3 |
| 218 | 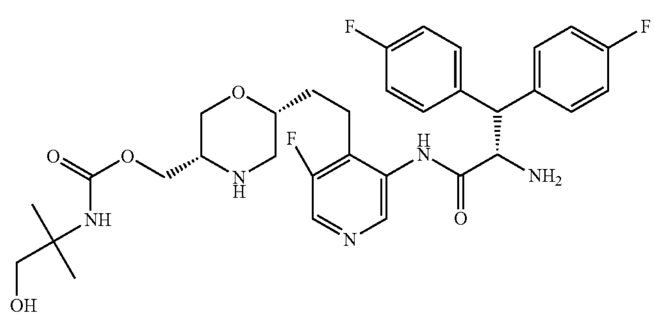 [SMILES: CC(C)(CO)NC(=O)OC[C@@H]1CO[C@H](CCc2c(F)cncc2NC(=O)[C@@H](N)C(c2ccc(F)cc2)c2ccc(F)cc2)CN1] | 4-fluoro-N-(5-fluoro-4-{2-[(2R,5S)-5-({[(2-hydroxy-1,1-dimethylethyl)carbamoyl]oxy}methyl)morpholin-2-yl]ethyl}pyridin-3-yl)-β-(4-fluorophenyl)-L-phenylalaninamide | 630.3 |
| 219 | 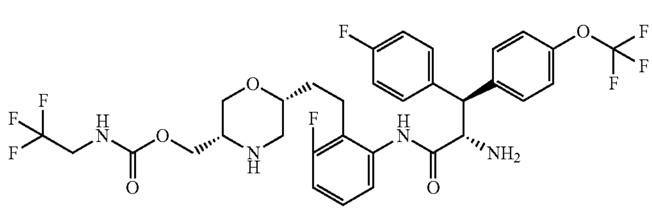 [SMILES: N[C@H](C(=O)Nc1cccc(F)c1CC[C@@H]1CN[C@H](COC(=O)NCC(F)(F)F)CO1)[C@@H](c1ccc(F)cc1)c1ccc(OC(F)(F)F)cc1] | (βR)-β-(4-fluorophenyl)-N-(3-fluoro-2-{2-[(2R,5S)-5-({[(2,2,2-trifluoroethyl)carbamoyl]oxy}methyl)morpholin-2-yl]ethyl}phenyl)-O-(trifluoromethyl)-L-tyrosinamide | 705.2 |

TABLE 2-continued

The following examples can be prepared using the procedures described above.

| Example | Structure | IUPAC Name | Mass [M + H]+ |
|---|---|---|---|
| 220 | 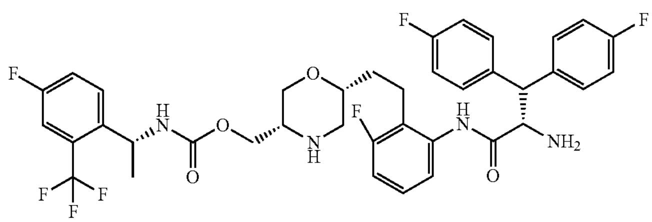 [SMILES: C[C@@H](NC(=O)OC[C@@H]1CO[C@H](CCc2c(F)cccc2NC(=O)[C@@H](N)C(c2ccc(F)cc2)c2ccc(F)cc2)CN1)c1ccc(F)cc1C(F)(F)F] | 4-fluoro-N-(3-fluoro-2-{2-[(2R,5S)-5-{[({(1R)-1-[4-fluoro-2-(trifluoromethyl)phenyl]ethyl}carbamoyl)oxy]methyl}morpholin-2-yl]ethyl}phenyl)-β-(4-fluorophenyl)-L-phenylalaninamide | 747.3 |
| 221 | 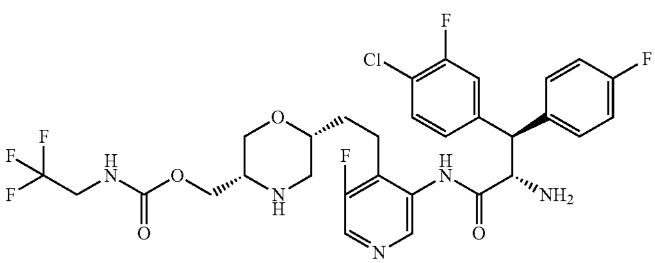 [SMILES: N[C@H](C(=O)Nc1cncc(F)c1CC[C@@H]1CN[C@H](COC(=O)NCC(F)(F)F)CO1)[C@H](c1ccc(F)cc1)c1ccc(Cl)c(F)c1] | (βR)-β-(4-chloro-3-fluorophenyl)-4-fluoro-N-(5-fluoro-4-{2-[(2R,5S)-5-({[(2,2,2-trifluoroethyl)carbamoyl]oxy}methyl)morpholin-2-yl]ethyl}pyridin-3-yl)-L-phenylalaninamide | 674.2 |
| 222 | 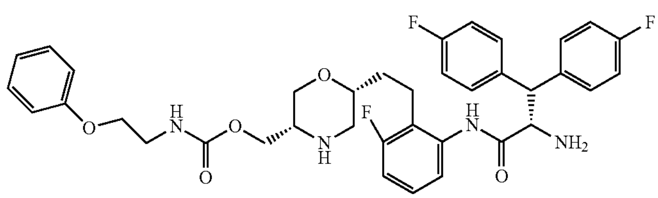 [SMILES: N[C@H](C(=O)Nc1cccc(F)c1CC[C@@H]1CN[C@H](COC(=O)NCCOc2ccccc2)CO1)C(c1ccc(F)cc1)c1ccc(F)cc1] | 4-fluoro-N-(3-fluoro-2-{2-[(2R,5S)-5-({[(2-phenoxyethyl)carbamoyl]oxy}methyl)morpholin-2-yl]ethyl}phenyl)-β-(4-fluorophenyl)-L-phenylalaninamide | 677.3 |
| 223 | 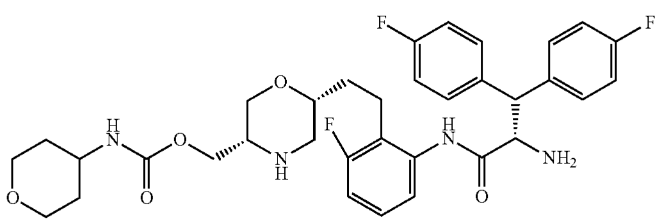 [SMILES: N[C@H](C(=O)Nc1cccc(F)c1CC[C@@H]1CN[C@H](COC(=O)NC2CCOCC2)CO1)C(c1ccc(F)cc1)c1ccc(F)cc1] | 4-fluoro-β-(4-fluorophenyl)-N-(3-fluoro-2-{2-[(2R,5S)-5-{[(tetrahydro-2H-pyran-4-ylcarbamoyl)oxy]methyl}morpholin-2-yl]ethyl}phenyl)-L-phenylalaninamide | 641.3 |
| 224 | 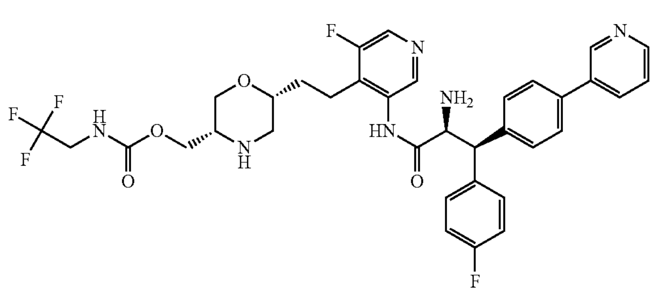 [SMILES: N[C@H](C(=O)Nc1cncc(F)c1CC[C@@H]1CN[C@H](COC(=O)NCC(F)(F)F)CO1)[C@H](c1ccc(F)cc1)c1ccc(-c2cccnc2)cc1] | (βS)-β-(4-fluorophenyl)-N-(5-fluoro-4-{2-[(2R,5S)-5-({[(2,2,2-trifluoroethyl)carbamoyl]oxy}methyl)morpholin-2-yl]ethyl}pyridin-3-yl)-4-pyridin-3-yl-L-phenylalaninamide | 699.3 |
| 225 | 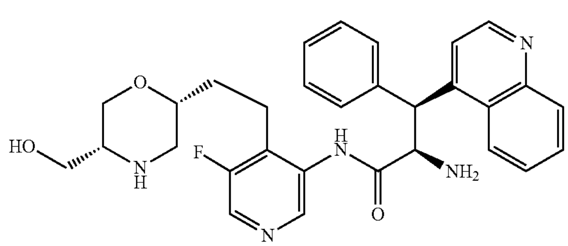 [SMILES: N[C@@H](C(=O)Nc1cncc(F)c1CC[C@@H]1CN[C@H](CO)CO1)[C@@H](c1ccccc1)c1ccnc2ccccc12] | (βS)-N-(5-fluoro-4-{2-[(2R,5R)-5-(hydroxymethyl)morpholin-2-yl]ethyl}pyridin-3-yl)-β-quinolin-4-yl-D-phenylalaninamide | 530.3 |

TABLE 2-continued

The following examples can be prepared using the procedures described above.

| Example | Structure | IUPAC Name | Mass [M + H]+ |
|---|---|---|---|
| 226 | 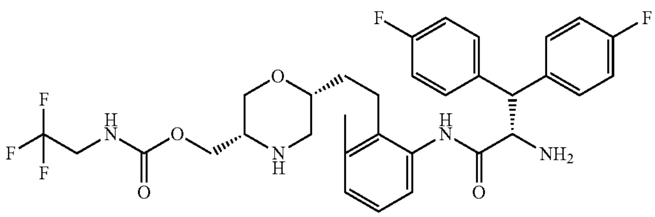 [SMILES: Cc1cccc(NC(=O)[C@@H](N)C(c2ccc(F)cc2)c2ccc(F)cc2)c1CC[C@@H]1CN[C@H](COC(=O)NCC(F)(F)F)CO1] | 4-fluoro-β-(4-fluorophenyl)-N-(3-methyl-2-{2-[(2R,5S)-5-({[(2,2,2-trifluoroethyl)carbamoyl]oxy}methyl)morpholin-2-yl]ethyl}phenyl)-L-phenylalaninamide | 635.3 |
| 227 | 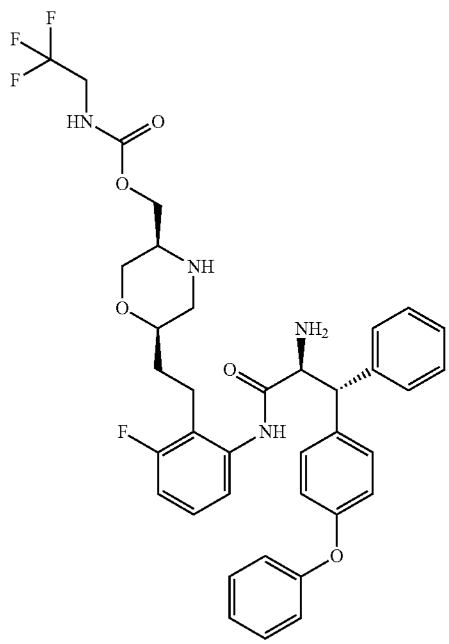 [SMILES: N[C@H](C(=O)Nc1cccc(F)c1CC[C@@H]1CN[C@H](COC(=O)NCC(F)(F)F)CO1)[C@H](c1ccccc1)c1ccc(Oc2ccccc2)cc1] | (βR)-N-(3-fluoro-2-{2-[(2R,5S)-5-({[(2,2,2-trifluoroethyl)carbamoyl]oxy}methyl)morpholin-2-yl]ethyl}phenyl)-O,β-diphenyl-L-tyrosinamide | 695.3 |
| 228 | 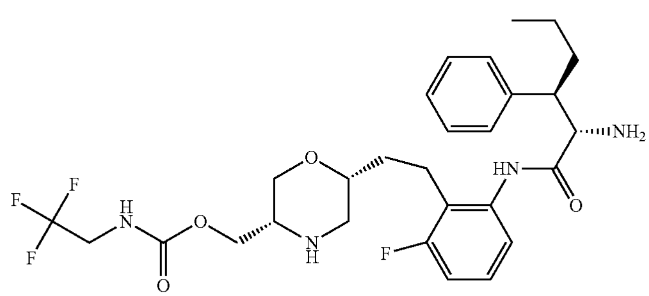 [SMILES: CCC[C@H](c1ccccc1)[C@H](N)C(=O)Nc1cccc(F)c1CC[C@@H]1CN[C@H](COC(=O)NCC(F)(F)F)CO1] | (βR)-N-(3-fluoro-2-{2-[(2R,5S)-5-({[(2,2,2-trifluoroethyl)carbamoyl]oxy}methyl)morpholin-2-yl]ethyl}phenyl)-β-propyl-L-phenylalaninamide | 569.3 |
| 229 | 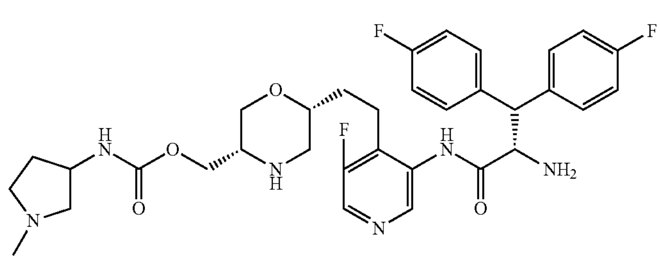 [SMILES: CN1CCC(NC(=O)OC[C@@H]2CO[C@H](CCc3c(F)cncc3NC(=O)[C@@H](N)C(c3ccc(F)cc3)c3ccc(F)cc3)CN2)C1] | 4-fluoro-N-(5-fluoro-4-{2-[(2R,5S)-5-({[(1-methylpyrrolidin-3-yl)carbamoyl]oxy}methyl)morpholin-2-yl]ethyl}pyridin-3-yl)-β-(4-fluorophenyl)-L-phenylalaninamide | 641.3 |

TABLE 2-continued

The following examples can be prepared using the procedures described above.

| Example | Structure | IUPAC Name | Mass [M + H]+ |
|---|---|---|---|
| 230 | 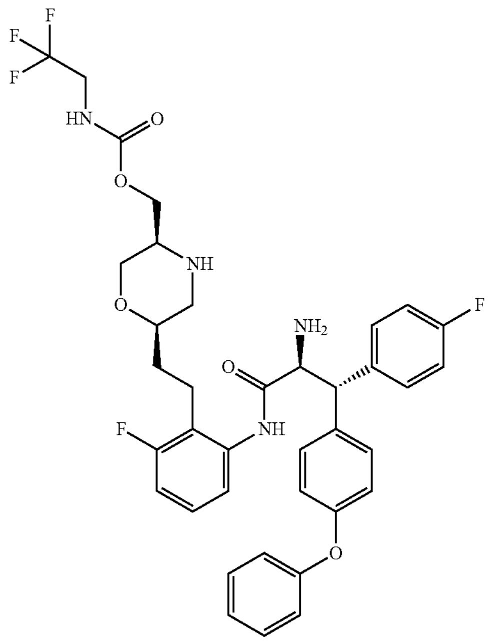 [SMILES: N[C@H](C(=O)Nc1cccc(F)c1CC[C@@H]1CN[C@H](COC(=O)NCC(F)(F)F)CO1)[C@H](c1ccc(F)cc1)c1ccc(Oc2ccccc2)cc1] | (βS)-β-(4-fluorophenyl)-N-(3-fluoro-2-{2-[(2R,5S)-5-({[(2,2,2-trifluoroethyl)carbamoyl]oxy}methyl)morpholin-2-yl]ethyl}phenyl)-O-phenyl-L-tyrosinamide | 713.3 |
| 231 | 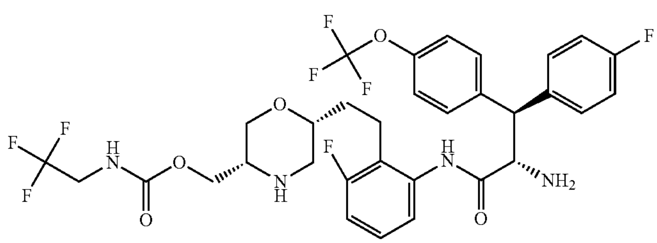 [SMILES: N[C@H](C(=O)Nc1cccc(F)c1CC[C@@H]1CN[C@H](COC(=O)NCC(F)(F)F)CO1)[C@H](c1ccc(F)cc1)c1ccc(OC(F)(F)F)cc1] | (βS)-β-(4-fluorophenyl)-N-(3-fluoro-2-{2-[(2R,5S)-5-({[(2,2,2-trifluoroethyl)carbamoyl]oxy}methyl)morpholin-2-yl]ethyl}phenyl)-O-(trifluoromethyl)-L-tyrosinamide | 705.2 |
| 232 | 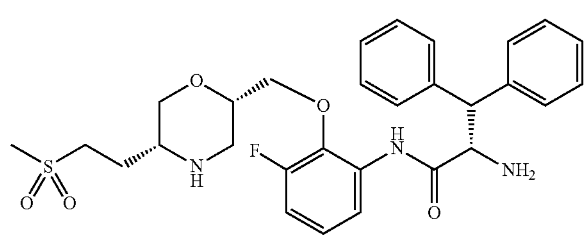 [SMILES: CS(=O)(=O)CC[C@@H]1CO[C@H](COc2c(F)cccc2NC(=O)[C@@H](N)C(c2ccccc2)c2ccccc2)CN1] | N-[3-fluoro-2-({(2S,5R)-5-[2-(methylsulfonyl)ethyl]morpholin-2-yl}methoxy)phenyl]-β-phenyl-L-phenylalaninamide | 556.2 |
| 233 | 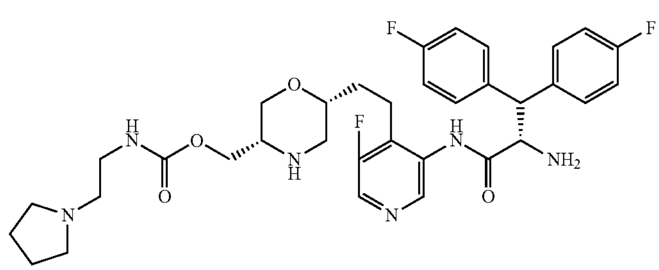 [SMILES: N[C@H](C(=O)Nc1cncc(F)c1CC[C@@H]1CN[C@H](COC(=O)NCCN2CCCC2)CO1)C(c1ccc(F)cc1)c1ccc(F)cc1] | 4-fluoro-β-(4-fluorophenyl)-N-(5-fluoro-4-{2-[(2R,5S)-5-({[(2-pyrrolidin-1-ylethyl)carbamoyl]oxy}methyl)morpholin-2-yl]ethyl}pyridin-3-yl)-L-phenylalaninamide | 655.3 |

TABLE 2-continued

The following examples can be prepared using the procedures described above.

| Example | Structure | IUPAC Name | Mass [M + H]+ |
|---|---|---|---|
| 234 | 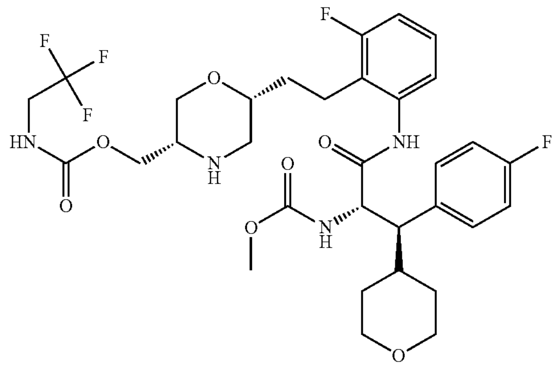 [SMILES: COC(=O)N[C@H](C(=O)Nc1cccc(F)c1CC[C@@H]1CN[C@H](COC(=O)NCC(F)(F)F)CO1)[C@@H](c1ccc(F)cc1)C1CCOCC1] | β-phenyl-N-[2-{2-[(2R,5S)-5-({[(2,2,2-trifluoroethyl)carbamoyl]oxy}methyl)morpholin-2-yl]ethyl}-3-(trifluoromethyl)phenyl]-L-phenylalaninamide | 653.3 |
| 235 | 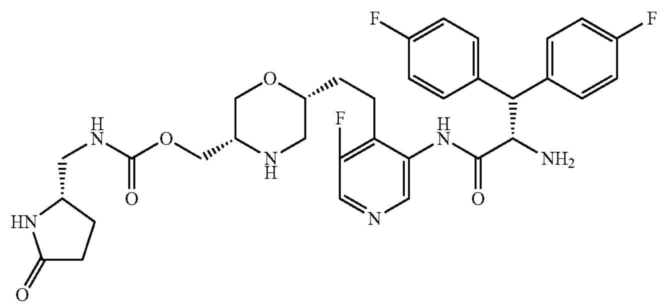 [SMILES: N[C@H](C(=O)Nc1cncc(F)c1CC[C@@H]1CN[C@H](COC(=O)NC[C@@H]2CCC(=O)N2)CO1)C(c1ccc(F)cc1)c1ccc(F)cc1] | 4-fluoro-N-(5-fluoro-4-{2-[(2R,5S)-5-{[({[(2S)-5-oxopyrrolidin-2-yl]methyl}carbamoyl)oxy]methyl}morpholin-2-yl]ethyl}pyridin-3-yl)-β-(4-fluorophenyl)-L-phenylalaninamide | 655.3 |
| 236 | 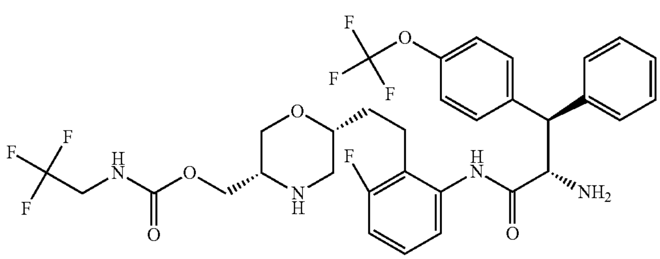 [SMILES: N[C@H](C(=O)Nc1cccc(F)c1CC[C@@H]1CN[C@H](COC(=O)NCC(F)(F)F)CO1)[C@H](c1ccccc1)c1ccc(OC(F)(F)F)cc1] | (βR)-N-(3-fluoro-2-{2-[(2R,5S)-5-({[(2,2,2-trifluoroethyl)carbamoyl]oxy}methyl)morpholin-2-yl]ethyl}phenyl)-β-phenyl-O-(trifluoromethyl)-L-tyrosinamide | 687.2 |
| 237 | 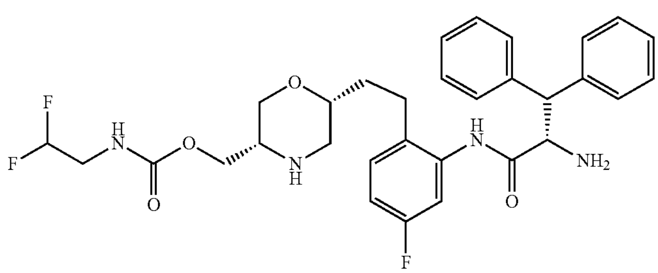 [SMILES: N[C@H](C(=O)Nc1cc(F)ccc1CC[C@@H]1CN[C@H](COC(=O)NCC(F)F)CO1)C(c1ccccc1)c1ccccc1] | N-(2-{2-[(2R,5S)-5-({[(2,2-difluoroethyl)carbamoyl]oxy}methyl)morpholin-2-yl]ethyl}-5-fluorophenyl)-β-phenyl-L-phenylalaninamide | 585.3 |
| 238 | 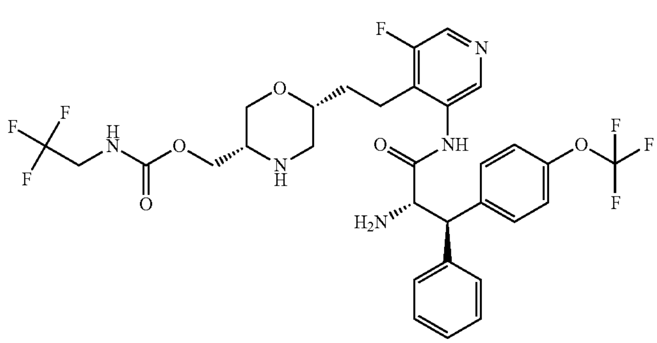 [SMILES: N[C@H](C(=O)Nc1cncc(F)c1CC[C@@H]1CN[C@H](COC(=O)NCC(F)(F)F)CO1)[C@H](c1ccccc1)c1ccc(OC(F)(F)F)cc1] | (βR)-N-(5-fluoro-4-{2-[(2R,5S)-5-({[(2,2,2-trifluoroethyl)carbamoyl]oxy}methyl)morpholin-2-yl]ethyl}pyridin-3-yl)-β-phenyl-O-(trifluoromethyl)-L-tyrosinamide | 688.2 |

TABLE 2-continued

The following examples can be prepared using the procedures described above.

| Example | Structure | IUPAC Name | Mass [M + H]+ |
|---|---|---|---|
| 239 | 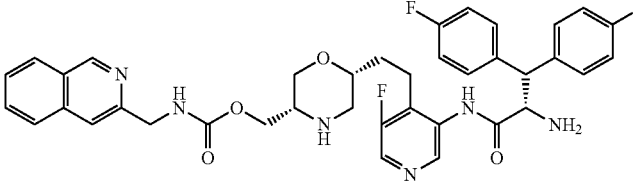 | {(3S,6R)-6-[2-(3-fluoro-5-{[4-fluoro-β-(4-fluorophenyl)-L-phenylalanyl]amino}pyridin-4-yl)ethyl]morpholin-3-yl}methyl (isoquinolin-3-ylmethyl)carbamate | 699.3 |
| 240 | 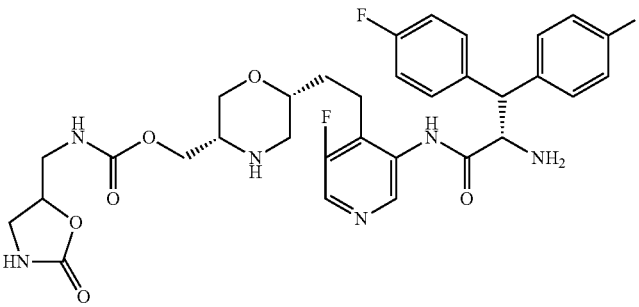 | 4-fluoro-N-[5-fluoro-4-(2-{(2R,5S)-5-[({[(2-oxo-1,3-oxazolidin-5-yl)methyl]carbamoyl}oxy)methyl]morpholin-2-yl}ethyl)pyridin-3-yl]-β-(4-fluorophenyl)-L-phenylalaninamide | 657.3 |
| 241 | 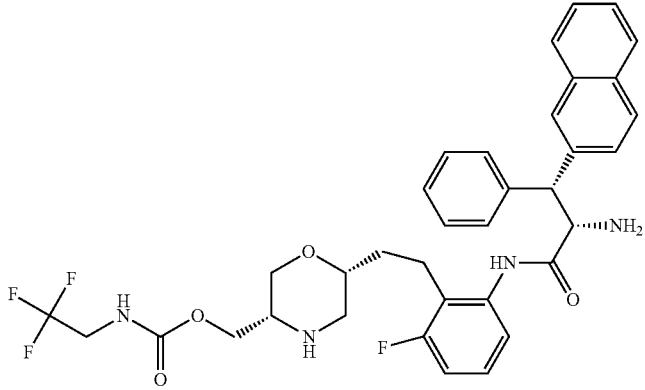 [SMILES: N[C@H](C(=O)Nc1cccc(F)c1CC[C@@H]1CN[C@H](COC(=O)NCC(F)(F)F)CO1)[C@H](c1ccccc1)c1ccc2ccccc2c1] | (βR)-N-(3-fluoro-2-{2-[(2R,5S)-5-({[(2,2,2-trifluoroethyl)carbamoyl]oxy}methyl)morpholin-2-yl]ethyl}phenyl)-β-naphthalen-2-yl-L-phenylalaninamide | 653.3 |
| 242 | 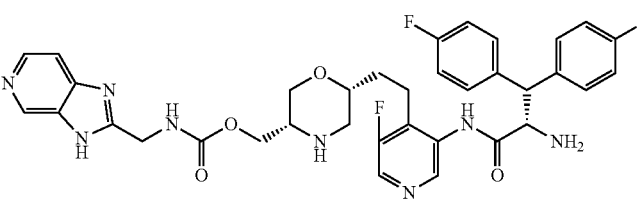 | 4-fluoro-N-(5-fluoro-4-{2-[(2R,5S)-5-({[(3H-imidazo[4,5-c]pyridin-2-ylmethyl)carbamoyl]oxy}methyl)morpholin-2-yl]ethyl}pyridin-3-yl)-β-(4-fluorophenyl)-L-phenylalaninamide | 689.3 |
| 243 | 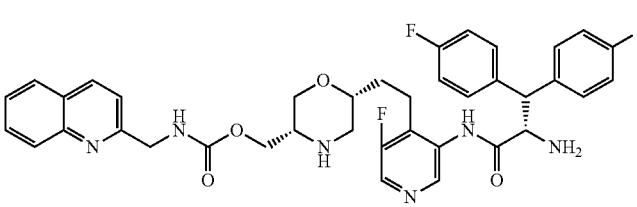 | {(3S,6R)-6-[2-(3-fluoro-5-{[4-fluoro-β-(4-fluorophenyl)-L-phenylalanyl]amino}pyridin-4-yl)ethyl]morpholin-3-yl}methyl (quinolin-2-ylmethyl)carbamate | 699.3 |

TABLE 2-continued

The following examples can be prepared using the procedures described above.

| Example | Structure | IUPAC Name | Mass [M + H]+ |
|---|---|---|---|
| 244 | 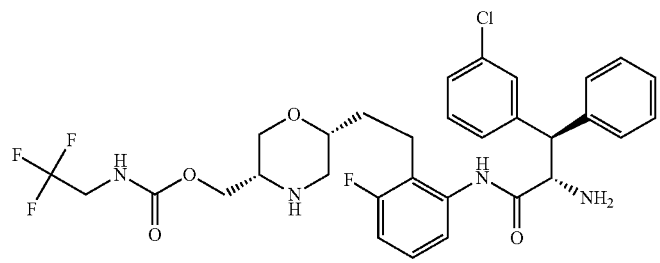 [SMILES: N[C@H](C(=O)Nc1cccc(F)c1CC[C@@H]1CN[C@H](COC(=O)NCC(F)(F)F)CO1)[C@H](c1ccccc1)c1cccc(Cl)c1] | (βR)-3-chloro-N-(3-fluoro-2-{2-[(2R,5S)-5-({[(2,2,2-trifluoroethyl)carbamoyl]oxy}methyl)morpholin-2-yl]ethyl}phenyl)-β-phenyl-L-phenylalaninamide | 637.2 |
| 245 | 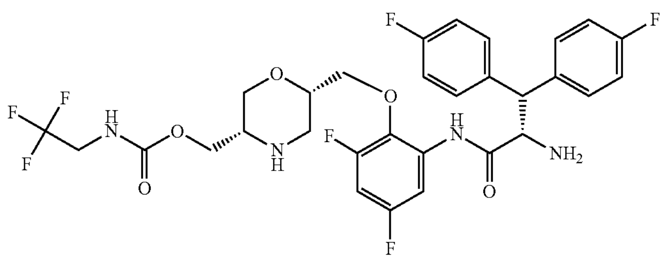 [SMILES: N[C@H](C(=O)Nc1cc(F)cc(F)c1OC[C@@H]1CN[C@H](COC(=O)NCC(F)(F)F)CO1)C(c1ccc(F)cc1)c1ccc(F)cc1] | N-(3,5-difluoro-2-{[(2S,5S)-5-({[(2,2,2-trifluoroethyl)carbamoyl]oxy}methyl)morpholin-2-yl]methoxy}phenyl)-4-fluoro-β-(4-fluorophenyl)-L-phenylalaninamide | 659.2 |
| 246 | 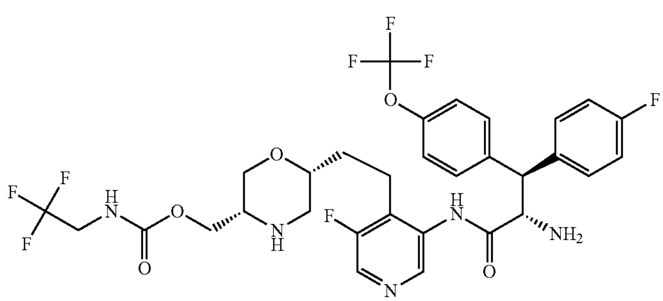 [SMILES: N[C@H](C(=O)Nc1cncc(F)c1CC[C@@H]1CN[C@H](COC(=O)NCC(F)(F)F)CO1)[C@H](c1ccc(F)cc1)c1ccc(OC(F)(F)F)cc1] | (βS)-β-(4-fluorophenyl)-N-(5-fluoro-4-{2-[(2R,5S)-5-({[(2,2,2-trifluoroethyl)carbamoyl]oxy}methyl)morpholin-2-yl]ethyl}pyridin-3-yl)-O-(trifluoromethyl)-L-tyrosinamide | 706.2 |
| 247 | 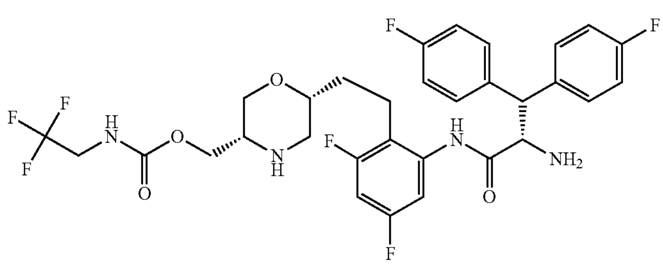 [SMILES: N[C@H](C(=O)Nc1cc(F)cc(F)c1CC[C@@H]1CN[C@H](COC(=O)NCC(F)(F)F)CO1)C(c1ccc(F)cc1)c1ccc(F)cc1] | N-(3,5-difluoro-2-{2-[(2R,5S)-5-({[(2,2,2-trifluoroethyl)carbamoyl]oxy}methyl)morpholin-2-yl]ethyl}phenyl)-4-fluoro-β-(4-fluorophenyl)-L-phenylalaninamide | 657.2 |
| 248 | 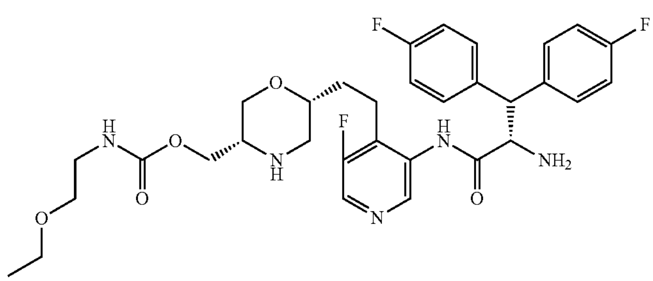 [SMILES: CCOCCNC(=O)OC[C@@H]1CO[C@H](CCc2c(F)cncc2NC(=O)[C@@H](N)C(c2ccc(F)cc2)c2ccc(F)cc2)CN1] | N-(4-{2-[(2R,5S)-5-({[(2-ethoxyethyl)carbamoyl]oxy}methyl)morpholin-2-yl]ethyl}-5-fluoropyridin-3-yl)-4-fluoro-β-(4-fluorophenyl)-L-phenylalaninamide | 630.3 |

TABLE 2-continued

The following examples can be prepared using the procedures described above.

| Example | Structure | IUPAC Name | Mass [M + H]+ |
|---|---|---|---|
| 249 | 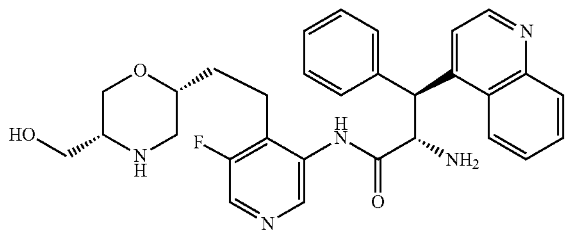 [SMILES: N[C@H](C(=O)Nc1cncc(F)c1CC[C@@H]1CN[C@H](CO)CO1)[C@@H](c1ccccc1)c1ccnc2ccccc12] | (βS)-N-(5-fluoro-4-{2-[(2R,5R)-5-(hydroxymethyl)morpholin-2-yl]ethyl}pyridin-3-yl)-β-quinolin-4-yl-L-phenylalaninamide | 530.3 |
| 250 | 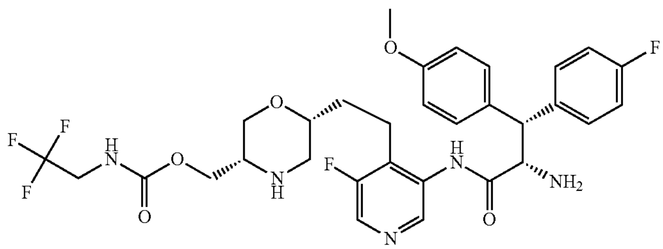 [SMILES: COc1ccc([C@H](c2ccc(F)cc2)[C@H](N)C(=O)Nc2cncc(F)c2CC[C@@H]2CN[C@H](COC(=O)NCC(F)(F)F)CO2)cc1] | (βR)-β-(4-fluorophenyl)-N-(5-fluoro-4-{2-[(2R,5S)-5-({[(2,2,2-trifluoroethyl)carbamoyl]oxy}methyl)morpholin-2-yl]ethyl}pyridin-3-yl)-O-methyl-L-tyrosinamide | 652.3 |
| 251 | 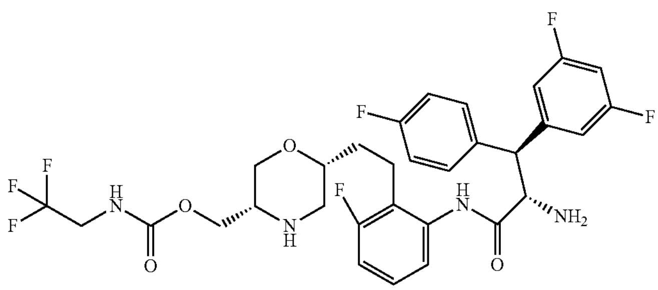 [SMILES: N[C@H](C(=O)Nc1cccc(F)c1CC[C@@H]1CN[C@H](COC(=O)NCC(F)(F)F)CO1)[C@@H](c1ccc(F)cc1)c1cc(F)cc(F)c1] | (βS)-3,5-difluoro-β-(4-fluorophenyl)-N-(3-fluoro-2-{2-[(2R,5S)-5-({[(2,2,2-trifluoroethyl)carbamoyl]oxy}methyl)morpholin-2-yl]ethyl}phenyl)-L-phenylalaninamide | 657.2 |
| 252 | 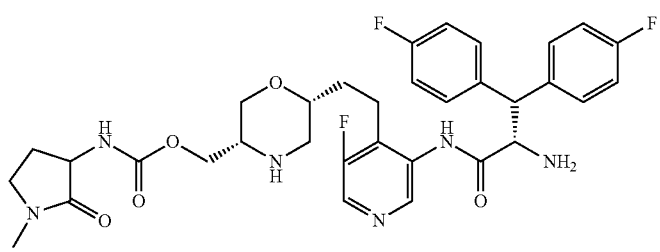 [SMILES: CN1CCC(NC(=O)OC[C@@H]2CO[C@H](CCc3c(F)cncc3NC(=O)[C@@H](N)C(c3ccc(F)cc3)c3ccc(F)cc3)CN2)C1=O] | 4-fluoro-N-(5-fluoro-4-{2-[(2R,5S)-5-({[(1-methyl-2-oxopyrrolidin-3-yl)carbamoyl]oxy}methyl)morpholin-2-yl]ethyl}pyridin-3-yl)-β-(4-fluorophenyl)-L-phenylalaninamide | 655.3 |
| 253 | 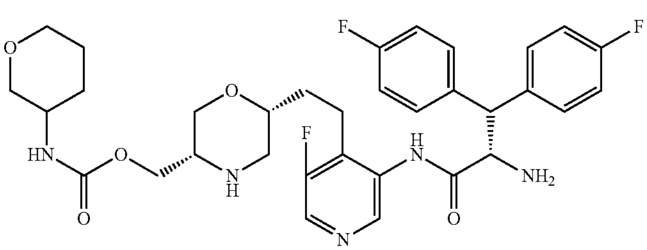 [SMILES: N[C@H](C(=O)Nc1cncc(F)c1CC[C@@H]1CN[C@H](COC(=O)NC2CCCOC2)CO1)C(c1ccc(F)cc1)c1ccc(F)cc1] | 4-fluoro-β-(4-fluorophenyl)-N-(5-fluoro-4-{2-[(2R,5S)-5-{[(tetrahydro-2H-pyran-3-ylcarbamoyl)oxy]methyl}morpholin-2-yl]ethyl}pyridin-3-yl)-L-phenylalaninamide | 642.3 |

TABLE 2-continued

The following examples can be prepared using the procedures described above.

| Example | Structure | IUPAC Name | Mass [M + H]+ |
|---|---|---|---|
| 254 | 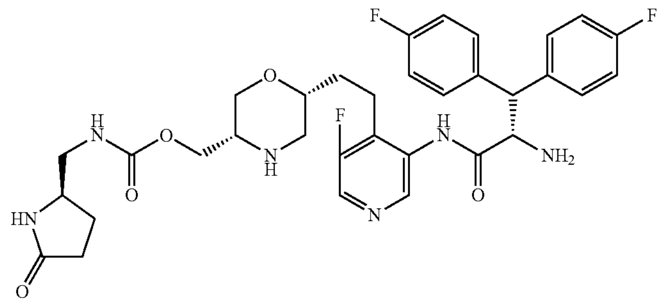 [SMILES: N[C@H](C(=O)Nc1cncc(F)c1CC[C@@H]1CN[C@H](COC(=O)NC[C@H]2CCC(=O)N2)CO1)C(c1ccc(F)cc1)c1ccc(F)cc1] | 4-fluoro-N-(5-fluoro-4-{2-[(2R,5S)-5-{[({[(2R)-5-oxopyrrolidin-2-yl]methyl}carbamoyl)oxy]methyl}morpholin-2-yl]ethyl}pyridin-3-yl)-β-(4-fluorophenyl)-L-phenylalaninamide | 655.3 |
| 255 | 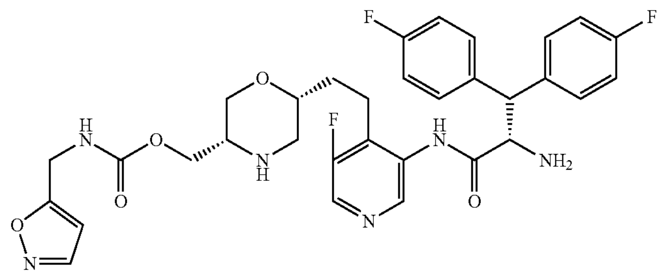 [SMILES: N[C@H](C(=O)Nc1cncc(F)c1CC[C@@H]1CN[C@H](COC(=O)NCc2ccno2)CO1)C(c1ccc(F)cc1)c1ccc(F)cc1] | 4-fluoro-N-(5-fluoro-4-{2-[(2R,5S)-5-({[(isoxazol-5-ylmethyl)carbamoyl]oxy}methyl)morpholin-2-yl]ethyl}pyridin-3-yl)-β-(4-fluorophenyl)-L-phenylalaninamide | 639.3 |
| 256 | 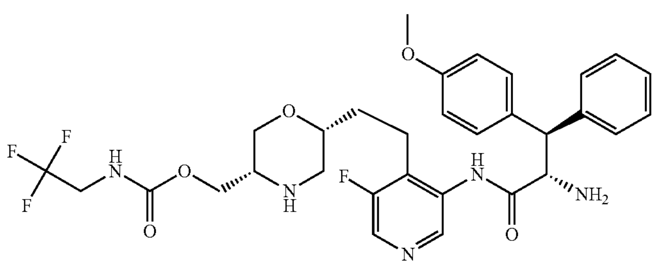 [SMILES: COc1ccc([C@@H](c2ccccc2)[C@H](N)C(=O)Nc2cncc(F)c2CC[C@@H]2CN[C@H](COC(=O)NCC(F)(F)F)CO2)cc1] | (βR)-N-(5-fluoro-4-{2-[(2R,5S)-5-({[(2,2,2-trifluoroethyl)carbamoyl]oxy}methyl)morpholin-2-yl]ethyl}pyridin-3-yl)-O-methyl-β-phenyl-L-tyrosinamide | 634.3 |
| 257 | 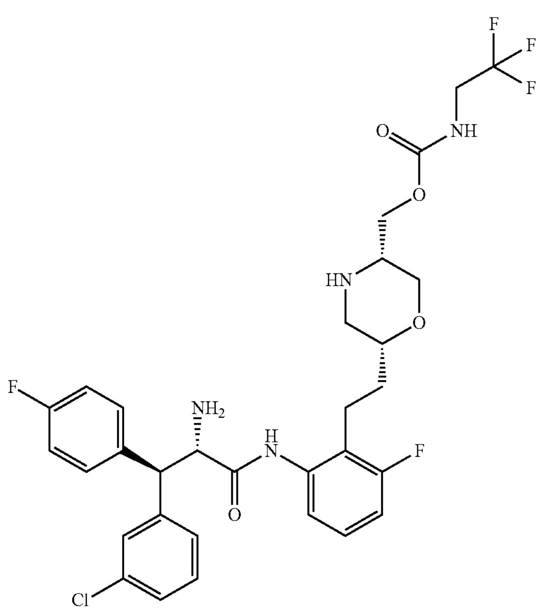 [SMILES: N[C@H](C(=O)Nc1cccc(F)c1CC[C@@H]1CN[C@H](COC(=O)NCC(F)(F)F)CO1)[C@H](c1ccc(F)cc1)c1cccc(Cl)c1] | (βR)-β-(3-chlorophenyl)-4-fluoro-N-(3-fluoro-2-{2-[(2R,5S)-5-({[(2,2,2-trifluoroethyl)carbamoyl]oxy}methyl)morpholin-2-yl]ethyl}phenyl)-L-phenylalaninamide | 655.2 |

TABLE 2-continued

The following examples can be prepared using the procedures described above.

| Example | Structure | IUPAC Name | Mass [M + H]+ |
|---|---|---|---|
| 258 | 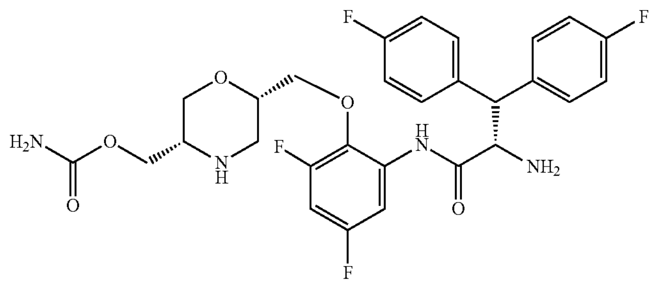 [SMILES: NC(=O)OC[C@@H]1CO[C@H](COc2c(F)cc(F)cc2NC(=O)[C@@H](N)C(c2ccc(F)cc2)c2ccc(F)cc2)CN1] | N-[2-({(2S,5S)-5-[(carbamoyloxy)methyl]morpholin-2-yl}methoxy)-3,5-difluorophenyl]-4-fluoro-β-(4-fluorophenyl)-L-phenylalaninamide | 577.2 |
| 259 | 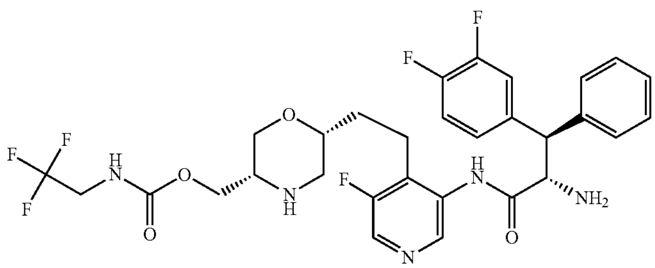 [SMILES: N[C@H](C(=O)Nc1cncc(F)c1CC[C@@H]1CN[C@H](COC(=O)NCC(F)(F)F)CO1)[C@H](c1ccccc1)c1ccc(F)c(F)c1] | (βR)-β-(3,4-difluorophenyl)-N-(5-fluoro-4-{2-[(2R,5S)-5-({[(2,2,2-trifluoroethyl)carbamoyl]oxy}methyl)morpholin-2-yl]ethyl}pyridin-3-yl)-L-phenylalaninamide | 640.2 |
| 260 | 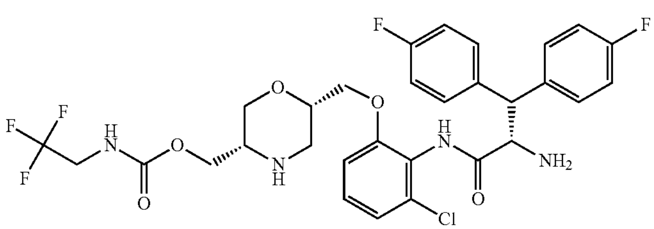 [SMILES: N[C@H](C(=O)Nc1c(Cl)cccc1OC[C@@H]1CN[C@H](COC(=O)NCC(F)(F)F)CO1)C(c1ccc(F)cc1)c1ccc(F)cc1] | N-(2-chloro-6-{[(2S,5S)-5-({[(2,2,2-trifluoroethyl)carbamoyl]oxy}methyl)morpholin-2-yl]methoxy}phenyl)-4-fluoro-β-(4-fluorophenyl)-L-phenylalaninamide | 657.2 |
| 261 | 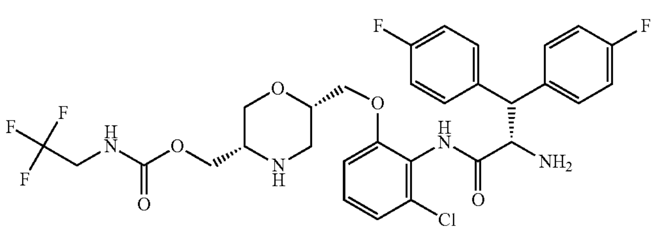 [SMILES: N[C@H](C(=O)Nc1c(Cl)cccc1OC[C@@H]1CN[C@H](COC(=O)NCC(F)(F)F)CO1)C(c1ccc(F)cc1)c1ccc(F)cc1] | N-(2-chloro-6-{[(2S,5S)-5-({[(2,2,2-trifluoroethyl)carbamoyl]oxy}methyl)morpholin-2-yl]methoxy}phenyl)-4-fluoro-β-(4-fluorophenyl)-L-phenylalaninamide | 657.2 |
| 262 | 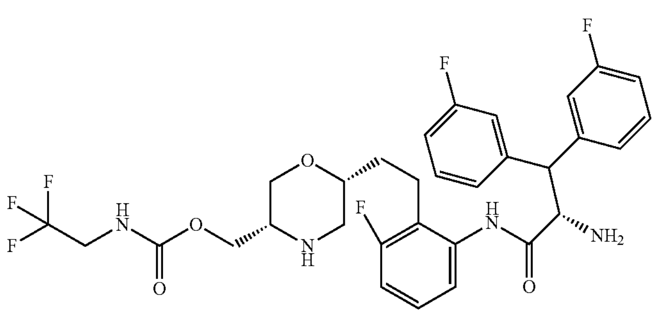 [SMILES: N[C@H](C(=O)Nc1cccc(F)c1CC[C@@H]1CN[C@H](COC(=O)NCC(F)(F)F)CO1)C(c1cccc(F)c1)c1cccc(F)c1] | 3-fluoro-β-(3-fluorophenyl)-N-(3-fluoro-2-{2-[(2R,5S)-5-({[(2,2,2-trifluoroethyl)carbamoyl]oxy}methyl)morpholin-2-yl]ethyl}phenyl)-L-phenylalaninamide | 639.2 |

TABLE 2-continued

The following examples can be prepared using the procedures described above.

| Example | Structure | IUPAC Name | Mass [M + H]+ |
|---|---|---|---|
| 263 | 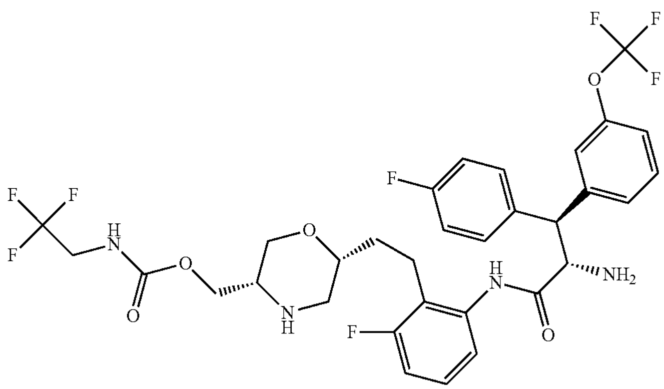 [SMILES: N[C@H](C(=O)Nc1cccc(F)c1CC[C@@H]1CN[C@H](COC(=O)NCC(F)(F)F)CO1)[C@@H](c1ccc(F)cc1)c1cccc(OC(F)(F)F)c1] | (βS)-4-fluoro-N-(3-fluoro-2-{2-[(2R,5S)-5-({[(2,2,2-trifluoroethyl)carbamoyl]oxy}methyl)morpholin-2-yl]ethyl}phenyl)-β-[3-(trifluoromethoxy)phenyl]-L-phenylalaninamide | 705.2 |
| 264 | 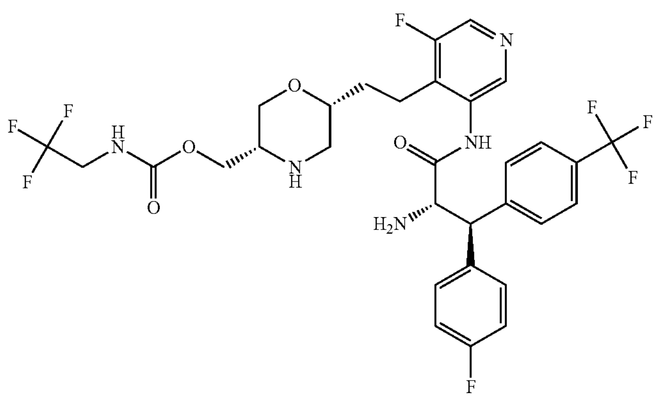 [SMILES: N[C@H](C(=O)Nc1cncc(F)c1CC[C@@H]1CN[C@H](COC(=O)NCC(F)(F)F)CO1)[C@H](c1ccc(F)cc1)c1ccc(C(F)(F)F)cc1] | (βS)-β-(4-fluorophenyl)-N-(5-fluoro-4-{2-[(2R,5S)-5-({[(2,2,2-trifluoroethyl)carbamoyl]oxy}methyl)morpholin-2-yl]ethyl}pyridin-3-yl)-4-(trifluoromethyl)-L-phenylalaninamide | 690.2 |
| 265 | 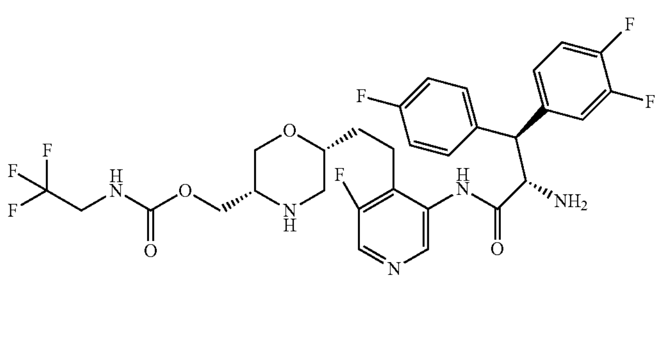 [SMILES: N[C@H](C(=O)Nc1cncc(F)c1CC[C@@H]1CN[C@H](COC(=O)NCC(F)(F)F)CO1)[C@@H](c1ccc(F)cc1)c1ccc(F)c(F)c1] | (βS)-3,4-difluoro-β-(4-fluorophenyl)-N-(5-fluoro-4-{2-[(2R,5S)-5-({[(2,2,2-trifluoroethyl)carbamoyl]oxy}methyl)morpholin-2-yl]ethyl}pyridin-3-yl)-L-phenylalaninamide | 658.2 |

TABLE 2-continued

The following examples can be prepared using the procedures described above.

| Example | Structure | IUPAC Name | Mass [M + H]+ |
|---|---|---|---|
| 266 | 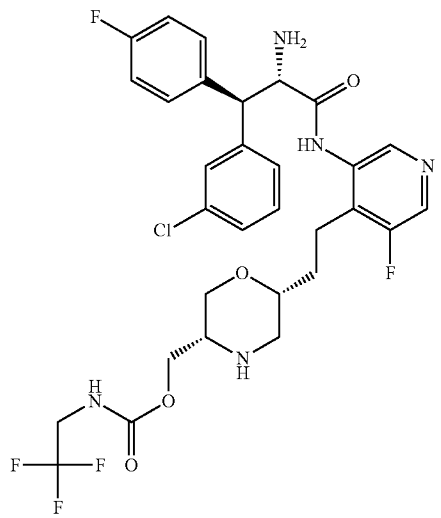 [SMILES: N[C@H](C(=O)Nc1cncc(F)c1CC[C@@H]1CN[C@H](COC(=O)NCC(F)(F)F)CO1)[C@H](c1ccc(F)cc1)c1cccc(Cl)c1] | (βR)-3-chloro-β-(4-fluorophenyl)-N-(5-fluoro-4-{2-[(2R,5S)-5-({[(2,2,2-trifluoroethyl)carbamoyl]oxy}methyl)morpholin-2-yl]ethyl}pyridin-3-yl)-L-phenylalaninamide | 656.2 |
| 267 | 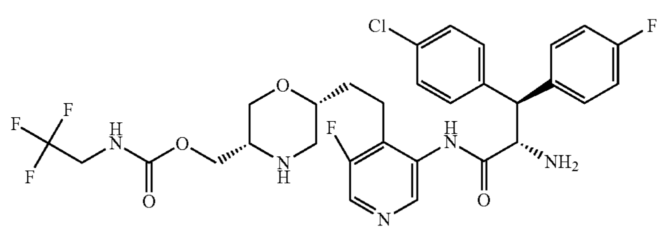 [SMILES: N[C@H](C(=O)Nc1cncc(F)c1CC[C@@H]1CN[C@H](COC(=O)NCC(F)(F)F)CO1)[C@H](c1ccc(F)cc1)c1ccc(Cl)cc1] | (βR)-β-(4-chlorophenyl)-4-fluoro-N-(5-fluoro-4-{2-[(2R,5S)-5-({[(2,2,2-trifluoroethyl)carbamoyl]oxy}methyl)morpholin-2-yl]ethyl}pyridin-3-yl)-L-phenylalaninamide | 656.2 |
| 268 | 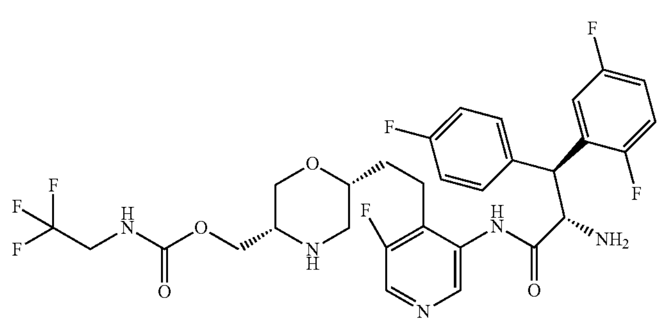 [SMILES: N[C@H](C(=O)Nc1cncc(F)c1CC[C@@H]1CN[C@H](COC(=O)NCC(F)(F)F)CO1)[C@@H](c1ccc(F)cc1)c1cc(F)ccc1F] | (βS)-2,5-difluoro-β-(4-fluorophenyl)-N-(5-fluoro-4-{2-[(2R,5S)-5-({[(2,2,2-trifluoroethyl)carbamoyl]oxy}methyl)morpholin-2-yl]ethyl}pyridin-3-yl)-L-phenylalaninamide | 658.2 |

TABLE 2-continued

The following examples can be prepared using the procedures described above.

| Example | Structure | IUPAC Name | Mass [M + H]+ |
|---|---|---|---|
| 269 | 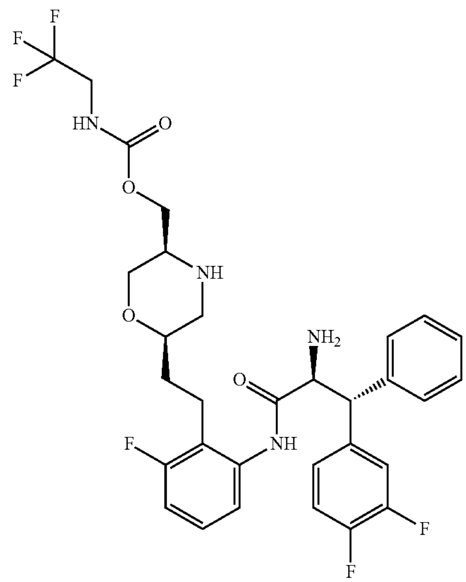 [SMILES: N[C@H](C(=O)Nc1cccc(F)c1CC[C@@H]1CN[C@H](COC(=O)NCC(F)(F)F)CO1)[C@H](c1ccccc1)c1ccc(F)c(F)c1] | (βR)-β-(3,4-difluorophenyl)-N-(3-fluoro-2-{2-[(2R,5S)-5-({[(2,2,2-trifluoroethyl)carbamoyl]oxy}methyl)morpholin-2-yl]ethyl}phenyl)-L-phenylalaninamide | 639.2 |
| 270 | 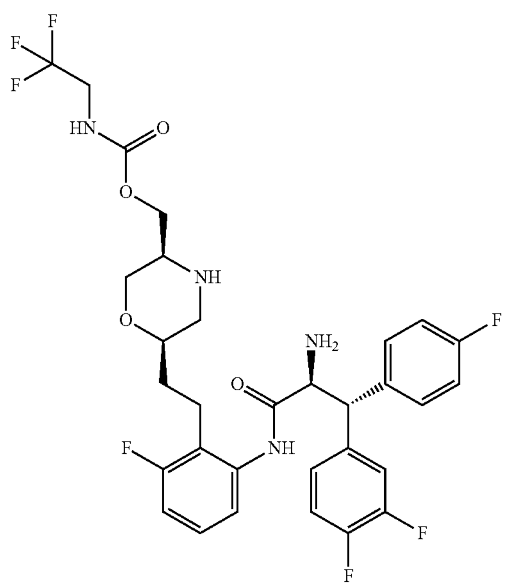 [SMILES: N[C@H](C(=O)Nc1cccc(F)c1CC[C@@H]1CN[C@H](COC(=O)NCC(F)(F)F)CO1)[C@H](c1ccc(F)cc1)c1ccc(F)c(F)c1] | (βR)-β-(3,4-difluorophenyl)-4-fluoro-N-(3-fluoro-2-{2-[(2R,5S)-5-({[(2,2,2-trifluoroethyl)carbamoyl]oxy}methyl)morpholin-2-yl]ethyl}phenyl)-L-phenylalaninamide | 657.2 |
| 271 | 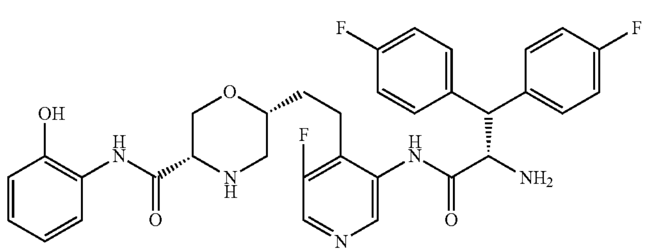 [SMILES: N[C@H](C(=O)Nc1cncc(F)c1CC[C@@H]1CN[C@H](C(=O)Nc2ccccc2O)CO1)C(c1ccc(F)cc1)c1ccc(F)cc1] | 4-fluoro-N-[5-fluoro-4-(2-{(2R,5S)-5-[(2-hydroxyphenyl)carbamoyl]morpholin-2-yl}ethyl)pyridin-3-yl]-β-(4-fluorophenyl)-L-phenylalaninamide | 620.2 |

TABLE 2-continued

The following examples can be prepared using the procedures described above.

| Example | Structure | IUPAC Name | Mass [M + H]+ |
|---|---|---|---|
| 272 | 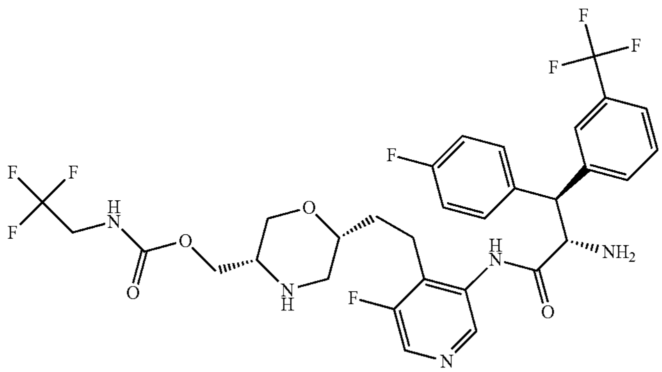 [SMILES: N[C@H](C(=O)Nc1cncc(F)c1CC[C@@H]1CN[C@H](COC(=O)NCC(F)(F)F)CO1)[C@@H](c1ccc(F)cc1)c1cccc(C(F)(F)F)c1] | (βS)-4-fluoro-N-(5-fluoro-4-{2-[(2R,5S)-5-({[(2,2,2-trifluoroethyl)carbamoyl]oxy}methyl)morpholin-2-yl]ethyl}pyridin-3-yl)-β-[3-(trifluoromethyl)phenyl]-L-phenylalaninamide | 690.2 |
| 273 | 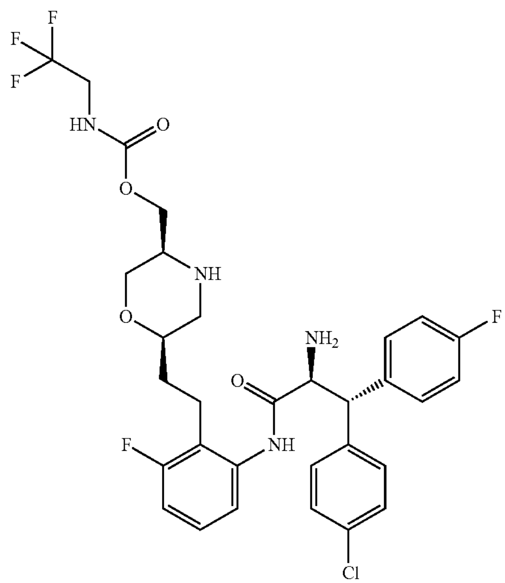 [SMILES: N[C@H](C(=O)Nc1cccc(F)c1CC[C@@H]1CN[C@H](COC(=O)NCC(F)(F)F)CO1)[C@H](c1ccc(F)cc1)c1ccc(Cl)cc1] | (βR)-β-(4-chlorophenyl)-4-fluoro-N-(3-fluoro-2-{2-[(2R,5S)-5-({[(2,2,2-trifluoroethyl)carbamoyl]oxy}methyl)morpholin-2-yl]ethyl}phenyl)-L-phenylalaninamide | 655.2 |
| 274 | 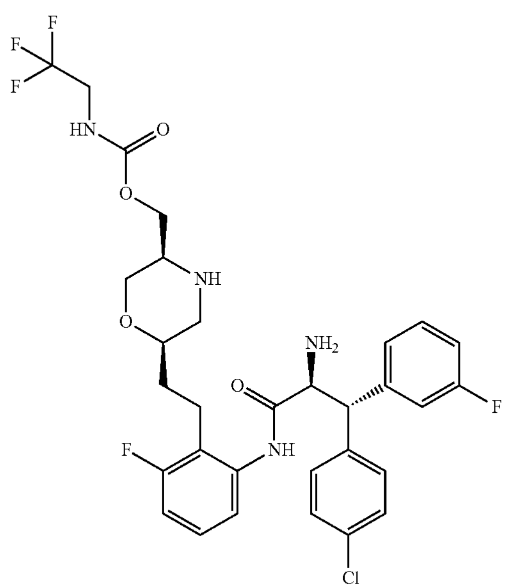 [SMILES: N[C@H](C(=O)Nc1cccc(F)c1CC[C@@H]1CN[C@H](COC(=O)NCC(F)(F)F)CO1)[C@@H](c1ccc(Cl)cc1)c1cccc(F)c1] | (βS)-β-(4-chlorophenyl)-3-fluoro-N-(3-fluoro-2-{2-[(2R,5S)-5-({[(2,2,2-trifluoroethyl)carbamoyl]oxy}methyl)morpholin-2-yl]ethyl}phenyl)-L-phenylalaninamide | 655.2 |

TABLE 2-continued

The following examples can be prepared using the procedures described above.

| Example | Structure | IUPAC Name | Mass [M + H]+ |
|---|---|---|---|
| 275 | 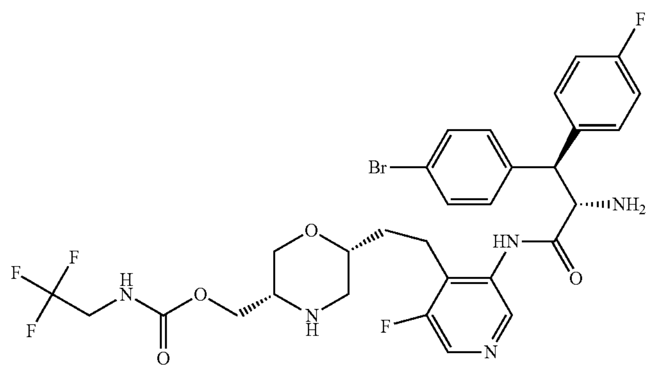 [SMILES: N[C@H](C(=O)Nc1cncc(F)c1CC[C@@H]1CN[C@H](COC(=O)NCC(F)(F)F)CO1)[C@H](c1ccc(F)cc1)c1ccc(Br)cc1] | (βR)-4-bromo-β-(4-fluorophenyl)-N-(5-fluoro-4-{2-[(2R,5S)-5-({[(2,2,2-trifluoroethyl)carbamoyl]oxy}methyl)morpholin-2-yl]ethyl}pyridin-3-yl)-L-phenylalaninamide | 700.2 |
| 276 | 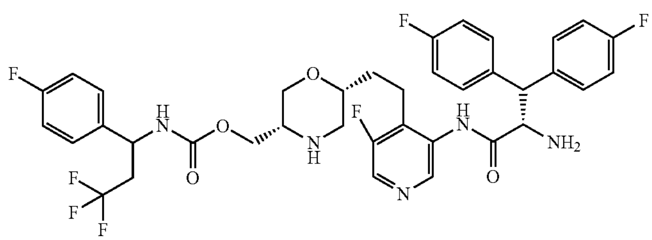 [SMILES: N[C@H](C(=O)Nc1cncc(F)c1CC[C@@H]1CN[C@H](COC(=O)NC(CC(F)(F)F)c2ccc(F)cc2)CO1)C(c1ccc(F)cc1)c1ccc(F)cc1] | 4-fluoro-β-(4-fluorophenyl)-N-[5-fluoro-4-(2-{(2R,5S)-5-[({[3,3,3-trifluoro-1-(4-fluorophenyl)propyl]carbamoyl}oxy)methyl]morpholin-2-yl}ethyl)pyridin-3-yl]-L-phenylalaninamide | 748.3 |

TABLE 3

The following examples can be prepared using the procedures described above.

| Example | Structure | IUPAC Name | Mass [M + H]+ |
|---|---|---|---|
| 277 | 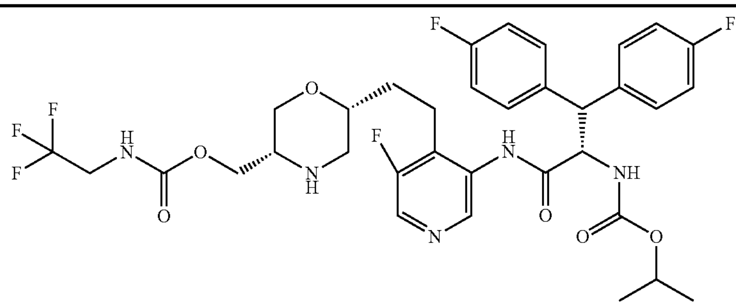 | 4-fluoro-β-(4-fluorophenyl)-N-(5-fluoro-4-{2-[(2R,5S)-5-({[(2,2,2-trifluoroethyl)carbamoyl]oxy}methyl)morpholin-2-yl]ethyl}pyridin-3-yl)-Nα-[(1-methylethoxy)carbonyl]-L-phenylalaninamide | 726.3 |
| 278 | 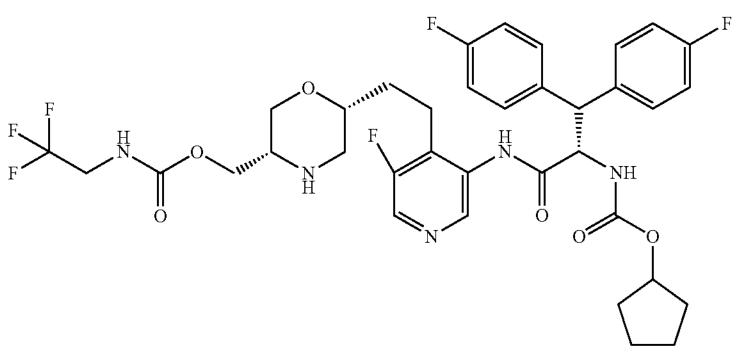 [SMILES: O=C(NCC(F)(F)F)OC[C@@H]1CO[C@H](CCc2c(F)cncc2NC(=O)[C@@H](NC(=O)OC2CCCC2)C(c2ccc(F)cc2)c2ccc(F)cc2)CN1] | Nα-[(cyclopentyloxy)carbonyl]-4-fluoro-β-(4-fluorophenyl)-N-(5-fluoro-4-{2-[(2R,5S)-5-({[(2,2,2-trifluoroethyl)carbamoyl]oxy}methyl)morpholin-2-yl]ethyl}pyridin-3-yl)-L-phenylalaninamide | 752.3 |

TABLE 3-continued

The following examples can be prepared using the procedures described above.

| Example | Structure | IUPAC Name | Mass [M + H]+ |
|---------|-----------|------------|---------------|
| 279 | 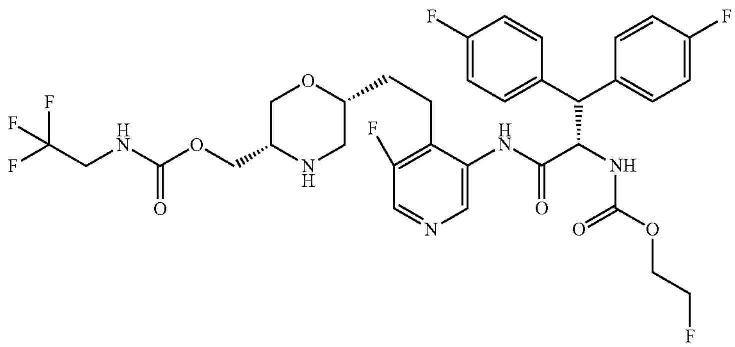 [SMILES: O=C(NCC(F)(F)F)OC[C@@H]1CO[C@H](CCc2c(F)cncc2NC(=O)[C@@H](NC(=O)OCCF)C(c2ccc(F)cc2)c2ccc(F)cc2)CN1] | 4-fluoro-Nα-[(2-fluoroethoxy)carbonyl]-β-(4-fluorophenyl)-N-(5-fluoro-4-{2-[(2R,5S)-5-({[(2,2,2-trifluoroethyl)carbamoyl]oxy}methyl)morpholin-2-yl]ethyl}pyridin-3-yl)-L-phenylalaninamide | 730.2 |
| 280 | 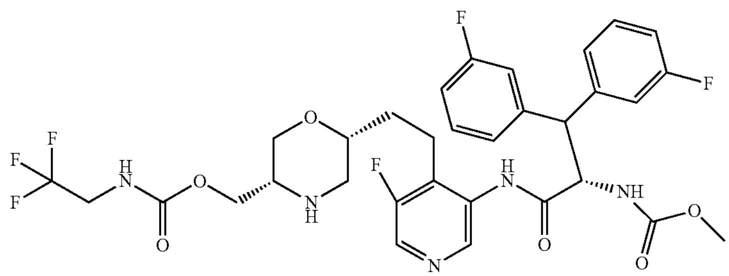 [SMILES: COC(=O)N[C@H](C(=O)Nc1cncc(F)c1CC[C@@H]1CN[C@H](COC(=O)NCC(F)(F)F)CO1)C(c1cccc(F)c1)c1cccc(F)c1] | 3-fluoro-β-(3-fluorophenyl)-N-(5-fluoro-4-{2-[(2R,5S)-5-({[(2,2,2-trifluoroethyl)carbamoyl]oxy}methyl)morpholin-2-yl]ethyl}pyridin-3-yl)-Nα-(methoxycarbonyl)-L-phenylalaninamide | 698.2 |
| 281 | 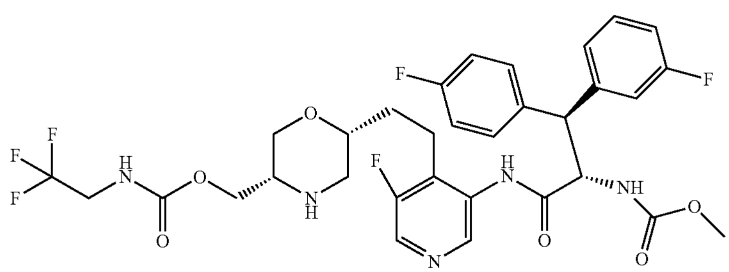 [SMILES: COC(=O)N[C@H](C(=O)Nc1cncc(F)c1CC[C@@H]1CN[C@H](COC(=O)NCC(F)(F)F)CO1)[C@@H](c1ccc(F)cc1)c1cccc(F)c1] | (βS)-3-fluoro-β-(4-fluorophenyl)-N-(5-fluoro-4-{2-[(2R,5S)-5-({[(2,2,2-trifluoroethyl)carbamoyl]oxy}methyl)morpholin-2-yl]ethyl}pyridin-3-yl)-Nα-(methoxycarbonyl)-L-phenylalaninamide | 697.3 |
| 282 | 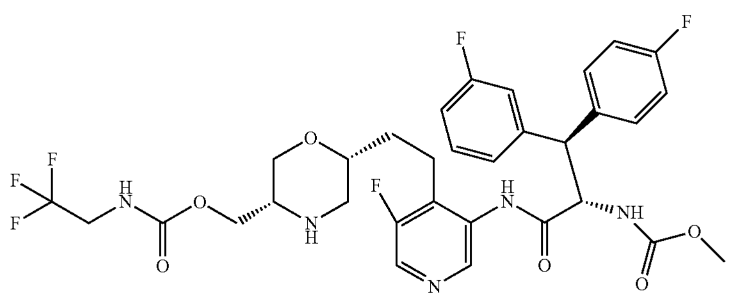 [SMILES: COC(=O)N[C@H](C(=O)Nc1cncc(F)c1CC[C@@H]1CN[C@H](COC(=O)NCC(F)(F)F)CO1)[C@H](c1ccc(F)cc1)c1cccc(F)c1] | (βR)-4-fluoro-β-(3-fluorophenyl)-N-(5-fluoro-4-{2-[(2R,5S)-5-({[(2,2,2-trifluoroethyl)carbamoyl]oxy}methyl)morpholin-2-yl]ethyl}pyridin-3-yl)-Nα-(methoxycarbonyl)-L-phenylalaninamide | 698.2 |
| 283 | 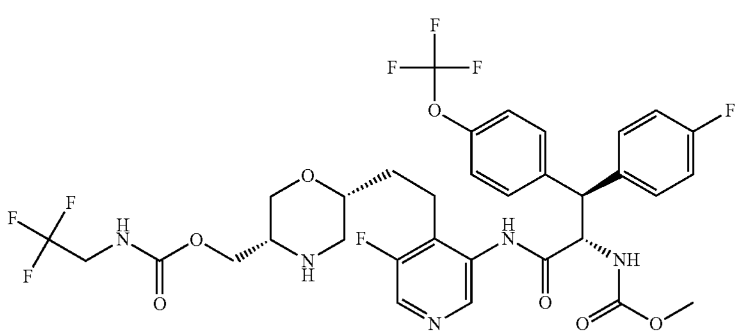 [SMILES: COC(=O)N[C@H](C(=O)Nc1cncc(F)c1CC[C@@H]1CN[C@H](COC(=O)NCC(F)(F)F)CO1)[C@H](c1ccc(F)cc1)c1ccc(OC(F)(F)F)cc1] | (βS)-β-(4-fluorophenyl)-N-(5-fluoro-4-{2-[(2R,5S)-5-({[2,2,2-trifluoroethyl)carbamoyl]oxy}methyl)morpholin-2-yl]ethyl}pyridin-3-yl)-Nα-(methoxycarbonyl)-O-(trifluoromethyl)-L-tyrosinamide | 764.2 |

TABLE 3-continued

The following examples can be prepared using the procedures described above.

| Example | Structure | IUPAC Name | Mass [M + H]+ |
|---|---|---|---|
| 284 | 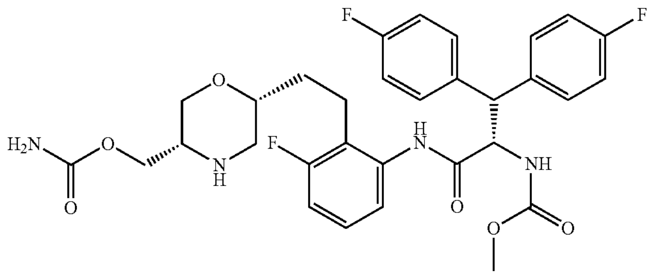 [SMILES: COC(=O)N[C@H](C(=O)Nc1cccc(F)c1CC[C@@H]1CN[C@H](COC(N)=O)CO1)C(c1ccc(F)cc1)c1ccc(F)cc1] | N-[2-(2-{(2R,5S)-5-[(carbamoyloxy)methyl]morpholin-2-yl}ethyl)-3-fluorophenyl]-4-fluoro-β-(4-fluorophenyl)-Nα-(methoxycarbonyl)-L-phenylalaninamide | 615.2 |
| 285 | 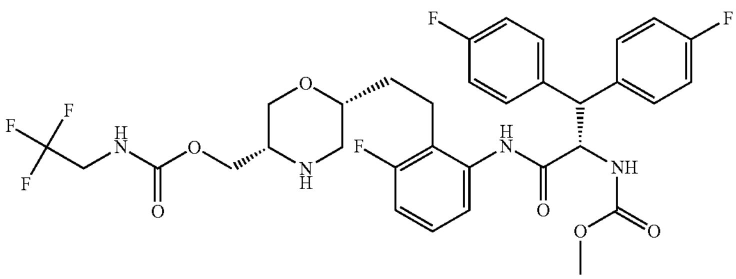 [SMILES: COC(=O)N[C@H](C(=O)Nc1cccc(F)c1CC[C@@H]1CN[C@H](COC(=O)NCC(F)(F)F)CO1)C(c1ccc(F)cc1)c1ccc(F)cc1] | 4-fluoro-β-(4-fluorophenyl)-N-(3-fluoro-2-{2-[(2R,5S)-5-({[2,2,2-trifluoroethyl)carbamoyl]oxy}methyl)morpholin-2-yl]ethyl}phenyl)-Nα-(methoxycarbonyl)-L-phenylalaninamide | 697.2 |
| 286 | 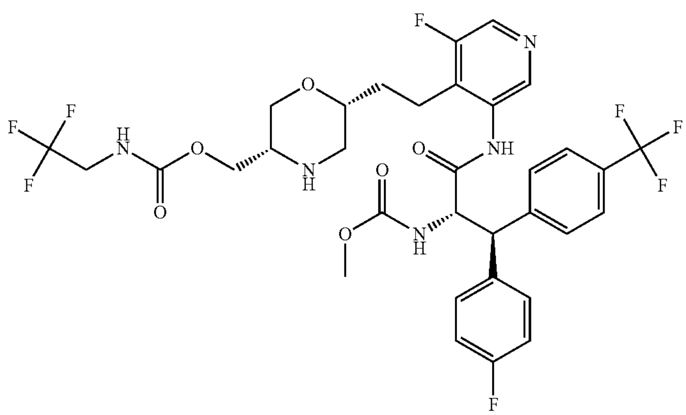 [SMILES: COC(=O)N[C@H](C(=O)Nc1cncc(F)c1CC[C@@H]1CN[C@H](COC(=O)NCC(F)(F)F)CO1)[C@H](c1ccc(F)cc1)c1ccc(C(F)(F)F)cc1] | (βS)-β-(4-fluorophenyl)-N-(5-fluoro-4-{2-[(2R,5S)-5-({[2,2,2-trifluoroethyl)carbamoyl]oxy}methyl)morpholin-2-yl]ethyl}pyridin-3-yl)-Nα-(methoxycarbonyl)-4-(trifluoromethyl)-L-phenylalaninamide | 748.2 |
| 287 | 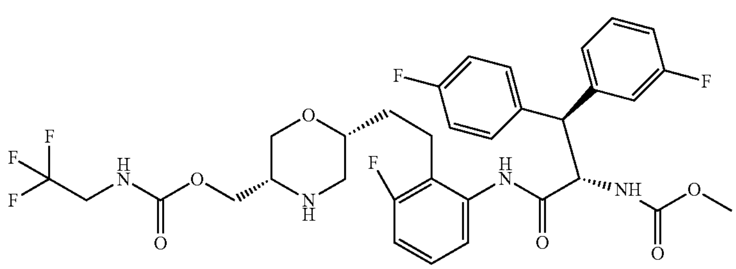 [SMILES: COC(=O)N[C@H](C(=O)Nc1cccc(F)c1CC[C@@H]1CN[C@H](COC(=O)NCC(F)(F)F)CO1)[C@@H](c1ccc(F)cc1)c1cccc(F)c1] | (βS)-3-fluoro-β-(4-fluorophenyl)-N-(3-fluoro-2-{2-[(2R,5S)-5-({[2,2,2-trifluoroethyl)carbamoyl]oxy}methyl)morpholin-2-yl]ethyl}phenyl)-Nα-(methoxycarbonyl)-L-phenylalaninamide | 697.2 |
| 288 | 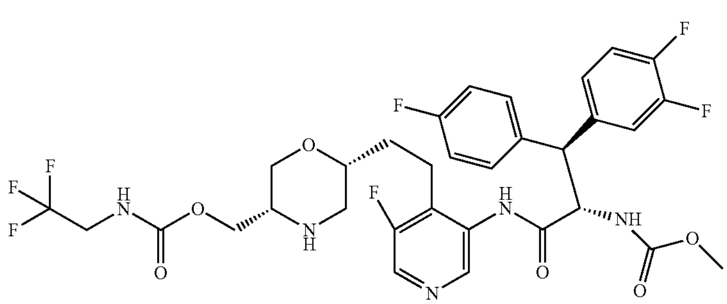 [SMILES: COC(=O)N[C@H](C(=O)Nc1cncc(F)c1CC[C@@H]1CN[C@H](COC(=O)NCC(F)(F)F)CO1)[C@@H](c1ccc(F)cc1)c1ccc(F)c(F)c1] | (βS)-3,4-difluoro-β-(4-fluorophenyl)-N-(5-fluoro-4-{2-[(2R,5S)-5-({[2,2,2-trifluoroethyl)carbamoyl]oxy}methyl)morpholin-2-yl]ethyl}pyridin-3-yl)-Nα-(methoxycarbonyl)-L-phenylalaninamide | 716.2 |

TABLE 3-continued

The following examples can be prepared using the procedures described above.

| Example | Structure | IUPAC Name | Mass [M + H]+ |
|---|---|---|---|
| 289 | 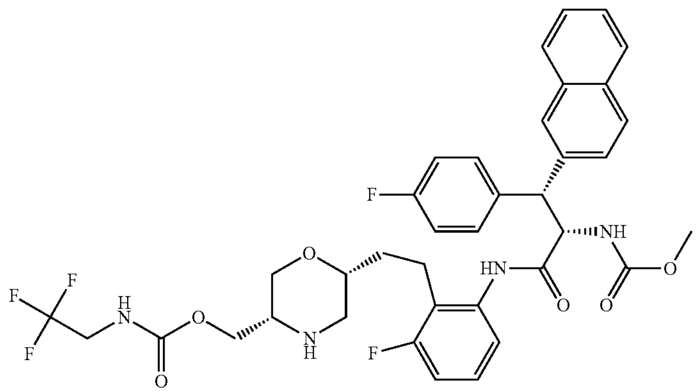 [SMILES: COC(=O)N[C@H](C(=O)Nc1cccc(F)c1CC[C@@H]1CN[C@H](COC(=O)NCC(F)(F)F)CO1)[C@H](c1ccc(F)cc1)c1ccc2ccccc2c1] | (βR)-4-fluoro-N-(3-fluoro-2-{2-[(2R,5S)-5-({[2,2,2-trifluoroethyl)carbamoyl]oxy}methyl)morpholin-2-yl]ethyl}phenyl)-Nα-(methoxycarbonyl)-β-naphthalen-2-yl-L-phenylalaninamide | 729.3 |
| 290 | 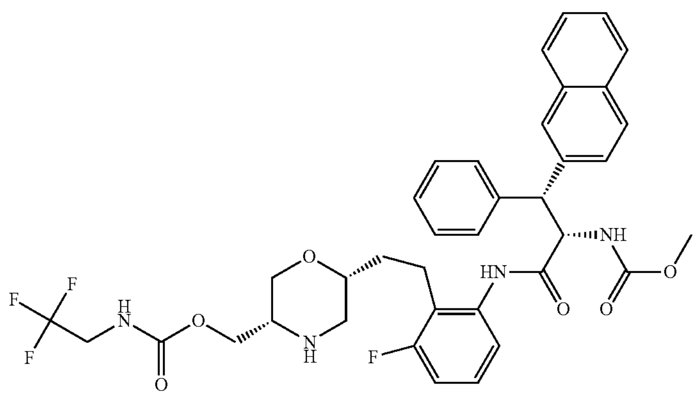 [SMILES: COC(=O)N[C@H](C(=O)Nc1cccc(F)c1CC[C@@H]1CN[C@H](COC(=O)NCC(F)(F)F)CO1)[C@H](c1ccccc1)c1ccc2ccccc2c1] | (βR)-N-(3-fluoro-2-{2-[(2R,5S)-5-({[(2,2,2-trifluoroethyl)carbamoyl]oxy}methyl)morpholin-2-yl]ethyl}phenyl)-Nα-(methoxycarbonyl)-β-naphthalen-2-yl-L-phenylalaninamide | 711.3 |
| 291 | 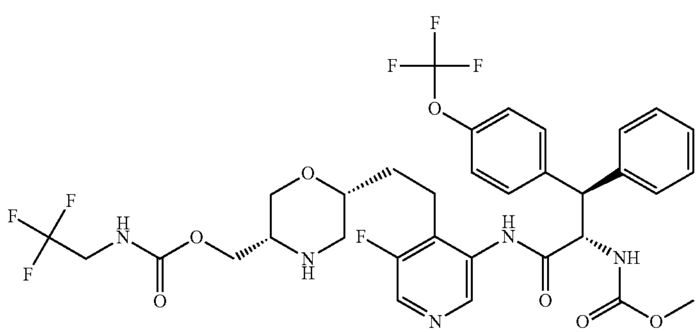 [SMILES: COC(=O)N[C@H](C(=O)Nc1cncc(F)c1CC[C@@H]1CN[C@H](COC(=O)NCC(F)(F)F)CO1)[C@H](c1ccccc1)c1ccc(OC(F)(F)F)cc1] | (βR)-N-(5-fluoro-4-{2-[(2R,5S)-5-({[(2,2,2-trifluoroethyl)carbamoyl]oxy}methyl)morpholin-2-yl]ethyl}pyridin-3-yl)-Nα-(methoxycarbonyl)-β-phenyl-O-(trifluoromethyl)-L-tyrosinamide | 746.2 |
| 292 | 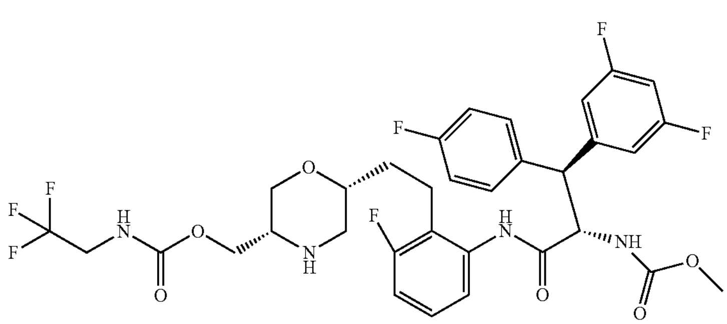 [SMILES: COC(=O)N[C@H](C(=O)Nc1cccc(F)c1CC[C@@H]1CN[C@H](COC(=O)NCC(F)(F)F)CO1)[C@@H](c1ccc(F)cc1)c1cc(F)cc(F)c1] | (βS)-3,5-difluoro-β-(4-fluorophenyl)-N-(3-fluoro-2-{2-[(2R,5S)-5-({[(2,2,2-trifluoroethyl)carbamoyl]oxy}methyl)morpholin-2-yl]ethyl}phenyl)-Nα-(methoxycarbonyl)-L-phenylalaninamide | 715.2 |

TABLE 3-continued

The following examples can be prepared using the procedures described above.

| Example | Structure | IUPAC Name | Mass [M + H]+ |
|---|---|---|---|
| 293 | 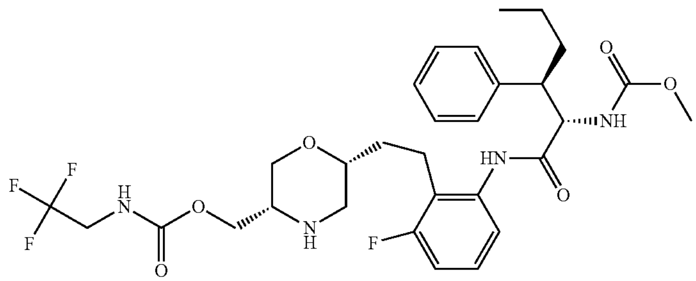 [SMILES: CCC[C@H](c1ccccc1)[C@H](NC(=O)OC)C(=O)Nc1cccc(F)c1CC[C@@H]1CN[C@H](COC(=O)NCC(F)(F)F)CO1] | (βR)-N-(3-fluoro-2-{2-[(2R,5S)-5-({[(2,2,2-trifluoroethyl)carbamoyl]oxy}methyl)morpholin-2-yl]ethyl}phenyl)-Nα-(methoxycarbonyl)-β-propyl-L-phenylalaninamide | 627.3 |
| 294 | 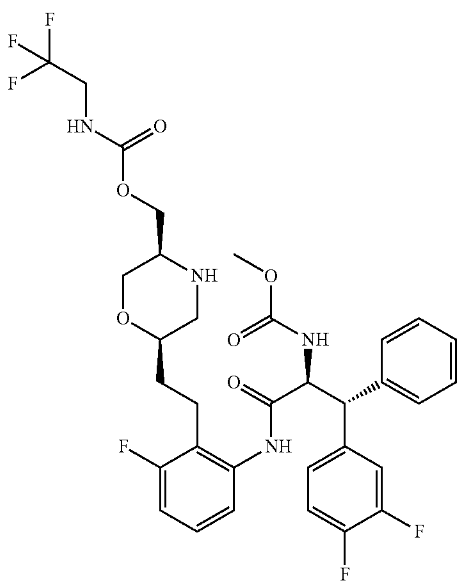 [SMILES: COC(=O)N[C@H](C(=O)Nc1cccc(F)c1CC[C@@H]1CN[C@H](COC(=O)NCC(F)(F)F)CO1)[C@H](c1ccccc1)c1ccc(F)c(F)c1] | (βR)-β-(3,4-difluorophenyl)-N-(3-fluoro-2-{2-[(2R,5S)-5-({[(2,2,2-trifluoroethyl)carbamoyl]oxy}methyl)morpholin-2-yl]ethyl}phenyl)-Nα-(methoxycarbonyl)-L-phenylalaninamide | 697.2 |
| 295 | 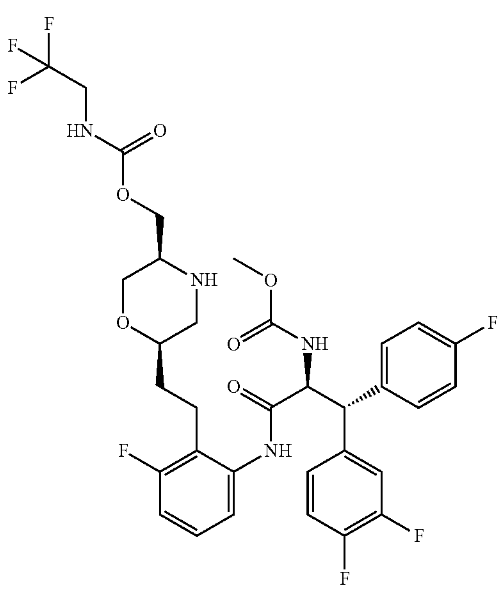 [SMILES: COC(=O)N[C@H](C(=O)Nc1cccc(F)c1CC[C@@H]1CN[C@H](COC(=O)NCC(F)(F)F)CO1)[C@H](c1ccc(F)cc1)c1ccc(F)c(F)c1] | (βR)-β-(3,4-difluorophenyl)-4-fluoro-N-(3-fluoro-2-{2-[(2R,5S)-5-({[(2,2,2-trifluoroethyl)carbamoyl]oxy}methyl)morpholin-2-yl]ethyl}phenyl)-Nα-(methoxycarbonyl)-L-phenylalaninamide | 715.2 |

TABLE 3-continued

The following examples can be prepared using the procedures described above.

| Example | Structure | IUPAC Name | Mass [M + H]+ |
|---|---|---|---|
| 296 | 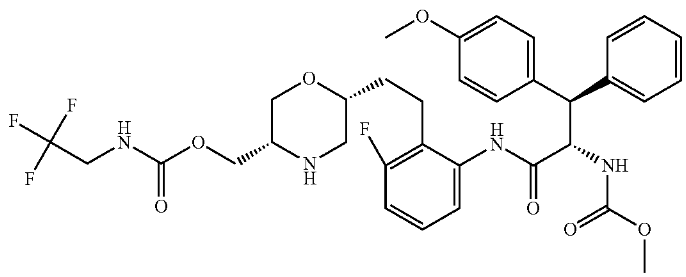 [SMILES: COC(=O)N[C@H](C(=O)Nc1cccc(F)c1CC[C@@H]1CN[C@H](COC(=O)NCC(F)(F)F)CO1)[C@H](c1ccccc1)c1ccc(OC)cc1] | (βR)-N-(3-fluoro-2-{2-[(2R,5S)-5-({[(2,2,2-trifluoroethyl)carbamoyl]oxy}methyl)morpholin-2-yl]ethyl}phenyl)-Nα-(methoxycarbonyl)-O-methyl-β-phenyl-L-tyrosinamide | 691.3 |
| 297 | 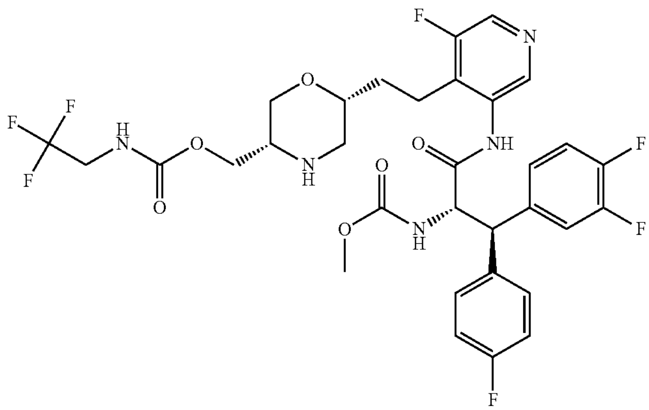 [SMILES: COC(=O)N[C@H](C(=O)Nc1cncc(F)c1CC[C@@H]1CN[C@H](COC(=O)NCC(F)(F)F)CO1)[C@H](c1ccc(F)cc1)c1ccc(F)c(F)c1] | (βR)-3,4-difluoro-β-(4-fluorophenyl)-N-(5-fluoro-4-{2-[(2R,5S)-5-({[(2,2,2-trifluoroethyl)carbamoyl]oxy}methyl)morpholin-2-yl]ethyl}pyridin-3-yl)-Nα-(methoxycarbonyl)-L-phenylalaninamide | 716.2 |
| 298 | 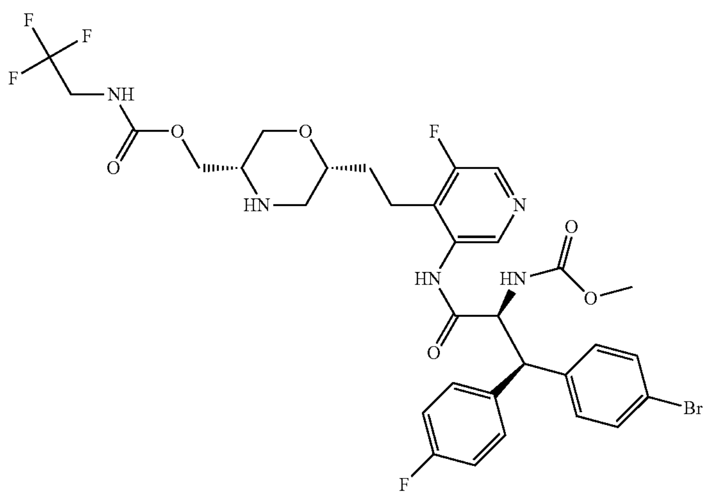 [SMILES: COC(=O)N[C@H](C(=O)Nc1cncc(F)c1CC[C@@H]1CN[C@H](COC(=O)NCC(F)(F)F)CO1)[C@H](c1ccc(F)cc1)c1ccc(Br)cc1] | (βR)-β-(4-bromophenyl)-4-fluoro-N-(5-fluoro-4-{2-[(2R,5S)-5-({[(2,2,2-trifluoroethyl)carbamoyl]oxy}methyl)morpholin-2-yl]ethyl}pyridin-3-yl)-Nα-(methoxycarbonyl)-L-phenylalaninamide | 758.2 |
| 299 | 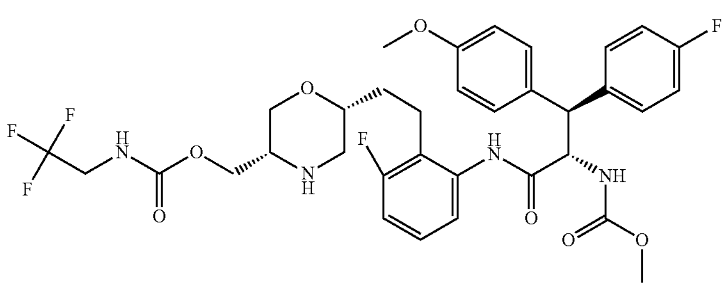 [SMILES: COC(=O)N[C@H](C(=O)Nc1cccc(F)c1CC[C@@H]1CN[C@H](COC(=O)NCC(F)(F)F)CO1)[C@H](c1ccc(F)cc1)c1ccc(OC)cc1] | (βS)-β-(4-fluorophenyl)-N-(3-fluoro-2-{2-[(2R,5S)-5-({[(2,2,2-trifluoroethyl)carbamoyl]oxy}methyl)morpholin-2-yl]ethyl}phenyl)-Nα-(methoxycarbonyl)-O-methyl-L-tyrosinamide | 709.3 |

TABLE 3-continued

The following examples can be prepared using the procedures described above.

| Example | Structure | IUPAC Name | Mass [M + H]+ |
|---|---|---|---|
| 300 | 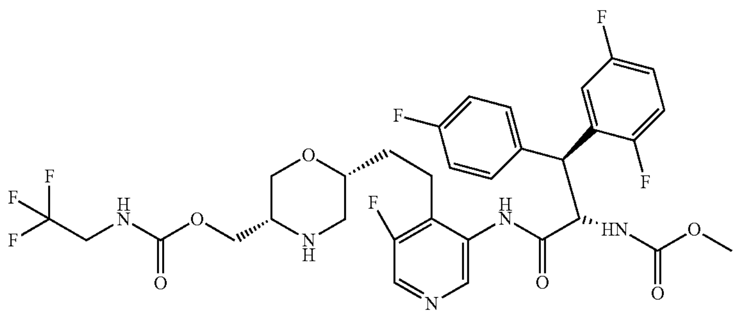 | (βS)-2,5-difluoro-β-(4-fluorophenyl)-N-(5-fluoro-4-{2-[(2R,5S)-5-({[(2,2,2-trifluoroethyl)carbamoyl]oxy}methyl)morpholin-2-yl]ethyl}pyridin-3-yl)-Nα-(methoxycarbonyl)-L-phenylalaninamide | 716.2 |
| 301 | 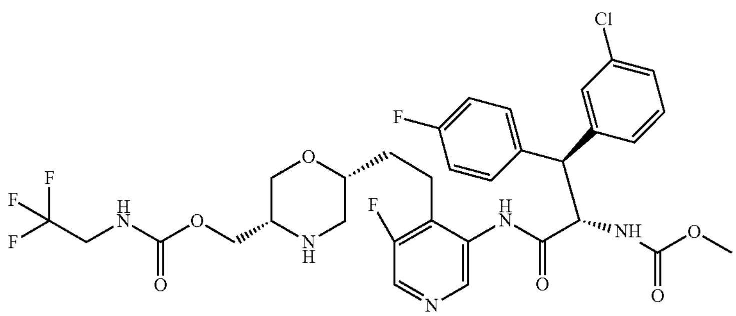 [SMILES: COC(=O)N[C@H](C(=O)Nc1cncc(F)c1CC[C@@H]1CN[C@H](COC(=O)NCC(F)(F)F)CO1)[C@@H](c1ccc(F)cc1)c1cccc(Cl)c1] | (βS)-3-chloro-β-(4-fluorophenyl)-N-(5-fluoro-4-{2-[(2R,5S)-5-({[(2,2,2-trifluoroethyl)carbamoyl]oxy}methyl)morpholin-2-yl]ethyl}pyridin-3-yl)-Nα-(methoxycarbonyl)-L-phenylalaninamide | 714.2 |
| 302 | 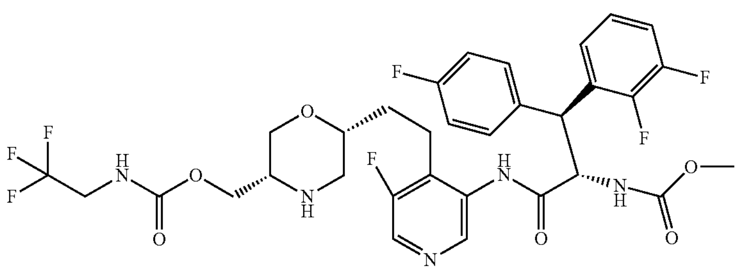 [SMILES: COC(=O)N[C@H](C(=O)Nc1cncc(F)c1CC[C@@H]1CN[C@H](COC(=O)NCC(F)(F)F)CO1)[C@@H](c1ccc(F)cc1)c1cccc(F)c1F] | (βS)-2,3-difluoro-β-(4-fluorophenyl)-N-(5-fluoro-4-{2-[(2R,5S)-5-({[(2,2,2-trifluoroethyl)carbamoyl]oxy}methyl)morpholin-2-yl]ethyl}pyridin-3-yl)-Nα-(methoxycarbonyl)-L-phenylalaninamide | 716.2 |
| 303 | 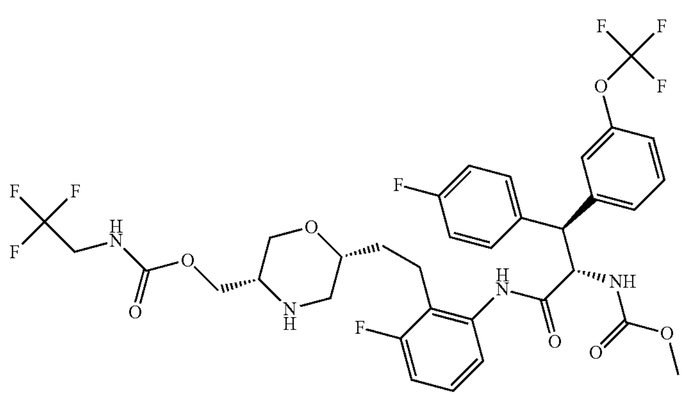 [SMILES: COC(=O)N[C@H](C(=O)Nc1cccc(F)c1CC[C@@H]1CN[C@H](COC(=O)NCC(F)(F)F)CO1)[C@@H](c1ccc(F)cc1)c1cccc(OC(F)(F)F)c1] | (βS)-4-fluoro-N-(3-fluoro-2-{2-[(2R,5S)-5-({[(2,2,2-trifluoroethyl)carbamoyl]oxy}methyl)morpholin-2-yl]ethyl}phenyl)-Nα-(methoxycarbonyl)-β-[3-(trifluoromethoxy)phenyl]-L-phenylalaninamide | 763.2 |

TABLE 3-continued

The following examples can be prepared using the procedures described above.

| Example | Structure | IUPAC Name | Mass [M + H]+ |
|---------|-----------|------------|---------------|
| 304 | 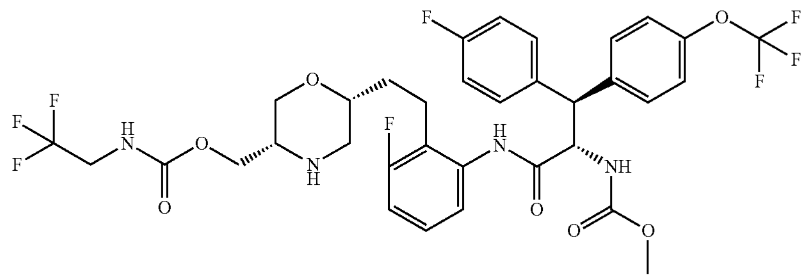 [SMILES: COC(=O)N[C@H](C(=O)Nc1cccc(F)c1CC[C@@H]1CN[C@H](COC(=O)NCC(F)(F)F)CO1)[C@@H](c1ccc(F)cc1)c1ccc(OC(F)(F)F)cc1] | (βR)-β-(4-fluorophenyl)-N-(3-fluoro-2-{2-[(2R,5S)-5-({[(2,2,2-trifluoroethyl)carbamoyl]oxy}methyl)morpholin-2-yl]ethyl}phenyl)-Nα-(methoxy-carbonyl)-O-(trifluoromethyl)-L-tyrosinamide | 763.2 |
| 305 | 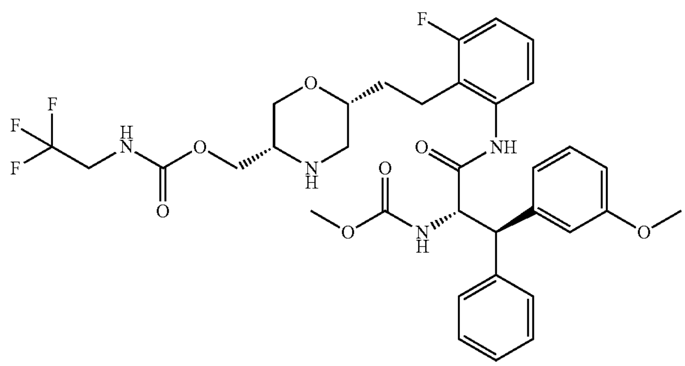 [SMILES: COC(=O)N[C@H](C(=O)Nc1cccc(F)c1CC[C@@H]1CN[C@H](COC(=O)NCC(F)(F)F)CO1)[C@H](c1ccccc1)c1cccc(OC)c1] | (βR)-N-(3-fluoro-2-{2-[(2R,5S)-5-({[(2,2,2-trifluoroethyl)carbamoyl]oxy}methyl)morpholin-2-yl]ethyl}phenyl)-3-methoxy-Nα-(methoxy-carbonyl)-β-phenyl-L-phenylalaninamide | 691.3 |
| 306 | 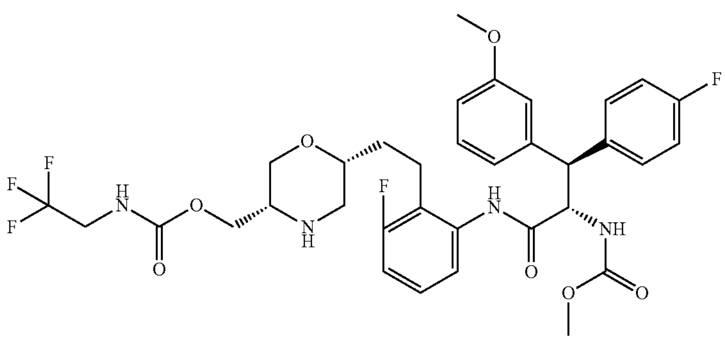 [SMILES: COC(=O)N[C@H](C(=O)Nc1cccc(F)c1CC[C@@H]1CN[C@H](COC(=O)NCC(F)(F)F)CO1)[C@H](c1ccc(F)cc1)c1cccc(OC)c1] | (βR)-4-fluoro-N-(3-fluoro-2-{2-[(2R,5S)-5-({[(2,2,2-trifluoroethyl)carbamoyl]oxy}methyl)morpholin-2-yl]ethyl}phenyl)-Nα-(methoxy-carbonyl)-β-(3-methoxyphenyl)-L-phenylalaninamide | 709.3 |
| 307 | 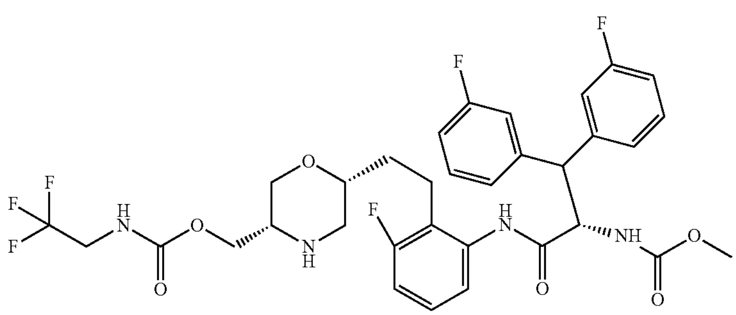 [SMILES: COC(=O)N[C@H](C(=O)Nc1cccc(F)c1CC[C@@H]1CN[C@H](COC(=O)NCC(F)(F)F)CO1)C(c1cccc(F)c1)c1cccc(F)c1] | 3-fluoro-β-(3-fluorophenyl)-N-(3-fluoro-2-{2-[(2R,5S)-5-({[(2,2,2-trifluoroethyl)carbamoyl]oxy}methyl)morpholin-2-yl]ethyl}phenyl)-Nα-(methoxy-carbonyl)-L-phenylalaninamide | 697.2 |

Assay for Inhibition of Microbial Expressed HIV Protease ("Pepcleav")

Studies of the inhibition of the wildtype HIV-1 protease (which was expressed in *Escherichia coli*) were carried out with a peptide substrate [Val-Ser-Gln-Asn-(βnaphthyl)Ala-Pro-Ile-Val (SEQ ID NO:1)]. The inhibitor is first preincubated with the HIV-1 protease (wild type) enzyme in assay buffer (50 mM sodium acetate, pH 5.5, 100 mM NaCl, and 0.1% BSA) for 30 minutes at room temperature. Substrate is added to 400 micromolar in a total volume of 20 microliters containing 20 picomolar HIV-1 protease (final) and the reaction is incubated for 1 hour at 30° C. The reaction is quenched with the addition of formic acid and indinavir to 0.012% and 150 nM final concentrations, respectively. The product formation is determined after separation of product and substrate on a Zorbax Eclipse XDB-C 18 column connected to an API 4000 mass spectrometer (Applied Biosystems) with multiple reaction monitoring (transitions were 644.5/428.9 and 615.4/

422.2 (M1/M3) for product and indinavir respectively). The extent of inhibition of the reaction is determined from the peak area of the products. Analysis of the products, independently synthesized, provided quantitation standards and confirmation of the product composition. Representative compounds of the present invention exhibit inhibition of HIV-1 protease in this assay.

Antiviral Assays in Cell Culture ("Spread")

Acute Infection Assay ("Spread") data were generated using HIV-1 (H9IIIB strain) infection of MT-4 human T-lymphoid cells in 10% FBS, and according to the methods disclosed by J. P. Vacca et al, "L-735,524: An orally bioavailable human immunodeficiency virus type 1 protease inhibitor," Proc. Natl. Acad. Sci. USA, Vol. 91, pp. 4096-4100 (April 1994).

Data Tables 1 to 5 displays data regarding Pepcleave and Spread data for each of the example compounds. Both columns of data in the table reflect the mean of at least two independent experiments

DATA TABLE 1

| Example | Pepcleav (nM) | Spread (nM) |
|---|---|---|
| 1 | 65 | |
| 2 | 1.4 | |
| 3 | 15 | |
| 4 | 25 | |
| 5 | 80 | |
| 6 | 9.9 | |
| 7 | 0.8 | |
| 8 | 41 | |
| 9 | 88 | |
| 10 | 17 | |
| 11 | 80 | |
| 12 | 3.6 | |
| 13 | 110 | |
| 14 | 17 | |
| 15 | 4.1 | |
| 16 | 5.9 | |
| 17 | 27 | |
| 18 | 28 | |
| 19 | 48 | |
| 20 | 78 | |
| 21 | 52 | |
| 22 | 58 | |
| 23 | 80 | |
| 24 | 85 | |
| 25 | 120 | |
| 26 | 210 | |
| 27 | 180 | |
| 28 | 250 | |
| 29 | 18 | |
| 30 | 32 | |
| 31 | 29 | |
| 32 | 21 | |
| 33 | 5.7 | |
| 34 | 14 | |
| 35 | 60 | |
| 36 | 24 | |
| 37 | 180 | |
| 38 | 0.6 | |
| 39 | 2.3 | |
| 40 | 52 | |
| 41 | 2.9 | |
| 42 | 17 | |
| 43 | 96 | |
| 44 | 26 | |
| 45 | 21 | |
| 46 | 50 | |
| 47 | 84 | |
| 48 | 91 | |
| 49 | 94 | |
| 50 | 49 | |
| 51 | 38 | |
| 52 | 96 | |
| 53 | 12 | |
| 54 | 26 | |
| 55 | 30 | |
| 56 | 34 | |
| 57 | 50 | |
| 58 | 66 | |
| 59 | 71 | |
| 60 | 72 | |
| 61 | 160 | |
| 62 | 130 | |
| 63 | 49 | |
| 64 | 56 | |
| 65 | 43 | |
| 66 | 100 | |
| 67 | 26 | |
| 68 | 0.03 | |
| 69 | 3.4 | |
| 70 | 24 | |
| 71 | 1.3 | |
| 72 | 14 | |
| 73 | 21 | |
| 74 | 10 | |
| 75 | 4.1 | |
| 76 | 52 | |
| 77 | 15 | |
| 78 | 59 | |
| 79 | 3.6 | 37 |
| 80 | 9.4 | 45 |
| 81 | 0.4 | 25 |
| 82 | 11 | 40 |
| 83 | | 64 |
| 84 | 670 | |
| 85 | | 87 |
| 87 | | 2200 |
| 88 | | 450 |
| 89 | 1.4 | 13 |
| 90 | 2.4 | 49 |
| 91 | 3.0 | 16 |
| 92 | 4.4 | 43 |
| 93 | 1.7 | 52 |

DATA TABLE 2

| Example | Pepcleav (nM) | Spread (nM) |
|---|---|---|
| 95 | 0.4 | 16 |
| 96 | 9.9 | 73 |
| 97 | 0.8 | 17 |
| 98 | | 28 |
| 99 | | 20 |
| 100 | | 39 |
| 102 | | 37 |
| 104 | | 26 |
| 106 | | 6.5 |
| 107 | 0.3 | 11 |
| 108 | | 860 |
| 109 | | 340 |
| 110 | | 6.9 |
| 111 | | 25 |
| 112 | | 200 |
| 113 | | 320 |
| 114 | | 14 |
| 115 | | 30 |
| 116 | 17 | 47 |
| 117 | | 18 |
| 118 | | 17 |
| 119 | 6.9 | |
| 120 | | 20 |
| 121 | 2.5 | 10 |
| 122 | | 44 |
| 123 | 3.2 | 19 |
| 127 | | 71 |
| 128 | | 91 |
| 129 | 8.6 | |

DATA TABLE 2-continued

| Example | Pepcleav (nM) | Spread (nM) |
|---|---|---|
| 130 | 68 | 26 |
| 133 | | 23 |
| 134 | | 28 |
| 136 | | 60 |
| 137 | | 9.8 |
| 138 | | 31 |
| 139 | | 108 |
| 140 | 2.1 | 21 |
| 141 | 180 | |
| 142 | | 150 |
| 143 | | 40 |
| 144 | | 170 |

DATA TABLE 3

| Example | Pepcleav (nM) | Spread (nM) |
|---|---|---|
| 146 | 13 | 47 |
| 147 | 4.9 | 120 |
| 148 | 22 | 150 |
| 149 | 1.4 | 14 |
| 150 | 11 | 130 |
| 151 | 100 | 290 |
| 152 | | 88 |
| 153 | | 130 |
| 154 | 5.1 | 150 |
| 155 | 6.1 | 58 |
| 156 | 10 | 26 |
| 157 | 9.6 | 18 |
| 158 | | 34 |
| 159 | | 380 |
| 160 | | 31 |
| 161 | 12 | 70 |
| 162 | 510 | |
| 163 | 1100 | |
| 164 | 3.4 | 63 |
| 165 | 4.5 | 40 |
| 166 | 14 | 37 |
| 167 | 1.5 | 1250 |
| 168 | | 13 |
| 169 | | 73 |
| 170 | | 61 |
| 171 | | 68 |
| 172 | | 60 |
| 173 | | 37 |
| 174 | | 120 |
| 175 | | 39 |
| 176 | | 73 |
| 177 | | 41 |
| 178 | | 85 |
| 179 | | 240 |
| 180 | | 310 |
| 181 | | 50 |
| 182 | | 17 |
| 183 | | 690 |
| 184 | | 15 |
| 185 | | 68 |
| 186 | | 66 |
| 187 | | 210 |
| 188 | | 50 |

DATA TABLE 4

| Example | Pepcleav (nM) | Spread (nM) |
|---|---|---|
| 189 | 1730 | |
| 190 | 510 | |
| 191 | 130 | |
| 192 | 130 | |
| 193 | 120 | 1400 |
| 194 | 100 | |
| 195 | 91 | |
| 196 | 79 | |

DATA TABLE 4-continued

| Example | Pepcleav (nM) | Spread (nM) |
|---|---|---|
| 197 | 68 | |
| 198 | 44 | |
| 199 | 41 | |
| 200 | 31 | |
| 201 | 28 | 80 |
| 202 | 28 | 65 |
| 203 | 28 | |
| 204 | 26 | |
| 205 | 24 | 58 |
| 206 | 21 | 120 |
| 207 | 20 | 110 |
| 208 | 18 | 100 |
| 209 | 16 | |
| 210 | 13 | |
| 211 | 12 | |
| 212 | 11 | 810 |
| 213 | 6.1 | 61 |
| 214 | 5.2 | 58 |
| 215 | 3.5 | 25 |
| 216 | 3.3 | 2000 |
| 217 | 2.7 | 94 |
| 218 | 2.1 | |
| 219 | | 140 |
| 221 | 1.1 | 22 |
| 222 | | 53 |
| 223 | | 1400 |
| 224 | | 260 |
| 225 | 2700 | |
| 226 | 360 | |
| 227 | 340 | |
| 228 | 190 | |
| 229 | 190 | |
| 230 | 180 | |
| 231 | 150 | |
| 232 | 150 | |
| 233 | 110 | |
| 234 | 110 | |
| 235 | 97 | 5000 |
| 236 | 69 | 580 |
| 237 | 69 | 190 |
| 238 | 69 | 470 |
| 239 | 45 | 420 |
| 240 | 39 | 5000 |
| 241 | 32 | 360 |
| 242 | 25 | 600 |
| 243 | 24 | 240 |
| 244 | 22 | 120 |
| 245 | 16 | 360 |
| 246 | 13 | 390 |
| 247 | 12 | 260 |
| 248 | 9.8 | 55 |
| 249 | 9.4 | 3000 |
| 250 | 8.3 | 63 |
| 251 | 8.2 | 32 |
| 252 | 7.7 | 160 |
| 253 | 7.7 | 24 |
| 254 | 7.6 | 1100 |
| 255 | 6.4 | 210 |
| 256 | 5.7 | 100 |
| 257 | 5.1 | 51 |
| 258 | 5.0 | 260 |
| 259 | 5.0 | 66 |
| 260 | 4.8 | 190 |
| 261 | 4.3 | 170 |
| 262 | 4.0 | 15 |
| 263 | 3.7 | 48 |
| 264 | 3.6 | 77 |
| 265 | 3.1 | 36 |
| 266 | 3.1 | 50 |
| 267 | 3.1 | 51 |
| 268 | 2.8 | 44 |
| 269 | 2.7 | 25 |
| 270 | 2.1 | 22 |
| 271 | 2.0 | 810 |
| 272 | 2.0 | 32 |
| 273 | 1.4 | 20 |

DATA TABLE 4-continued

| Example | Pepcleav (nM) | Spread (nM) |
|---|---|---|
| 274 | 1.3 | 11 |
| 275 | 0.4 | 25 |
| 276 | 0.2 | 28 |

DATA TABLE 5

| Example | Pepcleav (nM) | Spread (nM) |
|---|---|---|
| 277 | 3.2 | 23 |
| 278 | 3.2 | 38 |
| 279 | 1.9 | 57 |
| 280 | 1.0 | 15 |
| 281 | 0.9 | 14 |
| 282 | 3.7 | 25 |
| 283 | 14 | 69 |
| 284 | 12 | 19 |
| 285 | 13 | 21 |
| 286 | 4.6 | 37 |
| 287 | 6.0 | 17 |
| 288 | 3.2 | 16 |
| 289 | 16 | 310 |
| 290 | 30 | 600 |
| 291 | 28 | 110 |
| 292 | 3.6 | 16 |
| 293 | 100 | 80 |
| 294 | 3.8 | 14 |
| 295 | 2.5 | 13 |
| 296 | 23 | 120 |
| 297 | 1.0 | 15 |
| 298 | 0.3 | 14 |
| 299 | 15 | 32 |
| 300 | 1.6 | 18 |
| 301 |  | 25 |
| 302 |  | 15 |
| 303 | 5.3 | 24 |
| 304 |  | 33 |
| 305 | 230 | 42 |
| 306 | 170 |  |
| 307 | 3.0 | 14 |

While the foregoing specification teaches the principles of the present invention, with examples provided for the purpose of illustration, the practice of the invention encompasses all of the usual variations, adaptations and/or modifications that come within the scope of the following claims. All publications, patents and patent applications cited herein are incorporated by reference in their entirety into the disclosure.

What is claimed is:

1. A compound of Formula I:

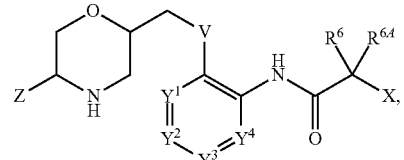

or a pharmaceutically acceptable salt thereof, wherein:

V is $CH_2$ or O;

$Y^1$, $Y^2$, $Y^3$ and $Y^4$ are independently selected from C(R) and N;

each X is independently selected from H and $NR^7R^8$;

Z is selected from the group consisting of

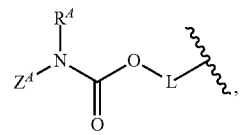

(1)

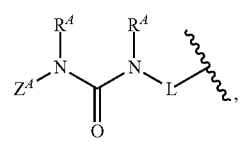

(2)

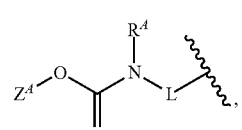

(3)

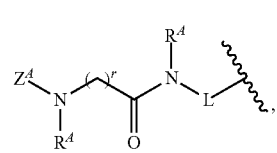

(4)

SEQUENCE LISTING

```
<160> NUMBER OF SEQ ID NOS: 1

<210> SEQ ID NO 1
<211> LENGTH: 8
<212> TYPE: PRT
<213> ORGANISM: Artificial Sequence
<220> FEATURE:
<223> OTHER INFORMATION: HIV-1 Protease Peptide
<220> FEATURE:
<221> NAME/KEY: MISC_FEATURE
<223> OTHER INFORMATION: Xaa = betanaphthyl alanine
<220> FEATURE:
<221> NAME/KEY: misc_feature
<222> LOCATION: (5)..(5)
<223> OTHER INFORMATION: Xaa can be any naturally occurring amino acid

<400> SEQUENCE: 1

Val Ser Gln Asn Xaa Pro Ile Val
1               5
```

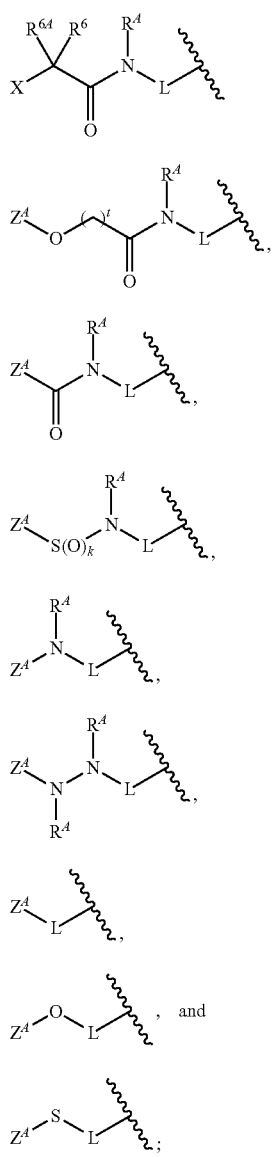

(5)

(6)

(7)

(8)

(9)

(10)

(11)

(12) , and (13)

L is a linker selected from
(a) a bond,
(b) —CH₂—,
(c) —C(O)—,
(d) —CH₂—C(O)— or —C(O)—CH₂—,
(e) —CH₂—CH₂—C(O)— or —C(O)—CH₂—CH₂—, and (f)

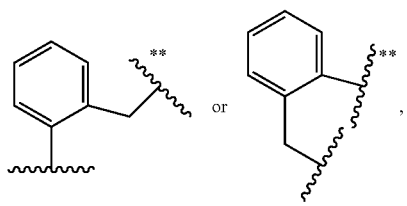

wherein ** shows the point of attachment to the morpholine and when Z is

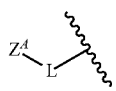

then L is not a bond;

R is selected from H, halo, hydroxy, $C_{1-4}$alkyl, $C_{1-4}$alkoxy, $C_{1-4}$alkyl-$S(O)_k$—, $CF_3$, CN, benzyl, or two R groups on adjacent atoms may be joined together with the atoms to which they are attached to form a fused phenyl, pyridine, pyridazine, pyrimidine, pyrazine, or triazine, each of which is optionally substituted with 1 to 4 substituents independently selected from the group consisting of: halo, $C_{1-4}$alkyl, $C_{1-4}$alkoxy, $CF_3$ and CN;

each k is independently 0, 1 or 2;

each r and t are independently 1, 2, 3 or 4;

$Z^A$ is selected from the group consisting of:
(1) hydrogen,
(2) $C_{1-10}$ alkyl,
(3) $C_{2-10}$alkenyl,
(4) $C_{3-7}$ cycloalkyl,
(5) AryA,
(6) HetA,
(7) HetB, wherein said $C_{1-10}$ alkyl, $C_{2-10}$alkenyl and $C_{3-7}$ cycloalkyl are optionally substituted with 1 to 6 substituents as allowed by valence independently selected from the group consisting of: fluoro, hydroxy, carbamoyl, $C_{3-6}$ cycloalkyl, C(O)O—$C_{1-6}$ alkyl, C(O)OH, C(O)—$C_{1-6}$ alkyl, N(H)—$C_{1-6}$ alkyl, N(—$C_{1-6}$ alkyl)₂, ArylA, HetA and HetB;

each $R^A$ is independently H or $C_{1-6}$ alkyl;

or $Z^A$ and $R^A$ and the nitrogen atom to which they are attached may be joined together to form a 5-, 6- or 7-membered mono-cyclic, or 9- or 10-membered bi-cyclic, saturated, aromatic or partially aromatic ring, said ring optionally containing 1 to 3 additional heteroatoms selected from O, S and N, and said ring optionally substituted with from 1 to 3 $X^A$;

each $R^6$ independently is:

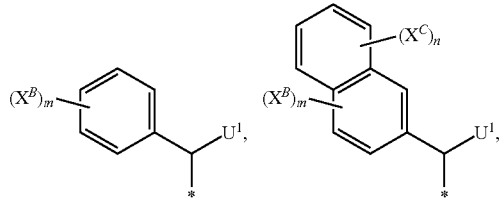

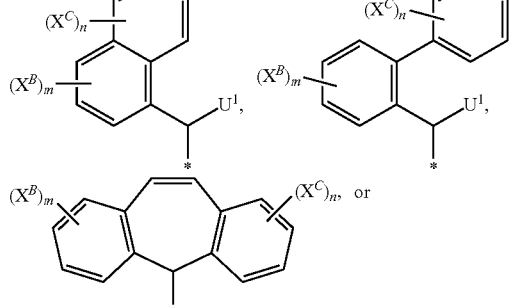

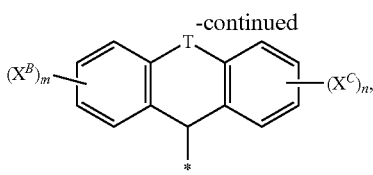

wherein the asterisk (*) denotes the point of attachment to the rest of the compound and $U^1$ is selected from H, $C_{1-10}$alkyl, ArylA, HetA and HetB;

each $R^{6A}$ independently is H or $C_{1-6}$ alkyl;

alternatively, $R^6$ and $R^{6A}$ together with the carbon to which they are attached form a $C_{3-6}$ cycloalkyl which is optionally substituted with phenyl, wherein the phenyl is optionally substituted with from 1 to 3 $X^D$;

each $X^A$, each $X^B$, each $X^C$, each $X^D$, each $Y^B$ and each $Y^C$ are independently selected from the group consisting of:
(1) $C_{1-6}$ alkyl,
(2) $C_{3-6}$ cycloalkyl,
(3) $C_{1-6}$ haloalkyl,
(4) OH,
(5) O—$C_{1-6}$ alkyl,
(6) O—$C_{1-6}$ haloalkyl,
(7) O—$C_{3-6}$ cycloalkyl,
(8) SH,
(9) S—$C_{1-6}$ alkyl,
(10) S—$C_{1-6}$ haloalkyl,
(11) S—$C_{3-6}$ cycloalkyl,
(12) halo,
(13) CN,
(14) $NO_2$,
(15) $NH_2$,
(16) N(H)—$C_{1-6}$ alkyl,
(17) N(—$C_{1-6}$ alkyl)$_2$,
(18) N(H)C(O)—$C_{1-6}$ alkyl,
(19) N(H)CH(O),
(20) CH(O),
(21) C(O)—$C_{1-6}$ alkyl,
(22) C(O)OH,
(23) C(O)O—$C_{1-6}$ alkyl,
(24) C(O)$NH_2$,
(25) C(O)N(H)—$C_{1-6}$ alkyl,
(26) C(O)N(—$C_{1-6}$ alkyl)$_2$,
(27) C(O)N(H)C(O)—$C_{1-6}$ alkyl,
(28) C(O)N(H)CH(O)
(29) $SO_2$H,
(30) $SO_2$—$C_{1-6}$ alkyl;
(31) phenyl, benzyl or phenoxy, each optionally substituted with 1 to 5 substituents selected from halogen and $C_{1-6}$ alkyl,
(32) HetA, —O-HetA or —$CH_2$-HetA, optionally substituted with 1 to 5 substituents selected from halogen and $C_{1-6}$ alkyl,
(33) trimethylsilyl, and
(34) $C_{2-6}$alkenyl, wherein $C_{1-6}$ alkyl in each instance of (1), (3) (5), (6), (9), (10), (16), (17), (18), (21), (23), (25), (26), (27), (30), (31) and (32) above is optionally substituted with 1 to 6 substituents as allowed by valence selected from the group consisting of:
(a) $C_{1-6}$ haloalkyl,
(b) OH
(c) O—$C_{1-6}$ alkyl,
(d) O—$C_{1-6}$ haloalkyl,
(e) O—$C_{3-6}$ cycloalkyl,
(f) SH,
(g) S—$C_{1-6}$ alkyl,
(h) halo,
(i) CN,
(j) $NO_2$,
(k) $NH_2$,
(l) N(H)—$C_{1-6}$ alkyl,
(m) N(—$C_{1-6}$ alkyl)$_2$,
(n) C(O)—$C_{1-6}$ alkyl,
(o) C(O)OH,
(p) C(O)O—$C_{1-6}$ alkyl, and
(q) $SO_2$—$C_{1-6}$ alkyl;

T is O, S, S(O), or $SO_2$;

m is an integer equal to 0, 1, 2, or 3;

n is an integer equal to 0, 1, 2, or 3;

$R^7$ is H, $C_{1-6}$ alkyl, $C_{3-6}$ cycloalkyl, $C_{1-6}$ alkyl substituted with $C_{3-6}$ cycloalkyl, C(O)—$R^K$ or $SO_2$—$R^K$;

$R^8$ is H, $C_{1-6}$ alkyl, $C_{1-6}$ haloalkyl and $C_{3-6}$ cycloalkyl;

$R^K$ is:
(1) $C_{1-6}$ alkyl,
(2) $C_{3-6}$ cycloalkyl,
(3) $C_{1-6}$ alkyl substituted with $C_{3-6}$ cycloalkyl,
(4) O—$C_{1-6}$ alkyl,
(5) O—$C_{1-6}$ alkyl substituted with O—$C_{1-6}$ alkyl,
(6) O—$C_{1-6}$ fluoroalkyl,
(7) C(O)O—$C_{1-6}$ alkyl,
(8) $C_{1-6}$ alkyl substituted with C(O)O—$C_{1-6}$ alkyl,
(9) $C_{1-6}$ alkyl substituted with C(O)OH,
(10) $C_{1-6}$ alkyl substituted with C(O)—$C_{1-6}$ alkyl,
(11) N(H)—$C_{1-6}$ alkyl,
(12) N(—$C_{1-6}$ alkyl)$_2$,
(13) $C_{1-6}$ alkyl substituted with $NH_2$, N(H)—$C_{1-6}$ alkyl, or N(—$C_{1-6}$ alkyl)$_2$,
(14) AryA,
(15) $C_{1-6}$ alkyl substituted with AryA,
(16) O—$C_{1-6}$ alkyl substituted with AryA,
(17) HetA,
(18) $C_{1-6}$ alkyl substituted with HetA,
(19) O—$C_{1-6}$ alkyl substituted with HetA,
(20) HetB,
(21) O-HetB, or
(22) O—$C_{1-6}$ alkyl substituted with HetB;

each AryA is an aryl which is independently phenyl or naphthyl, wherein the phenyl or naphthyl is optionally substituted with from 1 to 3 $Y^B$;

each HetA is a heteroaryl which is independently (i) a 5- or 6-membered monocyclic heteroaromatic ring containing from 1 to 3 heteroatoms independently selected from N, O and S, or (ii) is a 9-, 10- or 11-membered bicyclic heteroaromatic ring containing from 1 to 4 heteroatoms independently selected from N, O and S; wherein the monoclyclic ring (i) or the bicyclic ring (ii) is optionally substituted with from 1 to 3 $Y^C$; and each HetB is independently a 4- to 7-membered, saturated or unsaturated, non-aromatic heterocyclic ring containing at least one carbon atom and from 1 to 4 heteroatoms independently selected from N, O and S, where each S is optionally oxidized to S(O) or $S(O)_2$, and wherein the saturated or unsaturated heterocyclic ring is optionally substituted with from 1 to 3 substituents each of which is independently halogen, CN, $C_{1-6}$ alkyl, OH, oxo, O—$C_{1-6}$ alkyl, $C_{1-6}$ haloalkyl, O—$C_{1-6}$ haloalkyl, C(O)$NH_2$, C(O)N(H)—$C_{1-6}$ alkyl, C(O)N(—$C_{1-6}$ alkyl)$_2$, C(O)H, C(O)—$C_{1-6}$ alkyl, $CO_2$H, $CO_2$—$C_{1-6}$ alkyl, $SO_2$H, or $SO_2$—$C_{1-6}$ alkyl.

2. The compound according to claim 1 wherein $R^6$ is:

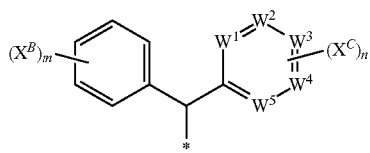

wherein $W^1$ to $W^5$ are independently C or N, with the proviso that no more that three are N, and $R^{6A}$ is H.

3. The compound according to claim 1 wherein Z is

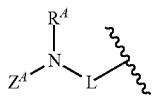

and L is —C(O)—.

4. The compound according to claim 1 wherein Z is

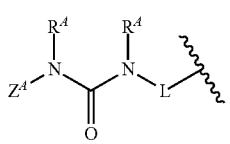

and L is —CH$_2$—.

5. The compound according to claim 1 wherein Z is

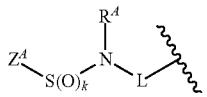

and L is —CH$_2$—.

6. The compound according to claim 1 wherein Z is

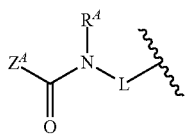

and L is —CH$_2$—.

7. The compound according to claim 1 wherein Z is

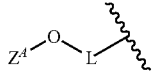

and L is —CH$_2$—.

8. The compound according to claim 1 wherein Z is

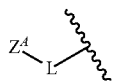

and L is —CH$_2$—.

9. The compound according to claim 1 wherein Z is

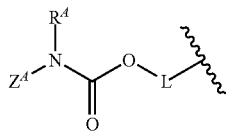

and L is —CH$_2$—.

10. The compound according to claim 1 wherein Z is

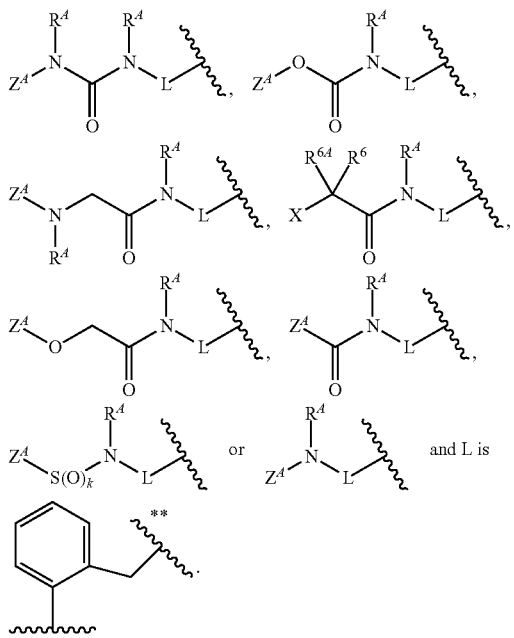

11. The compound according to claim 1 of Formula Ia (Ia)

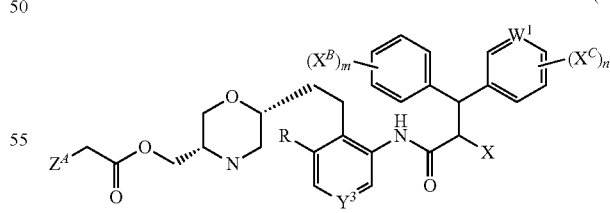

or a pharmaceutically acceptable salt thereof, wherein $W^1$ is C or N.

12. The compound according to claim 11 wherein:
R is H or fluoro,
$Y^3$ is CH or N,
$X^B$ and $X^C$ are independently selected from halo, —OCH$_3$, —CF$_3$ and —OCF$_3$, and
m and n are independently 0, 1 or 2.

13. The compound according to claim 12 wherein X is selected from: H, —NH$_2$ and —N(H)—C(O)—OR$^8$.

14. The compound according to any one of claim 1, wherein W$^1$ is C, one X$^B$ group is present and substituted at the 4-position, one or two X$^C$ groups are present and substituted at the 3- or 3,5-positions respectively, and the X$^B$ group is a different group with respect to either X$^C$ group.

15. The compound according to any one of claim 1 wherein Z$^A$ is selected from the group consisting of:
(1) hydrogen,
(2) C$_{1-10}$ alkyl,
(3) C$_{2-10}$alkenyl, and
(4) C$_{3-7}$ cycloalkyl,
wherein said C$_{1-10}$ alkyl, C$_{2-10}$alkenyl and C$_{3-7}$ cycloalky are optionally substituted with 1 to 6 substituents as allowed by valence independently selected from the group consisting of: fluoro, hydroxy, carbamoyl, C$_{3-6}$ cycloalkyl, C(O)O—C$_{1-6}$ alkyl, C(O)OH, C(O)—C$_{1-6}$ alkyl, N(H)—C$_{1-6}$ alkyl, N(—C$_{1-6}$ alkyl)$_2$, ArylA, HetA and HetB.

16. The compound according to claim 15 wherein Z$^A$ is C$_{1-10}$ alkyl, optionally substituted with 1 to 6 substituents as allowed by valence independently selected from the group consisting of: fluoro and hydroxy.

17. The compound according to claim 16 wherein Z$^A$ is —(CH$_2$)$_{0-4}$—CF$_3$.

18. A compound selected from the group consisting of:
(3S,6R)-6-[2-(2-{[N-(methoxycarbonyl)-β-phenyl-L-phenylalanyl]amino}phenyl)ethyl]morpholine-3-carboxylic acid;
N-(2-{2-[(2R,5S)-5-(benzylcarbamoyl)morpholin-2-yl]ethyl}phenyl)-Nα-(methoxycarbonyl)-β-phenyl-L-phenylalaninamide;
N-(2-{2-[(2R,5S)-5-(ethylcarbamoyl)morpholin-2-yl]ethyl}phenyl)-Nα-(methoxycarbonyl)-β-phenyl-L-phenylalaninamide;
Nα-(methoxycarbonyl)-β-phenyl-N-(2-{2-[(2R,5S)-5-(tetrahydrofuran-3-ylcarbamoyl)morpholin-2-yl]ethyl}phenyl)-L-phenylalaninamide;
Nα-(methoxycarbonyl)-β-phenyl-N-(2-{2-[(2R,5S)-5-(pyrrolidin-1-ylcarbonyl)morpholin-2-yl]ethyl}phenyl)-L-phenylalaninamide;
Nα-(methoxycarbonyl)-β-phenyl-N-[2-(2-{(2R,5S)-5-[(2-phenylethyl)carbamoyl]morpholin-2-yl}ethyl)phenyl]-L-phenylalaninamide;
Nα-(methoxycarbonyl)-β-phenyl-N-(2-{2-[(2R,5S)-5-(phenylcarbamoyl)morpholin-2-yl]ethyl}phenyl)-L-phenylalaninamide;
N-(2-{2-[(2R,5S)-5-(tert-butylcarbamoyl)morpholin-2-yl]ethyl}phenyl)-Nα-(methoxycarbonyl)-β-phenyl-L-phenylalaninamide;
Nα-(methoxycarbonyl)-β-phenyl-N-[2-(2-{(2R,5S)-5-[(2-phenylhydrazinyl)carbonyl]morpholin-2-yl}ethyl)phenyl]-L-phenylalaninamide;
Nα-(methoxycarbonyl)-β-phenyl-N-[2-(2-{(2R,5S)-5-[(phenylsulfonyl)carbamoyl]morpholin-2-yl}ethyl)phenyl]-L-phenylalaninamide;
methyl [(1S)-2-[(2-{2-[(2R,5S)-5-(aminocarbonyl)morpholin-2-yl]ethyl}phenyl)amino]-1-(diphenylmethyl)-2-oxoethyl]carbamate;
N-(2-{2-[(2R,5S)-5-({[(2-fluorobenzyl)carbamoyl]oxy}methyl)morpholin-2-yl]ethyl}phenyl)-Nα-(methoxycarbonyl)-β-phenyl-L-phenylalaninamide;
N-(2-{2-[(2R,5S)-5-({[(3R,3aS,6aR)-hexahydrofuro[2,3-b]furan-3-ylcarbamoyl]oxy}methyl)morpholin-2-yl]ethyl}phenyl)-Nα-(methoxycarbonyl)-β-phenyl-L-phenylalaninamide;
N-[2-(2-{(2R,5S)-5-[({[(1S,2R)-2-hydroxy-2,3-dihydro-1H-inden-1-yl]carbamoyl}oxy)methyl]morpholin-2-yl}ethyl)phenyl]-Nα-(methoxycarbonyl)-β-phenyl-L-phenylalaninamide;
N-(2-{2-[(2R,5S)-5-{[(2,3-dihydro-1H-inden-1-ylcarbamoyl)oxy]methyl}morpholin-2-yl]ethyl}phenyl)-Nα-(methoxycarbonyl)-β-phenyl-L-phenylalaninamide;
methyl N-[(1S)-1-benzhydryl-2-[[2-[2-[(2R,5S)-5-[(4-fluorophenyl)methylcarbamoyloxymethyl]morpholin-2-yl]ethyl]phenyl]amino]-2-oxo-ethyl]carbamate;
methyl N-[(1S)-1-benzhydryl-2-oxo-2-[[2-[2-[(2R,5S)-5-(2,2,2-trifluoroethylcarbamoyloxymethyl)morpholin-2-yl]ethyl]phenyl]amino]ethyl]carbamate;
methyl N-[(1S)-1-benzhydryl-2-[[2-[2-[(2R,5S)-5-(8-isoquinolylmethylcarbamoyloxymethyl)morpholin-2-yl]ethyl]phenyl]amino]-2-oxo-ethyl]carbamate;
methyl N-[(1S)-1-benzhydryl-2-oxo-2-[[2-[2-[(2R,5S)-5-(thiazol-5-ylmethylcarbamoyloxymethyl)morpholin-2-yl]ethyl]phenyl]amino]ethyl]carbamate;
methyl N-[(1S)-1-benzhydryl-2-oxo-2-[[2-[2-[(2R,5S)-5-(3-pyridylmethylcarbamoyloxymethyl)morpholin-2-yl]ethyl]phenyl]amino]ethyl]carbamate;
methyl N-[(1S)-1-benzhydryl-2-[[2-[2-[(2R,5S)-5-(2,1,3-benzoxadiazol-5-ylmethylcarbamoyloxymethyl)morpholin-2-yl]ethyl]phenyl]amino]-2-oxo-ethyl]carbamate;
methyl N-[(1S)-1-benzhydryl-2-[[2-[2-[(2R,5S)-5-(cyclopropylmethylcarbamoyloxymethyl)morpholin-2-yl]ethyl]phenyl]amino]-2-oxo-ethyl]carbamate;
methyl N-[(1S)-1-benzhydryl-2-[[2-[2-[(2R,5S)-5-(cyclobutylcarbamoyloxymethyl)morpholin-2-yl]ethyl]phenyl]amino]-2-oxo-ethyl]carbamate;
methyl N-[(1S)-1-benzhydryl-2-[[2-[2-[(2R,5S)-5-(2,2-difluoroethylcarbamoyloxymethyl)morpholin-2-yl]ethyl]phenyl]amino]-2-oxo-ethyl]carbamate;
methyl N-[(1S)-1-benzhydryl-2-[[2-[2-[(2R,5S)-5-(diethylcarbamoyloxymethyl)morpholin-2-yl]ethyl]phenyl]amino]-2-oxo-ethyl]carbamate;
methyl N-[(1S)-1-benzhydryl-2-[[2-[2-[(2R,5S)-5-(dimethylcarbamoyloxymethyl)morpholin-2-yl]ethyl]phenyl]amino]-2-oxo-ethyl]carbamate;
[(3S,6R)-6-[2-[2-[[(2S)-2-(methoxycarbonylamino)-3,3-diphenyl-propanoyl]amino]phenyl]ethyl]morpholin-3-yl]methyl pyrrolidine-1-carboxylate;
methyl N-[(1S)-1-benzhydryl-2-[[2-[2-[(2R,5S)-5-(2-dimethylaminoethylcarbamoyloxymethyl)morpholin-2-yl]ethyl]phenyl]amino]-2-oxo-ethyl]carbamate;
N-[2-(2-{(2R,5S)-5-[({[(3S,4R)-4-fluorotetrahydrofuran-3-yl]carbamoyl}oxy) methyl]morpholin-2-yl}ethyl)phenyl]-Nα-(methoxycarbonyl)-β-phenyl-L-phenylalaninamide;
Nα-(methoxycarbonyl)-N-(2-{2-[(2R,5S)-5-{[(methylcarbamoyl)oxy]methyl}morpholin-2-yl]ethyl}phenyl)-β-phenyl-L-phenylalaninamide;
N-(2-{2-[(2R,5S)-5-({[(1-cyclopropyl-2,2,2-trifluoroethyl)carbamoyl]oxy}methyl)morpholin-2-yl]ethyl}phenyl)-Nα-(methoxycarbonyl)-β-phenyl-L-phenylalaninamide;
N-(3-{2-[(2R,5S)-5-({[(4-fluorobenzyl)carbamoyl]oxy}methyl)morpholin-2-yl]ethyl}pyridin-2-yl)-Nα-(methoxycarbonyl)-β-phenyl-L-phenylalaninamide;
N-(4-{2-[(2R,5S)-5-({[(4-fluorobenzyl)carbamoyl]oxy}methyl)morpholin-2-yl]ethyl}pyridin-3-yl)-Nα-(methoxycarbonyl)-β-phenyl-L-phenylalaninamide;

Nα-(methoxycarbonyl)-β-phenyl-N-(4-{2-[(2R,5S)-5-({[(2,2,2-trifluoroethyl) carbamoyl]oxy}methyl)morpholin-2-yl]ethyl}pyridin-3-yl)-L-phenylalaninamide;

Nα-(methoxycarbonyl)-N-(2-methoxy-4-{2-[(2R,5S)-5-({[(2,2,2-trifluoroethyl)carbamoyl]oxy}methyl)morpholin-2-yl]ethyl}pyridin-3-yl)-β-phenyl-L-phenylalaninamide;

N-(4-{2-[(2R,5S)-5-({[(4-fluorobenzyl)carbamoyl]oxy}methyl)morpholin -2-yl]ethyl}pyrimidin-5-yl)-Nα-(methoxycarbonyl)-β-phenyl-L-phenylalaninamide;

Nα-(methoxycarbonyl)-β-phenyl-N-(4-{2-[(2R,5S)-5-({[(2,2,2-trifluoroethyl)carbamoyl]oxy}methyl)morpholin-2-yl]ethyl}pyrimidin-5-yl)-L-phenylalaninamide;

N-(4-{2-[(2R,5S)-5-({[(4-fluorobenzyl)carbamoyl]oxy}methyl) morpholin-2-yl]ethyl}-2-oxo-1,2-dihydropyridin-3-yl)-Nα-(methoxycarbonyl)-β-phenyl-L-phenylalaninamide;

Nα-(methoxycarbonyl)-N-(2-oxo-4-{2-[(2R,5S)-5-({[(2,2,2-trifluoroethyl)carbamoyl]oxy}methyl)morpholin-2-yl]ethyl}-1,2-dihydropyridin-3-yl)-β-phenyl-L-phenylalaninamide;

N-α-(methoxycarbonyl)-β-phenyl-N-(2-{2-[(2R,5R)-5-{[(phenylcarbamoyl)amino]methyl}morpholin-2-yl]ethyl}phenyl)-L-phenylalaninamide;

methyl N-[(1S)-1-benzhydryl-2-oxo-2-[[2-[2-[(2R,5R)-5-[(pyridazin-3-ylcarbamoylamino)methyl]morpholin-2-yl]ethyl]phenyl]amino]ethyl]carbamate;

methyl N-[(1S)-1-benzhydryl-2-oxo-2-[[2-[2-[(2R,5R)-5-[(2-pyridylcarbamoylamino)methyl]morpholin-2-yl]ethyl]phenyl]amino]ethyl]carbamate;

methyl N-[(1S)-1-benzhydryl-2-oxo-2-[[2-[2-[(2R,5R)-5-[(1H-pyrazol-3-ylcarbamoylamino)methyl]morpholin-2-yl]ethyl]phenyl]amino]ethyl]carbamate;

methyl N-[(1S)-1-benzhydryl-2-oxo-2-[[2-[2-[(2R,5R)-5-[(triazolo[1,5-a]pyridin-6-ylsulfonylamino)methyl]morpholin-2-yl]ethyl]phenyl]amino]ethyl]carbamate;

methyl N-[(1S)-1-benzhydryl-2-oxo-2-[[2-[2-[(2R,5R)-5-[[[6-(trifluoromethyl)-2-pyridyl]sulfonylamino]methyl]morpholin-2-yl]ethyl]phenyl]amino]ethyl]carbamate;

methyl N-[(1S)-1-benzhydryl-2-[[2-[2-[(2R,5R)-5-[(cyclopropylsulfonylamino)methyl]morpholin-2-yl]ethyl]phenyl]amino]-2-oxo-ethyl]carbamate;

methyl N-[(1S)-1-benzhydryl-2-oxo-2-[[2-[2-[(2R,5R)-5-[(2-pyridylsulfonylamino)methyl]morpholin-2-yl]ethyl]phenyl]amino]ethyl]carbamate;

N-(2-{2-[(2R,5R)-5-({[(4-aminophenyl)sulfonyl]amino}methyl) morpholin-2-yl]ethyl}phenyl)-Nα-(methoxycarbonyl)-β-phenyl-L-phenylalaninamide;

N-(2-{2-[(2R,5R)-5-{[(benzylsulfonyl)amino]methyl}morpholin-2-yl]ethyl}phenyl) -Nα-(methoxycarbonyl)-β-phenyl-L-phenylalaninamide;

Nα-(methoxycarbonyl)-N-(2-{2-[(2R,5R)-5-{[(phenoxycarbonyl)amino]methyl}morpholin-2-yl]ethyl}phenyl)-β-phenyl-L-phenylalaninamide;

Nα-(methoxycarbonyl)-β-phenyl-N-(2-{2-[(2R,5R)-5-{[(phenylcarbonyl)amino]methyl}morpholin-2-yl]ethyl}phenyl)-L-phenylalaninamide;

Nα-(methoxycarbonyl)-β-phenyl-N-(2-{2-[(2R,5R)-5-{[(phenylacetyl)amino]methyl}morpholin-2-yl]ethyl}phenyl)-L-phenylalaninamide;

methyl N-[(1S)-1-benzhydryl-2-oxo-2-[[2-[2-[(2R,5R)-5-[(pyridazine-3-carbonylamino)methyl]morpholin-2-yl]ethyl]phenyl]amino]ethyl]carbamate;

methyl N-[(1S)-1-benzhydryl-2-[[2-[2-[(2R,5R)-5-[[(2-chlorobenzoyl)amino]methyl]morpholin-2-yl]ethyl]phenyl]amino]-2-oxo-ethyl]carbamate;

methyl N-[(1S)-1-benzhydryl-2-[[2-[2-[(2R,5R)-5-[(1H-indole-2-carbonylamino)methyl]morpholin-2-yl]ethyl]phenyl]amino]-2-oxo-ethyl]carbamate;

methyl N-[(1S)-1-benzhydryl-2-[[2-[2-[(2R,5R)-5-[[(2,6-dimethylbenzoyl)amino]methyl]morpholin-2-yl]ethyl]phenyl]amino]-2-oxo-ethyl]carbamate;

methyl N-[(1S)-1-benzhydryl-2-[[2-[2-[(2R,5R)-5-[[(3-fluoro-6-oxo-1H-pyridine-2-carbonyl)amino]methyl]morpholin-4-ium-2-yl]ethyl]phenyl]amino]-2-oxo-ethyl]carbamate;

methyl N-[(1S)-1-benzhydryl-2-oxo-2-[[2-[2-[(2R,5R)-5-[(pyrazolo[1,5-a]pyrimidine-2-carbonylamino)methyl]morpholin-2-yl]ethyl]phenyl]amino]ethyl]carbamate;

methyl N-[(1S)-1-benzhydryl-2-oxo-2-[[2-[2-[(2R,5R)-5-[[[5-(2-pyridyl)-1H-pyrazole-3-carbonyl]amino]methyl]morpholin-2-yl]ethyl]phenyl]amino]ethyl]carbamate;

N-(2-{2-[(2R,5R)-5-(hydroxymethyl)morpholin-2-yl]ethyl}phenyl)-Nα-(methoxycarbonyl)-β-phenyl-L-phenylalaninamide;

Nα-(methoxycarbonyl)-β-phenyl-N-[2-(2-{(2R,5S)-5-[(phenylsulfanyl)methyl]morpholin-2-yl}ethyl)phenyl]-L-phenylalaninamide;

Nα-(methoxycarbonyl)-N-(2-{2-[(2R,5S)-5-(phenoxymethyl)morpholin-2-yl]ethyl}phenyl)-β-phenyl-L-phenylalaninamide;

Nα-(methoxycarbonyl)-β-phenyl-N-[2-(2-{(2R,5R)-5-[(4-phenyl-1H-1,2,3-triazol-1-yl)methyl]morpholin-2-yl}ethyl)phenyl]-L-phenylalaninamide;

Nα-(methoxycarbonyl)-β-phenyl-N-(2-{2-[(2R,5R)-5-{[4-(trimethylsilyl)-1H-1,2,3-triazol-1-yl]methyl}morpholin-2-yl]ethyl}phenyl)-L-phenylalaninamide;

Nα-(methoxycarbonyl)-β-phenyl-N-(2-{2-[(2R,5R)-5-(1H-1,2,3-triazol-1-ylmethyl)morpholin-2-yl]ethyl}phenyl)-L-phenylalaninamide;

methyl {(1S)-1-(diphenylmethyl)-2-oxo-2-[(2-{2-[(2R,5R)-5-(3-phenylpropyl)morpholin-2-yl]ethyl}phenyl)amino]ethyl}carbamate;

dimethyl [(2R,5R)-morpholine-2,5-diylbis {ethane-2,1-diylbenzene-2,1-diylimino[(2S)-1-oxo-3,3-diphenylpropane-1,2-diyl]}]biscarbamate;

methyl N-[(1S)-1-benzhydryl-2-[[2-[2-[(2R,5R)-5-[2-[2-[[2-(methoxycarbonylamino)acetyl]amino]phenyl]ethyl]morpholin-2-yl]ethyl]phenyl]amino]-2-oxo -ethyl]carbamate;

methyl N-[(1S)-1-benzhydryl-2-[[2-[2-[(2R,5R)-5-[2-[2-[(2-methoxyacetyl)amino]phenyl]ethyl]morpholin-2-yl]ethyl]phenyl]amino]-2-oxo-ethyl]carbamate;

methyl N-[(1S)-1-benzhydryl-2-oxo-2-[[2-[2-[(2R,5R)-5-[2-[2-(3-phenylpropanoylamino)phenyl]ethyl]morpholin-2-yl]ethyl]phenyl]amino]ethyl]carbamate;

methyl N-[(1S)-1-[[2-[2-[(2R,5R)-5-[2-(2-aminophenyl)ethyl]morpholin-2-yl]ethyl]phenyl]carbamoyl]-2,2-diphenyl-ethyl]carbamate;

N-(2-{2-[(2R,5R)-5-(2-{2-[(benzylsulfonyl)amino]phenyl}ethyl)morpholin-2-yl]ethyl}phenyl)-Nα-(methoxycarbonyl)-β-phenyl-L-phenylalaninamide;

methyl N-[(1S)-1-benzhydryl-2-[[2-[2-[(2R,5R)-5-[2-(2-benzyloxycarbonylaminophenyl)ethyl]morpholin-2-yl]ethyl]phenyl]amino]-2-oxo -ethyl]carbamate;

methyl N-[(1S)-1-benzhydryl-2-[[2-[2-[(2R,5R)-5-[2-[2-(benzylcarbamoylamino)phenyl]ethyl]morpholin-2-yl]ethyl]phenyl]amino]-2-oxo-ethyl]carbamate;

methyl N-[(1S)-1-benzhydryl-2-[[2-[2-[(2R,5R)-5-[2-[2-(methoxycarbonylamino)phenyl]ethyl]morpholin-2-yl]ethyl]phenyl]amino]-2-oxo-ethyl]carbamate;

methyl N-[(1S)-1-benzhydryl-2-[[2-[2-[(2R,5R)-5-[2-[2-(ethylcarbamoylamino)phenyl]ethyl]morpholin-2-yl]ethyl]phenyl]amino]-2-oxo-ethyl]carbamate;

N-(2-{2-fluoro-2-[(2S,5S)-5-({[(4-fluorobenzyl)carbamoyl]oxy}methyl) morpholin-2-yl]ethyl}phenyl)-Nα-(methoxycarbonyl)-β-phenyl-L-phenylalaninamide;

4-Fluoro-β-(4-fluorophenyl)-N-(5-fluoro-4-{2-[(2R,5S)-5-({[(2,2,2-trifluoroethyl)carbamoyl]oxy}methyl)morpholin-2-yl]ethyl}pyridin-3-yl)-L-phenylalaninamide trihydrochloride;

4-Fluoro-β-(4-fluorophenyl)-N-(3-fluoro-2-{2-[(2R,5S)-5-({[(2,2,2-trifluoroethyl)carbamoyl]oxy}methyl)morpholin-2-yl]ethyl}phenyl)-L-phenylalaninamide dihydrochloride;

((3S,6R)-6-(2-(3-(3,3-bis(4-fluorophenyl)propanamido)-5-fluoropyridin-4-yl)ethyl)morpholin-3-yl)methyl ((6-chloropyridin-2-yl)methyl)carbamate;

((3S,6S)-6-((2-((S)-2-amino-3,3-bis(4-fluorophenyl)propanamido)-6-fluorophenoxy)methyl)morpholin-3-yl) methyl (2,2,2-trifluoroethyl)carbamate;

2S-Amino-3,3-di-(4-fluorophenyl)-N-(5-fluoro-4-(2-((2R,5R)-5-(2,2,2-trifluoroethoxycarbonylaminomethyl)morpholine-2-yl)ethyl)pyridin-3-yl)propanamide;

Nα-(methoxycarbonyl)-β-phenyl-N-(2-{2-[(2R,5R)-5-({[(tetrahydrofuran-3-yloxy)carbonyl]amino}methyl)morpholin-2-yl]ethyl}phenyl)-L-phenylalaninamide;

2,2,2-trifluoroethyl ({(3R,6R)-6-[2-(3-{[3,3-bis(4-fluorophenyl)propanoyl]amino}-5-fluoropyridin-4-yl)ethyl]morpholin-3-yl}methyl)carbamate;

(2S,3S)-2-Methoxycarbonylamino-3-(4-Fluorophenyl)-3-(3,5-difluorophenyl)-N-(5-fluoro-4-(2-((2R,5R)-5-(2,2,2-trifluoroethoxycarbonylaminomethyl)morpholine-2-yl)ethyl)pyridin-3-yl)propanamide;

2,2,2-trifluoroethyl ({(3R,6R)-6-[2-(2-{[3,3-bis(4-fluorophenyl)propanoyl]amino}-6-fluorophenyl)ethyl]morpholin-3-yl}methyl)carbamate;

4-fluoro-β-(4-fluorophenyl)-N-(3-fluoro-2-{2-[(2R,5R)-5-({[(2,2,2-trifluoroethoxy)carbonyl]amino}methyl)morpholin-2-yl]ethyl}phenyl)-L-phenylalaninamide;

(3S)-3-(4-Fluorophenyl)-3-(3,5-difluorophenyl)-N-(5-fluoro-4-((2R,5R)-5-(2,2,2-trifluoroethylaminocarbonyloxymethyl)morpholine-2-yl)ethyl)pyridin-3-yl)propanamide;

(2S,3S)-2-Amino-3-(4-fluorophenyl)-3-(3,5-difluorophenyl)-N-(5-fluoro-4-(2-((2R,5R)-5-(2,2,2-trifluoroethylaminocarbonyloxymethyl)morpholine-2-yl)ethyl)pyridin-3-yl)propanamide;

(2S,3S)-2-(Methoxycarbonylamino)-3-(4-fluorophenyl)-3-(3,5-difluorophenyl)-N-(5-fluoro-4-(2-((2R,5R)-5-(2,2,2-trifluoroethylaminocarbonyloxymethyl)morpholine-2-yl)ethyl)pyridin-3-yl)propanamide;

(2S,3R)-2-Amino-3-(3-fluorophenyl)-3-(4-fluorophenyl)-N-(5-fluoro-4-(2-((2R,5R)-5-(2,2,2-trifluoroethylaminocarbonyloxymethyl)morpholine-2-yl)ethyl)pyridin-3-yl)propanamide;

(2S,3S)-2-Amino-3-(3-chlorophenyl)-3-(4-fluorophenyl)-N-(5-fluoro-4-(2-((2R,5R)-5-(2,2,2-trifluoroethylaminocarbonyloxymethyl)morpholine-2-yl)ethyl)pyridin-3-yl)propanamide;

(βR)-4-Chloro-3-fluoro-β-(3-fluorophenyl)-N-(5-fluoro-4-{2-[(2R,5S)-5-({[(2,2,2-trifluoroethyl)carbamoyl]oxy}methyl)morpholin-2-yl]ethyl}pyridin-3-yl)-L-phenylalaninamide;

(βR)-β-(4-Chlorophenyl)-N-(5-fluoro-4-{2-[(2R,5S)-5-({[(2,2,2-trifluoroethyl)carbamoyl]oxy}methyl)morpholin-2-yl]ethyl}pyridin-3-yl)-L-phenylalaninamide;

(βR)-4-Fluoro-N-(5-fluoro-4-{2-[(2R,5S)-5-({[(2,2,2-trifluoroethyl)carbamoyl]oxy}methyl)morpholin-2-yl]ethyl}pyridin-3-yl)-β-naphthalen-2-yl-L-phenylalaninamide;

(βS)-β-(4-Chlorophenyl)-3,5-difluoro-N-(5-fluoro-4-{2-[(2R,5S)-5-({[(2,2,2-trifluoroethyl)carbamoyl]oxy}methyl)morpholin-2-yl]ethyl}pyridin-3-yl)-L-phenylalaninamide;

(βS)-β-(4-Chlorophenyl)-N-(5-fluoro-4-{2-[(2R,5S)-5-({[(2,2,2-trifluoroethyl)carbamoyl]oxy}methyl)morpholin-2-yl]ethyl}pyridin-3-yl)-3-(trifluoromethoxy)-L-phenylalaninamide;

(βR)-β-(3,4-Difluorophenyl)-3-fluoro-N-(3-fluoro-2-{2-[(2R,5S)-5-({[(2,2,2-trifluoroethyl)carbamoyl]oxy}methyl)morpholin-2-yl]ethyl}phenyl)-L-phenylalaninamide;

{(3S,6R)-6-[2-(2-{[(3R)-3-(1,3-Benzodioxol-5-yl)-3-(4-chlorophenyl)-L-alanyl]amino}-6-fluorophenyl)ethyl]morpholin-3-yl}methyl (2,2,2-trifluoroethyl)carbamate;

{(3S,6R)-6-[2-(2-{[(βS)-4-Chloro-β-(quinolin-4-yl)-L-phenylalanyl]amino}-6-fluorophenyl)ethyl]morpholin-3-yl}methyl (2,2,2-trifluoroethyl)carbamate;

(βR)-β-(4-Cyanophenyl)-3,4-difluoro-N-(3-fluoro-2-{2-[(2R,5S)-5-({[(2,2,2-trifluoroethyl)carbamoyl]oxy}methyl)morpholin-2-yl]ethyl}phenyl)-L-phenylalaninamide;

(βS)-4-Chloro-β-(3-fluorophenyl)-N-(5-fluoro-4-{2-[(2R,5S)-5-({[(2,2,2-trifluoroethyl)carbamoyl]oxy}methyl)morpholin-2-yl]ethyl}pyridin-3-yl)-Nα-(methoxycarbonyl)-L-phenylalaninamide;

(βS)-β-1,3-Benzodioxol-5-yl-4-chloro-N-(5-fluoro-4-{2-[(2R,5S)-5-({[(2,2,2-trifluoroethyl)carbamoyl]oxy}methyl)morpholin-2-yl]ethyl}pyridin-3-yl)-Nα-(methoxycarbonyl)-L-phenylalaninamide;

(βS)-β-(4-Chlorophenyl)-3,5-difluoro-N-(5-fluoro-4-{2-[(2R,5S)-5-({[(2,2,2-trifluoroethyl)carbamoyl]oxy}methyl)morpholin-2-yl]ethyl}pyridin-3-yl)-Nα-(methoxycarbonyl)-L-phenylalaninamide;

(βS)-β-(4-Chlorophenyl)-N-(5-fluoro-4-{2-[(2R,5S)-5-({[(2,2,2-trifluoroethyl)carbamoyl]oxy}methyl)morpholin-2-yl]ethyl}pyridin-3-yl)-Nα-(methoxycarbonyl)-3-(trifluoromethoxy)-L-phenylalaninamide;

(βR)-β-(4-Chlorophenyl)-N-(5-fluoro-4-{2-[(2R,5S)-5-({[(2,2,2-trifluoroethyl)carbamoyl]oxy}methyl)morpholin-2-yl]ethyl}pyridin-3-yl)-Nα-(methoxycarbonyl)-L-phenylalaninamide;

4-Chloro-β-(4-chlorophenyl)-N-(3-fluoro-2-{2-[(2R,5S)-5-({[(2,2,2-trifluoroethyl)carbamoyl]oxy}methyl)morpholin-2-yl]ethyl}phenyl)-Nα-(methoxycarbonyl)-L-phenylalaninamide;

(βR)-3-Chloro-N-(3-fluoro-2-{2-[(2R,5S)-5-({[(2,2,2-trifluoroethyl)carbamoyl]oxy}methyl)morpholin-2-yl]ethyl}phenyl)-Nα-(methoxycarbonyl)-O-methyl-β-phenyl-L-tyrosinamide;

(βS)-β-1,3-Benzodioxol-5-yl-4-chloro-N-(3-fluoro-2-{2-[(2R,5S)-5-({[(2,2,2-trifluoroethyl)carbamoyl]oxy}methyl)morpholin-2-yl]ethyl}phenyl)-Nα-(methoxycarbonyl)-L-phenylalaninamide;

(βS)-4-Fluoro-N-(3-fluoro-2-{2-[(2R,5S)-5-({[(2,2,2-trifluoroethyl)carbamoyl]oxy}methyl)morpholin-2-yl]ethyl}phenyl)-Nα-(methoxycarbonyl)-β-[2-(trifluoromethoxy)phenyl]-L-phenylalaninamide;

(βR)-4-Fluoro-N-(3-fluoro-2-{2-[(2R,5S)-5-({[(2,2,2-tri-fluoroethyl)carbamoyl]oxy}methyl)morpholin-2-yl]ethyl}phenyl)-Nα-(methoxycarbonyl)-β-pyridin-4-yl-L-phenylalaninamide;

[(3S,6R)-6-{2-[2-Fluoro-6-({(3R)-3-(3-fluorophenyl)-3-[4-(methylsulfonyl)phenyl]propanoyl}amino)phenyl]ethyl}morpholin-3-yl]methyl (2,2,2-trifluoroethyl)carbamate;

{(3S,6R)-6-[2-(3-{[(3S)-3-(4-Chlorophenyl)-3-(2,3-dihydro-1-benzofuran-5-yl)propanoyl]amino}-5-fluoropyridin-4-yl)ethyl]morpholin-3-yl}methyl (2,2,2-trifluoroethyl)carbamate;

{(3S,6R)-6-[2-(3-{[(3R)-3-(4-Cyanophenyl)-3-(3,4-difluorophenyl)propanoyl]amino}-5-fluoropyridin-4-yl)ethyl]morpholin-3-yl}methyl (2,2,2-trifluoroethyl)carbamate;

N-[2-(2-{(2R,5S)-5-[(Carbamoyloxy)methyl]morpholin-2-yl}ethyl)-3-fluorophenyl]-4-fluoro-β-(4-fluorophenyl)-L-phenylalaninamide;

(βS)—N-[2-({(2S,5S)-5-[(Carbamoyloxy)methyl]morpholin-2-yl}methoxy)-3-fluorophenyl]-4-fluoro-β-(3-fluorophenyl)-Nα-(methoxycarbonyl)-L-phenylalaninamide;

(βS)—N-[2-(2-{(2R,5S)-5-[(Carbamoyloxy)methyl]morpholin-2-yl}ethyl)-3-fluorophenyl]-4-fluoro-β-(3-fluorophenyl)-Nα-(methoxycarbonyl)-L-phenylalaninamide;

N-[4-(2-{(2R,5S)-5-[(Carbamoyloxy)methyl]morpholin-2-yl}ethyl)-5-fluoropyridin-3-yl]-4-fluoro-β-(4-fluorophenyl)-L-phenylalaninamide;

(βS)—N-[2-(2-{(2R,5S)-5-[(Carbamoyloxy)methyl]morpholin-2-yl}ethyl)-3-fluorophenyl]-4-fluoro-β-(3-fluorophenyl)-L-phenylalaninamide;

4-Fluoro-N-(3-fluoro-2-{2-[(2R,5S)-5-({[(2-hydroxy-2-methylpropyl)carbamoyl]oxy}methyl)morpholin-2-yl]ethyl}phenyl)-β-(4-fluorophenyl)-Nα-(methoxycarbonyl)-L-phenylalaninamide;

4-Fluoro-β-(4-fluorophenyl)-N-(3-fluoro-2-{2-[(2R,5S)-5-({[(3S)-tetrahydro-2H-pyran-3-ylcarbamoyl]oxy}methyl)morpholin-2-yl]ethyl}phenyl)-L-phenylalaninamide;

4-Fluoro-N-[5-fluoro-4-(2-{(2R,5S)-5-[({[(2-methyltetrahydrofuran-2-yl)methyl]carbamoyl}oxy)methyl]morpholin-2-yl}ethyl)pyridin-3-yl]-β-(4-fluorophenyl)-L-phenylalaninamide;

(βR)-4-Chloro-3-fluoro-β-(3-fluorophenyl)-N-(3-fluoro-2-{2-[(2R,5S)-5-({[(3R)-tetrahydro-2H-pyran-3-ylcarbamoyl]oxy}methyl)morpholin-2-yl]ethyl}phenyl)-Nα-(methoxycarbonyl)-L-phenylalaninamide;

(βS)-β-(3,5-Difluorophenyl)-4-fluoro-N-(5-fluoro-4-{2-[(2R,5S)-5-({[(3R)-tetrahydro-2H-pyran-3-ylcarbamoyl]oxy}methyl)morpholin-2-yl]ethyl}pyridin-3-yl)-Nα-(methoxycarbonyl)-D-phenylalaninamide;

4-Fluoro-N-[3-fluoro-2-(2-{(2R,5S)-5-[({[(5-methylisoxazol-3-yl)methyl]carbamoyl}oxy)methyl]morpholin-2-yl}ethyl)phenyl]-β-(4-fluorophenyl)-Nα-(methoxycarbonyl)-L-phenylalaninamide;

(βR)-4-Fluoro-N-(5-fluoro-4-{2-[(2R,5S)-5-({[(2,2,2-trifluoroethyl)carbamoyl]oxy}methyl)morpholin-2-yl]ethyl}pyridin-3-yl)-β-(tetrahydro-2H-pyran-4-yl)-L-phenylalaninamide;

(βR)-4-Fluoro-N-(3-fluoro-2-{2-[(2R,5S)-5-({[(2,2,2-trifluoroethyl)carbamoyl]oxy}methyl)morpholin-2-yl]ethyl}phenyl)-β-(tetrahydro-2H-pyran-4-yl)-L-phenylalaninamide;

(βR)-4-Chloro-3-fluoro-N-(3-fluoro-2-{2-[(2R,5S)-5-({[(2,2,2-trifluoroethyl)carbamoyl]oxy}methyl)morpholin-2-yl]ethyl}phenyl)-Nα-(methoxycarbonyl)-β-(tetrahydro-2H-pyran-4-yl)-L-phenylalaninamide;

(βR)-4-Fluoro-N-(3-fluoro-2-{2-[(2R,5S)-5-({[(2,2,2-trifluoroethyl)carbamoyl]oxy}methyl)morpholin-2-yl]ethyl}phenyl)-Nα-(methoxycarbonyl)-β-(tetrahydro-2H-pyran-4-yl)-L-phenylalaninamide;

(βR)-4-Chloro-3-fluoro-N-(3-fluoro-2-{2-[(2R,5S)-5-({[(2,2,2-trifluoroethyl)carbamoyl]oxy}methyl)morpholin-2-yl]ethyl}phenyl)-β-(tetrahydro-2H-pyran-4-yl)-L-phenylalaninamide;

(βS)-4-Chloro-3-fluoro-β-(5-fluoropyridin-3-yl)-N-(3-fluoro-2-{2-[(2R,5S)-5-({[(2,2,2-trifluoroethyl)carbamoyl]oxy}methyl)morpholin-2-yl]ethyl}phenyl)-Nα-(methoxycarbonyl)-L-phenylalaninamide;

[(3S,6R)-6-{2-[3-Fluoro-5-({(3S)-3-(4-fluorophenyl)-3-[6-(trifluoromethyl)pyridin-3-yl]propanoyl}amino)pyridin-4-yl]ethyl}morpholin-3-yl]methyl (2,2,2-trifluoroethyl)carbamate;

(βS)-4-Chloro-β-(3-fluoropyridin-4-yl)-N-(3-fluoro-2-{2-[(2R,5S)-5-({[(2,2,2-trifluoroethyl)carbamoyl]oxy}methyl)morpholin-2-yl]ethyl}phenyl)-Nα-(methoxycarbonyl)-L-phenylalaninamide;

(βS)-3,4-Difluoro-β-(5-fluoropyridin-3-yl)-N-(5-fluoro-4-{2-[(2R,5S)-5-({[(2,2,2-trifluoroethyl)carbamoyl]oxy}methyl)morpholin-2-yl]ethyl}pyridin-3-yl)-Nα-(methoxycarbonyl)-L-phenylalaninamide;

(βS)-4-Chloro-β-(3-fluoropyridin-4-yl)-N-(3-fluoro-2-{2-[(2R,5S)-5-({[(2,2,2-trifluoroethyl)carbamoyl]oxy}methyl)morpholin-2-yl]ethyl}phenyl)-L-phenylalaninamide;

(βS)-4-Chloro-β-(5-fluoropyridin-3-yl)-N-(3-fluoro-2-{2-[(2R,5S)-5-({[(2,2,2-trifluoroethyl)carbamoyl]oxy}methyl)morpholin-2-yl]ethyl}phenyl)-Nα-(methoxycarbonyl)-L -phenylalaninamide;

{(3S,6R)-6-[2-(2-Fluoro-6-{[(3S)-3-(4-fluorophenyl)-3-(3-fluoropyridin-4-yl)propanoyl]amino}phenyl)ethyl]morpholin-3-yl}methyl (2,2,2-trifluoroethyl)carbamate;

[(3S,6R)-6-{2-[2-Fluoro-6-({(3S)-3-(4-fluorophenyl)-3-[5-(trifluoromethyl)pyridin-3-yl]propanoyl}amino)phenyl]ethyl}morpholin-3-yl]methyl (2,2,2-trifluoroethyl)carbamate;

4-Fluoro-β-(4-fluorophenyl)-N-(5-fluoro-4-{2-[(2R,5S)-5-({[(2,2,2-trifluoroethyl)carbamoyl]oxy}methyl)morpholin-2-yl]ethyl}pyridin-3-yl)-Nα-[(2-methylpropoxy)carbonyl]-L-phenylalaninamide;

4-Fluoro-β-(4-fluorophenyl)-N-(5-fluoro-4-{2-[(2R,5S)-5-({[(2,2,2-trifluoroethyl)carbamoyl]oxy}methyl)morpholin-2-yl]ethyl}pyridin-3-yl)-Nα-[(2,2,2-trifluoroethoxy)carbonyl]-L-phenylalaninamide;

4-Fluoro-β-(4-fluorophenyl)-N-(3-fluoro-2-{2-[(2R,5S)-5-({[(2,2,2-trifluoroethyl)carbamoyl]oxy}methyl)morpholin-2-yl]ethyl}phenyl)-Nα-[(1-methylcyclopropyl)carbonyl]-L-phenylalaninamide;

N-({(3R,6R)-6-[2-(3-{[3,3-Bis(4-fluorophenyl)propanoyl]amino}-5-fluoropyridin-4-yl)ethyl]morpholin-3-yl}methyl)-3,3,3-trifluoropropanamide;

N-({(3R,6R)-6-[2-(2-{[3,3-Bis(4-fluorophenyl)propanoyl]amino}-6-fluorophenyl)ethyl]morpholin-3-yl}methyl)-3,3,3-trifluoropropanamide;

(βS)-β-(3,5-Difluorophenyl)-N-(3,6-difluoro-2-{2-[(2R,5S)-5-({[(2,2,2-trifluoroethyl)carbamoyl]oxy}methyl)morpholin-2-yl]ethyl}phenyl)-4-fluoro-Nα-(methoxycarbonyl)-L-phenylalaninamide;

[(3S,6R)-6-(2-{3-[(3,3-diphenylpropanoyl)amino]-5-fluoropyridin-4-yl}ethyl)morpholin-3-yl]methyl (2,2,2-trifluoroethyl)carbamate;

{(3S,6R)-6-[2-(2-{[(3S)-3-(3,5-difluorophenyl)-3-(4-fluorophenyl)propanoyl]amino}-6-fluorophenyl)ethyl]morpholin-3-yl}methyl (2,2,2-trifluoroethyl)carbamate;

{(3S,6R)-6-[2-(3-{[(3R)-3-cyclohexyl-3-(4-fluorophenyl)propanoyl]amino}-5-fluoropyridin-4-yl)ethyl]morpholin-3-yl}methyl (2,2,2-trifluoroethyl)carbamate;

{(3S,6R)-6-[2-(3-{[(3S)-3-(2,5-difluorophenyl)-3-(4-fluorophenyl)propanoyl]amino}-5-fluoropyridin-4-yl)ethyl]morpholin-3-yl}methyl (2,2,2-trifluoroethyl)carbamate;

{(3S,6R)-6-[2-(2-{[(3R)-3-(4-chlorophenyl)-3-phenylpropanoyl]amino}-6-fluorophenyl)ethyl]morpholin-3-yl}methyl (2,2,2-trifluoroethyl)carbamate;

{(3S,6R)-6-[2-(2-fluoro-6-{[(3S)-3-(4-fluorophenyl)-3-(4-methoxyphenyl)propanoyl]amino}phenyl)ethyl]morpholin-3-yl}methyl (2,2,2-trifluoroethyl)carbamate;

[(3S,6R)-6-(2-{2-[(3,3-diphenylpropanoyl)amino]-6-fluorophenyl}ethyl)morpholin-3-yl]methyl carbamate;

{(3S,6R)-6-[2-(2-{[(3S)-3-(2,3-difluorophenyl)-3-(4-fluorophenyl)propanoyl]amino}-6-fluorophenyl)ethyl]morpholin-3-yl}methyl (2,2,2-trifluoroethyl)carbamate;

{(3S,6R)-6-[2-(2-{[(3R)-3-(4-chlorophenyl)-3-(4-fluorophenyl)propanoyl]amino}-6-fluorophenyl)ethyl]morpholin-3-yl}methyl (2,2,2-trifluoroethyl)carbamate;

{(3S,6R)-6-[2-(2-{[(3R)-3-(4-bromophenyl)-3-(4-fluorophenyl)propanoyl]amino}-6-fluorophenyl)ethyl]morpholin-3-yl}methyl (2,2,2-trifluoroethyl)carbamate;

{(3S,6R)-6-[2-(2-{[(3S)-3-(2,4-difluorophenyl)-3-(4-fluorophenyl)propanoyl]amino}-6-fluorophenyl)ethyl]morpholin-3-yl}methyl carbamate;

{(3S,6R)-6-[2-(2-fluoro-6-{[(3S)-3-(4-fluorophenyl)-3-(3-fluoropyridin-4-yl)propanoyl]amino}phenyl)ethyl]morpholin-3-yl}methyl carbamate;

{(3S,6R)-6-[2-(3-fluoro-5-{[(3S)-3-(2-fluorophenyl)-3-(4-fluorophenyl)propanoyl]amino}pyridin-4-yl)ethyl]morpholin-3-yl}methyl (2,2,2-trifluoroethyl)carbamate;

[(3S,6R)-6-{2-[2-fluoro-6-({(3R)-3-(4-fluorophenyl)-3-[4-(trifluoromethoxy)phenyl]propanoyl}amino)phenyl]ethyl}morpholin-3-yl]methyl (2,2,2-trifluoroethyl)carbamate;

{(3S,6R)-6-[2-(2-{[(3S)-3-(3-cyanophenyl)-3-(4-fluorophenyl)propanoyl]amino}-6-fluorophenyl)ethyl]morpholin-3-yl}methyl (2,2,2-trifluoroethyl)carbamate;

{(3S,6R)-6-[2-(2-fluoro-6-{[(3R)-3-(4-fluorophenyl)-3-(5-fluoropyridin-3-yl)propanoyl]amino}phenyl)ethyl]morpholin-3-yl}methyl (2,2,2-trifluoroethyl)carbamate;

{(3S,6R)-6-[2-(2-fluoro-6-{[(3R)-3-phenyl-3-pyridin-4-ylpropanoyl]amino}phenyl)ethyl]morpholin-3-yl}methyl (2,2,2-trifluoroethyl)carbamate;

{(3S,6R)-6-[2-(2-{[(3S)-4-cyclopropyl-3-phenylbutanoyl]amino}-6-fluorophenyl)ethyl]morpholin-3-yl}methyl (2,2,2-trifluoroethyl)carbamate;

[(3S,6R)-6-{2-[2-({(3S)-3-(4-chlorophenyl)-3-[3-(methylsulfonyl)phenyl]propanoyl}amino)-6-fluorophenyl]ethyl}morpholin-3-yl]methyl (2,2,2-trifluoroethyl)carbamate;

{(3S,6R)-6-[2-(3-{[3,3-bis(4-fluorophenyl)propanoyl]amino}-5-fluoropyridin-4-yl)ethyl]morpholin-3-yl}methyl [1-(hydroxymethyl)propyl]carbamate;

{(3S,6R)-6-[2-(3-{[3,3-bis(4-fluorophenyl)propanoyl]amino}-5-fluoropyridin-4-yl)ethyl]morpholin-3-yl}methyl [(2-methyltetrahydrofuran-2-yl)methyl]carbamate;

{(3S,6R)-6-[2-(3-{[3,3-bis(4-fluorophenyl)propanoyl]amino}-5-fluoropyridin-4-yl)ethyl]morpholin-3-yl}methyl [2,2,2-trifluoro-1-(hydroxymethyl)ethyl]carbamate;

{(3S,6R)-6-[2-(3-{[3,3-bis(4-fluorophenyl)propanoyl]amino}-5-fluoropyridin-4-yl)ethyl]morpholin-3-yl}methyl [2-(phenylamino)ethyl]carbamate;

{(3S,6R)-6-[2-(3-{[3,3-bis(4-fluorophenyl)propanoyl]amino}-5-fluoropyridin-4-yl)ethyl]morpholin-3-yl}methyl (tetrahydrofuran-2-ylmethyl)carbamate;

{(3S,6R)-6-[2-(3-{[3,3-bis(4-fluorophenyl)propanoyl]amino}-5-fluoropyridin-4-yl)ethyl]morpholin-3-yl}methyl (2-phenoxyethyl)carbamate;

{(3S,6R)-6-[2-(3-{[3,3-bis(4-fluorophenyl)propanoyl]amino}-5-fluoropyridin-4-yl)ethyl]morpholin-3-yl}methyl [1-(tetrahydrofuran-2-yl)ethyl]carbamate;

{(3S,6R)-6-[2-(3-{[3,3-bis(4-fluorophenyl)propanoyl]amino}-5-fluoropyridin-4-yl)ethyl]morpholin-3-yl}methyl [2-(3,5-dimethyl-1H-pyrazol-1-yl)ethyl]carbamate;

{(3S,6R)-6-[2-(3-{[3,3-bis(4-fluorophenyl)propanoyl]amino}-5-fluoropyridin-4-yl)ethyl]morpholin-3-yl}methyl tetrahydrofuran-3-ylcarbamate;

{(3S,6R)-6-[2-(3-{[3,3-bis(4-fluorophenyl)propanoyl]amino}-5-fluoropyridin-4-yl)ethyl]morpholin-3-yl}methyl [(5-ethyl-1,2,4-oxadiazol-3-yl)methyl]carbamate;

{(3S,6R)-6-[2-(3-{[3,3-bis(4-fluorophenyl)propanoyl]amino}-5-fluoropyridin-4-yl)ethyl]morpholin-3-yl}methyl (1-cyclopropyl-2-hydroxyethyl)carbamate;

{(3S,6R)-6-[2-(3-{[3,3-bis(4-fluorophenyl)propanoyl]amino}-5-fluoropyridin-4-yl)ethyl]morpholin-3-yl}methyl (4-fluorobenzyl)carbamate;

{(3S,6R)-6-[2-(3-{[3,3-bis(4-fluorophenyl)propanoyl]amino}-5-fluoropyridin-4-yl)ethyl]morpholin-3-yl}methyl methylcarbamate;

{(3S,6R)-6-[2-(2-{[(3S)-3-(2-cyanopyridin-3-yl)-3-(4-fluorophenyl)propanoyl]amino}-6-fluorophenyl)ethyl]morpholin-3-yl}methyl (2,2,2-trifluoroethyl)carbamate;

{(3S,6R)-6-[2-(3-{[(3R)-3-(3-chloro-4-methoxyphenyl)-β-phenylpropanoyl]amino}-5-fluoropyridin-4-yl)ethyl]morpholin-3-yl}methyl (2,2,2-trifluoroethyl)carbamate;

[(3S,6R)-6-{2-[3-fluoro-5-({(3S)-3-(4-fluorophenyl)-3-[2-(trifluoromethyl)phenyl]propanoyl}amino)pyridin-4-yl]ethyl}morpholin-3-yl]methyl (2,2,2-trifluoroethyl)carbamate;

[(3S,6R)-6-{2-[3-fluoro-5-({(3R)-3-(4-fluorophenyl)-3-[4-(2-methoxyethoxy)phenyl]propanoyl}amino)pyridin-4-yl]ethyl}morpholin-3-yl]methyl (2,2,2-trifluoroethyl)carbamate;

{(3S,6R)-6-[2-(3-{[(3R)-3-(4-chloro-3-fluorophenyl)-3-(4-fluorophenyl)propanoyl]amino}-5-fluoropyridin-4-yl)ethyl]morpholin-3-yl}methyl (2,2,2-trifluoroethyl)carbamate;

{(3S,6R)-6-[2-(2-fluoro-6-{[(3S)-3-(4-fluorophenyl)-3-thiophen-3-ylpropanoyl]amino}phenyl)ethyl]morpholin-3-yl}methyl (2,2,2-trifluoroethyl)carbamate;

[(3S,6R)-6-{2-[3-fluoro-5-({(3S)-3-(4-fluorophenyl)-3-[5-(trifluoromethyl)pyridin-3-yl]propanoyl}amino)pyridin-4-yl]ethyl}morpholin-3-yl]methyl (2,2,2-trifluoroethyl)carbamate;

{(3S,6R)-6-[2-(3-{[3,3-bis(4-fluorophenyl)propanoyl] amino}-5-fluoropyridin-4-yl)ethyl]morpholin-3-yl}methyl [(2R)-2-hydroxy-2,3-dihydro-1H-inden-1-yl]carbamate;

{(3S,6R)-6-[2-(3-{[3,3-bis(4-fluorophenyl)propanoyl] amino}-5-fluoropyridin-4-yl)ethyl]morpholin-3-yl}methyl [2-methyl-1-(1-methylethyl)propyl]carbamate;

{(3S,6R)-6-[2-(3-{[3,3-bis(4-fluorophenyl)propanoyl] amino}-5-fluoropyridin-4-yl)ethyl]morpholin-3-yl}methyl [(2S)-2-carbamoylcyclohexyl]carbamate;

{(3S,6R)-6-[2-(3-{[3,3-bis(4-fluorophenyl)propanoyl] amino}-5-fluoropyridin-4-yl)ethyl]morpholin-3-yl}methyl (isoxazol-5-ylmethyl)carbamate;

2-cyclopropyl-N-(5-fluoro-4-{2-[(2R,5S)-5-({[(2,2,2-trifluoroethyl)carbamoyl]oxy}methyl)morpholin-2-yl] ethyl}pyridin-3-yl)-L-phenylalaninamide;

{(3S,6R)-6-[2-(3-{[(2S)-2-amino-3-naphthalen-1-ylpropanoyl]amino}-5-fluoropyridin-4-yl)ethyl]morpholin-3-yl}methyl (2,2,2-trifluoroethyl)carbamate;

{(3S,6R)-6-[2-(3-{[(2S)-2-amino-3-naphthalen-1-ylpropanoyl]amino}-5-fluoropyridin-4-yl)ethyl]morpholin-3-yl}methyl (4-fluorobenzyl)carbamate;

N-(2-{[(2R,5S)-5-({[(2,2-difluoroethyl)carbamoyl] oxy}methyl)morphpholin-2-yl]ethyl}-4-fluorophenyl)-β-phenyl-L-phenylalaninamide;

4-fluoro-β-(4-fluorophenyl)-N-(3-fluoro-2-{(1S)-1-[(2S, 5S)-5-({[(2,2,2-trifluoroethyl)carbamoyl]oxy}methyl) morpholin-2-yl]ethoxy}phenyl)-L-phenylalaninamide;

4-fluoro-β-(4-fluorophenyl)-N-(5-fluoro-4-{2-[(2R,5S)-5-({[(1-pyridin-4-ylcyclobutyl)carbamoyl] oxy}methyl)morpholin-2-yl]ethyl}pyridin-3-yl)-L-phenylalaninamide;

4-fluoro-N-(3-fluoro-2-{(1S)-1-[(2S,5S)-5-({[(4-fluorobenzyl)carbamoyl]oxy}methyl)morpholin-2-yl] ethoxy}phenyl)-3-(4-fluorophenyl)-L-phenylalaninamide;

N-(4-fluoro-2-{2-[(2R,5S)-5-({[(2,2,2-trifluoroethyl)carbamoyl]oxy}methyl)morpholin-2-yl]ethyl}phenyl)-β-phenyl-L-phenylalaninamide;

{(3S,6R)-6-[2-(3-fluoro-5-{[4-fluoro-β-(4-fluorophenyl)-L-phenylalanyl]amino}pyridin-4-yl)ethyl]morpholin-3-yl}methyl morpholine-4-carboxylate;

4-fluoro-β-(4-fluorophenyl)-N-(3-fluoro-2-{2-[(2R,5S)-5-({[(pyridin-4-ylmethyl)carbamoyl]oxy}methyl)morpholin-2-yl]ethyl}phenyl)-L-phenylalaninamide;

(βS)—N-(3-fluoro-2-{2-[(2R,5S)-5-({[(4-fluorobenzyl) carbamoyl]oxy}methyl)morpholin-2-yl]ethyl}phenyl)-β-propyl-L-phenylalaninamide;

4-fluoro-β-(4-fluorophenyl)-N-(2-fluoro-6-{[(2S,5S)-5-({[(2,2,2-trifluoroethyl)carbamoyl]oxy}methyl)morpholin-2-yl]methoxy}phenyl)-L-phenylalaninamide;

4-fluoro-β-(4-fluorophenyl)-N-(3-fluoro-2-{2-[(2R,5S)-5-({[(pyridin-3-ylmethyl)carbamoyl]oxy}methyl)morpholin-2-yl]ethyl}phenyl)-L-phenylalaninamide;

4-fluoro-β-(4-fluorophenyl)-N-(5-fluoro-4-{2-[(2R,5S)-5-({[(2,2,2-trifluoroethyl)carbamoyl]oxy}methyl)morpholin-2-yl]ethyl}pyridin-3-yl)-Nα-methyl-L-phenylalaninamide;

4-fluoro-β-(4-fluorophenyl)-N-(5-fluoro-4-{[(2S,5S)-5-({[(2,2,2-trifluoroethyl)carbamoyl]oxy}methyl)morpholin-2-yl]methoxy}pyridin-3-yl)-L-phenylalaninamide;

2-chloro-N-(3-fluoro-2-{2-[(2R,5S)-5-({[(4-fluorobenzyl)carbamoyl]oxy}methyl)morpholin-2-yl] ethyl}phenyl)-L-phenylalaninamide;

4-fluoro-N-(5-fluoro-4-{2-[(2R,5S)-5-{[(methylcarbamoyl)oxy]methyl}morpholin-2-yl]ethyl}pyridin-3-yl)-β-(4-fluorophenyl)-L-phenylalaninamide;

N-[4-({(2S,5S)-5-[(carbamoyloxy)methyl]morpholin-2-yl}methoxy)-5-fluoropyridin-3-yl]-4-fluoro-β-(4-fluorophenyl)-L-phenylalaninamide;

N-(4-{2-[(2R,5S)-5-{[(ethylcarbamoyl)oxy] methyl}morpholin-2-yl]ethyl}-5-fluoropyridin-3-yl)-4-fluoro-β-(4-fluorophenyl)-L-phenylalaninamide;

4-fluoro-β-(4-fluorophenyl)-N-(5-fluoro-4-{2-[(2R,5S)-5-({[(tetrahydro-2H-pyran-4-ylmethyl)carbamoyl] oxy}methyl)morpholin-2-yl]ethyl}pyridin-3-yl)-L-phenylalaninamide;

N-[4-(2-{(2R,5S)-5-[({[(1,1-dioxidotetrahydrothiophen-3-yl)methyl]carbamoyl}oxy)methyl]morpholin-2-yl}ethyl)-5-fluoropyridin-3-yl]-4-fluoro-β-(4-fluorophenyl)-L-phenylalaninamide;

4-fluoro-N-[3-fluoro-2-({(2S,5S)-5-[({[(1S)-1-(4-fluorophenyl)ethyl]carbamoyl}oxy)methyl]morpholin-2-yl}methoxy)phenyl]-3-(4-fluorophenyl) -L-phenylalaninamide;

4-fluoro-N-[5-fluoro-4-(2-{(2R,5S)-5-[({[(3R,4R)-4-fluorotetrahydrofuran-3-yl]carbamoyl}oxy)methyl] morpholin-2-yl}ethyl)pyridin-3-yl]-β-(4-fluorophenyl)-L-phenylalaninamide;

4-fluoro-N-[3-fluoro-2-(2-{(2R,5S)-5-[({[(1S)-1-(4-fluorophenyl)ethyl]carbamoyl}oxy)methyl]morpholin-2-yl}ethyl)phenyl]-β-(4-fluorophenyl)-L-phenylalaninamide;

4-fluoro-β-(4-fluorophenyl)-N-(5-fluoro-4-{2-[(2R,5S)-5-({[(tetrahydro-2H-pyran-2-ylmethyl)carbamoyl] oxy}methyl)morpholin-2-yl]ethyl}pyridin-3-yl)-L-phenylalaninamide;

4-fluoro-β-(4-fluorophenyl)-N-(5-fluoro-4-{2-[(2R,5S)-5-({[(1-pyridin-2-ylcyclopropyl)carbamoyl] oxy}methyl)morpholin-2-yl]ethyl}pyridin-3-yl)-L-phenylalaninamide;

4-fluoro-β-(4-fluorophenyl)-N-[5-fluoro-4-(2-{(2R,5S)-5-[({[(2R)-tetrahydrofuran-2-ylmethyl] carbamoyl}oxy)methyl]morpholin-2-yl}ethyl)pyridin-3-yl]-L-phenylalaninamide;

4-fluoro-β-(4-fluorophenyl)-N-[5-fluoro-4-(2-{(2R,5S)-5-[({[(1R)-1-(trifluoromethyl)propyl]carbamoyl}oxy) methyl]morpholin-2-yl}ethyl)pyridin-3-yl]-L-phenylalaninamide;

N-(4-{2-[(2R,5S)-5-({[(3,3-difluorocyclobutyl)carbamoyl]oxy}methyl)morpholin-2-yl]ethyl}-5-fluoropyridin-3-yl)-4-fluoro-β-(4-fluorophenyl)-L-phenylalaninamide;

4-fluoro-N-(5-fluoro-4-{2-[(2R,5S)-5-({[(2-hydroxy-1,1-dimethylethyl)carbamoyl]oxy}methyl)morpholin-2-yl] ethyl}pyridin-3-yl)-β-(4-fluorophenyl)-L-phenylalaninamide;

(βR)-β-(4-fluorophenyl)-N-(3-fluoro-2-{2-[(2R,5S)-5-({[(2,2,2-trifluoroethyl)carbamoyl]oxy}methyl)morpholin-2-yl]ethyl}phenyl)-O-(trifluoromethyl)-L-tyrosinamide;

4-fluoro-N-(3-fluoro-2-{2-[(2R,5S)-5-{[({(1R)-1-[4-fluoro-2-(trifluoromethyl)phenyl]ethyl}carbamoyl) oxy]methyl}morpholin-2-yl]ethyl}phenyl)-3-(4-fluorophenyl)-L-phenylalaninamide;

(βR)-β-(4-chloro-3-fluorophenyl)-4-fluoro-N-(5-fluoro-4-{2-[(2R,5S)-5-({[(2,2,2-trifluoroethyl)carbamoyl] oxy}methyl)morpholin-2-yl]ethyl}pyridin-3-yl)-L-phenylalaninamide;

4-fluoro-N-(3-fluoro-2-{2-[(2R,5S)-5-({[(2-phenoxyethyl)carbamoyl]oxy}methyl)morpholin-2-yl]ethyl}phenyl)-β-(4-fluorophenyl)-L-phenylalaninamide;

4-fluoro-β-(4-fluorophenyl)-N-(3-fluoro-2-{2-[(2R,5S)-5-{[(tetrahydro-2H-pyran-4-ylcarbamoyl)oxy]methyl}morpholin-2-yl]ethyl}phenyl)-L-phenylalaninamide;

(βS)-β-(4-fluorophenyl)-N-(5-fluoro-4-{2-[(2R,5S)-5-({[(2,2,2-trifluoroethyl)carbamoyl]oxy}methyl)morpholin-2-yl]ethyl}pyridin-3-yl)-4-pyridin-3-yl-L-phenylalaninamide;

(βS)—N-(5-fluoro-4-{2-[(2R,5R)-5-(hydroxymethyl)morpholin-2-yl]ethyl}pyridin-3-yl)-β-quinolin-4-yl-D-phenylalaninamide;

4-fluoro-β-(4-fluorophenyl)-N-(3-methyl-2-{2-[(2R,5S)-5-({[(2,2,2-trifluoroethyl)carbamoyl]oxy}methyl)morpholin-2-yl]ethyl}phenyl)-L-phenylalaninamide;

(βR)—N-(3-fluoro-2-{2-[(2R,5S)-5-({[(2,2,2-trifluoroethyl)carbamoyl]oxy}methyl)morpholin-2-yl]ethyl}phenyl)-O,β-diphenyl-L-tyrosinamide;

(βR)—N-(3-fluoro-2-{2-[(2R,5S)-5-({[(2,2,2-trifluoroethyl)carbamoyl]oxy}methyl)morpholin-2-yl]ethyl}phenyl)-β-propyl-L-phenylalaninamide;

4-fluoro-N-(5-fluoro-4-{2-[(2R,5S)-5-({[(1-methylpyrrolidin-3-yl)carbamoyl]oxy}methyl)morpholin-2-yl]ethyl}pyridin-3-yl)-β-(4-fluorophenyl)-L-phenylalaninamide;

(βS)-β-(4-fluorophenyl)-N-(3-fluoro-2-{2-[(2R,5S)-5-({[(2,2,2-trifluoroethyl)carbamoyl]oxy}methyl)morpholin-2-yl]ethyl}phenyl)-O-phenyl-L-tyrosinamide;

(βS)-β-(4-fluorophenyl)-N-(3-fluoro-2-{2-[(2R,5S)-5-({[(2,2,2-trifluoroethyl)carbamoyl]oxy}methyl)morpholin-2-yl]ethyl}phenyl)-O-(trifluoromethyl)-L-tyrosinamide;

N-[3-fluoro-2-({(2S,5R)-5-[2-(methylsulfonyl)ethyl]morpholin-2-yl}methoxy)phenyl]-β-phenyl-L-phenylalaninamide;

4-fluoro-β-(4-fluorophenyl)-N-(5-fluoro-4-{2-[(2R,5S)-5-({[(2-pyrrolidin-1-ylethyl)carbamoyl]oxy}methyl)morpholin-2-yl]ethyl}pyridin-3-yl)-L-phenylalaninamide;

β-phenyl-N-[2-{2-[(2R,5S)-5-({[(2,2,2-trifluoroethyl)carbamoyl]oxy}methyl)morpholin-2-yl]ethyl}-3-(trifluoromethyl)phenyl]-L-phenylalaninamide;

4-fluoro-N-(5-fluoro-4-{2-[(2R,5S)-5-{[({[(2S)-5-oxopyrrolidin-2-yl]methyl}carbamoyl)oxy]methyl}morpholin-2-yl]ethyl}pyridin-3-yl)-β-(4-fluorophenyl)-L-phenylalaninamide;

(βR)—N-(3-fluoro-2-{2-[(2R,5S)-5-({[(2,2,2-trifluoroethyl)carbamoyl]oxy}methyl)morpholin-2-yl]ethyl}phenyl)-β-phenyl-O-(trifluoromethyl)-L-tyrosinamide;

N-(2-{2-[(2R,5S)-5-({[(2,2-difluoroethyl)carbamoyl]oxy}methyl)morphpholin-2-yl]ethyl}-5-fluorophenyl)-β-phenyl-L-phenylalaninamide;

(βR)—N-(5-fluoro-4-{2-[(2R,5S)-5-({[(2,2,2-trifluoroethyl)carbamoyl]oxy}methyl)morpholin-2-yl]ethyl}pyridin-3-yl)-β-phenyl-O-(trifluoromethyl)-L-tyrosinamide;

{(3S,6R)-6-[2-(3-fluoro-5-{[4-fluoro-β-(4-fluorophenyl)-L-phenylalanyl]amino}pyridin-4-yl)ethyl]morpholin-3-yl}methyl (isoquinolin-3-ylmethyl)carbamate;

4-fluoro-N-[5-fluoro-4-(2-{(2R,5S)-5-[({[(2-oxo-1,3-oxazolidin-5-yl)methyl]carbamoyl}oxy)methyl]morpholin-2-yl}ethyl)pyridin-3-yl]-β-(4-fluorophenyl)-L-phenylalaninamide;

(βR)—N-(3-fluoro-2-{2-[(2R,5S)-5-({[(2,2,2-trifluoroethyl)carbamoyl]oxy}methyl)morpholin-2-yl]ethyl}phenyl)-β-naphthalen-2-yl-L-phenylalaninamide;

4-fluoro-N-(5-fluoro-4-{2-[(2R,5S)-5-({[(3H-imidazo[4,5-c]pyridin-2-ylmethyl)carbamoyl]oxy}methyl)morpholin-2-yl]ethyl}pyridin-3-yl)-β-(4-fluorophenyl)-L-phenylalaninamide;

{(3S,6R)-6-[2-(3-fluoro-5-{[4-fluoro-β-(4-fluorophenyl)-L-phenylalanyl]amino}pyridin-4-yl)ethyl]morpholin-3-yl}methyl (quinolin-2-ylmethyl)carbamate;

(βR)-3-chloro-N-(3-fluoro-2-{2-[(2R,5S)-5-({[(2,2,2-trifluoroethyl)carbamoyl]oxy}methyl)morpholin-2-yl]ethyl}phenyl)-β-phenyl-L-phenylalaninamide;

N-(3,5-difluoro-2-{[(2S,5S)-5-({[(2,2,2-trifluoroethyl)carbamoyl]oxy}methyl)morpholin-2-yl]methoxy}phenyl)-4-fluoro-β-(4-fluorophenyl)-L-phenylalaninamide;

(βS)-β-(4-fluorophenyl)-N-(5-fluoro-4-{2-[(2R,5S)-5-({[(2,2,2-trifluoroethyl)carbamoyl]oxy}methyl)morpholin-2-yl]ethyl}pyridin-3-yl)-O-(trifluoromethyl)-L-tyrosinamide;

N-(3,5-difluoro-2-{2-[(2R,5S)-5-({[(2,2,2-trifluoroethyl)carbamoyl]oxy}methyl)morpholin-2-yl]ethyl}phenyl)-4-fluoro-β-(4-fluorophenyl)-L-phenylalaninamide;

N-(4-{2-[(2R,5S)-5-({[(2-ethoxyethyl)carbamoyl]oxy}methyl)morpholin-2-yl]ethyl}-5-fluoropyridin-3-yl)-4-fluoro-β-(4-fluorophenyl)-L-phenylalaninamide;

(βS)—N-(5-fluoro-4-{2-[(2R,5R)-5-(hydroxymethyl)morpholin-2-yl]ethyl}pyridin-3-yl)-β-quinolin-4-yl-L-phenylalaninamide;

(βR)-β-(4-fluorophenyl)-N-(5-fluoro-4-{2-[(2R,5S)-5-({[(2,2,2-trifluoroethyl)carbamoyl]oxy}methyl)morpholin-2-yl]ethyl}pyridin-3-yl)-O-methyl-L-tyrosinamide;

(βS)-3,5-difluoro-β-(4-fluorophenyl)-N-(3-fluoro-2-{2-[(2R,5S)-5-({[(2,2,2-trifluoroethyl)carbamoyl]oxy}methyl)morpholin-2-yl]ethyl}phenyl)-L-phenylalaninamide;

4-fluoro-N-(5-fluoro-4-{2-[(2R,5S)-5-({[(1-methyl-2-oxopyrrolidin-3-yl)carbamoyl]oxy}methyl)morpholin-2-yl]ethyl}pyridin-3-yl)-β-(4-fluorophenyl)-L-phenylalaninamide;

4-fluoro-β-(4-fluorophenyl)-N-(5-fluoro-4-{2-[(2R,5S)-5-{[(tetrahydro-2H-pyran-3-ylcarbamoyl)oxy]methyl}morpholin-2-yl]ethyl}pyridin-3-yl)-L-phenylalaninamide;

4-fluoro-N-(5-fluoro-4-{2-[(2R,5S)-5-{[({[(2R)-5-oxopyrrolidin-2-yl]methyl}carbamoyl)oxy]methyl}morpholin-2-yl]ethyl}pyridin-3-yl)-β-(4-fluorophenyl)-L-phenylalaninamide;

4-fluoro-N-(5-fluoro-4-{2-[(2R,5S)-5-({[(isoxazol-5-ylmethyl)carbamoyl]oxy}methyl)morpholin-2-yl]ethyl}pyridin-3-yl)-β-(4-fluorophenyl)-L-phenylalaninamide;

(βR)—N-(5-fluoro-4-{2-[(2R,5S)-5-({[(2,2,2-trifluoroethyl)carbamoyl]oxy}methyl)morpholin-2-yl]ethyl}pyridin-3-yl)-O-methyl-β-phenyl-L-tyrosinamide;

(βR)-β-(3-chlorophenyl)-4-fluoro-N-(3-fluoro-2-{2-[(2R,5S)-5-({[(2,2,2-trifluoroethyl)carbamoyl]oxy}methyl)morpholin-2-yl]ethyl}phenyl)-L-phenylalaninamide;

N-[2-({(2S,5S)-5-[(carbamoyloxy)methyl]morpholin-2-yl}methoxy)-3,5-difluorophenyl]-4-fluoro-β-(4-fluorophenyl)-L-phenylalaninamide;

(βR)-β-(3,4-difluorophenyl)-N-(5-fluoro-4-{2-[(2R,5S)-5-({[(2,2,2-trifluoroethyl)carbamoyl]oxy}methyl)morpholin-2-yl]ethyl}pyridin-3-yl)-L-phenylalaninamide;

N-(2-chloro-6-{[(2S,5S)-5-({[(2,2,2-trifluoroethyl)carbamoyl]oxy}methyl)morpholin-2-yl]methoxy}phenyl)-4-fluoro-β-(4-fluorophenyl)-L-phenylalaninamide;

N-(2-chloro-6-{[(2S,5S)-5-({[(2,2,2-trifluoroethyl)carbamoyl]oxy}methyl)morpholin-2-yl]methoxy}phenyl)-4-fluoro-β-(4-fluorophenyl)-L-phenylalaninamide;

3-fluoro-β-(3-fluorophenyl)-N-(3-fluoro-2-{2-[(2R,5S)-5-({[(2,2,2-trifluoroethyl)carbamoyl]oxy}methyl)morpholin-2-yl]ethyl}phenyl)-L-phenylalaninamide;

(βS)-4-fluoro-N-(3-fluoro-2-{2-[(2R,5S)-5-({[(2,2,2-trifluoroethyl)carbamoyl]oxy}methyl)morpholin-2-yl]ethyl}phenyl)-β-[3-(trifluoromethoxy)phenyl]-L-phenylalaninamide;

(βS)-β-(4-fluorophenyl)-N-(5-fluoro-4-{2-[(2R,5S)-5-({[(2,2,2-trifluoroethyl)carbamoyl]oxy}methyl)morpholin-2-yl]ethyl}pyridin-3-yl)-4-(trifluoromethyl)-L-phenylalaninamide;

(βS)-3,4-difluoro-β-(4-fluorophenyl)-N-(5-fluoro-4-{2-[(2R,5S)-5-({[(2,2,2-trifluoroethyl)carbamoyl]oxy}methyl)morpholin-2-yl]ethyl}pyridin-3-yl)-L-phenylalaninamide;

(βR)-3-chloro-β-(4-fluorophenyl)-N-(5-fluoro-4-{2-[(2R,5S)-5-({[(2,2,2-trifluoroethyl)carbamoyl]oxy}methyl)morpholin-2-yl]ethyl}pyridin-3-yl)-L-phenylalaninamide;

(βR)-β-(4-chlorophenyl)-4-fluoro-N-(5-fluoro-4-{2-[(2R,5S)-5-({[(2,2,2-trifluoroethyl)carbamoyl]oxy}methyl)morpholin-2-yl]ethyl}pyridin-3-yl)-L-phenylalaninamide;

(βS)-2,5-difluoro-β-(4-fluorophenyl)-N-(5-fluoro-4-{2-[(2R,5S)-5-({[(2,2,2-trifluoroethyl)carbamoyl]oxy}methyl)morpholin-2-yl]ethyl}pyridin-3-yl)-L-phenylalaninamide;

(βR)-β-(3,4-difluorophenyl)-N-(3-fluoro-2-{2-[(2R,5S)-5-({[(2,2,2-trifluoroethyl)carbamoyl]oxy}methyl)morpholin-2-yl]ethyl}phenyl)-L-phenylalaninamide;

(βR)-β-(3,4-difluorophenyl)-4-fluoro-N-(3-fluoro-2-{2-[(2R,5S)-5-({[(2,2,2-trifluoroethyl)carbamoyl]oxy}methyl)morpholin-2-yl]ethyl}phenyl)-L-phenylalaninamide;

4-fluoro-N-[5-fluoro-4-(2-{(2R,5S)-5-[(2-hydroxyphenyl)carbamoyl]morpholin-2-yl}ethyl)pyridine-3-yl]-β-(4-fluorophenyl)-L-phenylalaninamide;

(βS)-4-fluoro-N-(5-fluoro-4-{2-[(2R,5S)-5-({[(2,2,2-trifluoroethyl)carbamoyl]oxy}methyl)morpholin-2-yl]ethyl}pyridin-3-yl)-β-[3-(trifluoromethyl)phenyl]-L-phenylalaninamide;

(βR)-β-(4-chlorophenyl)-4-fluoro-N-(3-fluoro-2-{2-[(2R,5S)-5-({[(2,2,2-trifluoroethyl)carbamoyl]oxy}methyl)morpholin-2-yl]ethyl}phenyl)-L-phenylalaninamide;

(βS)-β-(4-chlorophenyl)-3-fluoro-N-(3-fluoro-2-{2-[(2R,5S)-5-({[(2,2,2-trifluoroethyl)carbamoyl]oxy}methyl)morpholin-2-yl]ethyl}phenyl)-L-phenylalaninamide;

(βR)-4-bromo-β-(4-fluorophenyl)-N-(5-fluoro-4-{2-[(2R,5S)-5-({[(2,2,2-trifluoroethyl)carbamoyl]oxy}methyl)morpholin-2-yl]ethyl}pyridin-3-yl)-L-phenylalaninamide;

4-fluoro-β-(4-fluorophenyl)-N-[5-fluoro-4-(2-{(2R,5S)-5-[({[3,3,3-trifluoro-1-(4-fluorophenyl)propyl]carbamoyl}oxy)methyl]morpholin-2-yl}ethyl)pyridin-3-yl]-L-phenylalaninamide;

4-fluoro-β-(4-fluorophenyl)-N-(5-fluoro-4-{2-[(2R,5S)-5-({[(2,2,2-trifluoroethyl)carbamoyl]oxy}methyl)morpholin-2-yl]ethyl}pyridin-3-yl)-Nα-[(1-methylethoxy)carbonyl]-L-phenylalaninamide;

Nα-[(cyclopentyloxy)carbonyl]-4-fluoro-β-(4-fluorophenyl)-N-(5-fluoro-4-{2-[(2R,5S)-5-({[(2,2,2-trifluoroethyl)carbamoyl]oxy}methyl)morpholin-2-yl]ethyl}pyridin-3-yl)-L-phenylalaninamide;

4-fluoro-Nα-[(2-fluoroethoxy)carbonyl]-β-(4-fluorophenyl)-N-(5-fluoro-4-{2-[(2R,5S)-5-({[(2,2,2-trifluoroethyl)carbamoyl]oxy}methyl)morpholin-2-yl]ethyl}pyridin-3-yl)-L-phenylalaninamide;

3-fluoro-β-(3-fluorophenyl)-N-(5-fluoro-4-{2-[(2R,5S)-5-({[(2,2,2-trifluoroethyl)carbamoyl]oxy}methyl)morpholin-2-yl]ethyl}pyridin-3-yl)-Nα-(methoxycarbonyl)-L-phenylalaninamide;

(βS)-3-fluoro-β-(4-fluorophenyl)-N-(5-fluoro-4-{2-[(2R,5S)-5-({[(2,2,2-trifluoroethyl)carbamoyl]oxy}methyl)morpholin-2-yl]ethyl}pyridin-3-yl)-Nα-(methoxycarbonyl)-L-phenylalaninamide;

(βR)-4-fluoro-β-(3-fluorophenyl)-N-(5-fluoro-4-{2-[(2R,5S)-5-({[(2,2,2-trifluoroethyl)carbamoyl]oxy}methyl)morpholin-2-yl]ethyl}pyridin-3-yl)-Nα-(methoxycarbonyl)-L-phenylalaninamide;

(βS)-β-(4-fluorophenyl)-N-(5-fluoro-4-{2-[(2R,5S)-5-({[(2,2,2-trifluoroethyl)carbamoyl]oxy}methyl)morpholin-2-yl]ethyl}pyridin-3-yl)-Nα-(methoxycarbonyl)-O-(trifluoromethyl)-L-tyrosinamide;

N-[2-(2-{(2R,5S)-5-[(carbamoyloxy)methyl]morpholin-2-yl}ethyl)-3-fluorophenyl]-4-fluoro-β-(4-fluorophenyl)-Nα-(methoxycarbonyl)-L-phenylalaninamide;

4-fluoro-β-(4-fluorophenyl)-N-(3-fluoro-2-{2-[(2R,5S)-5-({[(2,2,2-trifluoroethyl)carbamoyl]oxy}methyl)morpholin-2-yl]ethyl}phenyl)-Nα-(methoxycarbonyl)-L-phenylalaninamide;

(βS)-β-(4-fluorophenyl)-N-(5-fluoro-4-{2-[(2R,5S)-5-({[(2,2,2-trifluoroethyl)carbamoyl]oxy}methyl)morpholin-2-yl]ethyl}pyridin-3-yl)-Nα-(methoxycarbonyl)-4-(trifluoromethyl)-L-phenylalaninamide;

(βS)-3-fluoro-β-(4-fluorophenyl)-N-(3-fluoro-2-{2-[(2R,5S)-5-({[(2,2,2-trifluoroethyl)carbamoyl]oxy}methyl)morpholin-2-yl]ethyl}phenyl)-Nα-(methoxycarbonyl)-L-phenylalaninamide;

(βS)-3,4-difluoro-β-(4-fluorophenyl)-N-(5-fluoro-4-{2-[(2R,5S)-5-({[(2,2,2-trifluoroethyl)carbamoyl]oxy}methyl)morpholin-2-yl]ethyl}pyridin-3-yl)-Nα-(methoxycarbonyl)-L-phenylalaninamide;

(βR)-4-fluoro-N-(3-fluoro-2-{2-[(2R,5S)-5-({[(2,2,2-trifluoroethyl)carbamoyl]oxy}methyl)morpholin-2-yl]ethyl}phenyl)-Nα-(methoxycarbonyl)-β-naphthalen-2-yl-L-phenylalaninamide;

(βR)—N-(3-fluoro-2-{2-[(2R,5S)-5-({[(2,2,2-trifluoroethyl)carbamoyl]oxy}methyl)morpholin-2-yl]ethyl}phenyl)-Nα-(methoxycarbonyl)-β-naphthalen-2-yl-L-phenylalaninamide;

(βR)—N-(5-fluoro-4-{2-[(2R,5S)-5-({[(2,2,2-trifluoroethyl)carbamoyl]oxy}methyl)morpholin-2-yl]ethyl}pyridin-3-yl)-Nα-(methoxycarbonyl)-β-phenyl-O-(trifluoromethyl)-L-tyrosinamide;

(βS)-3,5-difluoro-β-(4-fluorophenyl)-N-(3-fluoro-2-{2-[(2R,5S)-5-({[(2,2,2-trifluoroethyl)carbamoyl]oxy}methyl)morpholin-2-yl]ethyl}phenyl)-Nα-(methoxycarbonyl)-L-phenylalaninamide;

(βR)—N-(3-fluoro-2-{2-[(2R,5S)-5-({[(2,2,2-trifluoroethyl)carbamoyl]oxy}methyl)morpholin-2-yl]ethyl}phenyl)-Nα-(methoxycarbonyl)-β-propyl-L-phenylalaninamide;

(βR)-β-(3,4-difluorophenyl)-N-(3-fluoro-2-{2-[(2R,5S)-5-({[(2,2,2-trifluoroethyl)carbamoyl]oxy}methyl)morpholin-2-yl]ethyl}phenyl)-Nα-(methoxycarbonyl)-L-phenylalaninamide;

(βR)-β-(3,4-difluorophenyl)-4-fluoro-N-(3-fluoro-2-{2-[(2R,5S)-5-({[(2,2,2-trifluoroethyl)carbamoyl]oxy}methyl)morpholin-2-yl]ethyl}phenyl)-Nα-(methoxycarbonyl)-L-phenylalaninamide;

(βR)—N-(3-fluoro-2-{2-[(2R,5S)-5-({[(2,2,2-trifluoroethyl)carbamoyl]oxy}methyl)morpholin-2-yl]ethyl}phenyl)-Nα-(methoxycarbonyl)-O-methyl-β-phenyl-L-tyrosinamide;

(βR)-3,4-difluoro-β-(4-fluorophenyl)-N-(5-fluoro-4-{2-[(2R,5S)-5-({[(2,2,2-trifluoroethyl)carbamoyl]oxy}methyl)morpholin-2-yl]ethyl}pyridin-3-yl)-Nα-(methoxycarbonyl)-L-phenylalaninamide;

(βR)-β-(4-bromophenyl)-4-fluoro-N-(5-fluoro-4-{2-[(2R,5S)-5-({[(2,2,2-trifluoroethyl)carbamoyl]oxy}methyl)morpholin-2-yl]ethyl}pyridin-3-yl)-Nα-(methoxycarbonyl)-L-phenylalaninamide;

(βS)-β-(4-fluorophenyl)-N-(3-fluoro-2-{2-[(2R,5S)-5-({[(2,2,2-trifluoroethyl)carbamoyl]oxy}methyl)morpholin-2-yl]ethyl}phenyl)-Nα-(methoxycarbonyl)-O-methyl-L-tyrosinamide;

(βS)-2,5-difluoro-β-(4-fluorophenyl)-N-(5-fluoro-4-{2-[(2R,5S)-5-({[(2,2,2-trifluoroethyl)carbamoyl]oxy}methyl)morpholin-2-yl]ethyl}pyridin-3-yl)-Nα-(methoxycarbonyl)-L-phenylalaninamide;

(βS)-3-chloro-β-(4-fluorophenyl)-N-(5-fluoro-4-{2-[(2R,5S)-5-({[(2,2,2-trifluoroethyl)carbamoyl]oxy}methyl)morpholin-2-yl]ethyl}pyridin-3-yl)-Nα-(methoxycarbonyl)-L-phenylalaninamide;

(βS)-2,3-difluoro-β-(4-fluorophenyl)-N-(5-fluoro-4-{2-[(2R,5S)-5-({[(2,2,2-trifluoroethyl)carbamoyl]oxy}methyl)morpholin-2-yl]ethyl}pyridin-3-yl)-Nα-(methoxycarbonyl)-L-phenylalaninamide;

(βS)-4-fluoro-N-(3-fluoro-2-{2-[(2R,5S)-5-({[(2,2,2-trifluoroethyl)carbamoyl]oxy}methyl)morpholin-2-yl]ethyl}phenyl)-Nα-(methoxycarbonyl)-β-[3-(trifluoromethoxy)phenyl]-L-phenylalaninamide;

(βR)-β-(4-fluorophenyl)-N-(3-fluoro-2-{2-[(2R,5S)-5-({[(2,2,2-trifluoroethyl)carbamoyl]oxy}methyl)morpholin-2-yl]ethyl}phenyl)-Nα-(methoxycarbonyl)-O-(trifluoromethyl)-L-tyrosinamide;

(βR)—N-(3-fluoro-2-{2-[(2R,5S)-5-({[(2,2,2-trifluoroethyl)carbamoyl]oxy}methyl)morpholin-2-yl]ethyl}phenyl)-3-methoxy-Nα-(methoxycarbonyl)-β-phenyl-L-phenylalaninamide;

(βR)-4-fluoro-N-(3-fluoro-2-{2-[(2R,5S)-5-({[(2,2,2-trifluoroethyl)carbamoyl]oxy}methyl)morpholin-2-yl]ethyl}phenyl)-Nα-(methoxycarbonyl)-β-(3-methoxyphenyl)-L-phenylalaninamide; and 3-fluoro-β-(3-fluorophenyl)-N-(3-fluoro-2-{2-[(2R,5S)-5-({[(2,2,2-trifluoroethyl)carbamoyl]oxy}methyl)morpholin-2-yl]ethyl}phenyl)-Nα-(methoxycarbonyl)-L-phenylalaninamide;

and pharmaceutically acceptable salts thereof.

19. A pharmaceutical composition comprising an effective amount of a compound according to any one of claim 1 or a pharmaceutically acceptable salt thereof, and a pharmaceutically acceptable carrier.

20. A method for the treatment of infection by HIV or for the treatment or delay in the onset of AIDS in a subject infected with HIV, which comprises administering to the subject an effective amount of the compound according to claim 1 or a pharmaceutically acceptable salt thereof.

21. A pharmaceutical composition comprising an effective amount of a compound according to any one of claim 1, or a pharmaceutically acceptable salt thereof, and a pharmaceutically acceptable carrier and further comprising an effective amount of an anti-HIV agent selected from the group consisting of HIV antiviral agents, immunomodulators, and anti-infective agents.

22. The pharmaceutical composition of claim 21, wherein the anti-HIV agent is an antiviral selected from the group consisting of HIV protease inhibitors, HIV reverse transcriptase inhibitors, HIV integrase inhibitors, HIV fusion inhibitors, HIV entry inhibitors, and HIV maturation inhibitors.

23. The compound selected from:

Nα-(methoxycarbonyl)-β-phenyl-N-(2-{2-[(2R,5S)-5-(phenylcarbamoyl)morpholin-2-yl]ethyl}phenyl)-L-phenylalaninamide, (βR)-β-(4-Chlorophenyl)-N-(5-fluoro-4-{2-[(2R,5S)-5-({[(2,2,2-trifluoroethyl)carbamoyl]oxy}methyl)morpholin-2-yl]ethyl}pyridin-3-yl)-L-phenylalaninamide, (βS)-β-(4-Chlorophenyl)-3,5-difluoro-N-(5fluoro-4-{2-[(2R,5S)-5-({[(2,2,2-trifluoroethyl)carbamoyl]oxy}methyl)morpholin-2-yl]ethyl}pyridin-3-yl)-L-phenylalaninamide, (βR)-β-(4-Chlorophenyl)-N-(5-fluoro-4-{2-{(2R,5S)-5-({[(2,2,2-trifluoroethyl)carbamoyl]oxy}methyl)morpholin-2-yl]ethyl}pyridin-3-yl)-Nα-(methoxycarbonyl)-L-phenylalaninamide, βR)-4-bromo-β-(4-fluorophenyl)-N-(5-fluoro-4-{2-[(2R,5S)-5-({[(2,2,2-trifluoroethyl)carbamoyl]oxy}methyl)morpholin-2-yl]ethyl}pyridin-3-yl)-L-phenylalaninamide, 4-fluoro-β-(4-fluorophenyl)-N-[5-fluoro-4-(2-{(2R,5S)-5-[({[3,3,3-trifluoro-1-(4-fluorophenyl)propyl]carbamoyl}oxy)methyl]morpholin-2-yl}ethyl)pyridin-3-yl]-L-phenylalaninamide, or a pharmaceutically acceptable salt thereof.

* * * * *